US006476193B1

(12) United States Patent
Nandabalan et al.

(10) Patent No.: US 6,476,193 B1
(45) Date of Patent: Nov. 5, 2002

(54) NLK1 PROTEIN AND NLK1 PROTEIN COMPLEXES

(75) Inventors: Krishnan Nandabalan, Guilford, CT (US); Vincent P. Schulz, Madison, CT (US); Meija Yang, East Lyme, CT (US)

(73) Assignee: CuraGen Corporation, New Haven, CT (US)

( * ) Notice: Subject to any disclaimer, the term of this patent is extended or adjusted under 35 U.S.C. 154(b) by 0 days.

(21) Appl. No.: 09/167,206

(22) Filed: Oct. 6, 1998

(51) Int. Cl.[7] .................... C07K 14/00; A61K 38/00; C07H 21/02; C07H 21/04
(52) U.S. Cl. .................. 530/350; 530/350; 530/324; 514/2; 435/320.1; 435/252.3; 435/194; 435/6; 435/15; 435/91.1; 536/23.1
(58) Field of Search .................... 435/320.1, 252.3, 435/6, 15, 91.1, 194; 536/23.1; 530/350, 324

(56) References Cited

FOREIGN PATENT DOCUMENTS

| WO | WO 98/27994 | 7/1998 |
| WO | WO 41376 A | 8/1999 |

OTHER PUBLICATIONS

Hillier et al., Gene Bank Accession No. AA143467, Nov. 8 (1997).*
Aitken, 1995. "14–3 proteins on the MAP." Trends Biochem Sci. 20: 95–97.
Aitken, et al., 1995. "14–3–3 α and δ are the phosphorylated forms of Ras–activating 14–3 β and ζ." J Biol Chem. 270: 5706–5709.
Barbacid. 1995. "Neurotrophic factors and their receptors." Curr. Opin. Cell. Biol., 7: 148–155.
Bazan, et al. 1997. "Experimental models and their use in studies of diabetic retinal microangiopathy." Therapie, 52: 447–51.
Braverman, et al. 1996. "Anti–oncogenic effects of tropomyosin: isoform specificity and importance of protein coding sequences." Oncogene, 13:537–545.
Conklin, et al. 1995. "14–3–3 proteins associate with cdc25 phosphatases." Proc. Natl. Acad. Sci. USA, 92:7892–7896.
Drelich, et al. 1993. "Conserved residues Pro–109 and Asp–116 are required for interaction of the human immunodeficiency virus type 1 integrase protein with its viral DNA substrate." J. Virol., 67: 5041–5044.
Durfee, et al. 1993. "The retinoblastoma protein associates with the protein phosphatase type 1 catalytic subunit." Genes Dev, 7: 555–569.
Ehrhard, et al. 1993. "Expression of functional trk protooncogene in human monocytes." Proc. Natl. Acad. Sci. USA, 90: 5423–5427.
Ermisch, et al. 1995. "Protein gene product (PGP) 9.5 in diagnostic (neuro–) oncology. An immunomorphological study." Clin. Neuropathol., 14: 130–136.

Fields, et al. 1989. "A novel genetic system to detect protein–protein interactions." Nature, 340: 245–246.
Franzen, et al. 1996. "Expression of tropomyosin isoforms in benign and malignant human breast lesions." Br. J. Cancer, 73: 909–913.
Fry, et al., 1995a. "Substrate specificity and cell cycle regulation of the Nek2 protein kinase, a potential human homolog of the mitotic regulator NIMA of *Aspergillus nidulans*." J. Biol. Chem., 270: 12899–12905.
Fry, et al., 1995b. "Cell cycl. The NIMA kinase joins forces with Cdc2." Curr. Biol., 5: 1122–11.
Fry, et al. 1997. "Characterization of mammalian NIMA––related kinases." Meth. Enzym., 283: 270–282.
Fry, et al. 1998. "A centrosomal function for the human Nek2 protein kinase, a member of the NIMA family of cell cycle regulators." EMBO J., 17: 470–481.
Good, et al. 1997. "Expression of small therapeutic RNAs in human cell nuclei." GeneTherapy, 4:45–54.
Grassi, et al. 1996. "Ribozymes: structure, function, and potential therapy for dominant genetic disorders." Annals of Med., 28: 499–510.
Hall. 1997. "The roles of calmodulin, actin, and vimentin in steroid synthesis by adrenal cells." Steroids, 62: 185–189.
Hatzfield, et al. 1996. "Cloning and characterization of a new armadillo family member, p0071, associated with the junctional plaque: evidence for a subfamily of closely related proteins." J. Cell Sci., 109: 2767–2778.
Hoehner, et al. 1995. "Association of neurotrophic receptor expression and differentiation in human neuroblastoma." Am. J. Pathol., 147: 102–113.
Honore, et al. 1990. "Nucleotide sequence of cDNA covering the complete coding part of the human vimentin gene." Nucl Acids Res. 18:6692.
Kalpana, et al. 1994. "Binding and stimulation of HIV–1 integrase by a human homolog of yeast transcription factor SNF5." Science, 266: 2002–2006.
Koller, et al. 1989. "Inactivating the beta 2–microglobulin locus in mouse embryonic stem cells by homologous recombination." Proc. Natl. Acad. Sci. USA, 86: 8932–8935.

(List continued on next page.)

Primary Examiner—Karen Cochrane Carlson
Assistant Examiner—Chih-Min Kam
(74) Attorney, Agent, or Firm—Mintz Levin; Ivor R. Elrifi; Naomi S. Biswas

(57) ABSTRACT

The present invention discloses complexes of the Nlk1 protein with proteins identified as interacting with the Nlk1 protein (Nlk1 protein-IPs) by a modified, improved yeast two hybrid assay system. The proteins which were identified to interact with the Nlk1 protein, and thus form complexes, included: TrkA, protein phosphatase 1α, 14-3-3ε, α-tropomyosin, vimentin, p0071, Ini-1, IP-1, IP-2, IP-3, IP-4 and IP-5, as well as derivatives, fragments analogs and homologs thereof. Methodologies of screening these aforementioned complexes for efficacy in treating and/or preventing various diseases and disorders, particularly, neoplasia, neurodegenerative disease, hypertrophic cardiomyopathy, viral infections and metabolic diseases and disorders are also disclosed herein.

46 Claims, 28 Drawing Sheets

OTHER PUBLICATIONS

Lafarge–Frayssinet, et al., 1995. "Cellular genes possibly involved in the transformation process of the human melanoma cell line XP44 RO (Mel)." Anticancer Res. 15: 1205–1213.

Lu, et al. 1995. "Evidence for a NIMA–like mitotic pathway in vertebrate cells." Cell, 81: 413–424.

MacLeod, et al. 1988. "Human hTM alpha gene: expression in muscle and nonmuscle tissue." Mol. Cell. Biol., 8: 433–440.

Matsushima, et al. 1993. "Expression of trkA cDNA in neuroblastoma mediates differentiation in vitro and in vivo." Mol. Cell. Biol., 13: 7447–7456.

Mayer, et al. 1991. "The role of protein ubiquitination in neurodegenerative disease." Acta Biol. Hung., 42: 21–26.

Muragaki, et al. 1997. "Nerve growth factor induces apoptosis in human medulloblastoma cell lines that express TrkA receptors." J. Neurosci., 17: 530–542.

Ogihara, et al. 1997. "14–3–3 protein binds to insulin receptor substrate–1, one of the binding sites of which is in the phosphotyrosine binding domain." J. Biol. Chem., 272: 25267–25274.

Pu, et al., 1995b. "Mitotic destruction of the cell cycle regulated NIMA protein kinase of *Aspergillus nidulans* is required for mitotic exit." EMBO J., 14: 995–1003.

Rhee, et al. 1997. "The NIMA–related kinase 2, Nek2, is expressed in specific stages of the meiotoc cell cycle and associates with meiotic chromosomes." Development, 124: 2167–1277.

Saadat, et al. 1995. "Neoplastic alterations in subcellular distribution of type 1 alpha protein phosphatase in rat ascites hepatoma cells." Cancer Lett., 94: 165–170.

Schultz, et al. 1994. "Cell cycle–dependent expression of Nek2, a novel human protein kinase related to the NIMA mitotic regulator of *Aspergillus nidulans*." Cell Growth Diff., 5: 625–632.

Seroz, et al., 1995. "TFIIH: a link between transcription, DNA repair and cell cycle regulation." Curr Opin Genet Dev. 5: 217–222.

Simcha, et al. 1996. "Suppression of tumorigenicity by plakoglobin: an augmenting effect of N–cadherin." J. Cell. Biol., 133: 199–209.

Song, et al. 1993. "Cloning and characterization of a human protein phosphatase 1–encoding cDNA." Gene, 129: 291–295.

Swanson, et al. 1996. "A ubiquitin C–terminal hydrolase gene on the proximal short arm of the X chromosome: implications for X–linked retinal disorders." Hum. Mol. Genet., 5: 533–538.

Tanaka, et al. 1995. "trk A gene expression in neuroblastoma. The clinical significance of an immunohistochemical study." Cancer, 76: 1086–1095.

Thompson, et al. 1994. "Collagen induced NMP–2 activation in human breast cancer." Breast Cancer Res. Treat., 31: 357–370.

Tomlinson, et al. 1996. "Neurotrophins and peripheral neuropathy." Philos. Trans. R. Soc. Lond. B Biol. Sc., 351: 455–462.

Wheeler–Jones, et al. 1996. "Identification of 14–3–3 proteins in human platelets: effects of synthetic peptides on protein kinase C activation." Biochem. J., 315: 41–47.

Wu, et al. 1996. "Epstein–Barr virus nuclear protein 2 (EBNA2) binds to a component of hte human SNF–SWI complex, hSNF5/Inil." J. Virol., 70: 6020–6028.

Fry et al., "C–Napl, a Novel Centrosomal Coiled–Coil Protein and Candidate Substrate of the Cell Cycle–regulated Protein Kinase Nek2", J. Cell Biol. 141(7):1563–74, 1998.

Kramer et al., "Monoclonal Antibody to Human TRK–A: a Diagnostic and Therapeutic Potential in Neuroblastoma", Eur. J. Cancer 33(12):2090–91, 1997.

Martin–Zanca et al., "A human oncogene formed by the fusion of truncated tropomyosin and protein tyrosine kinase sequences", Nature 319:743–48, 1986.

Rovelli et al., "Chimeric tumor necrosis factor–TrkA receptors reveal that ligan–dependent activation of the trkA tyrosine kinase is sufficient for differentiation and survival of PC12 cells", Proc. Nat. Acad. Sci. USA. 90:8717–21, 1993.

\* cited by examiner

1   GGCACGAGTAGGGGTGGCGGGTCAGTGCTGCTCGGGGGCTTCTCC
46  ATCCAGGTCCCTGGAGTTCCTGGTCCCTGGAGCTCCGCACTTGGC

91  GCGCAACCTGCGTGAGGCAGCGCGACTCTGGCGACTGGCCGGCCA
                                                M

136 TGCCTTCCCGGGCTGAGGACTATGAAGTGTTGTACACCATTGGCA
    etProSerArgAlaGluAspTyrGluValLeuTyrThrIleGlyT

181 CAGGCTCCTACGGCCGCTGCCAGAAGATCCGGAGGAAGAGTGATG
    hrGlySerTyrGlyArgCysGlnLysIleArgArgLysSerAspG

226 GCAAGATATTAGTTTGGAAAGAACTTGACTATGGCTCCATGACAG
    lyLysIleLeuValTrpLysGluLeuAspTyrGlySerMetThrG

271 AAGCTGAGAAACAGATGCTTGTTTCTGAAGTGAATTTGCTTCGTG
    luAlaGluLysGlnMetLeuValSerGluValAsnLeuLeuArgG

316 AACTGAAACATCCAAACATCGTTCGTTACTATGATCGGATTATTG
    luLeuLysHisProAsnIleValArgTyrTyrAspArgIleIleA

361 ACCGGACCAATACAACACTGTACATTGTAATGGAATATTGTGAAG
    spArgThrAsnThrThrLeuTyrIleValMetGluTyrCysGluG

406 GAGGGGATCTGGCTAGTGTAATTACAAAGGGAACCAAGGAAAGGC
    lyGlyAspLeuAlaSerValIleThrLysGlyThrLysGluArgG

451 AATACTTAGATGAAGAGTTTGTTCTTCGAGTGATGACTCAGTTGA
    inTyrLeuAspGluGluPheValLeuArgValMetThrGlnLeuT

496 CTCTGGCCCTGAAGGAATGCCACAGACGAAGTGATGGTGGTCATA
    hrLeuAlaLeuLysGluCysHisArgArgSerAspGlyGlyHisT

541 CCGTATTGCATCGGGATCTTAAACCAGCCAATGTTTTCCTGGATG
    hrValLeuHisArgAspLeuLysProAlaAsnValPheLeuAspG

586 GCAAGCAAAACGTCAAGCTTGGAGACTTTGGGCTAGCTAGAATAT
    lyLysGlnAsnValLysLeuGlyAspPheGlyLeuAlaArgIleL

631 TAAACCATGACACGAGTTTTGCAAAAACATTTGTTGGCACACCTT
    euAsnHisAspThrSerPheAlaLysThrPheValGlyThrProT

676 ATTACATGTCTCCTGAACAAATGAATCGCATGTCCTACAATGAGA
    yrTyrMetSerProGluGluMetAsnArgMetSerTyrAsnGluL

721 AATCAGATATCTGGTCATTGGGCTGCTTGCTGTATGAGTTATGTG
    ysSerAspIleTrpSerLeuGlyCysLeuLeuTyrGluLeuCysA

766 CATTAATGCCTCCATTTACAGCTTTTAGCCAGAAAGAACTCGCTG
    laLeuMetProProPheThrAlaPheSerGlnLysGluLeuAlaG

811 GGAAAATCAGAGAAGGCAAATTCAGGCGAATTCCATACCGTTACT
    lyLysIleArgGluGlyLysPheArgArgIleProTyrArgTyrS

Fig. 1A

```
 856  CTGATGAATTGAATGAAATTATTACGAGGATGTTAAACTTAAAGG
      erAspGluLeuAsnGluIleIleThrArgMetLeuAsnLeuLysA

901  ATTACCATCGACCTTCTGTTGAAGAAATTCTTGAGAACCCTTTAA
      spTyrHisArgProSerValGluGluIleLeuGluAsnProLeuI

946  TAGCAGATTTGGTTGCAGACGAGCAAAGAAGAAATCTTGAGAGAA
      leAlaAspLeuValAlaAspGluGlnArgArgAsnLeuGluArgA

991  GAGGGCGACAATTAGGAGAGCCAGAAAAATCGCAGGATTCCAGCC
      rgGlyArgGlnLeuGlyGluProGluLysSerGlnAspSerSerP

1036  CTGTATTGAGTGAGCTGAAACTGAAGGAAATTCAGTTACAGGAGC
      roValLeuSerGluLeuLysLeuLysGluIleGlnLeuGlnGluA

1081  GAGAGCGAGCTCTCAAAGCAAGAGAAGAAAGATTGGAGCAGAAAG
      rgGluArgAlaLeuLysAlaArgGluGluArgLeuGluGlnLysG

1126  AACAGGAGCTTTGTGTTCGTGAGAGACTAGCAGAGGACAAACTGG
      luGlnGluLeuCysValArgGluArgLeuAlaGluAspLysLeuA

1171  CTAGAGCAGAAAATCTGTTGAAGAACTACAGCTTGCTAAAGGAAC
      laArgAlaGluAsnLeuLeuLysAsnTyrSerLeuLeuLysGluA

1216  GGAAGTTCCTGTCTCTGGCAAGTAATCCAGAACTTCTTAATCTTC
      rgLysPheLeuSerLeuAlaSerAsnProGluLeuLeuAsnLeuP

1261  CATCCTCAGTAATTAAGAAGAAAGTTCATTTCAGTGGGGAAAGTA
      roSerSerValIleLysLysLysValHisPheSerGlyGluSerL

1306  AAGAGAACATCATGAGGAGTGAGAATTCTGAGAGTCAGCTCACAT
      ysGluAsnIleMetArgSerGluAsnSerGluSerGlnLeuThrS

1351  CTAAGTCCAAGTGCAAGGACCTGAAGAAAAGGCTTCACGCTGCCC
      erLysSerLysCysLysAspLeuLysLysArgLeuHisAlaAlaG

1396  AGCTGCGGGCTCAAGCCCTGTCAGATATTGAGAAAAATTACCAAC
      lnLeuArgAlaGlnAlaLeuSerAspIleGluLysAsnTyrGlnL

1441  TGAAAAGCAGACAGATCCTGGGCATGCGCTAGCCAGGTAGAGAGA
      euLysSerArgGlnIleLeuGlyMetArg

1486  CACAGAGCTGTGTACAGGATGTAATATTACCAACCTTTAAAGACT
1531  GATATTCAAATGCTGTAGTGTTAATACTTGGCCCCATGAGCCAT
1576  GCCTTTCTGTATAGTACACATGATATTTCGGAATTGGTTTTACTG
1621  TTCTTCAGCAACTATTGTACAAAATGTTCACATTTAATTTTTCTT
1666  TCTTCTTTTAAGAACATATTATAAAAGAATACTTTCTTGGTTGG
1711  GCTTTTAATCCTGTGTGTGATTACTAGTAGGAACATGAGATGTGA
1756  CATTCTAAATCTTGGGAGAAAAAATAATATTAGGAAAAAAATATT
1801  TATGCAGGAAGAGTAGCACTCACTGAATAGTTTTAAATGACTGAG
1846  TGGTATGCTTACAATTGTCATGTCTAGATTTAAATTTTAAGTCTG
1891  AGATTTTAAATGTTTTTGAGCTTAGAAAACCCAGTTAGATGCAAT
1936  TTGGTCATTAATACCATGACATCTTGCTTATAAATATTCCATTGC
1981  TCTGTAGTTCAAATCTGTTAGCTTTGTGAAAATTCATCACTGTGA
2026  TGTTTGTATTCTTTTTTTTTTTTCTGTTTAACAGAATATGAGCTGT
2071  CTGTCATTTACCTACTTCTTTCCCACTAAATAAAGAATTCTTCA

2116  GTTA
```

Fig. 1B

```
  1  GTCGACCGGAGGGCAGGAGGAGCAGGAGGAGCAGGAGCAGGAGGA
 46  GCAGGAGGAGCAGGAGGAGCAGGAGGAGCAGGAGGAGCAGGAACA
 91  GGAGGAGGAGGAGGAGGAGAAGGAGGAGCAGGAAGAGCAGGAGGA
136  GGAGGAGCAGGAGCAGGAGGAGCAGGAGGGAGAGGAGGCTGCAAC
181  GCCGAGCGGAGGAGGCAGGAACCGGAGCGCGAGCAGTAGCTGGGT

226  GGGCACCATGGCTGGGATCACCACCATCGAGGCGGTGAAGCGCAA
         metAlaGlyIleThrThrIleGluAlaValLysArgLy 271  GATCCAGGTTCTGCAGCAGCAGGCAGATGATGCAGAGGAGCGAGC
     sIleGlnValLeuGlnGlnGlnAlaAspAspAlaGluGluArgAl 316  TGAGCGCCTCCAGCGAGAAGTTGAGGGAGAAAGGCGGGCCCGGGA
     aGluArgLeuGlnArgGluValGluGlyGluArgArgAlaArgGl 361  ACAGGCTGAGGCTGAGGTGGCCTCCTTGAACCGTAGGATCCAGCT
     uGlnAlaGluAlaGluValAlaSerLeuAsnArgArgIleGlnLe 406  GGTTGAAGAAGAGCTGGACCGTGCTCAGGAGCGCCTGGCCACTGC
     uValGluGluGluLeuAspArgAlaGlnGluArgLeuAlaThrAl 451  CCTGCAAAAGCTGGAAGAAGCTGAAAAAGCTGCTGATGAGAGTGA
     aLeuGlnLysLeuGluGluAlaGluLysAlaAlaAspGluSerGl 496  GAGAGGTATGAAGGTTATTGAAAACCGGGCCTTAAAAGATGAAGA
     uArgGlyMetLysValIleGluAsnArgAlaLeuLysAspGluGl 541  AAAGATGGAACTCCAGGAAATCCAACTCGAAGAAGCTAAGCACAT
     uLysMetGluLeuGlnGluIleGlnLeuGluGluAlaLysHisIl 586  TGCAGAAGAGGCAGATAGGAAGTATGAAGAGGTGGCTCGTAAGTT
     eAlaGluGluAlaAspArgLysTyrGluGluValAlaArgLysLe 631  GGTGATCATTGAAGGAGACTTGGAACGCACAGAGGAACGAGCTGA
     uValIleIleGluGlyAspLeuGluArgThrGluGluArgAlaGl 676  GCTGGCAGAGTCGCGTTGCCGAGAGATGGATGAGCAGATTAGACT
     uLeuAlaGluSerArgCysArgGluMetAspGluGlnIleArgLe 721  GATGGACCAGAACCTGAAGTGTCTGAGTGCTGCCGAAGAAAAGTA
     uMetAspGlnAsnLeuLysCysLeuSerAlaAlaGluGluLysTy 766  CTCTCAAAAAGAAGATAAATATGAGGAAGAAATCAAGATTCTTAC
     rSerGlnLysGluAspLysTyrGluGluGluIleLysIleLeuTh 811  TGATAAACTCAAGGAGGCAGAGACCCGTGCTGAGTTTGCTGAGAG
     rAspLysLeuLysGluAlaGluThrArgAlaGluPheAlaGluAr 856  ATCGGTAGCCAAGCTGGAAAAGACAATTGATGACCTGGAAGACAC
     gSerValAlaLysLeuGluLysThrIleAspAspLeuGluAspTh 901  TAACAGCACATCTGGAGACCCGGTGGAGAAGAAGGACGAAACACC
     rAsnSerThrSerGlyAspProValGluLysLysAspGluThrPr
```

Fig. 2A

```
 946  TTTTGGGGTCTCGGTGGCTGTGGGCCTGGCCGTCTTTGCCTGCCT
      oPheGlyValSerValAlaValGlyLeuAlaValPheAlaCysLe

991  CTTCCTTTCTACGCTGCTCCTTGTGCTCAACAAATGTGGACGGAG
      uPheLeuSerThrLeuLeuLeuValLeuAsnLysCysGlyArgAr

1036  AAACAAGTTTGGGATCAACCGCCCGGCTGTGCTGGCTCCAGAGGA
      gAsnLysPheGlyIleAsnArgProAlaValLeuAlaProGluAs

1081  TGGGCTGGCCATGTCCCTGCATTTCATGACATTGGGTGGCAGCTC
      pGlyLeuAlaMetSerLeuHisPheMetThrLeuGlyGlySerSe

1126  CCTGTCCCCCACCGAGGGCAAAGGCTCTGGGCTCCAAGGCCACAT
      rLeuSerProThrGluGlyLysGlySerGlyLeuGlnGlyHisIl

1171  CATCGAGAACCCACAATACTTCAGTGATGCCTGTGTTCACCACAT
      eIleGluAsnProGlnTyrPheSerAspAlaCysValHisHisIl

1216  CAAGCGCCGGGACATCGTGCTCAAGTGGGAGCTGGGGGAGGGCGC
      eLysArgArgAspIleValLeuLysTrpGluLeuGlyGluGlyAl

1261  CTTTGGGAAGGTCTTCCTTGCTGAGTGCCACAACCTCCTGCCTGA
      aPheGlyLysValPheLeuAlaGluCysHisAsnLeuLeuProGl

1306  GCAGGACAAGATGCTGGTGGCTGTCAAGGCACTGAAGGAGGCGTC
      uGlnAspLysMetLeuValAlaValLysAlaLeuLysGluAlaSe

1351  CGAGAGTGCTCGGCAGGACTTCCAACGTGAGGCTGAGCTGCTCAC
      rGluSerAlaArgGlnAspPheGlnArgGluAlaGluLeuLeuTh

1396  CATGCTGCAGCACCAGCACATCGTGCGCTTCTTCGGCGTCTGCAC
      rMetLeuGlnHisGlnHisIleValArgPhePheGlyValCysTh

1441  CGAGGGCCGCCCCCTGCTCATGGTCTTCGAGTATATGCGGCACGG
      rGluGlyArgProLeuLeuMetValPheGluTyrMetArgHisGl

1486  GGACCTCAACCGCTTCCTCCGATCCCATGGACCCGATGCCAAGCT
      yAspLeuAsnArgPheLeuArgSerHisGlyProAspAlaLysLe

1531  GCTGGCTGGTGGGAGGATGTGGCTCCAGGCCCCCTGGGTCTGGG
      uLeuAlaGlyGlyGluAspValAlaProGlyProLeuGlyLeuGl

1576  GCAGCTGCTGGCCGTGGCTAGCCAGGTCGCTGCGGGGATGGTGTA
      yGlnLeuLeuAlaValAlaSerGlnValAlaAlaGlyMetValTy

1621  CCTGGCGGGTCTGCATTTTGTGCACCGGGACCTGGCCACACGCAA
      rLeuAlaGlyLeuHisPheValHisArgAspLeuAlaThrArgAs

1666  CTGTCTAGTGGGCCAGGGACTGGTGGTCAAGATTGGTGATTTTGG
      nCysLeuValGlyGlnGlyLeuValValLysIleGlyAspPheGl

1711  CATGAGCAGGGATATCTACAGCACCGACTATTACCGTGTGGGAGG
      yMetSerArgAspIleTyrSerThrAspTyrTyrArgValGlyGl

1756  CCGCACCATGCTGCCCATTCGCTGGATGCCGCCCGAGAGCATCCT
      yArgThrMetLeuProIleArgTrpMetProProGluSerIleLe
```

Fig. 2B

```
1801   GTACCGTAAGTTCACCACCGAGAGCGACGTGTGGAGCTTCGGCGT
       uTyrArgLysPheThrThrGluSerAspValTrpSerPheGlyVa

1846   GGTGCTCTGGGAGATCTTCACCTACGGCAAGCAGCCCTGGTACCA
       lValLeuTrpGluIlePheThrTyrGlyLysGlnProTrpTyrGl

1891   GCTCTCCAACACGGAGGCAATCGACTGCATCACGCAGGGACGTGA
       nLeuSerAsnThrGluAlaIleAspCysIleThrGlnGlyArgGl

1936   GTTGGAGCGGCCACGTGCCTGCCCACCAGAGGTCTACGCCATCAT
       uLeuGluArgProArgAlaCysProProGluValTyrAlaIleMe

1981   GCGGGGCTGCTGGCAGCGGGAGCCCAGCAACGCCACAGCATCAAG
       tArgGlyCysTrpGlnArgGluProSerAsnAlaThrAlaSerAr

2026   GATGTGCACGCCCGGCTGCAAGCCCTGGCCTAGGCACCTCCTGTC
       gMetCysThrProGlyCysLysProTrpProArgHisLeuLeuSe

2071   TACCTGGATGTCCTGGGCTAGGGGGCCGGCCCAGGGGCTGGGAGT
       rThrTrpMetSerTrpAlaArgGlyProAlaGlnGlyLeuGlyVa

2116   GGTTAGCCGGAATACTGGGGCCTGCCCTCAGCATCCCCCATAGCT
       lValSerArgAsnThrGlyAlaCysProGlnHisProPro

2161   CCCAGCAGCCCCAGGGTGATCTCGAAGTATCTAATTCGCCCTCAG
2206   CATGTGGGAAGGGACAGGTGGGGGCTGGGAGTAGAGGATGTTCCT
2251   GCTTCTCTAGGCAAGGTCCCGTCGTAGCAATTATATTTATTATGG
2296   GAATTC
```

Fig. 2C

| | |
|---|---|
| 1 | GGGCAAGGAGCTGCTGGCTGGACGGCGGCATGTCCGACAGCGAGA |
| | MetSerAspSerGluL |
| 46 | AGCTCAACCTGGACTCGATCATCGGGCGCCTGCTGGAAGTGCAGG |
| | ysLeuAsnLeuAspSerIleIleGlyArgLeuLeuGluValGlnG |
| 91 | GCTCGCGGCCTGGCAAGAATGTACAGCTGACAGAGAACGAGATCC |
| | lySerArgProGlyLysAsnValGlnLeuThrGluAsnGluIleA |
| 136 | GCGGTCTGTGCCTGAAATCCCGGGAGATTTTTCTGAGCCAGCCCA |
| | rgGlyLeuCysLeuLysSerArgGluIlePheLeuSerGlnProI |
| 181 | TTCTTCTGGAGCTGGAGGCACCCCTCAAGATCTGCGGTGACATAC |
| | leLeuLeuGluLeuGluAlaProLeuLysIleCysGlyAspIleH |
| 226 | ACGGCCAGTACTACGACCTTCTGCGACTATTTGAGTATGGCGGTT |
| | isGlyGlnTyrTyrAspLeuLeuArgLeuPheGluTyrGlyGlyP |
| 271 | TCCCTCCCGAGAGCAACTACCTCTTTCTGGGGGACTATGTGGACA |
| | heProProGluSerAsnTyrLeuPheLeuGlyAspTyrValAspA |
| 316 | GGGGCAAGCAGTCCTTGGAGACCATCTGCCTGCTGCTGGCCTATA |
| | rgGlyLysGlnSerLeuGluThrIleCysLeuLeuLeuAlaTyrL |
| 361 | AGATCAAGTACCCCGAGAACTTCTTCCTGCTCCGTGGGAACCACG |
| | ysIleLysTyrProGluAsnPhePheLeuLeuArgGlyAsnHisG |
| 406 | AGTGTGCCAGCATCAACCGCATCTATGGTTTCTACGATGAGTGCA |
| | luCysAlaSerIleAsnArgIleTyrGlyPheTyrAspGluCysL |
| 451 | AGAGACGCTACAACATCAAACTGTGGAAAACCTTCACTGACTGCT |
| | ysArgArgTyrAsnIleLysLeuTrpLysThrPheThrAspCysP |
| 496 | TCAACTGCCTGCCCATCGCGGCCATAGTGGACGAAAAGATCTTCT |
| | heAsnCysLeuProIleAlaAlaIleValAspGluLysIlePheC |
| 541 | GCTGCCACGGAGGCCTGTCCCCGGACCTGCAGTCTATGGAGCAGA |
| | ysCysHisGlyGlyLeuSerProAspLeuGlnSerMetGluGlnI |
| 586 | TTCGGCGGATCATGCGGCCCACAGATGTGCCTGACCAGGGCCTGC |
| | leArgArgIleMetArgProThrAspValProAspGlnGlyLeuL |
| 631 | TGTGTGACCTGCTGTGGTCTGACCCTGACAAGGACGTGCAGGGCT |
| | euCysAspLeuLeuTrpSerAspProAspLysAspValGlnGlyT |
| 676 | GGGGCGAGAACGACCGTGGCGTCTCTTTTACCTTTGGAGCCGAGG |
| | rpGlyGluAsnAspArgGlyValSerPheThrPheGlyAlaGluV |
| 721 | TGGTGGCCAAGTTCCTCCACAAGCACGACTTGGACCTCATCTGCC |
| | alValAlaLysPheLeuHisLysHisAspLeuAspLeuIleCysA |

Fig. 3A

```
766   GAGCACACCAGGTGGTAGAAGACGGCTATGAGTTCTTTGCCAAGC
      rgAlaHisGlnValValGluAspGlyTyrGluPhePheAlaLysA

811   GGCAGCTGGTGACACTTTTCTCAGCTCCCAACTACTGTGGCGAGT
      rgGlnLeuValThrLeuPheSerAlaProAsnTyrCysGlyGluP

856   TTGACAATGCTGGCGCCATGATGAGTGTGGACGAGACCCTCATGT
      heAspAsnAlaGlyAlaMetMetSerValAspGluThrLeuMetC

901   GCTCTTTCCAGATCCTCAAGCCCGCCGACAAGAACAAGGGGAAGT
      ysSerPheGlnIleLeuLysProAlaAspLysAsnLysGlyLysT

946   ACGGGCAGTTCAGTGGCCTGAACCCTGGAGGCCGACCCATCACCC
      yrGlyGlnPheSerGlyLeuAsnProGlyGlyArgProIleThrP

991   CACCCCGCAATTCCGCCAAAGCCAAGAAATAGCCCCCGCACACCA
      roProArgAsnSerAlaLysAlaLysLys

1036  CCCTGTGCCCCAGATGATGGATTGATTGTACAGAAATCATGCTGC
1081  CATGCTGGGGGGGGGTCACCCCGACCCCTAAGGCCCACCTGTCAC
1126  GGGGAACATGGAGCCTTGGTGTATTTTTCTTTTCTTTTTTTAATG
1171  AATCAATAGCAGCGTCCAGTCCCCAGGGCTGCTTCCTGCCTGCA
1216  CCTGCGGTACTGTGAGCAGGATCCTGGGGCCGAGGCTGCAGCTCA
1261  GGGCAACGGCAGGCCAGGTCGTGGGTCTCCAGCCGTGCTTGGCCT
1306  CAGGCTGGCAGCCCGGATCCTGGGGCAACCCATCTGGTCTCTTGA
1351  ATAAAGGTCAAAGCTGG
```

Fig. 3B

| | |
|---|---|
| 1 | ATGGATGATCGAGAGGATCTGGTGTACCAGGCGAAGCTGGCCGAG<br>MetAspAspArgGluAspLeuValTyrGluAlaLysLeuAlaGlu |
| 46 | CAGGCTGAGCGATACGACGAAATGGTGGAGTCAATGAAGAAAGTA<br>GlnAlaGluArgTyrAspGluMetValGluSerMetLysLysVal |
| 91 | GCAGGGATGGATGTGGAGCTGACAGTTGAAGAAAGAAACCTCCTA<br>AlaGlyMetAspValGluLeuThrValGluGluArgAsnLeuLeu |
| 136 | TCTGTTGCATATAAGAATGTGATTGGAGCTAGAAGAGCCTCCTGG<br>SerValAlaTyrLysAsnValIleGlyAlaArgArgAlaSerTrp |
| 181 | AGAATAATCAGCAGCATTGAACAGAAAGAAGAAAACAAGGGAGGA<br>ArgIleIleSerSerIleGluGlnLysGluGluAsnLysGlyGly |
| 226 | GAAGACAAGCTAAAAATGATTCGGGAATATCGGCAAATGGTTGAG<br>GluAspLysLeuLysMetIleArgGluTyrArgGlnMetValGlu |
| 271 | ACTGAGCTAAAGTTAATCTGTTGTGACATTCTGGATGTACTGGAC<br>ThrGluLeuLysLeuIleCysCysAspIleLeuAspValLeuAsp |
| 316 | AAACACCTCATTCCAGCAGCTAACACTGGCGAGTCCAAGGTTTTC<br>LysHisLeuIleProAlaAlaAsnThrGlyGluSerLysValPhe |
| 361 | TATTATAAAATGAAAGGGGACTACCACAGGTATCTGGCAGAATTT<br>TyrTyrLysMetLysGlyAspTyrHisArgTyrLeuAlaGluPhe |
| 406 | GCCACAGGAAACGACAGGAAGGAGGCTGCGGAGAACAGCCTAGTG<br>AlaThrGlyAsnAspArgLysGluAlaAlaGluAsnSerLeuVal |
| 451 | GCTTATAAAGCTGCTAGTGATATTGCAATGACAGAACTTCCACCA<br>AlaTyrLysAlaAlaSerAspIleAlaMetThrGluLeuProPro |
| 496 | ACGCATCCTATTCGCTTAGGTCTTGCTCTCAATTTTTCCGTATTC<br>ThrHisProIleArgLeuGlyLeuAlaLeuAsnPheSerValPhe |
| 541 | TACTACGAAATTCTTAATTCCCCTGACCGTGCCTGCAGGTTGGCA<br>TyrTyrGluIleLeuAsnSerProAspArgAlaCysArgLeuAla |

Fig. 4A

586  AAAGCAGCTTTTGATGATGCAATTGCAGAACTGGATACGCTGAGT
     LysAlaAlaPheAspAspAlaIleAlaGluLeuAspThrLeuSer

631  GAAGAAAGCTATAAGGACTCTACACTTATCATGCAGTTGTTACGT
     GluGluSerTyrLysAspSerThrLeuIleMetGlnLeuLeuArg

676  GATAATCTGACACTATGGACTTCAGACATGCAGGGTGACGGTGAA
     AspAsnLeuThrLeuTrpThrSerAspMetGlnGlyAspGlyGlu

721  GAGCAGAATAAAGAAGCGCTGCAGGACGTGGAAGACGAAAATCAG
     GluGlnAsnLysGluAlaLeuGlnAspValGluAspGluAsnGln

766  TGAGACATAAGCCAACAAGAGAAACCA
     AspIleSerGlnGlnGluLysPro

Fig. 4B

| | |
|---|---|
| 1 | CCGCGCGCTCGCCCCGCCGCTCCTGCTGCAGCCCCAGGCCCCTCG |
| 46 | CCGCCGCCACCATGGACGCCATCAAGAAGAAGATGCAGATGCTGA<br>               MetAspAlaIleLysLysLysMetGlnMetLeuLys |
| 91 | AGCTCGACAAGGAGAACGCCTTGGATCGAGCTGAGCAGGCGGAGG<br>LeuAspLysGluAsnAlaLeuAspArgAlaGluGlnAlaGluAla |
| 136 | CCGACAAGAAGGCGGCGGAAGACAGGAGCAAGCAGCTGGAAGATG<br>AspLysLysAlaAlaGluAspArgSerLysGlnLeuGluAspGlu |
| 181 | AGCTGGTGTCACTGCAAAAGAAACTCAAGGGCACCGAAGATGAAC<br>LeuValSerLeuGlnLysLysLeuLysGlyThrGluAspGluLeu |
| 226 | TGGACAAATACTCTGAGGCTCTCAAAGATGCCCAGGAGAAGCTGG<br>AspLysTyrSerGluAlaLeuLysAspAlaGlnGluLysLeuGlu |
| 271 | AGCTGGCAGAGAAAAAGGCCACCGATGCTGAAGCCGACGTAGCTT<br>LeuAlaGluLysLysAlaThrAspAlaGluAlaAspValAlaSer |
| 316 | CTCTGAACAGACGCATCCAGCTGGTTGAGGAAGAGTTGGATCGTG<br>LeuAsnArgArgIleGlnLeuValGluGluGluLeuAspArgAla |
| 361 | CCCAGGAGCGTCTGGCAACAGCTTTGCAGAAGCTGGAGGAAGCTG<br>GlnGluArgLeuAlaThrAlaLeuGlnLysLeuGluGluAlaGlu |
| 406 | AGAAGGCAGCAGATGAGAGTGAGAGAGGCATGAAAGTCATTGAGA<br>LysAlaAlaAspGluSerGluArgGlyMetLysValIleGluSer |
| 451 | GTCGAGCCCAAAAAGATGAAGAAAAAATGGAAATTCAGGAGATCC<br>ArgAlaGlnLysAspGluGluLysMetGluIleGlnGluIleGln |
| 496 | AACTGAAAGAGGCCAAGCACATTGCTGAAGATGCCGACCGCAAAT<br>LeuLysGluAlaLysHisIleAlaGluAspAlaAspArg<u>LysTyr</u> |
| 541 | ACGAAGAGGTGGCCCGTAAGCTGGTCATCATTGAGAGCGACCTGG<br>GluGluValAlaArgLysLeuValIleIleGluSerAspLeuGlu |
| 586 | AACGTGCAGAGGAGCGGGCTGAGCTCTCAGAAGGCAAATGTGCCG<br>ArgAlaGluGluArgAlaGluLeuSerGluGlyLysCysAlaGlu |
| 631 | AGCTTGAAGAAGAATTGAAAACTGTGACGAACAACTTGAAGTCAC<br>LeuGluGluGluLeuLysThrValThrAsnAsnLeuLysSerLeu |
| 676 | TGGAGGCTCAGGCTGAGAAGTACTCGCAGAAGGAAGACAGATATG<br>GluAlaGlnAlaGluLysTyrSerGlnLysGluAspArgTyrGlu |
| 721 | AGGAAGAGATCAAGGTCCTTTCCGACAAGCTGAAGGAGGCTGAGA<br>GluGluIleLysValLeuSerAspLysLeuLysGluAlaGluThr |
| 766 | CTCGGGCTGAGTTTGCGGAGAGGTCAGTAACTAAATTGGAGAAAA<br>ArgAlaGluPheAlaGluArgSerValThrLysLeuGluLysSer |

Fig. 5A

811  GCATTGATGACTTAGAAGACGAGCTGTACGCTCAGAAACTGAAGT
     IleAspAspLeuGluAspGluLeuTyrAlaGlnLysLeuLysTyr

856  ACAAAGCCATCAGCGAGGAGCTGGACCACGCTCTCAACGATATGA
     LysAlaIleSerGluGluLeuAspHisAlaLeuAsnAspMetThr

901  CTTCCATATAAGTTTCTTTGCTTCACTTCTCCCAAGACTCCCTCG
     SerIleValSerLeuLeuHisPheSerGlnAspSerLeuValGlu

946  TCGAGCTGGATGTCCCACCTCTCTGAGCTCTGCATTTGTCTATTC
     LeuAspValProProLeuAlaLeuHisLeuSerIleLeuGlnLeu

991  TCCAGCTGACCCTGGTTCTCTCTCTTAGCATCCTGCCTTAGAGCC
     ThrLeuValLeuSerLeuSerIleLeuProSerGlnAlaHisThr

1036 AGGCACACACTGTGCTTTCTATTGTACAGAAGCTCTTCGTTTCAG
     ValLeuSerIleValGlnLysLeuPheValSerValSerAsnLys

1081 TGTCAAATAAACACTGTGTAAGCTAAAAAAA
     HisCysValSerLys

Fig. 5B

1    CGCGCCACCGCCGCCGCCCAGGCCATCGCCACCCTCCGCAGCCAT
                                                 Me

46   GTCCACCAGGTCCGTGTCCTCGTCCTCCTACCGCAGGATGTTCGG
     TserThrArgSerValSerSerSerSerTyrArgArgMetPheGl 91   CGGCCCGGGCACCGCGAGCCGGCCGAGCTCCAGCCGGAGCTACGT
     yGlyProGlyThrAlaSerArgProSerSerSerArgSerTyrVa 136  GACTACGTCCACCCGCACCTACAGCCTGGGCAGCGCGCTGCGCCC
     lThrThrSerThrArgThrTyrSerLeuGlySerAlaLeuArgPr 181  CAGCACCAGCCGCAGCCTCTACGCCTCGTCCCCGGGCGGCGTGTA
     oSerThrSerArgSerLeuTyrAlaSerSerProGlyGlyValTy 226  TGCCACGCGCTCCTCTGCCGTGCGCCTGCGGAGCAGCGTGCCCGG
     rAlaThrArgSerSerAlaValArgLeuArgSerSerValProGl 271  GGTGCGGCTCCTGCAGGACTCGGTGGACTTCTCGCTGGCCGACGC
     yValArgLeuLeuGlnAspSerValAspPheSerLeuAlaAspAl 316  CATCAACACCGAGTTCAAGAACACCCGCACCAACGAGAAGGTGGA
     aIleAsnThrGluPheLysAsnThrArgThrAsnGluLysValGl 361  GCTGCAGGAGCTGAATGACCGCTTCGCCAACTACATCGACAAGGT
     uLeuGlnGluLeuAsnAspArgPheAlaAsnTyrIleAspLysVa 406  GCGCTTCCTGGAGCAGCAGAATAAGATCCTGCTGGCCGAGCTCGA
     lArgPheLeuGluGlnGlnAsnLysIleLeuLeuAlaGluLeuGl 451  GCAGCTCAAGGGCCAAGGCAAGTCGCGCCTGGGGGACCTCTACGA
     uGlnLeuLysGlyGlnGlyLysSerArgLeuGlyAspLeuTyrGl 496  GGAGGAGATGCGGGAGCTGCGCCGGCAGGTGGACCAGCTAACCAA
     uGluGluMetArgGluLeuArgArgGlnValAspGlnLeuThrAs 541  CGACAAAGCCCGCGTCGAGGTGGAGCGCGACAACCTGGCCGAGGA
     nAspLysAlaArgValGluValGluArgAspAsnLeuAlaGluAs 586  CATCATGCGCCTCCGGGAGAAATTGCAGGAGGAGATGCTTCAGAG
     pIleMetArgLeuArgGluLysLeuGlnGluGluMetLeuGlnAr 631  AGAGGAAGCCGAAAACACCCTGCAATCTTTCAGACAGGATGTTGA
     gGluGluAlaGluAsnThrLeuGlnSerPheArgGlnAspValAs 676  CAATGCGTCTCTGGCACGTCTTGACCTTGAACGCAAAGTGGAATC
     pAsnAlaSerLeuAlaArgLeuAspLeuGluArgLysValGluSe 721  TTTGCAAGAAGAGATTGCCTTTTTGAAGAAACTCCACGAAGAGGA
     rLeuGlnGluGluIleAlaPheLeuLysLysLeuHisGluGluGl 766  AATCCAGGAGCTGCAGGCTCAGATTCAGGAACAGCATGTCCAAAT
     uIleGlnGluLeuGlnAlaGlnIleGlnGluGlnHisValGlnIl

Fig. 6A

| | |
|---|---|
| 811 | CGATGTGGATGTTTCCAAGCCTGACCTCACGGCTGCCCTGCGTGA |
| | eAspValAspValSerLysProAspLeuThrAlaAlaLeuArgAs |
| 856 | CGTACGTCAGCAATATGAAAGTGTGGCTGCCAAGAACCTGCAGGA |
| | pValArgGlnGlnTyrGluSerValAlaAlaLysAsnLeuGlnGl |
| 901 | GGCAGAAGAATGGTACAAATCCAAGTTTGCTGACCTCTCTGAGGC |
| | uAlaGluGluTrpTyrLysSerLysPheAlaAspLeuSerGluAl |
| 946 | TGCCAACCGGAACAATGACGCCCTGCGCCAGGCAAAGCAGGAGTC |
| | AAlaAsnArgAsnAsnAspAlaLeuArgGlnAlaLysGlnGluSe |
| 991 | CACTGAGTACCGGAGACAGGTGCAGTCCCTCACCTGTGAAGTGGA |
| | rThrGluTyrArgArgGlnValGlnSerLeuThrCysGluValAs |
| 1036 | TGCCCTTAAAGGAACCAATGAGTCCCTGGAACGCCAGATGCGTGA |
| | pAlaLeuLysGlyThrAsnGluSerLeuGluArgGlnMetArgGl |
| 1081 | AATGGAAGAGAACTTTGCCGTTGAAGCTGCTAACTACCAAGACAC |
| | uMetGluGluAsnPheAlaValGluAlaAlaAsnTyrGlnAspTh |
| 1126 | TATTGGCCGCCTGCAGGATGAGATTCAGAATATGAAGGAGGAAAT |
| | rIleGlyArgLeuGlnAspGluIleGlnAsnMetLysGluGluMe |
| 1171 | GGCTCGTCACCTTCGTGAATACCAAGACCTGCTCAATGTTAAGAT |
| | tAlaArgHisLeuArgGluTyrGlnAspLeuLeuAsnValLysMe |
| 1216 | GGCCCTTGACATTGAGATTGCCACCTACAGGAAGCTGCTGGAAGG |
| | tAlaLeuAspIleGluIleAlaThrTyrArgLysLeuLeuGluGl |
| 1261 | CGAGGAGAGCAGGATTTCTCTGCCTCTTCCAAACTTTTCCTCCCT |
| | yGluGluSerArgIleSerLeuProLeuProAsnPheSerSerLe |
| 1306 | GAACCTGAGGGAAACTAATCTGGATTCACTCCCTCTGGTTGATAC |
| | uAsnLeuArgGluThrAsnLeuAspSerLeuProLeuValAspTh |
| 1351 | CCACTCAAAAAGGACACTTCTGATTAAGACGGTTGAAACTAGAGA |
| | rHisSerLysArgThrLeuLeuIleLysThrValGluThrArgAs |
| 1396 | TGGACAGGTTATCAACGAAACTTCTCAGCATCACGATGACCTTGA |
| | pGlyGlnValIleAsnGluThrSerGlnHisHisAspAspLeuGl |
| 1441 | ATAAAAATTGCACACACTCAGTGCAGCAATATATTACCAGCAAGA |
| | u |
| 1486 | ATAAAAAGAAATCCATATCTTAAAGAAACAGCTTTCAAGTGCCT |
| 1531 | TTCTGCAGTTTTTCAGGAGCGCAAGATAGATTTGGAATAGGAATA |
| 1556 | AGCTCTAGTTCTTAACAACCGACACTCCTACAAGATTTAGAAAAA |
| 1621 | AGTTTACAACATAATCTAGTTTACAGAAAAATCTTGTGCTAGAAT |
| 1666 | ACTTTTTAAAGGTATTTTGAATACCATTAAAACTGCTTTTTTTTT |
| 1711 | TTCCAGCAAGTATCCAACCAACTTGGTTCTGCTTCAATAAATCTT |
| 1756 | TGGAAAAACTA |

Fig. 6B

```
  1  GNCTACTGTTGTTTTTGAGGGGCGGGCAGCCGCGCCGCCGCGGCA
 46  CTTTTTTAATTTTTTCGGGTGCCGCAGCAGCGACCCCTCGGCGCC
 91  GATGTCCCTGATCCCTGGAGCGACGACGGCCGCTGCCTAAGCTGG

136  GAAGAGGAATGCCAGCTCCTGAGCAGGCCTCATTGGTGGAGGAGG
                 MetProAlaProGluGlnAlaSerLeuValGluGluG

181  GGCAACCACAGACCCGCCAGGAAGCTGCCTCCACTGGCCCAGGCA
     lyGlnProGlnThrArgGlnGluAlaAlaSerThrGlyProGlyM

226  TGGAACCCGAGACCACAGCCACCACTATTCTAGCATCCGTGAAGG
     etGluProGluThrThrAlaThrThrIleLeuAlaSerValLysG

271  AGCAGGAGCTTCAGTTTCAGCGACTCACCCGAGAACTGGAAGTGG
     luGlnGluLeuGlnPheGlnArgLeuThrArgGluLeuGluValG

316  AAAGGCAGATTGTTGCCAGTCAGCTAGAAAGATGTAGGCTTGGAG
     luArgGlnIleValAlaSerGlnLeuGluArgCysArgLeuGlyA

361  CAGAATCACCAAGCATCGCCAGCACCAGCTCAACTGAGAAGTCAT
     laGluSerProSerIleAlaSerThrSerSerThrGluLysSerP

406  TTCCTTGGAGATCAACAGACGTGCCAAATACTGGTGTAAGCAAAC
     heProTrpArgSerThrAspValProAsnThrGlyValSerLysP

451  CTAGAGTTTCTGACGCTGTCCAGCCCAACAACTATCTCATCAGGA
     roArgValSerAspAlaValGlnProAsnAsnTyrLeuIleArgT

496  CAGAGCCAGAACAAGGAACCCTCTATTCACCAGAACAGACATCTC
     hrGluProGluGlnGlyThrLeuTyrSerProGluGlnThrSerL

541  TCCATGAAAGTGAGGGATCATTGGGTAACTCAAGAAGTTCAACAC
     euHisGluSerGluGlySerLeuGlyAsnSerArgSerSerThrG

586  AAATGAATTCTTATTCCGACAGTGGATACCAGGAAGCAGGGAGTT
     lnMetAsnSerTyrSerAspSerGlyTyrGlnGluAlaGlySerP

631  TCCACAACAGCCAGAACGTGAGCAAGGCAGACAACAGACAGCAGC
     heHisAsnSerGlnAsnValSerLysAlaAspAsnArgGlnGlnH

676  ATTCATTCATAGGATCAACTAACAACCATGTGGTGAGGAATTCAA
     isSerPheIleGlySerThrAsnAsnHisValValArgAsnSerA

721  GAGCTGAAGGACAAACACTGGTTCAGCCATCAGTAGCCAATCGGG
     rgAlaGluGlyGlnThrLeuValGlnProSerValAlaAsnArgA

766  CCATGAGAAGAGTTAGTTCAGTTCCATCTAGAGCACAGTCTCCTT
     laMetArgArgValSerSerValProSerArgAlaGlnSerProS

811  CTTATGTTATCAGCACAGGCGTGTCTCCTTCAAGGGGGTCTCTGA
     erTyrValIleSerThrGlyValSerProSerArgGlySerLeuA

856  GAACTTCTCTGGGTAGTGGATTTGGCTCTCCGTCAGTGACCGACC
     rgThrSerLeuGlySerGlyPheGlySerProSerValThrAspP
```

Fig. 7A

```
 901   CCCGACCTCTGAACCCCAGTGCATATTCCTCCACCACATTACCTG
       roArgProLeuAsnProSerAlaTyrSerSerThrThrLeuProA

946   CTGCACGGGCAGCCTCTCCGTACTCACAGAGACCCGCCTCCCCAA
       laAlaArgAlaAlaSerProTyrSerGlnArgProAlaSerProT

991   CAGCTATACGGCGGATTGGGTCAGTCACCTCCCGGCAGACCTCCA
       hrAlaIleArgArgIleGlySerValThrSerArgGlnThrSerA

1036   ATCCCAACGGACCAACCCCTCAATACCAAACCACCGCCAGAGTGG
       snProAsnGlyProThrProGlnTyrGlnThrThrAlaArgValG

1081   GGTCCCCACTGACCCTGACGGATGCACAGACTCGAGTAGCTTCCC
       lySerProLeuThrLeuTheAspAlaGlnThrArgValAlaSerP

1126   CATCCCAAGGCCAGGTGGGGTCGTCGTCCCCCAAACGCTCAGGGA
       roSerGlnGlyGlnValGlySerSerSerProLysArgSerGlyM

1171   TGACCGCCGTACCACAGCATCTGGGACCTTCACTGCAAAGGACTG
       etThrAlaValProGlnHisLeuGlyProSerLeuGlnArgThrV

1216   TTCATGACATGGAGCAATTCGGACAGCAGCAGTATGACATTTATG
       alHisAspMetGluGlnPheGlyGlnGlnGlnTyrAspIleTyrG

1261   AGAGGATGGTTCCACCCAGGCCAGACAGCCTGACAGGCTTACGGA
       luArgMetValProProArgProAspSerLeuThrGlyLeuArgS

1306   GTTCCTATGCTAGTCAGCATAGTCAGCTTGGGCAAGACCTTCGTT
       erSerTyrAlaSerGlnHisSerGlnLeuGlyGlnAspLeuArgS

1351   CTGCCGTGTCTCCCGACTTGCACATTACTCCTATATATGAGGGGA
       erAlaValSerProAspLeuHisIleThrProIleTyrGluGlyA

1396   GGACCTATTACAGCCCAGTGTACCGCAGCCCAAACCATGGAACTG
       rgThrTyrTyrSerProValTyrArgSerProAsnHisGlyThrV

1441   TGGAGCTCCAAGGATCGCAGACGGCGTTGTATCGCACAGGTGTAT
       alGluLeuGlnGlySerGlnThrAlaLeuTyrArgThrGlyValS

1486   CAGGTATTGGAAATCTACAAAGGACATCCAGCCAACGAAGTACCC
       erGlyIleGlyAsnLeuGlnArgThrSerSerGlnArgSerThrL

1531   TTACATACCAAAGAAATAATTATGCTCTGAACACAACAGCTACCT
       euThrTyrGlnArgAsnAsnTyrAlaLeuAsnThrThrAlaThrT

1576   ACGCGGAGCCCTACAGGCCTATACAATACCGAGTGCAAGAGTGCA
       yrAlaGluProTyrArgProIleGlnTyrArgValGlnGluCysA

1621   ATTATAACAGGCTTCAGCATGCAGTGCCGGCTGATGATGGCACCA
       snTyrAsnArgLeuGlnHisAlaValProAlaAspAspGlyThrT

1666   CAAGATCCCCATCAATAGACAGCATTCAGAAGGACCCCAGGGAGT
       hrArgSerProSerIleAspSerIleGlnLysAspProArgGluP

1711   TTGCCTGGCGTGATCCTGAGTTGCCTGAGGTCATTCACATGCTTG
       heAlaTrpArgAspProGluLeuProGluValIleHisMetLeuG
```

Fig. 7B

```
1756  AGCACCAGTTCCCATCTGTTCAGGCAAATGCAGCGGCCTACCTGC
      luHisGlnPheProSerValGlnAlaAsnAlaAlaAlaTyrLeuG

1801  AGCACCTGTGCTTTGGTGACAACAAAGTGAAGATGGAGGTGTGTA
      lnHisLeuCysPheGlyAspAsnLysValLysMetGluValCysA

1846  GGTTAGGGGGAATCAAGCATCTGGTTGACCTTCTGGACCACAGAG
      rgLeuGlyGlyIleLysHisLeuValAspLeuLeuAspHisArgV

1891  TTTTGGAAGTTCAGAAGAATGCTTGTGGTGCCCTTCGAAACCTCG
      alLeuGluValGlnLysAsnAlaCysGlyAlaLeuArgAsnLeuV

1936  TTTTTGGCAAGTCTACAGATGAAAATAAAATAGCAATGAAGAATG
      alPheGlyLysSerThrAspGluAsnLysIleAlaMetLysAsnV

1981  TTGGTGGGATACCTGCCTTGTTGCGACTGTTGAGAAAATCTATTG
      alGlyGlyIleProAlaLeuLeuArgLeuLeuArgLysSerIleA

2026  ATGCAGAAGTAAGGGAGCTTGTTACAGGAGTTCTTTGGAATTTAT
      spAlaGluValArgGluLeuValThrGlyValLeuTrpAsnLeuS

2071  CCTCATGTGATGCTGTAAAAATGACAATCATTCGAGATGCTCTCT
      erSerCysAspAlaValLysMetThrIleIleArgAspAlaLeuS

2116  CAACCTTAACAAACACTGTGATTGTTCCACATTCTGGATGGAATA
      erThrLeuThrAsnThrValIleValProHisSerGlyTrpAsnA

2161  ACTCTTCTTTTGATGATGATCATAAAATTAAATTTCAGACTTCAC
      snSerSerPheAspAspAspHisLysIleLysPheGlnThrSerL

2206  TAGTTCTGCGTAACACGACAGGTTGCCTAAGGAACCTCACGTCCG
      euValLeuArgAsnThrThrGlyCysLeuArgAsnLeuThrSerA

2251  CGGGGGAAGAAGCTCGGAAGCAAATGCGGTCCTGCGAGGGGCTGG
      laGlyGluGluAlaArgLysGlnMetArgSerCysGluGlyLeuV

2296  TAGACTCACTGTTGTATGTGATCCACACGTGTGTGAACACATCCG
      alAspSerLeuLeuTyrValIleHisThrCysValAsnThrSerA

2341  ATTACGACAGCAAGACGGTGGAGAACTGCGTGTGCACCCTGAGGA
      spTyrAspSerLysThrValGluAsnCysValCysThrLeuArgA

2386  ACCTGTCCTATCGGCTGGAGCTGGAGGTGCCCCAGGCCCGGTTAC
      snLeuSerTyrArgLeuGluLeuGluValProGlnAlaArgLeuL

2431  TGGGACTGAACGAATTGGATGACTTACTAGGAAAAGAGTCTCCCA
      euGlyLeuAsnGluLeuAspAspLeuLeuGlyLysGluSerProS

2476  GCAAAGACTCTGAGCCAAGTTGCTGGGGGAAGAAGAAGAAAAAGA
      erLysAspSerGluProSerCysTrpGlyLysLysLysLysLysL

2521  AAAAGAGGACTCCGCAAGAAGATCAATGGGATGGAGTTGGTCCTA
      ysLysArgThrProGlnGluAspGlnTrpAspGlyValGlyProI

2566  TCCCAGGACTGTCGAAGTCCCCCAAAGGGGTTGAGATGCTGTGGC
      leProGlyLeuSerLysSerProLysGlyValGluMetLeuTrpH
```

Fig. 7C

2611  ACCCATCGGTGGTAAAACCATATCTGACTCTTCTAGCAGAAAGTT
      isProSerValValLysProTyrLeuThrLeuLeuAlaGluSerS

2656  CCAACCCAGCCACCTTGGAAGGCTCTGCAGGGTCTCTCCAGAACC
      erAsnProAlaThrLeuGluGlySerAlaGlySerLeuGlnAsnL

2701  TCTCTGCTAGCAACTGGAAGTTTGCAGCATATATCCGGGGCGGCC
      euSerAlaSerAsnTrpLysPheAlaAlaTyrIleArgGlyGlyA

2746  GTCCGAAAAGAAAAGGGCTCCCCATCCTTGTGGAGCTTCTGAGAA
      rgProLysArgLysGlyLeuProIleLeuValGluLeuLeuArgM

2791  TGGATAACGATAGAGTTGTTTCTTCCGGTGCAACAGCCTTGAGGA
      etAspAsnAspArgValValSerSerGlyAlaThrAlaLeuArgA

2836  ATATGGCACTAGATGTTCGCAACAAGGAGCTCATAGGCAAATACG
      snMetAlaLeuAspValArgAsnLysGluLeuIleGlyLysTyrA

2881  CCATGCGAGACCTGGTCAACCGGCTCCCCGGCGGCAATGGCCCCA
      laMetArgAspLeuValAsnArgLeuProGlyGlyAsnGlyProS

2926  GTGTCTTGTCTGATGAGACCATGGCAGCCATCTGCTGTGCTCTGC
      erValLeuSerAspGluThrMetAlaAlaIleCysCysAlaLeuH

2971  ACGAGGTCACCAGCAAAAACATGGAGAACGCAAAAGCCCTGGCCG
      isGluValThrSerLysAsnMetGluAsnAlaLysAlaLeuAlaA

3016  ACTCAGGAGGCATAGAGAAGCTGGTGAACATAACCAAAGGCAGGG
      spSerGlyGlyIleGluLysLeuValAsnIleThrLysGlyArgG

3061  GCGACAGATCATCTCTGAAAGTGGTGAAGGCAGCAGCCCAGGTCT
      lyAspArgSerSerLeuLysValValLysAlaAlaAlaGlnValL

3106  TGAATACATTATGGCAATATCGGGACCTCCGGAGCATTTATAAAA
      euAsnThrLeuTrpGlnTyrArgAspLeuArgSerIleTyrLysL

3151  AGGATGGGTGGAATCAGAACCATTTTATTACACCTGTGTCGACAT
      ysAspGlyTrpAsnGlnAsnHisPheIleThrProValSerThrL

3196  TGGAGCGAGACCGATTCAAATCACATCCTTCCTTGTCTACCACCA
      euGluArgAspArgPheLysSerHisProSerLeuSerThrThrA

3241  ACCAACAGATGTCACCCATCATTCAGTCAGTCGGCAGCACCTCTT
      snGlnGlnMetSerProIleIleGlnSerValGlySerThrSerS

3286  CCTCACCAGCACTGTTAGGAATCAGAGACCCTCGCTCTGAATACG
      erSerProAlaLeuLeuGlyIleArgAspProArgSerGluTyrA

3331  ATAGGACCCAGCCACCTATGCAGTATTACAATAGCCAAGGGGATG
      spArgThrGlnProProMetGlnTyrTyrAsnSerGlnGlyAspA

3376  CCACACATAAAGGCCTGTACCCTGGCTCCAGCAAACCTTCACCAA
      laThrHisLysGlyLeuTyrProGlySerSerLysProSerProI

3421  TTTACATCAGTTCCTATTCCTCACCAGCAAGAGAACAAAATAGAC
      leTyrIleSerSerTyrSerSerProAlaArgGluGlnAsnArgA

Fig. 7D

3466 GGCTACAGCATCAACAGCTGTATTATAGTCAAGATGACTCCAACA
     rgLeuGlnHisGlnGlnLeuTyrTyrSerGlnAspAspSerAsnA

3511 GAAAGAACTTTGATGCATACAGATTGTATTTGCAGTCTCCTCATA
     rgLysAsnPheAspAlaTyrArgLeuTyrLeuGlnSerProHisS

3556 GCTATGAAGATCCTTATTTTGATGACCGAGTTCACTTTCCAGCTT
     erTyrGluAspProTyrPheAspAspArgValHisPheProAlaS

3601 CTACTGATTACTCAACACAGTATGGACTGAAATCGACCACAAATT
     erThrAspTyrSerThrGlnTyrGlyLeuLysSerThrThrAsnT

3646 ATGTAGACTTTTATTCCACTAAACGACCTTCTTATAGAGCAGAAC
     yrValAspPheTyrSerThrLysArgProSerTyrArgAlaGluG

3691 AGTACCCAGGGTCCCCAGACTCATGGGTGTACGATCAAGATGCCC
     lnTyrProGlySerProAspSerTrpValTyrAspGlnAspAlaG

3736 AACAGAGGAACTCTTTCTTTCTAACCTTGTTCAGATTGAGGTGAA
     lnGlnArgAsnSerPhePheLeuThrLeuPheArgLeuArg

3781 AAGTCCATCTTGCTGATTTCATGATTGAAATGTGAAAGTGAAGTG
3826 GAAGGAATGAATGAAGTGTGTTTTTTTTTCCTTTTTGAGGAATTA
3871 TCAGGGGAATTCGATATCAAGCTTATCGATACCGTCGAC

Fig. 7E

| | |
|---|---|
| 1 | GCCCCGGCCCCGCCCCAGCCCTCCTGATCCCTCGCAGCCCGGCTC |
| 46 | CGGCCGCCCGCCTCTGCCGCCGCAATGATGATGATGGCGCTGAGC<br>                                    MetMetMetMetAlaLeuSer |
| 91 | AAGACCTTCGGGCAGAAGCCCGTGAAGTTCCAGCTGGAGGACGAC<br>LysThrPheGlyGlnLysProValLysPheGlnLeuGluAspAsp |
| 136 | GGCGAGTTCTACATGATCGGCTCCGAGGTGGGAAACTACCTCCGT<br>GlyGluPheTyrMetIleGlySerGluValGlyAsnTyrLeuArg |
| 181 | ATGTTCCGAGGTTCTCTGTACAAGAGATACCCCTCACTCTGGAGG<br>MetPheArgGlySerLeuTyrLysArgTyrProSerLeuTrpArg |
| 226 | CGACTAGCCACTGTGGAAGAGAGGAAGAAAATAGTTGCATCGTCA<br>ArgLeuAlaThrValGluGluArgLysLysIleValAlaSerSer |
| 271 | CATGGTAAAAAAACAAAACCTAACACTAAGGATCACGGATACACG<br>HisGlyLysLysThrLys<u>Pro</u>AsnThrLysAspHisGlyTyrThr |
| 316 | ACTCTAGCCACCAGTGTGACCCTGTTAAAAGCCTCGGAAGTGGAA<br>ThrLeuAlaThrSerValThrLeuLeuLysAlaSerGluValGlu |
| 361 | GAGATTCTGGATGGCAACGATGAGAAGTACAAGGCTGTGTCCATC<br>GluIleLeuAspGlyAsnAspGluLysTyrLysAlaValSerIle |
| 406 | AGCACAGAGCCCCCCACCTACCTCAGGGAACAGAAGGCCAAGAGG<br>SerThrGluProProThrTyrLeuArgGluGlnLysAlaLysArg |
| 451 | AACAGCCAGTGGGTACCCACCCTGTCCAACAGCTCCCACCACTTA<br>AsnSerGlnTrpValProThrLeuSerAsnSerSerHisHisLeu |
| 496 | GATGCCGTGCCATGCTCCACAACCATCAACAGGAACCGCATGGGC<br>AspAlaValPeoCysSerThrThrIleAsnArgAsnArgMetGly |
| 541 | CGAGACAAGAAGAGAACCTTCCCCCTTTGCTTTGATGACCATGAC<br>ArgAspLysLysArgThrPheProLeuCysPheAspAspHisAsp |
| 586 | CCAGCTGTGATCCATGAGAACGCATCTCAGCCCGAGGTGCTGGTC<br>ProAlaValIleHisGluAsnAlaSerGlnProGluValLeuVal |
| 631 | CCCATCCGGCTGGACATGGAGATCGATGGGCAGAAGCTGCGAGAC<br>ProIleArgLeuAspMetGluIleAspGlyGlnLysLeuArgAsp |
| 676 | GCCTTCACCTGGAACATGAATGAGAAGTTGATGACGCCTGAGATG<br>AlaPheThrTrpAsnMetAsnGluLysLeuMetThrProGluMet |
| 721 | TTTTCAGAAATCCTCTGTGACGATCTGGATTTGAACCCGCTGACG<br>PheSerGluIleLeuCysAspAspLeuAspLeuAsnProLeuThr |
| 766 | TTTGTGCCAGCCATCGCCTCTGCCATCAGACAGCAGATCGAGTCC<br>PheValProAlaIleAlaSerAlaIleArgGlnGlnIleGluSer |

Fig. 8A

```
811   TACCCCACGGACAGCATCCTGGAGGACCAGTCAGACCAGCGCGTC
      TyrProThrAspSerIleLeuGluAspGlnSerAspGlnArgVal

856   ATCATCAAGCTGAACATCCATGTGGGAAACATTTCCCTGGTGGAC
      IleIleLysLeuAsnIleHisValGlyAsnIleSerLeuValAsp

901   CAGTTTGAGTGGGACATGTCAGAGAAGGAGAACTCACCAGAGAAG
      GlnPheGluTrpAspMetSerGluLysGluAsnSerProGluLys

946   TTTGCCCTGAAGCTGTGCTCGGAGCTGGGGTTGGGCGGGGAGTTT
      PheAlaLeuLysLeuCysSerGluLeuGlyLeuGlyGlyGluPhe

991   GTCACCACCATCGCATACAGCATCCGGGGACAGCTGAGCTGGCAT
      ValThrThrIleAlaTyrSerIleArgGlyGlnLeuSerTrpHis

1036  CAGAAGACCTACGCCTTCAGCGAGAACCCTCTGCCCACAGTGGAG
      GlnLysThrTyrAlaPheSerGluAsnProLeuProThrValGlu

1081  ATTGCCATCCGGAACACGGGCGATGCGGACCAGTGGTGCCCACTG
      IleAlaIleArgAsnThrGlyAspAlaAspGlnTrpCysProLeu

1126  CTGGAGACTCTGACAGACGCTGAGATGGAGAAGAAGATCCGCGAC
      LeuGluThrLeuThrAspAlaGluMetGluLysLysIleArgAsp

1171  CAGGACAGGAACACGAGGCGGATGAGGCGTCTTGCCAACACGGGC
      GlnAspArgAsnThrArgArgMetArgArgLeuAlaAsnThrGly

1216  CCGGCCTGGTAACCAGCCCATCAGCACACGGCTCCCACGGAGCAT
      ProAlaTrp

1261  CTCAGAAGATTGGGCCGCCTCTCCTCCATCTTCTGGCAAGGACAG
1306  AGGCGAGGGGACAGCCCAGCGCCATCCTGAGGATCGGGTGGGGGT
1351  GGAGTGGGGGCTTCCAGGTGGCCCTTCCCGGTACACATTCCATTT
1396  GTTGAGCCCCAGTCCTGCCCCCCACCCCACCCTCCCTACCCCTCC
1441  CCAGTCTCTGGGGTCAGGAAGAAACCTTATTTTAGGTTGTGTTTT
1486  GTTTTTGTATAGGAGCCCCAGGCAGGGCTAGTAACAGTTTTTAAA
1531  TAAAAGGCAACAGGTCATGTTCAATTTCTTAAATCTAGTGTCTTT
1576  ATTTCTTCTGTTACAATAGTGTTGCTTGTGTAAGCAGGTTAGAGT
1621  GCACAGTGTCCCCAATTGTTCCTGGCACTGCAAAACCAAATTAAA
1666  CAATCCCACAAAGAATTCTGACATCAATGTGTTTTCCTCAGTCAG
1711  GTCTATTTCAAGATTCTAGAAGTTCCTTTTGTAAAACTTGCCTTT
1756  AAAACTCTTCCTCCTAATGCCATCAGATCTCTTAACATTGGCTCA
1806  CTGTGGGATCTTTCCTCTTAGGTTGAATTTCTACGTGAATATCAA
1846  AGTGCCTTTTTC
```

Fig. 8B

```
      ↓
  1 AGCCGCCGCATCGTGGAGCTGGAGGTGGGGGCTGAGATGGACGAC
    SerArgArgIleValGluLeuGluValGlyAlaGluMetAspAsp

46 ATGAAGGATCATGGAGGTGGCTGTGGGGTGGCCTTCTCCGCGCTG
    MetLysAspHisGlyGlyGlyCysGlyValAlaPheSerAlaLeu

91 GGTGGCGGAGAGTGCGGGGAGAGCTTGGACCTGCAGTTTGTCGAA
    GlyGlyGlyGluCysGlyGluSerLeuAspLeuGlnPheValGlu

136 GAGGAGGCCGAGCTGCTGCGGCGCTCCTACCAGAACAAGCTGCTG
    GluGluAlaGluLeuLeuArgArgSerTyrGlnAsnLysLeuLeu

181 CTGAACGAGCTGGCCAAGTTCCGCTCGGTGGCGCTGTCGGAGGAC
    LeuAsnGluLeuAlaLysPheArgSerValAlaLeuSerGluAsp

226 AGTTGTTCTGTGCTCAGCGAACCTTCACCCGCAAGCTGCAGATCG
    SerCysSerValLeuSerGluProSerProAlaSerCysArgSer

271 GCGAGCTCAGCGGCAAGGTCAAGAAGCTCGTGCTCCTCTCCAACC
    AlaSerSerAlaAlaArgSerArgSerSerCysSerSerProThr

316 TCCAGCGCTGTGACCTCGCCTCCTGCCAGCTGGAGACGGACGCCG
    SerSerAlaValThrSerProProAlaSerTrpArgArgThrPro

361 AGGC
    Arg
```

Fig. 9

```
                                      ↓
1     GCCCGCTGCGGCAGAGGAGGAGGAGCAGCAGGGAGCCGACGGGGC
      ProAlaAlaAlaGluGluGluGluGlnGlnGlyAlaAspGlyAl

46    CGCTGCCGAGGACGGGGCGGACGAGGCCGAGGCAGAGATCATCCA
      aAlaAlaGluAspGlyAlaAspGluAlaGluAlaGluIleIleGl

91    GCTGCTGAAGCGAGCCAAGTTGAGCATTATGAAAGATGAGCCAGA
      nLeuLeuLysArgAlaLysLeuSerIleMetLysAspGluProGl

136   AGAGGCTGAGTTAATTTTGCATGACGCTCTTCGTCTCGCCTATCA
      uGluAlaGluLeuIleLeuHisAspAlaLeuArgLeuAlaTyrGl

181   GACTGATAACAAGAAGGCCATCACTTACACTTATGATTTGATGGC
      nThrAspAsnLysLysAlaIleThrTyrThrTyrAspLeuMetAl

226   CAACTTAGCATTTATACGGGGTCAGCTTGAAAATGCTGAACAACT
      aAsnLeuAlaPheIleArgGlyGlnLeuGluAsnAlaGluGlnLe

271   TTTTAAAGCAACAATGAGTTACCTCCTTGGAGGGGGGCATGAAGC
      uPheLysAlaThrMetSerTyrLeuLeuGlyGlyGlyHisGluAl

316   AGGAGGACAATGCAATAATTTGAAATTTCCCTAAAGCTGGCCAGT
      aGlyGlyGlnCysAsnAsnLeuLysPhePro

361   ATCTATGCTTGCGCAGAACAGACAGGAATTTGCTGTTGCTGGCTA
406   TGAATTCTGCATTTCAACTCTAGAGGAAAAAATTGAAAGAGAAAA
451   GGAATTAGCAGAAGACATTATGTCAGTGGAAGAGAAAGCCATACC
496   CACCTCCTCTTGGGCATGTGCTTAGACGCCTGTGCTCGCTACCTT
541   CTGTTCTCCAAGCAGCCGTCACAGGCCCAAAGGATGTNTGAAAAG
586   CTCTGCAGATTTCT
```

Fig. 10

```
  1 CTTTTTTTAAATCTAGGAACAACTGTTAAACCTATATACTTACTA

46 CTTGCAGTTCCATGATGGCAAATGACTGACAGAAGATCATGTGTC
                    MetThrAspArgArgSerCysVal

91 CCTAGCTGGTTTTGGGGTCCAGTAGTAACCTTGCAAGATTGTCTT
    ProSerTrpPheTrpGlyProValValThrLeuGlnAspCysLeu

136 GCTGCCTTCTTTGCCAGAGATGAACTAAAAGGTGACAATATGTAC
    AlaAlaPhePheAlaArgAspGluLeuLysGlyAspAsnMetTyr

181 AGTTGTGAAAAATGCAAAAAGCTGAGAAATGGAGTGAAGTTTTGT
    SerCysGluLysCysLysLysLeuArgAsnGlyValLysPheCys

226 AAAGTACAAAACTTTCCTGAGATTTTGTGCATCCACCTTAAAAGA
    LysValGlnAsnPheProGluIleLeuCysIleHisLeuLysArg

271 TTCAGACATGAACTAATGTTTTCCACCAAAATCAGTACCCATGTT
    PheArgHisGluLeuMetPheSerThrLysIleSerThrHisVal

316 TCATTTCCGCTAGAAGGCTTGGATCTTCAGCCATTTCTTGCTAAG
    SerPheProLeuGluGlyLeuAspLeuGlnProPheLeuAlaLys

361 GATAGTCCAGCTCAAATTGTGACATATGATCTTCTGTCAGTCATT
    AspSerProAlaGlnIleValThrTyrAspLeuLeuSerValIle

406 TGCCATCATGGAACTGCAAGTAGTGGACACTATATAGCCTACTGC
    CysHisHisGlyThrAlaSerSerGlyHisTyrIleAlaTyrCys

451 CGAAACAATCTAAATAATCTCTGGTATGAATTTGATGATCAGAGT
    ArgAsnAsnLeuAsnAsnLeuTrpTyrGluPheAspAspGlnSer
                                                ↓
496 GTCACTGAAGTTTCAGAATCTACTGTACAAAATGCAGAAGCTTAC
    ValThrGluValSerGluSerThrValGlnAsnAlaGluAlaTyr

541 GTTCTTTTCTATAGGAAGAGCAGCGAAGAGGCACAAAAAGAGAGG
    ValLeuPheTyrArgLysSerSerGluGluAlaGlnLysGluArg

586 AGAAGGATATCAAATTTATTGAACATAATGGAACCAAGCCTCCTT
    ArgArgIleSerAsnLeuLeuAsnIleMetGluProSerLeuLeu

631 CAGTTTTATATTTCTCGACAGTGGCTTAATAAATTTAAGACCTTT
    GlnPheTyrIleSerArgGlnTrpLeuAsnLysPheLysThrPhe

676 GCCGAACCTGGCCCTATTTCAAATAATGACTTTCTTTGTATTCAT
    AlaGluProGlyProIleSerAsnAsnAspPheLeuCysIleHis

721 GGAGGTGTTCCTCCAAGAAAAGCTGGTTATATTGAAGACCTGGTT
    GlyGlyValProProArgLysAlaGlyTyrIleGluAspLeuVal

766 TTGATGCTGCCTCAGAACATTTGGGATAACCTATATAGCAGGTAT
    LeuMetLeuProGlnAsnIleTrpAspAsnLeuTyrSerArgTyr
```

Fig. 11A

811 GGTGGAGGACCAGCTGTCAACCATCTGTACATTTGTCATACTTGC
    GlyGlyGlyProAlaValAsnHisLeuTyrIleCysHisThrCys

856 CAAATTGAGGCGGAGAAAATTGAAAAAGAAGAAAAACTGAATTG
    GlnIleGluAlaGluLysIleGluLysArgArgLysThrGluLeu

901 GAAATTTTTATTCGGCTTAACAGAGCGTTCCAAAAAGAGGA
    GluIlePheIleArgLeuAsnArgAlaPheGlnLysArg

Fig. 11B

```
             ↓ ↓                                    ↓ ↓
  1  AGGCCGGCTTTCGGCGCGACGGTCGCCGCGTTCCATCGTCGCGCG
     ArgProAlaPheGlyAlaThrValAlaAlaPheHisArgArgAla
                  ↓             ↓
 46  GCCCTTCGGGGCCCGAGCCCCAATGTCGGGCCCCAACGGAGACCT
     AlaLeuArgGlyProSerProAsnValGlyProGlnArgArgPro

91  GGGGATGCCGGTGGAGGCGGGAGCGGAAGGCGAGGAGGACGGCTT
     GlyAspAlaGlyGlyGlySerGlyArgArgGlyGlyargLeu 136  CGGGGAAGCAGAATACGCTGCCATCAACTCCATGCTGGACCAGAT
     ArgGlySerArgIleArgCysHisGlnLeuHisAlaGlyProAsp 181  CAACTCCTGTCTGGACCACCTGGAGGAGAAGAATGACCACCTCCA
     GlnLeuLeuSerGlyProProGlyGlyGluGlu 226  CGCCCGCCTCCAGGAGCTGCTGGAGTCCAACCGGCAGACACGCCT
271  GGAGTTCCAGCAGCAGCTCGGGGAGGCCCCCAGTGATGCCAGCCC
316  CTAGGCTCCAAGAGCCCCCAACCGGGACCCAACCCTGCCTCCCTG
361  GGGCTAAGCTCTGGCCTGGGGCACTCACCCCCTGGCTTAGACAAC
406  TTCTCAAGGGCTTGGCCTTCAGGGGACCCTTGTGGGTCTTGCCTT
451  GCTGGGGCCACCTTTTCTTGCTTGGGGCTTCCCCTTTGGCCTACC
496  TTGGGGCCAAGCCCCTACCAACTTTGGATTGCCTTCTTGGGGGCC
541  AA
```

Fig. 12

```
            ↓
1     ACGAGGGCTTATGCAACTACAAGGATTCGTAGCCAAATTGGAAAC
      ThrArgAlaTyrAlaThrThrArgIleArgSerGlnIleGlyAsn

46    ACAGAGTCTGCGCTGAAGAAACTTGCTGAAGAAAACCCAGATTTA
      ThrGluSerAlaLeuLysLysLeuAlaGluGluAsnProAspLeu

91    CAAGAAGCATACATTGCAAAACAGATACGACTTAAATCAAAGCTG
      GlnGluAlaTyrIleAlaLysGlnIleArgLeuLysSerLysLeu

136   CTTGATCATGACAATGTCAAGTATTTGAAGAAAATTCTTGATGAG
      LeuAspHisAspAsnValLysTyrLeuLysLysIleLeuAspGlu

181   TTGGAGAAAGTCTTGGATCAGGTTGAAACTGAATTGCAAAGAAGA
      LeuGluLysValLeuAspGlnValGluThrGluLeuGlnArgArg

226   AATGAAGAAAACCCAGGTTCTTGACTGAGCTGCTCCTGTGCTTCC
      AsnGluGluAsnProGlySer

271   ATGAATGGCTGCATCTCATCTGGACGGGGATTCCATCAGCGCCTT
316   CCCTGGCCATTTAATAGATGGACTCGCCATCCTTCAAGGCCTTGT
361   GCAAATGTCAACTTTCTAAAAATTCGCTTTATTGGAGCTGGAAGG
406   GACTATCCTATTTTCTCTAGCCCTTTGTTTTGCCCT
```

Fig. 13

|  | Nek2 | p27(Kip1) |
|---|---|---|
| TrkA | + | - |
| Tropomyosin alpha | + | - |
| Vimentin | + | - |
| P0071 | + | - |
| PP-1 alpha | + | - |
| 14-3-3 epsilon | + | - |
| H. Ini1 | + | - |
| IP-1 | + | - |
| IP-2 | + | - |
| IP-3 | + | - |
| IP-4 | + | - |
| IP-5 | + | - |
| CDK2 | - | + |
| Vector | - | - |

Fig. 14

| NEK2 interactant GenBankAcc. | Description of the interactant | Nucleotide start-stop (ORF) Total nt | Frag start | No of isolat | Interacting amino acids | SEQ ID NO: | Assembly |
|---|---|---|---|---|---|---|---|
| TrkA (X03541) | Tropomyosin + kinase*,receptor for neutrophin, induces apoptosis, found in tumors | 233-2155 | 176 182 200 224 230 | 1 1 1 1 1 | 1-641 | 3, 4 | - |
| Protein phosphatase-1 (M63960) | In signal transduction (cycle cycle progression), Expressed in brain, Interacts with oncogenes, Associates with myosin | 30-1019 | 30 33 36 48 93 96 150 | 1 1 2 1 1 1 1 | 1-330 2-330 3-330 7-330 22-330 23-330 41-330 | 5, 6 | - |
| 14-3-3 epsilon (U28936) | Role in signal transduction | 1-765 | 214 223 427 | 2 4 1 | 72-263 75-263 143-263 | 7, 8 | - |
| Alpha tropomyosin (M19713) | Also called hTM-alpha. Binds to actin; found in cardiomyopathy | 55-906 | 535 | 2 | 161-347 | 9, 10 | - |
| Vimentin (X56134) | Intermediate filament protein, found in many tumors | 44-1441 | 581 | 1 | 180-466 | 11, 12 | - |
| P0071 (X81889) | Armadillo family member; involved in cell junctions | 144-3776 | 708 711 | 3 1 | 189-1208 190-1208 | 13, 14 | - |
| H. Inil (U04847) | Cellular protein binds HIV-1 integrase, may alter nucleosomal structure | 70-1224 | 289 | 1 | 74-385 | 15, 16 | - |
| IP-1 (cg30153.1.g5) | Novel protein with homologies to ERF-2 (=Tis1 1d and Keratin 13 (type I intermediate Filament); associated to the cytoskeleton. | 1-363 | 1 | 1 | 1-363 (core) | 17, 18 | - |
| IP-2 (AA143467) | contracile system protein, such as tropomyosin homolog protein | 2-346 (599) | 29 | 1 | 10-115 (carboxy-terminus) | 19, 20 | - |
| IP-3 (H67985) | ubiquitin hydroxylase homolog, Degradation of proteins, tumors | 67-939 (941) | 514 | 1 | 150-291 (amino-terminus) | 21, 22 | AA255861 H67985 AA251528 |
| IP-4 (cg50648.e3) | Collagen-homolog protein | 1-213 (542) | 1 4 40 43 52 64 | 15 3 3 1 1 1 | 1-71 (carboxy-terminus) | 23, 24 | cg50648e3 M62042 |
| IP-5 (cg50424b2) | tropomyosin homolog protein; has homolog motifs to transcriptional regulators | 1-246 (441) | 1 | 1 | 1-82 (carboxy-terminus) | 25, 26 | - |

Table 1

SEQUENCE LISTING

<160> NUMBER OF SEQ ID NOS: 26

<210> SEQ ID NO 1
<211> LENGTH: 2119
<212> TYPE: DNA
<213> ORGANISM: Homo sapiens
<220> FEATURE:
<221> NAME/KEY: CDS
<222> LOCATION: (135)..(1469)

<400> SEQUENCE: 1

```
ggcacgagta ggggtggcgg gtcagtgctg ctcgggggct tctccatcca ggtccctgga      60
gttcctggtc cctggagctc cgcacttggc gcgcaacctg cgtgaggcag cgcgactctg     120
gcgactggcc ggcc atg cct tcc cgg gct gag gac tat gaa gtg ttg tac      170
             Met Pro Ser Arg Ala Glu Asp Tyr Glu Val Leu Tyr
               1               5                  10 acc att ggc aca ggc tcc tac ggc cgc tgc cag aag atc cgg agg aag      218
Thr Ile Gly Thr Gly Ser Tyr Gly Arg Cys Gln Lys Ile Arg Arg Lys
             15                  20                  25 agt gat ggc aag ata tta gtt tgg aaa gaa ctt gac tat ggc tcc atg      266
Ser Asp Gly Lys Ile Leu Val Trp Lys Glu Leu Asp Tyr Gly Ser Met
 30                  35                  40 aca gaa gct gag aaa cag atg ctt gtt tct gaa gtg aat ttg ctt cgt      314
Thr Glu Ala Glu Lys Gln Met Leu Val Ser Glu Val Asn Leu Leu Arg
 45                  50                  55                  60 gaa ctg aaa cat cca aac atc gtt cgt tac tat gat cgg att att gac      362
Glu Leu Lys His Pro Asn Ile Val Arg Tyr Tyr Asp Arg Ile Ile Asp
             65                  70                  75 cgg acc aat aca aca ctg tac att gta atg gaa tat tgt gaa gga ggg      410
Arg Thr Asn Thr Thr Leu Tyr Ile Val Met Glu Tyr Cys Glu Gly Gly
             80                  85                  90 gat ctg gct agt gta att aca aag gga acc aag gaa agg caa tac tta      458
Asp Leu Ala Ser Val Ile Thr Lys Gly Thr Lys Glu Arg Gln Tyr Leu
         95                 100                 105 gat gaa gag ttt gtt ctt cga gtg atg act cag ttg act ctg gcc ctg      506
Asp Glu Glu Phe Val Leu Arg Val Met Thr Gln Leu Thr Leu Ala Leu
     110                 115                 120 aag gaa tgc cac aga cga agt gat ggt ggt cat acc gta ttg cat cgg      554
Lys Glu Cys His Arg Arg Ser Asp Gly Gly His Thr Val Leu His Arg
125                 130                 135                 140 gat ctt aaa cca gcc aat gtt ttc ctg gat ggc aag caa aac gtc aag      602
Asp Leu Lys Pro Ala Asn Val Phe Leu Asp Gly Lys Gln Asn Val Lys
             145                 150                 155 ctt gga gac ttt ggg cta gct aga ata tta aac cat gac acg agt ttt      650
Leu Gly Asp Phe Gly Leu Ala Arg Ile Leu Asn His Asp Thr Ser Phe
             160                 165                 170 gca aaa aca ttt gtt ggc aca cct tat tac atg tct cct gaa caa atg      698
Ala Lys Thr Phe Val Gly Thr Pro Tyr Tyr Met Ser Pro Glu Gln Met
         175                 180                 185 aat cgc atg tcc tac aat gag aaa tca gat atc tgg tca ttg ggc tgc      746
Asn Arg Met Ser Tyr Asn Glu Lys Ser Asp Ile Trp Ser Leu Gly Cys
     190                 195                 200 ttg ctg tat gag tta tgt gca tta atg cct cca ttt aca gct ttt agc      794
Leu Leu Tyr Glu Leu Cys Ala Leu Met Pro Pro Phe Thr Ala Phe Ser
205                 210                 215                 220 cag aaa gaa ctc gct ggg aaa atc aga gaa ggc aaa ttc agg cga att      842
Gln Lys Glu Leu Ala Gly Lys Ile Arg Glu Gly Lys Phe Arg Arg Ile
             225                 230                 235
```

| | | |
|---|---|---|
| cca tac cgt tac tct gat gaa ttg aat gaa att att acg agg atg tta<br>Pro Tyr Arg Tyr Ser Asp Glu Leu Asn Glu Ile Ile Thr Arg Met Leu<br>240 245 250 | | 890 |
| aac tta aag gat tac cat cga cct tct gtt gaa gaa att ctt gag aac<br>Asn Leu Lys Asp Tyr His Arg Pro Ser Val Glu Glu Ile Leu Glu Asn<br>255 260 265 | | 938 |
| cct tta ata gca gat ttg gtt gca gac gag caa aga aga aat ctt gag<br>Pro Leu Ile Ala Asp Leu Val Ala Asp Glu Gln Arg Arg Asn Leu Glu<br>270 275 280 | | 986 |
| aga aga ggg cga caa tta gga gag cca gaa aaa tcg cag gat tcc agc<br>Arg Arg Gly Arg Gln Leu Gly Glu Pro Glu Lys Ser Gln Asp Ser Ser<br>285 290 295 300 | | 1034 |
| cct gta ttg agt gag ctg aaa ctg aag gaa att cag tta cag gag cga<br>Pro Val Leu Ser Glu Leu Lys Leu Lys Glu Ile Gln Leu Gln Glu Arg<br>305 310 315 | | 1082 |
| gag cga gct ctc aaa gca aga gaa gaa aga ttg gag cag aaa gaa cag<br>Glu Arg Ala Leu Lys Ala Arg Glu Glu Arg Leu Glu Gln Lys Glu Gln<br>320 325 330 | | 1130 |
| gag ctt tgt gtt cgt gag aga cta gca gag gac aaa ctg gct aga gca<br>Glu Leu Cys Val Arg Glu Arg Leu Ala Glu Asp Lys Leu Ala Arg Ala<br>335 340 345 | | 1178 |
| gaa aat ctg ttg aag aac tac agc ttg cta aag gaa cgg aag ttc ctg<br>Glu Asn Leu Leu Lys Asn Tyr Ser Leu Leu Lys Glu Arg Lys Phe Leu<br>350 355 360 | | 1226 |
| tct ctg gca agt aat cca gaa ctt ctt aat ctt cca tcc tca gta att<br>Ser Leu Ala Ser Asn Pro Glu Leu Leu Asn Leu Pro Ser Ser Val Ile<br>365 370 375 380 | | 1274 |
| aag aag aaa gtt cat ttc agt ggg gaa agt aaa gag aac atc atg agg<br>Lys Lys Lys Val His Phe Ser Gly Glu Ser Lys Glu Asn Ile Met Arg<br>385 390 395 | | 1322 |
| agt gag aat tct gag agt cag ctc aca tct aag tcc aag tgc aag gac<br>Ser Glu Asn Ser Glu Ser Gln Leu Thr Ser Lys Ser Lys Cys Lys Asp<br>400 405 410 | | 1370 |
| ctg aag aaa agg ctt cac gct gcc cag ctg cgg gct caa gcc ctg tca<br>Leu Lys Lys Arg Leu His Ala Ala Gln Leu Arg Ala Gln Ala Leu Ser<br>415 420 425 | | 1418 |
| gat att gag aaa aat tac caa ctg aaa agc aga cag atc ctg ggc atg<br>Asp Ile Glu Lys Asn Tyr Gln Leu Lys Ser Arg Gln Ile Leu Gly Met<br>430 435 440 | | 1466 |
| cgc tagccaggta gagagacaca gagctgtgta caggatgtaa tattaccaac<br>Arg<br>445 | | 1519 |
| ctttaaagac tgatattcaa atgctgtagt gttgaatact tggccccatg agccatgcct | | 1579 |
| ttctgtatag tacacatgat atttcggaat tggtttact gttcttcagc aactattgta | | 1639 |
| caaaatgttc acatttaatt tttctttctt cttttaagaa catattataa aaagaatact | | 1699 |
| ttcttggttg ggcttttaat cctgtgtgtg attactagta ggaacatgag atgtgacatt | | 1759 |
| ctaaatcttg ggagaaaaaa taatattagg aaaaaaatat ttatgcagga agagtagcac | | 1819 |
| tcactgaata gttttaaatg actgagtggt atgcttacaa ttgtcatgtc tagatttaaa | | 1879 |
| ttttaagtct gagattttaa atgtttttga gcttagaaaa cccagttaga tgcaatttgg | | 1939 |
| tcattaatac catgacatct tgcttataaa tattccattg ctctgtagtt caaatctgtt | | 1999 |
| agctttgtga aaattcatca ctgtgatgtt tgtattcttt tttttttct gtttaacaga | | 2059 |
| atatgagctg tctgtcattt acctacttct ttcccactaa ataaaagaat tcttcagtta | | 2119 |

<210> SEQ ID NO 2
<211> LENGTH: 445

```
<212> TYPE: PRT
<213> ORGANISM: Homo sapiens

<400> SEQUENCE: 2

Met Pro Ser Arg Ala Glu Asp Tyr Glu Val Leu Tyr Thr Ile Gly Thr
 1               5                  10                  15

Gly Ser Tyr Gly Arg Cys Gln Lys Ile Arg Arg Lys Ser Asp Gly Lys
             20                  25                  30

Ile Leu Val Trp Lys Glu Leu Asp Tyr Gly Ser Met Thr Glu Ala Glu
         35                  40                  45

Lys Gln Met Leu Val Ser Glu Val Asn Leu Leu Arg Glu Leu Lys His
 50                  55                  60

Pro Asn Ile Val Arg Tyr Tyr Asp Arg Ile Ile Asp Arg Thr Asn Thr
 65                  70                  75                  80

Thr Leu Tyr Ile Val Met Glu Tyr Cys Glu Gly Gly Asp Leu Ala Ser
                 85                  90                  95

Val Ile Thr Lys Gly Thr Lys Glu Arg Gln Tyr Leu Asp Glu Glu Phe
                100                 105                 110

Val Leu Arg Val Met Thr Gln Leu Thr Leu Ala Leu Lys Glu Cys His
            115                 120                 125

Arg Arg Ser Asp Gly Gly His Thr Val Leu His Arg Asp Leu Lys Pro
130                 135                 140

Ala Asn Val Phe Leu Asp Gly Lys Gln Asn Val Lys Leu Gly Asp Phe
145                 150                 155                 160

Gly Leu Ala Arg Ile Leu Asn His Asp Thr Ser Phe Ala Lys Thr Phe
                165                 170                 175

Val Gly Thr Pro Tyr Tyr Met Ser Pro Glu Gln Met Asn Arg Met Ser
            180                 185                 190

Tyr Asn Glu Lys Ser Asp Ile Trp Ser Leu Gly Cys Leu Leu Tyr Glu
        195                 200                 205

Leu Cys Ala Leu Met Pro Pro Phe Thr Ala Phe Ser Gln Lys Glu Leu
210                 215                 220

Ala Gly Lys Ile Arg Glu Gly Lys Phe Arg Arg Ile Pro Tyr Arg Tyr
225                 230                 235                 240

Ser Asp Glu Leu Asn Glu Ile Ile Thr Arg Met Leu Asn Leu Lys Asp
                245                 250                 255

Tyr His Arg Pro Ser Val Glu Glu Ile Leu Glu Asn Pro Leu Ile Ala
            260                 265                 270

Asp Leu Val Ala Asp Glu Gln Arg Arg Asn Leu Glu Arg Arg Gly Arg
        275                 280                 285

Gln Leu Gly Glu Pro Glu Lys Ser Gln Asp Ser Ser Pro Val Leu Ser
290                 295                 300

Glu Leu Lys Leu Lys Glu Ile Gln Leu Gln Glu Arg Glu Arg Ala Leu
305                 310                 315                 320

Lys Ala Arg Glu Glu Arg Leu Glu Gln Lys Glu Gln Glu Leu Cys Val
                325                 330                 335

Arg Glu Arg Leu Ala Glu Asp Lys Leu Ala Arg Ala Glu Asn Leu Leu
            340                 345                 350

Lys Asn Tyr Ser Leu Leu Lys Glu Arg Lys Phe Leu Ser Leu Ala Ser
        355                 360                 365

Asn Pro Glu Leu Leu Asn Leu Pro Ser Ser Val Ile Lys Lys Lys Val
370                 375                 380

His Phe Ser Gly Glu Ser Lys Glu Asn Ile Met Arg Ser Glu Asn Ser
385                 390                 395                 400
```

```
Glu Ser Gln Leu Thr Ser Lys Ser Lys Cys Lys Asp Leu Lys Lys Arg
                405                 410                 415
Leu His Ala Ala Gln Leu Arg Ala Gln Ala Leu Ser Asp Ile Glu Lys
            420                 425                 430
Asn Tyr Gln Leu Lys Ser Arg Gln Ile Leu Gly Met Arg
        435                 440                 445

<210> SEQ ID NO 3
<211> LENGTH: 2301
<212> TYPE: DNA
<213> ORGANISM: Homo sapiens
<220> FEATURE:
<221> NAME/KEY: CDS
<222> LOCATION: (233)..(2155)

<400> SEQUENCE: 3
gtcgaccgga gggcaggagg agcaggagga gcaggagcag gaggagcagg aggagcagga      60
ggagcaggag gagcaggagg agcaggaaca ggaggaggag gaggaggaga aggaggagca     120
ggaagagcag gaggaggagg agcaggagca ggaggagcag gagggagagg aggctgcaac    180
gccgagcgga ggaggcagga accggagcgc gagcagtagc tgggtgggca cc atg gct   238
                                                             Met Ala
                                                               1 ggg atc acc acc atc gag gcg gtg aag cgc aag atc cag gtt ctg cag     286
Gly Ile Thr Thr Ile Glu Ala Val Lys Arg Lys Ile Gln Val Leu Gln
        5                  10                  15 cag cag gca gat gat gca gag gag cga gct gag cgc ctc cag cga gaa     334
Gln Gln Ala Asp Asp Ala Glu Glu Arg Ala Glu Arg Leu Gln Arg Glu
    20                  25                  30 gtt gag gga gaa agg cgg gcc cgg gaa cag gct gag gct gag gtg gcc     382
Val Glu Gly Glu Arg Arg Ala Arg Glu Gln Ala Glu Ala Glu Val Ala
35                  40                  45                  50 tcc ttg aac cgt agg atc cag ctg gtt gaa gaa gag ctg gac cgt gct     430
Ser Leu Asn Arg Arg Ile Gln Leu Val Glu Glu Glu Leu Asp Arg Ala
                55                  60                  65 cag gag cgc ctg gcc act gcc ctg caa aag ctg gaa gaa gct gaa aaa     478
Gln Glu Arg Leu Ala Thr Ala Leu Gln Lys Leu Glu Glu Ala Glu Lys
            70                  75                  80 gct gct gat gag agt gag aga ggt atg aag gtt att gaa aac cgg gcc     526
Ala Ala Asp Glu Ser Glu Arg Gly Met Lys Val Ile Glu Asn Arg Ala
        85                  90                  95 tta aaa gat gaa gaa aag atg gaa ctc cag gaa atc caa ctc gaa gaa     574
Leu Lys Asp Glu Glu Lys Met Glu Leu Gln Glu Ile Gln Leu Glu Glu
    100                 105                 110 gct aag cac att gca gaa gag gca gat agg aag tat gaa gag gtg gct     622
Ala Lys His Ile Ala Glu Glu Ala Asp Arg Lys Tyr Glu Glu Val Ala
115                 120                 125                 130 cgt aag ttg gtg atc att gaa gga gac ttg gaa cgc aca gag gaa cga     670
Arg Lys Leu Val Ile Ile Glu Gly Asp Leu Glu Arg Thr Glu Glu Arg
                135                 140                 145 gct gag ctg gca gag tcg cgt tgc cga gag atg gat gag cag att aga     718
Ala Glu Leu Ala Glu Ser Arg Cys Arg Glu Met Asp Glu Gln Ile Arg
            150                 155                 160 ctg atg gac cag aac ctg aag tgt ctg agt gct gcc gaa gaa aag tac     766
Leu Met Asp Gln Asn Leu Lys Cys Leu Ser Ala Ala Glu Glu Lys Tyr
        165                 170                 175 tct caa aaa gaa gat aaa tat gag gaa gaa atc aag att ctt act gat     814
Ser Gln Lys Glu Asp Lys Tyr Glu Glu Glu Ile Lys Ile Leu Thr Asp
    180                 185                 190
```

-continued

| | | |
|---|---|---|
| aaa ctc aag gag gca gag acc cgt gct gag ttt gct gag aga tcg gta<br>Lys Leu Lys Glu Ala Glu Thr Arg Ala Glu Phe Ala Glu Arg Ser Val<br>195                    200                    205                    210 | 862 |
| gcc aag ctg gaa aag aca att gat gac ctg gaa gac act aac agc aca<br>Ala Lys Leu Glu Lys Thr Ile Asp Asp Leu Glu Asp Thr Asn Ser Thr<br>                215                    220                    225 | 910 |
| tct gga gac ccg gtg gag aag aag gac gaa aca cct ttt ggg gtc tcg<br>Ser Gly Asp Pro Val Glu Lys Lys Asp Glu Thr Pro Phe Gly Val Ser<br>            230                    235                    240 | 958 |
| gtg gct gtg ggc ctg gcc gtc ttt gcc tgc ctc ttc ctt tct acg ctg<br>Val Ala Val Gly Leu Ala Val Phe Ala Cys Leu Phe Leu Ser Thr Leu<br>                245                    250                    255 | 1006 |
| ctc ctt gtg ctc aac aaa tgt gga cgg aga aac aag ttt ggg atc aac<br>Leu Leu Val Leu Asn Lys Cys Gly Arg Arg Asn Lys Phe Gly Ile Asn<br>260                    265                    270 | 1054 |
| cgc ccg gct gtg ctg gct cca gag gat ggg ctg gcc atg tcc ctg cat<br>Arg Pro Ala Val Leu Ala Pro Glu Asp Gly Leu Ala Met Ser Leu His<br>275                    280                    285                    290 | 1102 |
| ttc atg aca ttg ggt ggc agc tcc ctg tcc ccc acc gag ggc aaa ggc<br>Phe Met Thr Leu Gly Gly Ser Ser Leu Ser Pro Thr Glu Gly Lys Gly<br>                295                    300                    305 | 1150 |
| tct ggg ctc caa ggc cac atc atc gag aac cca caa tac ttc agt gat<br>Ser Gly Leu Gln Gly His Ile Ile Glu Asn Pro Gln Tyr Phe Ser Asp<br>            310                    315                    320 | 1198 |
| gcc tgt gtt cac cac atc aag cgc cgg gac atc gtg ctc aag tgg gag<br>Ala Cys Val His His Ile Lys Arg Arg Asp Ile Val Leu Lys Trp Glu<br>                325                    330                    335 | 1246 |
| ctg ggg gag ggc gcc ttt ggg aag gtc ttc ctt gct gag tgc cac aac<br>Leu Gly Glu Gly Ala Phe Gly Lys Val Phe Leu Ala Glu Cys His Asn<br>340                    345                    350 | 1294 |
| ctc ctg cct gag cag gac aag atg ctg gtg gct gtc aag gca ctg aag<br>Leu Leu Pro Glu Gln Asp Lys Met Leu Val Ala Val Lys Ala Leu Lys<br>355                    360                    365                    370 | 1342 |
| gag gcg tcc gag agt gct cgg cag gac ttc caa cgt gag gct gag ctg<br>Glu Ala Ser Glu Ser Ala Arg Gln Asp Phe Gln Arg Glu Ala Glu Leu<br>                375                    380                    385 | 1390 |
| ctc acc atg ctg cag cac cag cac atc gtg cgc ttc ttc ggc gtc tgc<br>Leu Thr Met Leu Gln His Gln His Ile Val Arg Phe Phe Gly Val Cys<br>            390                    395                    400 | 1438 |
| acc gag ggc cgc ccc ctg ctc atg gtc ttc gag tat atg cgg cac ggg<br>Thr Glu Gly Arg Pro Leu Leu Met Val Phe Glu Tyr Met Arg His Gly<br>                405                    410                    415 | 1486 |
| gac ctc aac cgc ttc ctc cga tcc cat gga ccc gat gcc aag ctg ctg<br>Asp Leu Asn Arg Phe Leu Arg Ser His Gly Pro Asp Ala Lys Leu Leu<br>420                    425                    430 | 1534 |
| gct ggt ggg gag gat gtg gct cca ggc ccc ctg ggt ctg ggg cag ctg<br>Ala Gly Gly Glu Asp Val Ala Pro Gly Pro Leu Gly Leu Gly Gln Leu<br>435                    440                    445                    450 | 1582 |
| ctg gcc gtg gct agc cag gtc gct gcg ggg atg gtg tac ctg gcg ggt<br>Leu Ala Val Ala Ser Gln Val Ala Ala Gly Met Val Tyr Leu Ala Gly<br>                455                    460                    465 | 1630 |
| ctg cat ttt gtg cac cgg gac ctg gcc aca cgc aac tgt cta gtg ggc<br>Leu His Phe Val His Arg Asp Leu Ala Thr Arg Asn Cys Leu Val Gly<br>            470                    475                    480 | 1678 |
| cag gga ctg gtg gtc aag att ggt gat ttt ggc atg agc agg gat atc<br>Gln Gly Leu Val Val Lys Ile Gly Asp Phe Gly Met Ser Arg Asp Ile<br>                485                    490                    495 | 1726 |
| tac agc acc gac tat tac cgt gtg gga ggc cgc acc atg ctg ccc att<br>Tyr Ser Thr Asp Tyr Tyr Arg Val Gly Gly Arg Thr Met Leu Pro Ile<br>500                    505                    510 | 1774 |

```
cgc tgg atg ccg ccc gag agc atc ctg tac cgt aag ttc acc acc gag      1822
Arg Trp Met Pro Pro Glu Ser Ile Leu Tyr Arg Lys Phe Thr Thr Glu
515                 520                 525                 530 agc gac gtg tgg agc ttc ggc gtg gtg ctc tgg gag atc ttc acc tac      1870
Ser Asp Val Trp Ser Phe Gly Val Val Leu Trp Glu Ile Phe Thr Tyr
                535                 540                 545 ggc aag cag ccc tgg tac cag ctc tcc aac acg gag gca atc gac tgc      1918
Gly Lys Gln Pro Trp Tyr Gln Leu Ser Asn Thr Glu Ala Ile Asp Cys
        550                 555                 560 atc acg cag gga cgt gag ttg gag cgg cca cgt gcc tgc cca cca gag      1966
Ile Thr Gln Gly Arg Glu Leu Glu Arg Pro Arg Ala Cys Pro Pro Glu
565                 570                 575 gtc tac gcc atc atg cgg ggc tgc tgg cag cgg gag ccc agc aac gcc      2014
Val Tyr Ala Ile Met Arg Gly Cys Trp Gln Arg Glu Pro Ser Asn Ala
        580                 585                 590 aca gca tca agg atg tgc acg ccc ggc tgc aag ccc tgg cct agg cac      2062
Thr Ala Ser Arg Met Cys Thr Pro Gly Cys Lys Pro Trp Pro Arg His
595                 600                 605                 610 ctc ctg tct acc tgg atg tcc tgg gct agg ggg ccg gcc cag ggg ctg      2110
Leu Leu Ser Thr Trp Met Ser Trp Ala Arg Gly Pro Ala Gln Gly Leu
                615                 620                 625 gga gtg gtt agc cgg aat act ggg gcc tgc cct cag cat ccc cca          2155
Gly Val Val Ser Arg Asn Thr Gly Ala Cys Pro Gln His Pro Pro
        630                 635                 640 tagctcccag cagccccagg gtgatctcga agtatctaat tcgccctcag catgtgggaa    2215
gggacaggtg ggggctggga gtagaggatg ttcctgcttc tctaggcaag gtcccgtcgt    2275
agcaattata tttattatgg gaattc                                         2301

<210> SEQ ID NO 4
<211> LENGTH: 641
<212> TYPE: PRT
<213> ORGANISM: Homo sapiens

<400> SEQUENCE: 4

Met Ala Gly Ile Thr Thr Ile Glu Ala Val Lys Arg Lys Ile Gln Val
 1               5                  10                  15

Leu Gln Gln Gln Ala Asp Asp Ala Glu Glu Arg Ala Glu Arg Leu Gln
                20                  25                  30

Arg Glu Val Glu Gly Glu Arg Arg Ala Arg Glu Gln Ala Glu Ala Glu
            35                  40                  45

Val Ala Ser Leu Asn Arg Arg Ile Gln Leu Val Glu Glu Glu Leu Asp
        50                  55                  60

Arg Ala Gln Glu Arg Leu Ala Thr Ala Leu Gln Lys Leu Glu Glu Ala
65                  70                  75                  80

Glu Lys Ala Ala Asp Glu Ser Glu Arg Gly Met Lys Val Ile Glu Asn
                85                  90                  95

Arg Ala Leu Lys Asp Glu Glu Lys Met Glu Leu Gln Glu Ile Gln Leu
            100                 105                 110

Glu Glu Ala Lys His Ile Ala Glu Ala Asp Arg Lys Tyr Glu Glu
        115                 120                 125

Val Ala Arg Lys Leu Val Ile Ile Glu Gly Asp Leu Glu Arg Thr Glu
        130                 135                 140

Glu Arg Ala Glu Leu Ala Glu Ser Arg Cys Arg Glu Met Asp Glu Gln
145                 150                 155                 160

Ile Arg Leu Met Asp Gln Asn Leu Lys Cys Leu Ser Ala Ala Glu Glu
                165                 170                 175
```

```
Lys Tyr Ser Gln Lys Glu Asp Lys Tyr Glu Glu Ile Lys Ile Leu
                180                 185                 190

Thr Asp Lys Leu Lys Glu Ala Glu Thr Arg Ala Glu Phe Ala Glu Arg
            195                 200                 205

Ser Val Ala Lys Leu Glu Lys Thr Ile Asp Asp Leu Glu Asp Thr Asn
            210                 215                 220

Ser Thr Ser Gly Asp Pro Val Glu Lys Lys Asp Glu Thr Pro Phe Gly
225                 230                 235                 240

Val Ser Val Ala Val Gly Leu Ala Val Phe Ala Cys Leu Phe Leu Ser
                245                 250                 255

Thr Leu Leu Val Leu Asn Lys Cys Gly Arg Arg Asn Lys Phe Gly
            260                 265                 270

Ile Asn Arg Pro Ala Val Leu Ala Pro Glu Asp Gly Leu Ala Met Ser
            275                 280                 285

Leu His Phe Met Thr Leu Gly Gly Ser Ser Leu Ser Pro Thr Glu Gly
            290                 295                 300

Lys Gly Ser Gly Leu Gln Gly His Ile Ile Glu Asn Pro Gln Tyr Phe
305                 310                 315                 320

Ser Asp Ala Cys Val His His Ile Lys Arg Arg Asp Ile Val Leu Lys
                325                 330                 335

Trp Glu Leu Gly Glu Gly Ala Phe Gly Lys Val Phe Leu Ala Glu Cys
            340                 345                 350

His Asn Leu Leu Pro Glu Gln Asp Lys Met Leu Val Ala Val Lys Ala
            355                 360                 365

Leu Lys Glu Ala Ser Glu Ser Ala Arg Gln Asp Phe Gln Arg Glu Ala
            370                 375                 380

Glu Leu Leu Thr Met Leu Gln His Gln His Ile Val Arg Phe Phe Gly
385                 390                 395                 400

Val Cys Thr Glu Gly Arg Pro Leu Leu Met Val Phe Glu Tyr Met Arg
                405                 410                 415

His Gly Asp Leu Asn Arg Phe Leu Arg Ser His Gly Pro Asp Ala Lys
            420                 425                 430

Leu Leu Ala Gly Gly Glu Asp Val Ala Pro Gly Pro Leu Gly Leu Gly
            435                 440                 445

Gln Leu Leu Ala Val Ala Ser Gln Val Ala Ala Gly Met Val Tyr Leu
450                 455                 460

Ala Gly Leu His Phe Val His Arg Asp Leu Ala Thr Arg Asn Cys Leu
465                 470                 475                 480

Val Gly Gln Gly Leu Val Val Lys Ile Gly Asp Phe Gly Met Ser Arg
                485                 490                 495

Asp Ile Tyr Ser Thr Asp Tyr Tyr Arg Val Gly Gly Arg Thr Met Leu
            500                 505                 510

Pro Ile Arg Trp Met Pro Pro Glu Ser Ile Leu Tyr Arg Lys Phe Thr
            515                 520                 525

Thr Glu Ser Asp Val Trp Ser Phe Gly Val Val Leu Trp Glu Ile Phe
            530                 535                 540

Thr Tyr Gly Lys Gln Pro Trp Tyr Gln Leu Ser Asn Thr Glu Ala Ile
545                 550                 555                 560

Asp Cys Ile Thr Gln Gly Arg Glu Leu Glu Arg Pro Arg Ala Cys Pro
                565                 570                 575

Pro Glu Val Tyr Ala Ile Met Arg Gly Cys Trp Gln Arg Glu Pro Ser
            580                 585                 590
```

```
Asn Ala Thr Ala Ser Arg Met Cys Thr Pro Gly Cys Lys Pro Trp Pro
            595                 600                 605

Arg His Leu Leu Ser Thr Trp Met Ser Trp Ala Arg Gly Pro Ala Gln
        610                 615                 620

Gly Leu Gly Val Val Ser Arg Asn Thr Gly Ala Cys Pro Gln His Pro
625                 630                 635                 640

Pro

<210> SEQ ID NO 5
<211> LENGTH: 1367
<212> TYPE: DNA
<213> ORGANISM: Homo sapiens
<220> FEATURE:
<221> NAME/KEY: CDS
<222> LOCATION: (30)..(1019)

<400> SEQUENCE: 5
gggcaaggag ctgctggctg gacggcggc atg tcc gac agc gag aag ctc aac        53
                                Met Ser Asp Ser Glu Lys Leu Asn
                                  1               5 ctg gac tcg atc atc ggg cgc ctg ctg gaa gtg cag ggc tcg cgg cct       101
Leu Asp Ser Ile Ile Gly Arg Leu Leu Glu Val Gln Gly Ser Arg Pro
 10              15                  20 ggc aag aat gta cag ctg aca gag aac gag atc cgc ggt ctg tgc ctg       149
Gly Lys Asn Val Gln Leu Thr Glu Asn Glu Ile Arg Gly Leu Cys Leu
 25                  30                  35                  40 aaa tcc cgg gag att ttt ctg agc cag ccc att ctt ctg gag ctg gag       197
Lys Ser Arg Glu Ile Phe Leu Ser Gln Pro Ile Leu Leu Glu Leu Glu
                 45                  50                  55 gca ccc ctc aag atc tgc ggt gac ata cac ggc cag tac tac gac ctt       245
Ala Pro Leu Lys Ile Cys Gly Asp Ile His Gly Gln Tyr Tyr Asp Leu
             60                  65                  70 ctg cga cta ttt gag tat ggc ggt ttc cct ccc gag agc aac tac ctc       293
Leu Arg Leu Phe Glu Tyr Gly Gly Phe Pro Pro Glu Ser Asn Tyr Leu
         75                  80                  85 ttt ctg ggg gac tat gtg gac agg ggc aag cag tcc ttg gag acc atc       341
Phe Leu Gly Asp Tyr Val Asp Arg Gly Lys Gln Ser Leu Glu Thr Ile
     90                  95                 100 tgc ctg ctg ctg gcc tat aag atc aag tac ccc gag aac ttc ttc ctg       389
Cys Leu Leu Leu Ala Tyr Lys Ile Lys Tyr Pro Glu Asn Phe Phe Leu
105                 110                 115                 120 ctc cgt ggg aac cac gag tgt gcc agc atc aac cgc atc tat ggt ttc       437
Leu Arg Gly Asn His Glu Cys Ala Ser Ile Asn Arg Ile Tyr Gly Phe
                125                 130                 135 tac gat gag tgc aag aga cgc tac aac atc aaa ctg tgg aaa acc ttc       485
Tyr Asp Glu Cys Lys Arg Arg Tyr Asn Ile Lys Leu Trp Lys Thr Phe
            140                 145                 150 act gac tgc ttc aac tgc ctg ccc atc gcg gcc ata gtg gac gaa aag       533
Thr Asp Cys Phe Asn Cys Leu Pro Ile Ala Ala Ile Val Asp Glu Lys
        155                 160                 165 atc ttc tgc tgc cac gga ggc ctg tcc ccg gac ctg cag tct atg gag       581
Ile Phe Cys Cys His Gly Gly Leu Ser Pro Asp Leu Gln Ser Met Glu
    170                 175                 180 cag att cgg cgg atc atg cgg ccc aca gat gtg cct gac cag ggc ctg       629
Gln Ile Arg Arg Ile Met Arg Pro Thr Asp Val Pro Asp Gln Gly Leu
185                 190                 195                 200 ctg tgt gac ctg ctg tgg tct gac cct gac aag gac gtg cag ggc tgg       677
Leu Cys Asp Leu Leu Trp Ser Asp Pro Asp Lys Asp Val Gln Gly Trp
                205                 210                 215 ggc gag aac gac cgt ggc gtc tct ttt acc ttt gga gcc gag gtg gtg       725
```

```
Gly Glu Asn Asp Arg Gly Val Ser Phe Thr Phe Gly Ala Glu Val Val
            220                 225                 230 gcc aag ttc ctc cac aag cac gac ttg gac ctc atc tgc cga gca cac      773
Ala Lys Phe Leu His Lys His Asp Leu Asp Leu Ile Cys Arg Ala His
        235                 240                 245 cag gtg gta gaa gac ggc tat gag ttc ttt gcc aag cgg cag ctg gtg      821
Gln Val Val Glu Asp Gly Tyr Glu Phe Phe Ala Lys Arg Gln Leu Val
    250                 255                 260 aca ctt ttc tca gct ccc aac tac tgt ggc gag ttt gac aat gct ggc      869
Thr Leu Phe Ser Ala Pro Asn Tyr Cys Gly Glu Phe Asp Asn Ala Gly
265                 270                 275                 280 gcc atg atg agt gtg gac gag acc ctc atg tgc tct ttc cag atc ctc      917
Ala Met Met Ser Val Asp Glu Thr Leu Met Cys Ser Phe Gln Ile Leu
                285                 290                 295 aag ccc gcc gac aag aac aag ggg aag tac ggg cag ttc agt ggc ctg      965
Lys Pro Ala Asp Lys Asn Lys Gly Lys Tyr Gly Gln Phe Ser Gly Leu
            300                 305                 310 aac cct gga ggc cga ccc atc acc cca ccc cgc aat tcc gcc aaa gcc     1013
Asn Pro Gly Gly Arg Pro Ile Thr Pro Pro Arg Asn Ser Ala Lys Ala
        315                 320                 325 aag aaa tagccccgc acaccaccct gtgcccaga tgatggattg attgtacaga        1069
Lys Lys
    330 aatcatgctg ccatgctggg gggggtcac cccgacccct aaggcccacc tgtcacgggg    1129 aacatggagc cttggtgtat ttttctttc tttttttaat gaatcaatag cagcgtccag    1189 tcccccaggg ctgcttcctg cctgcacctg cggtactgtg agcaggatcc tggggccgag   1249 gctgcagctc agggcaacgg caggccaggt cgtgggtctc cagccgtgct tggcctcagg   1309 ctggcagccc ggatcctggg gcaacccatc tggtctcttg aataaaggtc aaagctgg    1367

<210> SEQ ID NO 6
<211> LENGTH: 330
<212> TYPE: PRT
<213> ORGANISM: Homo sapiens

<400> SEQUENCE: 6

Met Ser Asp Ser Glu Lys Leu Asn Leu Asp Ser Ile Ile Gly Arg Leu
 1               5                  10                  15

Leu Glu Val Gln Gly Ser Arg Pro Gly Lys Asn Val Gln Leu Thr Glu
                20                  25                  30

Asn Glu Ile Arg Gly Leu Cys Leu Lys Ser Arg Glu Ile Phe Leu Ser
            35                  40                  45

Gln Pro Ile Leu Leu Glu Leu Glu Ala Pro Leu Lys Ile Cys Gly Asp
        50                  55                  60

Ile His Gly Gln Tyr Tyr Asp Leu Leu Arg Leu Phe Glu Tyr Gly Gly
 65                  70                  75                  80

Phe Pro Pro Glu Ser Asn Tyr Leu Phe Leu Gly Asp Tyr Val Asp Arg
                    85                  90                  95

Gly Lys Gln Ser Leu Glu Thr Ile Cys Leu Leu Leu Ala Tyr Lys Ile
                100                 105                 110

Lys Tyr Pro Glu Asn Phe Phe Leu Leu Arg Gly Asn His Glu Cys Ala
            115                 120                 125

Ser Ile Asn Arg Ile Tyr Gly Phe Tyr Asp Glu Cys Lys Arg Arg Tyr
        130                 135                 140

Asn Ile Lys Leu Trp Lys Thr Phe Thr Asp Cys Phe Asn Cys Leu Pro
145                 150                 155                 160
```

```
Ile Ala Ala Ile Val Asp Glu Lys Ile Phe Cys Cys His Gly Gly Leu
            165                 170                 175

Ser Pro Asp Leu Gln Ser Met Glu Gln Ile Arg Arg Ile Met Arg Pro
            180                 185                 190

Thr Asp Val Pro Asp Gln Gly Leu Leu Cys Asp Leu Leu Trp Ser Asp
            195                 200                 205

Pro Asp Lys Asp Val Gln Gly Trp Gly Glu Asn Asp Arg Gly Val Ser
            210                 215                 220

Phe Thr Phe Gly Ala Glu Val Ala Lys Phe Leu His Lys His Asp
225                 230                 235                 240

Leu Asp Leu Ile Cys Arg Ala His Gln Val Val Glu Asp Gly Tyr Glu
            245                 250                 255

Phe Phe Ala Lys Arg Gln Leu Val Thr Leu Phe Ser Ala Pro Asn Tyr
            260                 265                 270

Cys Gly Glu Phe Asp Asn Ala Gly Ala Met Met Ser Val Asp Glu Thr
            275                 280                 285

Leu Met Cys Ser Phe Gln Ile Leu Lys Pro Ala Asp Lys Asn Lys Gly
            290                 295                 300

Lys Tyr Gly Gln Phe Ser Gly Leu Asn Pro Gly Gly Arg Pro Ile Thr
305                 310                 315                 320

Pro Pro Arg Asn Ser Ala Lys Ala Lys Lys
            325                 330
```

<210> SEQ ID NO 7
<211> LENGTH: 792
<212> TYPE: DNA
<213> ORGANISM: Homo sapiens
<220> FEATURE:
<221> NAME/KEY: CDS
<222> LOCATION: (1)..(765)

<400> SEQUENCE: 7

```
atg gat gat cga gag gat ctg gtg tac cag gcg aag ctg gcc gag cag      48
Met Asp Asp Arg Glu Asp Leu Val Tyr Gln Ala Lys Leu Ala Glu Gln
  1               5                  10                  15 gct gag cga tac gac gaa atg gtg gag tca atg aag aaa gta gca ggg      96
Ala Glu Arg Tyr Asp Glu Met Val Glu Ser Met Lys Lys Val Ala Gly
                 20                  25                  30 atg gat gtg gag ctg aca gtt gaa gaa aga aac ctc cta tct gtt gca     144
Met Asp Val Glu Leu Thr Val Glu Glu Arg Asn Leu Leu Ser Val Ala
             35                  40                  45 tat aag aat gtg att gga gct aga aga gcc tcc tgg aga ata atc agc     192
Tyr Lys Asn Val Ile Gly Ala Arg Arg Ala Ser Trp Arg Ile Ile Ser
         50                  55                  60 agc att gaa cag aaa gaa gaa aac aag gga gga gaa gac aag cta aaa     240
Ser Ile Glu Gln Lys Glu Glu Asn Lys Gly Gly Glu Asp Lys Leu Lys
 65                  70                  75                  80 atg att cgg gaa tat cgg caa atg gtt gag act gag cta aag tta atc     288
Met Ile Arg Glu Tyr Arg Gln Met Val Glu Thr Glu Leu Lys Leu Ile
                 85                  90                  95 tgt tgt gac att ctg gat gta ctg gac aaa cac ctc att cca gca gct     336
Cys Cys Asp Ile Leu Asp Val Leu Asp Lys His Leu Ile Pro Ala Ala
            100                 105                 110 aac act ggc gag tcc aag gtt ttc tat tat aaa atg aaa ggg gac tac     384
Asn Thr Gly Glu Ser Lys Val Phe Tyr Tyr Lys Met Lys Gly Asp Tyr
            115                 120                 125 cac agg tat ctg gca gaa ttt gcc aca gga aac gac agg aag gag gct     432
His Arg Tyr Leu Ala Glu Phe Ala Thr Gly Asn Asp Arg Lys Glu Ala
            130                 135                 140
```

```
gcg gag aac agc cta gtg gct tat aaa gct gct agt gat att gca atg    480
Ala Glu Asn Ser Leu Val Ala Tyr Lys Ala Ala Ser Asp Ile Ala Met
145                 150                 155                 160 aca gaa ctt cca cca acg cat cct att cgc tta ggt ctt gct ctc aat    528
Thr Glu Leu Pro Pro Thr His Pro Ile Arg Leu Gly Leu Ala Leu Asn
                165                 170                 175 ttt tcc gta ttc tac tac gaa att ctt aat tcc cct gac cgt gcc tgc    576
Phe Ser Val Phe Tyr Tyr Glu Ile Leu Asn Ser Pro Asp Arg Ala Cys
            180                 185                 190 agg ttg gca aaa gca gct ttt gat gat gca att gca gaa ctg gat acg    624
Arg Leu Ala Lys Ala Ala Phe Asp Asp Ala Ile Ala Glu Leu Asp Thr
        195                 200                 205 ctg agt gaa gaa agc tat aag gac tct aca ctt atc atg cag ttg tta    672
Leu Ser Glu Glu Ser Tyr Lys Asp Ser Thr Leu Ile Met Gln Leu Leu
    210                 215                 220 cgt gat aat ctg aca cta tgg act tca gac atg cag ggt gac ggt gaa    720
Arg Asp Asn Leu Thr Leu Trp Thr Ser Asp Met Gln Gly Asp Gly Glu
225                 230                 235                 240 gag cag aat aaa gaa gcg ctg cag gac gtg gaa gac gaa aat cag         765
Glu Gln Asn Lys Glu Ala Leu Gln Asp Val Glu Asp Glu Asn Gln
                245                 250                 255 tgagacataa gccaacaaga gaaacca                                       792

<210> SEQ ID NO 8
<211> LENGTH: 255
<212> TYPE: PRT
<213> ORGANISM: Homo sapiens

<400> SEQUENCE: 8

Met Asp Asp Arg Glu Asp Leu Val Tyr Gln Ala Lys Leu Ala Glu Gln
  1               5                  10                  15

Ala Glu Arg Tyr Asp Glu Met Val Glu Ser Met Lys Lys Val Ala Gly
             20                  25                  30

Met Asp Val Glu Leu Thr Val Glu Glu Arg Asn Leu Leu Ser Val Ala
         35                  40                  45

Tyr Lys Asn Val Ile Gly Ala Arg Arg Ala Ser Trp Arg Ile Ile Ser
     50                  55                  60

Ser Ile Glu Gln Lys Glu Asn Lys Gly Gly Glu Asp Lys Leu Lys
 65                  70                  75                  80

Met Ile Arg Glu Tyr Arg Gln Met Val Glu Thr Glu Leu Lys Leu Ile
                 85                  90                  95

Cys Cys Asp Ile Leu Asp Val Leu Asp Lys His Leu Ile Pro Ala Ala
            100                 105                 110

Asn Thr Gly Glu Ser Lys Val Phe Tyr Tyr Lys Met Lys Gly Asp Tyr
        115                 120                 125

His Arg Tyr Leu Ala Glu Phe Ala Thr Gly Asn Asp Arg Lys Glu Ala
    130                 135                 140

Ala Glu Asn Ser Leu Val Ala Tyr Lys Ala Ala Ser Asp Ile Ala Met
145                 150                 155                 160

Thr Glu Leu Pro Pro Thr His Pro Ile Arg Leu Gly Leu Ala Leu Asn
                165                 170                 175

Phe Ser Val Phe Tyr Tyr Glu Ile Leu Asn Ser Pro Asp Arg Ala Cys
            180                 185                 190

Arg Leu Ala Lys Ala Ala Phe Asp Asp Ala Ile Ala Glu Leu Asp Thr
        195                 200                 205

Leu Ser Glu Glu Ser Tyr Lys Asp Ser Thr Leu Ile Met Gln Leu Leu
```

-continued

```
             210                 215                 220
Arg Asp Asn Leu Thr Leu Trp Thr Ser Asp Met Gln Gly Asp Gly Glu
225                 230                 235                 240

Glu Gln Asn Lys Glu Ala Leu Gln Asp Val Glu Asp Glu Asn Gln
                245                 250                 255

<210> SEQ ID NO 9
<211> LENGTH: 1111
<212> TYPE: DNA
<213> ORGANISM: Homo sapiens
<220> FEATURE:
<221> NAME/KEY: CDS
<222> LOCATION: (57)..(908)

<400> SEQUENCE: 9
ccgcgcgctc gccccgccgc tcctgctgca gccccaggcc cctcgccgcc gccacc atg      59
                                                                Met
                                                                1 gac gcc atc aag aag aag atg cag atg ctg aag ctc gac aag gag aac     107
Asp Ala Ile Lys Lys Lys Met Gln Met Leu Lys Leu Asp Lys Glu Asn
            5                  10                  15 gcc ttg gat cga gct gag cag gcg gag gcc gac aag aag gcg gcg gaa     155
Ala Leu Asp Arg Ala Glu Gln Ala Glu Ala Asp Lys Lys Ala Ala Glu
         20                  25                  30 gac agg agc aag cag ctg gaa gat gag ctg gtg tca ctg caa aag aaa     203
Asp Arg Ser Lys Gln Leu Glu Asp Glu Leu Val Ser Leu Gln Lys Lys
     35                  40                  45 ctc aag ggc acc gaa gat gaa ctg gac aaa tac tct gag gct ctc aaa     251
Leu Lys Gly Thr Glu Asp Glu Leu Asp Lys Tyr Ser Glu Ala Leu Lys
 50                  55                  60                  65 gat gcc cag gag aag ctg gag ctg gca gag aaa aag gcc acc gat gct     299
Asp Ala Gln Glu Lys Leu Glu Leu Ala Glu Lys Lys Ala Thr Asp Ala
                 70                  75                  80 gaa gcc gac gta gct tct ctg aac aga cgc atc cag ctg gtt gag gaa     347
Glu Ala Asp Val Ala Ser Leu Asn Arg Arg Ile Gln Leu Val Glu Glu
             85                  90                  95 gag ttg gat cgt gcc cag gag cgt ctg gca aca gct ttg cag aag ctg     395
Glu Leu Asp Arg Ala Gln Glu Arg Leu Ala Thr Ala Leu Gln Lys Leu
        100                 105                 110 gag gaa gct gag aag gca gca gat gag agt gag aga ggc atg aaa gtc     443
Glu Glu Ala Glu Lys Ala Ala Asp Glu Ser Glu Arg Gly Met Lys Val
    115                 120                 125 att gag agt cga gcc caa aaa gat gaa gaa aaa atg gaa att cag gag     491
Ile Glu Ser Arg Ala Gln Lys Asp Glu Glu Lys Met Glu Ile Gln Glu
130                 135                 140                 145 atc caa ctg aaa gag gcc aag cac att gct gaa gat gcc gac cgc aaa     539
Ile Gln Leu Lys Glu Ala Lys His Ile Ala Glu Asp Ala Asp Arg Lys
                150                 155                 160 tac gaa gag gtg gcc cgt aag ctg gtc atc att gag agc gac ctg gaa     587
Tyr Glu Glu Val Ala Arg Lys Leu Val Ile Ile Glu Ser Asp Leu Glu
            165                 170                 175 cgt gca gag gag cgg gct gag ctc tca gaa ggc aaa tgt gcc gag ctt     635
Arg Ala Glu Glu Arg Ala Glu Leu Ser Glu Gly Lys Cys Ala Glu Leu
        180                 185                 190 gaa gaa gaa ttg aaa act gtg acg aac aac ttg aag tca ctg gag gct     683
Glu Glu Glu Leu Lys Thr Val Thr Asn Asn Leu Lys Ser Leu Glu Ala
    195                 200                 205 cag gct gag aag tac tcg cag aag gaa gac aga tat gag gaa gag atc     731
Gln Ala Glu Lys Tyr Ser Gln Lys Glu Asp Arg Tyr Glu Glu Glu Ile
210                 215                 220                 225
```

```
aag gtc ctt tcc gac aag ctg aag gag gct gag act cgg gct gag ttt      779
Lys Val Leu Ser Asp Lys Leu Lys Glu Ala Glu Thr Arg Ala Glu Phe
            230                 235                 240 gcg gag agg tca gta act aaa ttg gag aaa agc att gat gac tta gaa      827
Ala Glu Arg Ser Val Thr Lys Leu Glu Lys Ser Ile Asp Asp Leu Glu
        245                 250                 255 gac gag ctg tac gct cag aaa ctg aag tac aaa gcc atc agc gag gag      875
Asp Glu Leu Tyr Ala Gln Lys Leu Lys Tyr Lys Ala Ile Ser Glu Glu
    260                 265                 270 ctg gac cac gct ctc aac gat atg act tcc ata taagtttctt tgcttcactt    928
Leu Asp His Ala Leu Asn Asp Met Thr Ser Ile
275                 280 ctcccaagac tccctcgtcg agctggatgt cccacctctc tgagctctgc atttgtctat    988
tctccagctg accctggttc tctctcttag catcctgcct tagagccagg cacacactgt   1048
gctttctatt gtacagaagc tcttcgtttc agtgtcaaat aaacactgtg taagctaaaa   1108
aaa                                                                  1111

<210> SEQ ID NO 10
<211> LENGTH: 284
<212> TYPE: PRT
<213> ORGANISM: Homo sapiens

<400> SEQUENCE: 10

Met Asp Ala Ile Lys Lys Met Gln Met Leu Lys Leu Asp Lys Glu
 1               5                  10                  15

Asn Ala Leu Asp Arg Ala Glu Gln Ala Glu Ala Asp Lys Lys Ala Ala
            20                  25                  30

Glu Asp Arg Ser Lys Gln Leu Glu Asp Glu Leu Val Ser Leu Gln Lys
        35                  40                  45

Lys Leu Lys Gly Thr Glu Asp Glu Leu Asp Lys Tyr Ser Glu Ala Leu
    50                  55                  60

Lys Asp Ala Gln Glu Lys Leu Glu Leu Ala Glu Lys Lys Ala Thr Asp
65                  70                  75                  80

Ala Glu Ala Asp Val Ala Ser Leu Asn Arg Arg Ile Gln Leu Val Glu
                85                  90                  95

Glu Glu Leu Asp Arg Ala Gln Glu Arg Leu Ala Thr Ala Leu Gln Lys
            100                 105                 110

Leu Glu Glu Ala Glu Lys Ala Ala Asp Glu Ser Glu Arg Gly Met Lys
        115                 120                 125

Val Ile Glu Ser Arg Ala Gln Lys Asp Glu Glu Lys Met Glu Ile Gln
    130                 135                 140

Glu Ile Gln Leu Lys Glu Ala Lys His Ile Ala Glu Asp Ala Asp Arg
145                 150                 155                 160

Lys Tyr Glu Glu Val Ala Arg Lys Leu Val Ile Ile Glu Ser Asp Leu
                165                 170                 175

Glu Arg Ala Glu Glu Arg Ala Glu Leu Ser Glu Gly Lys Cys Ala Glu
            180                 185                 190

Leu Glu Glu Glu Leu Lys Thr Val Thr Asn Asn Leu Lys Ser Leu Glu
        195                 200                 205

Ala Gln Ala Glu Lys Tyr Ser Gln Lys Glu Asp Arg Tyr Glu Glu Glu
    210                 215                 220

Ile Lys Val Leu Ser Asp Lys Leu Lys Glu Ala Glu Thr Arg Ala Glu
225                 230                 235                 240

Phe Ala Glu Arg Ser Val Thr Lys Leu Glu Lys Ser Ile Asp Asp Leu
                245                 250                 255
```

```
Glu Asp Glu Leu Tyr Ala Gln Lys Leu Lys Tyr Lys Ala Ile Ser Glu
            260                 265                 270

Glu Leu Asp His Ala Leu Asn Asp Met Thr Ser Ile
        275                 280

<210> SEQ ID NO 11
<211> LENGTH: 1766
<212> TYPE: DNA
<213> ORGANISM: Homo sapiens
<220> FEATURE:
<221> NAME/KEY: CDS
<222> LOCATION: (44)..(1441)

<400> SEQUENCE: 11
cgcgccaccg ccgccgccca ggccatcgcc accctccgca gcc atg tcc acc agg       55
                                               Met Ser Thr Arg
                                                 1 tcc gtg tcc tcg tcc tcc tac cgc agg atg ttc ggc ggc ccg ggc acc     103
Ser Val Ser Ser Ser Ser Tyr Arg Arg Met Phe Gly Gly Pro Gly Thr
  5              10                  15                  20 gcg agc cgg ccg agc tcc agc cgg agc tac gtg act acg tcc acc cgc     151
Ala Ser Arg Pro Ser Ser Ser Arg Ser Tyr Val Thr Thr Ser Thr Arg
             25                  30                  35 acc tac agc ctg ggc agc gcg ctg cgc ccc agc acc agc cgc agc ctc     199
Thr Tyr Ser Leu Gly Ser Ala Leu Arg Pro Ser Thr Ser Arg Ser Leu
         40                  45                  50 tac gcc tcg tcc ccg ggc ggc gtg tat gcc acg cgc tcc tct gcc gtg     247
Tyr Ala Ser Ser Pro Gly Gly Val Tyr Ala Thr Arg Ser Ser Ala Val
     55                  60                  65 cgc ctg cgg agc agc gtg ccc ggg gtg cgg ctc ctg cag gac tcg gtg     295
Arg Leu Arg Ser Ser Val Pro Gly Val Arg Leu Leu Gln Asp Ser Val
 70                  75                  80 gac ttc tcg ctg gcc gac gcc atc aac acc gag ttc aag aac acc cgc     343
Asp Phe Ser Leu Ala Asp Ala Ile Asn Thr Glu Phe Lys Asn Thr Arg
 85                  90                  95                 100 acc aac gag aag gtg gag ctg cag gag ctg aat gac cgc ttc gcc aac     391
Thr Asn Glu Lys Val Glu Leu Gln Glu Leu Asn Asp Arg Phe Ala Asn
                105                 110                 115 tac atc gac aag gtg cgc ttc ctg gag cag cag aat aag atc ctg ctg     439
Tyr Ile Asp Lys Val Arg Phe Leu Glu Gln Gln Asn Lys Ile Leu Leu
            120                 125                 130 gcc gag ctc gag cag ctc aag ggc caa ggc aag tcg cgc ctg ggg gac     487
Ala Glu Leu Glu Gln Leu Lys Gly Gln Gly Lys Ser Arg Leu Gly Asp
        135                 140                 145 ctc tac gag gag gag atg cgg gag ctg cgc cgg cag gtg gac cag cta     535
Leu Tyr Glu Glu Glu Met Arg Glu Leu Arg Arg Gln Val Asp Gln Leu
    150                 155                 160 acc aac gac aaa gcc cgc gtc gag gtg gag cgc gac aac ctg gcc gag     583
Thr Asn Asp Lys Ala Arg Val Glu Val Glu Arg Asp Asn Leu Ala Glu
165                 170                 175                 180 gac atc atg cgc ctc cgg gag aaa ttg cag gag gag atg ctt cag aga     631
Asp Ile Met Arg Leu Arg Glu Lys Leu Gln Glu Glu Met Leu Gln Arg
                185                 190                 195 gag gaa gcc gaa aac acc ctg caa tct ttc aga cag gat gtt gac aat     679
Glu Glu Ala Glu Asn Thr Leu Gln Ser Phe Arg Gln Asp Val Asp Asn
            200                 205                 210 gcg tct ctg gca cgt ctt gac ctt gaa cgc aaa gtg gaa tct ttg caa     727
Ala Ser Leu Ala Arg Leu Asp Leu Glu Arg Lys Val Glu Ser Leu Gln
        215                 220                 225 gaa gag att gcc ttt ttg aag aaa ctc cac gaa gag gaa atc cag gag     775
```

```
Glu Glu Ile Ala Phe Leu Lys Lys Leu His Glu Glu Ile Gln Glu
        230                 235                 240 ctg cag gct cag att cag gaa cag cat gtc caa atc gat gtg gat gtt        823
Leu Gln Ala Gln Ile Gln Glu Gln His Val Gln Ile Asp Val Asp Val
245                 250                 255                 260 tcc aag cct gac ctc acg gct gcc ctg cgt gac gta cgt cag caa tat        871
Ser Lys Pro Asp Leu Thr Ala Ala Leu Arg Asp Val Arg Gln Gln Tyr
                265                 270                 275 gaa agt gtg gct gcc aag aac ctg cag gag gca gaa gaa tgg tac aaa        919
Glu Ser Val Ala Ala Lys Asn Leu Gln Glu Ala Glu Glu Trp Tyr Lys
            280                 285                 290 tcc aag ttt gct gac ctc tct gag gct gcc aac cgg aac aat gac gcc        967
Ser Lys Phe Ala Asp Leu Ser Glu Ala Ala Asn Arg Asn Asn Asp Ala
        295                 300                 305 ctg cgc cag gca aag cag gag tcc act gag tac cgg aga cag gtg cag       1015
Leu Arg Gln Ala Lys Gln Glu Ser Thr Glu Tyr Arg Arg Gln Val Gln
    310                 315                 320 tcc ctc acc tgt gaa gtg gat gcc ctt aaa gga acc aat gag tcc ctg       1063
Ser Leu Thr Cys Glu Val Asp Ala Leu Lys Gly Thr Asn Glu Ser Leu
325                 330                 335                 340 gaa cgc cag atg cgt gaa atg gaa gag aac ttt gcc gtt gaa gct gct       1111
Glu Arg Gln Met Arg Glu Met Glu Glu Asn Phe Ala Val Glu Ala Ala
                345                 350                 355 aac tac caa gac act att ggc cgc ctg cag gat gag att cag aat atg       1159
Asn Tyr Gln Asp Thr Ile Gly Arg Leu Gln Asp Glu Ile Gln Asn Met
                360                 365                 370 aag gag gaa atg gct cgt cac ctt cgt gaa tac caa gac ctg ctc aat       1207
Lys Glu Glu Met Ala Arg His Leu Arg Glu Tyr Gln Asp Leu Leu Asn
            375                 380                 385 gtt aag atg gcc ctt gac att gag att gcc acc tac agg aag ctg ctg       1255
Val Lys Met Ala Leu Asp Ile Glu Ile Ala Thr Tyr Arg Lys Leu Leu
390                 395                 400 gaa ggc gag gag agc agg att tct ctg cct ctt cca aac ttt tcc tcc       1303
Glu Gly Glu Glu Ser Arg Ile Ser Leu Pro Leu Pro Asn Phe Ser Ser
405                 410                 415                 420 ctg aac ctg agg gaa act aat ctg gat tca ctc cct ctg gtt gat acc       1351
Leu Asn Leu Arg Glu Thr Asn Leu Asp Ser Leu Pro Leu Val Asp Thr
                425                 430                 435 cac tca aaa agg aca ctt ctg att aag acg gtt gaa act aga gat gga       1399
His Ser Lys Arg Thr Leu Leu Ile Lys Thr Val Glu Thr Arg Asp Gly
            440                 445                 450 cag gtt atc aac gaa act tct cag cat cac gat gac ctt gaa                1441
Gln Val Ile Asn Glu Thr Ser Gln His His Asp Asp Leu Glu
        455                 460                 465 taaaaattgc acacactcag tgcagcaata tattaccagc aagaataaaa aagaaatcca     1501
tatcttaaag aaacagcttt caagtgcctt tctgcagttt ttcaggagcg caagatagat    1561
ttggaatagg aataagctct agttcttaac aaccgacact cctacaagat ttagaaaaaa    1621
gtttacaaca taatctagtt tacagaaaaa tcttgtgcta gaatacttt taaaaggtat     1681 tttgaatacc attaaaactg cttttttttt tccagcaagt atccaaccaa cttggttctg   1741
cttcaataaa tctttggaaa aacta                                          1766

<210> SEQ ID NO 12
<211> LENGTH: 466
<212> TYPE: PRT
<213> ORGANISM: Homo sapiens

<400> SEQUENCE: 12
```

-continued

```
Met Ser Thr Arg Ser Val Ser Ser Ser Tyr Arg Arg Met Phe Gly
 1               5                    10                   15

Gly Pro Gly Thr Ala Ser Arg Pro Ser Ser Arg Ser Tyr Val Thr
            20                  25              30

Thr Ser Thr Arg Thr Tyr Ser Leu Gly Ser Ala Leu Arg Pro Ser Thr
            35                  40              45

Ser Arg Ser Leu Tyr Ala Ser Ser Pro Gly Gly Val Tyr Ala Thr Arg
 50                  55                  60

Ser Ser Ala Val Arg Leu Arg Ser Ser Val Pro Gly Val Arg Leu Leu
 65              70                  75                   80

Gln Asp Ser Val Asp Phe Ser Leu Ala Asp Ala Ile Asn Thr Glu Phe
                 85                  90                  95

Lys Asn Thr Arg Thr Asn Glu Lys Val Glu Leu Gln Glu Leu Asn Asp
             100                 105             110

Arg Phe Ala Asn Tyr Ile Asp Lys Val Arg Phe Leu Glu Gln Gln Asn
             115                 120                 125

Lys Ile Leu Leu Ala Glu Leu Glu Gln Leu Lys Gly Gln Gly Lys Ser
 130                 135                 140

Arg Leu Gly Asp Leu Tyr Glu Glu Met Arg Glu Leu Arg Arg Gln
145                 150                 155                 160

Val Asp Gln Leu Thr Asn Asp Lys Ala Arg Val Glu Val Glu Arg Asp
                165                 170                 175

Asn Leu Ala Glu Asp Ile Met Arg Leu Arg Glu Lys Leu Gln Glu Glu
                180                 185                 190

Met Leu Gln Arg Glu Glu Ala Glu Asn Thr Leu Gln Ser Phe Arg Gln
            195                 200                 205

Asp Val Asp Asn Ala Ser Leu Ala Arg Leu Asp Leu Glu Arg Lys Val
            210                 215                 220

Glu Ser Leu Gln Glu Glu Ile Ala Phe Leu Lys Lys Leu His Glu Glu
225                 230                 235                 240

Glu Ile Gln Glu Leu Gln Ala Gln Ile Gln Glu Gln His Val Gln Ile
                245                 250                 255

Asp Val Asp Val Ser Lys Pro Asp Leu Thr Ala Ala Leu Arg Asp Val
                260                 265                 270

Arg Gln Gln Tyr Glu Ser Val Ala Ala Lys Asn Leu Gln Glu Ala Glu
            275                 280                 285

Glu Trp Tyr Lys Ser Lys Phe Ala Asp Leu Ser Glu Ala Ala Asn Arg
            290                 295                 300

Asn Asn Asp Ala Leu Arg Gln Ala Lys Gln Glu Ser Thr Glu Tyr Arg
305                 310                 315                 320

Arg Gln Val Gln Ser Leu Thr Cys Glu Val Asp Ala Leu Lys Gly Thr
                325                 330                 335

Asn Glu Ser Leu Glu Arg Gln Met Arg Glu Met Glu Glu Asn Phe Ala
            340                 345                 350

Val Glu Ala Ala Asn Tyr Gln Asp Thr Ile Gly Arg Leu Gln Asp Glu
            355                 360                 365

Ile Gln Asn Met Lys Glu Glu Met Ala Arg His Leu Arg Glu Tyr Gln
    370                 375                 380

Asp Leu Leu Asn Val Lys Met Ala Leu Asp Ile Glu Ile Ala Thr Tyr
385                 390                 395                 400

Arg Lys Leu Leu Glu Gly Glu Glu Ser Arg Ile Ser Leu Pro Leu Pro
                405                 410                 415

Asn Phe Ser Ser Leu Asn Leu Arg Glu Thr Asn Leu Asp Ser Leu Pro
```

```
                        420                 425                 430
Leu Val Asp Thr His Ser Lys Arg Thr Leu Leu Ile Lys Thr Val Glu
            435                 440                 445
Thr Arg Asp Gly Gln Val Ile Asn Glu Thr Ser Gln His His Asp Asp
        450                 455                 460
Leu Glu
465

<210> SEQ ID NO 13
<211> LENGTH: 3909
<212> TYPE: DNA
<213> ORGANISM: Homo sapiens
<220> FEATURE:
<221> NAME/KEY: CDS
<222> LOCATION: (144)..(3776)
<220> FEATURE:
<221> NAME/KEY: misc_difference
<222> LOCATION: (2)
<223> OTHER INFORMATION: n can be any nucleotide, thus n=a, t, c, or g

<400> SEQUENCE: 13
gnctactgtt gttttgagg ggcgggcagc cgcgccgccg cggcactttt ttaatttttt        60
cgggtgccgc agcagcgacc cctcggcgcc gatgtccctg atccctggag cgacgacggc       120
cgctgcctaa gctgggaaga gga atg cca gct cct gag cag gcc tca ttg gtg      173
                         Met Pro Ala Pro Glu Gln Ala Ser Leu Val
                           1               5                  10 gag gag ggg caa cca cag acc cgc cag gaa gct gcc tcc act ggc cca        221
Glu Glu Gly Gln Pro Gln Thr Arg Gln Glu Ala Ala Ser Thr Gly Pro
                15                  20                  25 ggc atg gaa ccc gag acc aca gcc acc act att cta gca tcc gtg aag        269
Gly Met Glu Pro Glu Thr Thr Ala Thr Thr Ile Leu Ala Ser Val Lys
        30                  35                  40 gag cag gag ctt cag ttt cag cga ctc acc cga gaa ctg gaa gtg gaa        317
Glu Gln Glu Leu Gln Phe Gln Arg Leu Thr Arg Glu Leu Glu Val Glu
    45                  50                  55 agg cag att gtt gcc agt cag cta gaa aga tgt agg ctt gga gca gaa        365
Arg Gln Ile Val Ala Ser Gln Leu Glu Arg Cys Arg Leu Gly Ala Glu
60                  65                  70 tca cca agc atc gcc agc acc agc tca act gag aag tca ttt cct tgg       413
Ser Pro Ser Ile Ala Ser Thr Ser Ser Thr Glu Lys Ser Phe Pro Trp
 75                  80                  85                  90 aga tca aca gac gtg cca aat act ggt gta agc aaa cct aga gtt tct       461
Arg Ser Thr Asp Val Pro Asn Thr Gly Val Ser Lys Pro Arg Val Ser
                 95                 100                 105 gac gct gtc cag ccc aac aac tat ctc atc agg aca gag cca gaa caa       509
Asp Ala Val Gln Pro Asn Asn Tyr Leu Ile Arg Thr Glu Pro Glu Gln
            110                 115                 120 gga acc ctc tat tca cca gaa cag aca tct ctc cat gaa agt gag gga       557
Gly Thr Leu Tyr Ser Pro Glu Gln Thr Ser Leu His Glu Ser Glu Gly
        125                 130                 135 tca ttg ggt aac tca aga agt tca aca caa atg aat tct tat tcc gac       605
Ser Leu Gly Asn Ser Arg Ser Ser Thr Gln Met Asn Ser Tyr Ser Asp
    140                 145                 150 agt gga tac cag gaa gca ggg agt ttc cac aac agc cag aac gtg agc       653
Ser Gly Tyr Gln Glu Ala Gly Ser Phe His Asn Ser Gln Asn Val Ser
155                 160                 165                 170 aag gca gac aac aga cag cag cat tca ttc ata gga tca act aac aac       701
Lys Ala Asp Asn Arg Gln Gln His Ser Phe Ile Gly Ser Thr Asn Asn
                175                 180                 185 cat gtg gtg agg aat tca aga gct gaa gga caa aca ctg gtt cag cca       749
```

```
                His Val Val Arg Asn Ser Arg Ala Glu Gly Gln Thr Leu Val Gln Pro
                            190                 195                 200 tca gta gcc aat cgg gcc atg aga aga gtt agt tca gtt cca tct aga              797
Ser Val Ala Asn Arg Ala Met Arg Arg Val Ser Ser Val Pro Ser Arg
        205                 210                 215 gca cag tct cct tct tat gtt atc agc aca ggc gtg tct cct tca agg              845
Ala Gln Ser Pro Ser Tyr Val Ile Ser Thr Gly Val Ser Pro Ser Arg
    220                 225                 230 ggg tct ctg aga act tct ctg ggt agt gga ttt ggc tct ccg tca gtg              893
Gly Ser Leu Arg Thr Ser Leu Gly Ser Gly Phe Gly Ser Pro Ser Val
235                 240                 245                 250 acc gac ccc cga cct ctg aac ccc agt gca tat tcc tcc acc aca tta              941
Thr Asp Pro Arg Pro Leu Asn Pro Ser Ala Tyr Ser Ser Thr Thr Leu
                255                 260                 265 cct gct gca cgg gca gcc tct ccg tac tca cag aga ccc gcc tcc cca              989
Pro Ala Ala Arg Ala Ala Ser Pro Tyr Ser Gln Arg Pro Ala Ser Pro
            270                 275                 280 aca gct ata cgg cgg att ggg tca gtc acc tcc cgg cag acc tcc aat             1037
Thr Ala Ile Arg Arg Ile Gly Ser Val Thr Ser Arg Gln Thr Ser Asn
        285                 290                 295 ccc aac gga cca acc cct caa tac caa acc acc gcc aga gtg ggg tcc             1085
Pro Asn Gly Pro Thr Pro Gln Tyr Gln Thr Thr Ala Arg Val Gly Ser
    300                 305                 310 cca ctg acc ctg acg gat gca cag act cga gta gct tcc cca tcc caa             1133
Pro Leu Thr Leu Thr Asp Ala Gln Thr Arg Val Ala Ser Pro Ser Gln
315                 320                 325                 330 ggc cag gtg ggg tcg tcg tcc ccc aaa cgc tca ggg atg acc gcc gta             1181
Gly Gln Val Gly Ser Ser Ser Pro Lys Arg Ser Gly Met Thr Ala Val
                335                 340                 345 cca cag cat ctg gga cct tca ctg caa agg act gtt cat gac atg gag             1229
Pro Gln His Leu Gly Pro Ser Leu Gln Arg Thr Val His Asp Met Glu
            350                 355                 360 caa ttc gga cag cag cag tat gac att tat gag agg atg gtt cca ccc             1277
Gln Phe Gly Gln Gln Gln Tyr Asp Ile Tyr Glu Arg Met Val Pro Pro
        365                 370                 375 agg cca gac agc ctg aca ggc tta cgg agt tcc tat gct agt cag cat             1325
Arg Pro Asp Ser Leu Thr Gly Leu Arg Ser Ser Tyr Ala Ser Gln His
    380                 385                 390 agt cag ctt ggg caa gac ctt cgt tct gcc gtg tct ccc gac ttg cac             1373
Ser Gln Leu Gly Gln Asp Leu Arg Ser Ala Val Ser Pro Asp Leu His
395                 400                 405                 410 att act cct ata tat gag ggg agg acc tat tac agc cca gtg tac cgc             1421
Ile Thr Pro Ile Tyr Glu Gly Arg Thr Tyr Tyr Ser Pro Val Tyr Arg
                415                 420                 425 agc cca aac cat gga act gtg gag ctc caa gga tcg cag acg gcg ttg             1469
Ser Pro Asn His Gly Thr Val Glu Leu Gln Gly Ser Gln Thr Ala Leu
            430                 435                 440 tat cgc aca ggt gta tca ggt att gga aat cta caa agg aca tcc agc             1517
Tyr Arg Thr Gly Val Ser Gly Ile Gly Asn Leu Gln Arg Thr Ser Ser
        445                 450                 455 caa cga agt acc ctt aca tac caa aga aat aat tat gct ctg aac aca             1565
Gln Arg Ser Thr Leu Thr Tyr Gln Arg Asn Asn Tyr Ala Leu Asn Thr
    460                 465                 470 aca gct acc tac gcg gag ccc tac agg cct ata caa tac cga gtg caa             1613
Thr Ala Thr Tyr Ala Glu Pro Tyr Arg Pro Ile Gln Tyr Arg Val Gln
475                 480                 485                 490 gag tgc aat tat aac agg ctt cag cat gca gtg ccg gct gat gat ggc             1661
Glu Cys Asn Tyr Asn Arg Leu Gln His Ala Val Pro Ala Asp Asp Gly
                495                 500                 505
```

-continued

| | | |
|---|---|---|
| acc aca aga tcc cca tca ata gac agc att cag aag gac ccc agg gag<br>Thr Thr Arg Ser Pro Ser Ile Asp Ser Ile Gln Lys Asp Pro Arg Glu<br>510                              515                          520 | 1709 |
| ttt gcc tgg cgt gat cct gag ttg cct gag gtc att cac atg ctt gag<br>Phe Ala Trp Arg Asp Pro Glu Leu Pro Glu Val Ile His Met Leu Glu<br>525                              530                          535 | 1757 |
| cac cag ttc cca tct gtt cag gca aat gca gcg gcc tac ctg cag cac<br>His Gln Phe Pro Ser Val Gln Ala Asn Ala Ala Ala Tyr Leu Gln His<br>540                              545                          550 | 1805 |
| ctg tgc ttt ggt gac aac aaa gtg aag atg gag gtg tgt agg tta ggg<br>Leu Cys Phe Gly Asp Asn Lys Val Lys Met Glu Val Cys Arg Leu Gly<br>555                          560                          565                          570 | 1853 |
| gga atc aag cat ctg gtt gac ctt ctg gac cac aga gtt ttg gaa gtt<br>Gly Ile Lys His Leu Val Asp Leu Leu Asp His Arg Val Leu Glu Val<br>                          575                          580                          585 | 1901 |
| cag aag aat gct tgt ggt gcc ctt cga aac ctc gtt ttt ggc aag tct<br>Gln Lys Asn Ala Cys Gly Ala Leu Arg Asn Leu Val Phe Gly Lys Ser<br>                          590                          595                          600 | 1949 |
| aca gat gaa aat aaa ata gca atg aag aat gtt ggt ggg ata cct gcc<br>Thr Asp Glu Asn Lys Ile Ala Met Lys Asn Val Gly Gly Ile Pro Ala<br>                          605                          610                          615 | 1997 |
| ttg ttg cga ctg ttg aga aaa tct att gat gca gaa gta agg gag ctt<br>Leu Leu Arg Leu Leu Arg Lys Ser Ile Asp Ala Glu Val Arg Glu Leu<br>620                              625                          630 | 2045 |
| gtt aca gga gtt ctt tgg aat tta tcc tca tgt gat gct gta aaa atg<br>Val Thr Gly Val Leu Trp Asn Leu Ser Ser Cys Asp Ala Val Lys Met<br>635                              640                          645                          650 | 2093 |
| aca atc att cga gat gct ctc tca acc tta aca aac act gtg att gtt<br>Thr Ile Ile Arg Asp Ala Leu Ser Thr Leu Thr Asn Thr Val Ile Val<br>                          655                          660                          665 | 2141 |
| cca cat tct gga tgg aat aac tct tct ttt gat gat gat cat aaa att<br>Pro His Ser Gly Trp Asn Asn Ser Ser Phe Asp Asp Asp His Lys Ile<br>                          670                          675                          680 | 2189 |
| aaa ttt cag act tca cta gtt ctg cgt aac acg aca ggt tgc cta agg<br>Lys Phe Gln Thr Ser Leu Val Leu Arg Asn Thr Thr Gly Cys Leu Arg<br>                          685                          690                          695 | 2237 |
| aac ctc acg tcc gcg ggg gaa gaa gct cgg aag caa atg cgg tcc tgc<br>Asn Leu Thr Ser Ala Gly Glu Glu Ala Arg Lys Gln Met Arg Ser Cys<br>700                              705                          710 | 2285 |
| gag ggg ctg gta gac tca ctg ttg tat gtg atc cac acg tgt gtg aac<br>Glu Gly Leu Val Asp Ser Leu Leu Tyr Val Ile His Thr Cys Val Asn<br>715                              720                          725                          730 | 2333 |
| aca tcc gat tac gac agc aag acg gtg gag aac tgc gtg tgc acc ctg<br>Thr Ser Asp Tyr Asp Ser Lys Thr Val Glu Asn Cys Val Cys Thr Leu<br>                          735                          740                          745 | 2381 |
| agg aac ctg tcc tat cgg ctg gag ctg gag gtg ccc cag gcc cgg tta<br>Arg Asn Leu Ser Tyr Arg Leu Glu Leu Glu Val Pro Gln Ala Arg Leu<br>                          750                          755                          760 | 2429 |
| ctg gga ctg aac gaa ttg gat gac tta cta gga aaa gag tct ccc agc<br>Leu Gly Leu Asn Glu Leu Asp Asp Leu Leu Gly Lys Glu Ser Pro Ser<br>                          765                          770                          775 | 2477 |
| aaa gac tct gag cca agt tgc tgg ggg aag aag aag aaa aag aaa aag<br>Lys Asp Ser Glu Pro Ser Cys Trp Gly Lys Lys Lys Lys Lys Lys Lys<br>780                              785                          790 | 2525 |
| agg act ccg caa gaa gat caa tgg gat gga gtt ggt cct atc cca gga<br>Arg Thr Pro Gln Glu Asp Gln Trp Asp Gly Val Gly Pro Ile Pro Gly<br>795                              800                          805                          810 | 2573 |
| ctg tcg aag tcc ccc aaa ggg gtt gag atg ctg tgg cac cca tcg gtg<br>Leu Ser Lys Ser Pro Lys Gly Val Glu Met Leu Trp His Pro Ser Val<br>                          815                          820                          825 | 2621 |

```
gta aaa cca tat ctg act ctt cta gca gaa agt tcc aac cca gcc acc    2669
Val Lys Pro Tyr Leu Thr Leu Leu Ala Glu Ser Ser Asn Pro Ala Thr
            830                 835                 840 ttg gaa ggc tct gca ggg tct ctc cag aac ctc tct gct agc aac tgg    2717
Leu Glu Gly Ser Ala Gly Ser Leu Gln Asn Leu Ser Ala Ser Asn Trp
        845                 850                 855 aag ttt gca gca tat atc cgg ggc ggc cgt ccg aaa aga aaa ggg ctc    2765
Lys Phe Ala Ala Tyr Ile Arg Gly Gly Arg Pro Lys Arg Lys Gly Leu
    860                 865                 870 ccc atc ctt gtg gag ctt ctg aga atg gat aac gat aga gtt gtt tct    2813
Pro Ile Leu Val Glu Leu Leu Arg Met Asp Asn Asp Arg Val Val Ser
875                 880                 885                 890 tcc ggt gca aca gcc ttg agg aat atg gca cta gat gtt cgc aac aag    2861
Ser Gly Ala Thr Ala Leu Arg Asn Met Ala Leu Asp Val Arg Asn Lys
            895                 900                 905 gag ctc ata ggc aaa tac gcc atg cga gac ctg gtc aac cgg ctc ccc    2909
Glu Leu Ile Gly Lys Tyr Ala Met Arg Asp Leu Val Asn Arg Leu Pro
        910                 915                 920 ggc ggc aat ggc ccc agt gtc ttg tct gat gag acc atg gca gcc atc    2957
Gly Gly Asn Gly Pro Ser Val Leu Ser Asp Glu Thr Met Ala Ala Ile
    925                 930                 935 tgc tgt gct ctg cac gag gtc acc agc aaa aac atg gag aac gca aaa    3005
Cys Cys Ala Leu His Glu Val Thr Ser Lys Asn Met Glu Asn Ala Lys
940                 945                 950 gcc ctg gcc gac tca gga ggc ata gag aag ctg gtg aac ata acc aaa    3053
Ala Leu Ala Asp Ser Gly Gly Ile Glu Lys Leu Val Asn Ile Thr Lys
955                 960                 965                 970 ggc agg ggc gac aga tca tct ctg aaa gtg gtg aag gca gca gcc cag    3101
Gly Arg Gly Asp Arg Ser Ser Leu Lys Val Val Lys Ala Ala Ala Gln
            975                 980                 985 gtc ttg aat aca tta tgg caa tat cgg gac ctc cgg agc att tat aaa    3149
Val Leu Asn Thr Leu Trp Gln Tyr Arg Asp Leu Arg Ser Ile Tyr Lys
        990                 995                 1000 aag gat ggg tgg aat cag aac cat ttt att aca cct gtg tcg aca ttg    3197
Lys Asp Gly Trp Asn Gln Asn His Phe Ile Thr Pro Val Ser Thr Leu
    1005                1010                1015 gag cga gac cga ttc aaa tca cat cct tcc ttg tct acc acc aac caa    3245
Glu Arg Asp Arg Phe Lys Ser His Pro Ser Leu Ser Thr Thr Asn Gln
1020                1025                1030 cag atg tca ccc atc att cag tca gtc ggc agc acc tct tcc tca cca    3293
Gln Met Ser Pro Ile Ile Gln Ser Val Gly Ser Thr Ser Ser Ser Pro
1035                1040                1045                1050 gca ctg tta gga atc aga gac cct cgc tct gaa tac gat agg acc cag    3341
Ala Leu Leu Gly Ile Arg Asp Pro Arg Ser Glu Tyr Asp Arg Thr Gln
            1055                1060                1065 cca cct atg cag tat tac aat agc caa ggg gat gcc aca cat aaa ggc    3389
Pro Pro Met Gln Tyr Tyr Asn Ser Gln Gly Asp Ala Thr His Lys Gly
        1070                1075                1080 ctg tac cct ggc tcc agc aaa cct tca cca att tac atc agt tcc tat    3437
Leu Tyr Pro Gly Ser Ser Lys Pro Ser Pro Ile Tyr Ile Ser Ser Tyr
    1085                1090                1095 tcc tca cca gca aga gaa caa aat aga cgg cta cag cat caa cag ctg    3485
Ser Ser Pro Ala Arg Glu Gln Asn Arg Arg Leu Gln His Gln Gln Leu
1100                1105                1110 tat tat agt caa gat gac tcc aac aga aag aac ttt gat gca tac aga    3533
Tyr Tyr Ser Gln Asp Asp Ser Asn Arg Lys Asn Phe Asp Ala Tyr Arg
1115                1120                1125                1130 ttg tat ttg cag tct cct cat agc tat gaa gat cct tat ttt gat gac    3581
Leu Tyr Leu Gln Ser Pro His Ser Tyr Glu Asp Pro Tyr Phe Asp Asp
```

```
                   1135              1140                  1145
cga gtt cac ttt cca gct tct act gat tac tca aca cag tat gga ctg   3629
Arg Val His Phe Pro Ala Ser Thr Asp Tyr Ser Thr Gln Tyr Gly Leu
            1150                1155                1160 aaa tcg acc aca aat tat gta gac ttt tat tcc act aaa cga cct tct   3677
Lys Ser Thr Thr Asn Tyr Val Asp Phe Tyr Ser Thr Lys Arg Pro Ser
        1165                1170                1175 tat aga gca gaa cag tac cca ggg tcc cca gac tca tgg gtg tac gat   3725
Tyr Arg Ala Glu Gln Tyr Pro Gly Ser Pro Asp Ser Trp Val Tyr Asp
    1180                1185                1190 caa gat gcc caa cag agg aac tct ttc ttt cta acc ttg ttc aga ttg   3773
Gln Asp Ala Gln Gln Arg Asn Ser Phe Phe Leu Thr Leu Phe Arg Leu
1195                1200                1205                1210 agg tgaaaagtcc atcttgctga tttcatgatt gaaatgtgaa agtgaagtgg        3826
Arg aaggaatgaa tgaagtgtgt ttttttttcc tttttgagga attatcaggg gaattcgata 3886 tcaagcttat cgataccgtc gac                                         3909
```

<210> SEQ ID NO 14
<211> LENGTH: 1211
<212> TYPE: PRT
<213> ORGANISM: Homo sapiens

<400> SEQUENCE: 14

```
Met Pro Ala Pro Glu Gln Ala Ser Leu Val Glu Glu Gly Gln Pro Gln
 1               5                  10                  15

Thr Arg Gln Glu Ala Ala Ser Thr Gly Pro Gly Met Glu Pro Glu Thr
            20                  25                  30

Thr Ala Thr Thr Ile Leu Ala Ser Val Lys Glu Gln Glu Leu Gln Phe
        35                  40                  45

Gln Arg Leu Thr Arg Glu Leu Glu Val Glu Arg Gln Ile Val Ala Ser
    50                  55                  60

Gln Leu Glu Arg Cys Arg Leu Gly Ala Glu Ser Pro Ser Ile Ala Ser
65                  70                  75                  80

Thr Ser Ser Thr Glu Lys Ser Phe Pro Trp Arg Ser Thr Asp Val Pro
                85                  90                  95

Asn Thr Gly Val Ser Lys Pro Arg Val Ser Asp Ala Val Gln Pro Asn
            100                 105                 110

Asn Tyr Leu Ile Arg Thr Glu Pro Glu Gln Gly Thr Leu Tyr Ser Pro
        115                 120                 125

Glu Gln Thr Ser Leu His Glu Ser Glu Gly Ser Leu Gly Asn Ser Arg
    130                 135                 140

Ser Ser Thr Gln Met Asn Ser Tyr Ser Asp Ser Gly Tyr Gln Glu Ala
145                 150                 155                 160

Gly Ser Phe His Asn Ser Gln Asn Val Ser Lys Ala Asp Asn Arg Gln
                165                 170                 175

Gln His Ser Phe Ile Gly Ser Thr Asn Asn His Val Val Arg Asn Ser
            180                 185                 190

Arg Ala Glu Gly Gln Thr Leu Val Gln Pro Ser Val Ala Asn Arg Ala
        195                 200                 205

Met Arg Arg Val Ser Ser Val Pro Ser Arg Ala Gln Ser Pro Ser Tyr
    210                 215                 220

Val Ile Ser Thr Gly Val Ser Pro Ser Arg Gly Ser Leu Arg Thr Ser
225                 230                 235                 240

Leu Gly Ser Gly Phe Gly Ser Pro Ser Val Thr Asp Pro Arg Pro Leu
```

-continued

```
                245                 250                 255
Asn Pro Ser Ala Tyr Ser Ser Thr Thr Leu Pro Ala Ala Arg Ala Ala
                260                 265                 270
Ser Pro Tyr Ser Gln Arg Pro Ala Ser Pro Thr Ala Ile Arg Arg Ile
                275                 280                 285
Gly Ser Val Thr Ser Arg Gln Thr Ser Asn Pro Asn Gly Pro Thr Pro
                290                 295                 300
Gln Tyr Gln Thr Thr Ala Arg Val Gly Ser Pro Leu Thr Leu Thr Asp
305                 310                 315                 320
Ala Gln Thr Arg Val Ala Ser Pro Ser Gln Gly Val Gly Ser Ser
                325                 330                 335
Ser Pro Lys Arg Ser Gly Met Thr Ala Val Pro Gln His Leu Gly Pro
                340                 345                 350
Ser Leu Gln Arg Thr Val His Asp Met Glu Gln Phe Gly Gln Gln Gln
                355                 360                 365
Tyr Asp Ile Tyr Glu Arg Met Val Pro Pro Arg Pro Asp Ser Leu Thr
                370                 375                 380
Gly Leu Arg Ser Ser Tyr Ala Ser Gln His Ser Gln Leu Gly Gln Asp
385                 390                 395                 400
Leu Arg Ser Ala Val Ser Pro Asp Leu His Ile Thr Pro Ile Tyr Glu
                405                 410                 415
Gly Arg Thr Tyr Tyr Ser Pro Val Tyr Arg Ser Pro Asn His Gly Thr
                420                 425                 430
Val Glu Leu Gln Gly Ser Gln Thr Ala Leu Tyr Arg Thr Gly Val Ser
                435                 440                 445
Gly Ile Gly Asn Leu Gln Arg Thr Ser Ser Gln Arg Ser Thr Leu Thr
                450                 455                 460
Tyr Gln Arg Asn Asn Tyr Ala Leu Asn Thr Thr Ala Thr Tyr Ala Glu
465                 470                 475                 480
Pro Tyr Arg Pro Ile Gln Tyr Arg Val Gln Glu Cys Asn Tyr Asn Arg
                485                 490                 495
Leu Gln His Ala Val Pro Ala Asp Asp Gly Thr Thr Arg Ser Pro Ser
                500                 505                 510
Ile Asp Ser Ile Gln Lys Asp Pro Arg Glu Phe Ala Trp Arg Asp Pro
                515                 520                 525
Glu Leu Pro Glu Val Ile His Met Leu Glu His Gln Phe Pro Ser Val
                530                 535                 540
Gln Ala Asn Ala Ala Ala Tyr Leu Gln His Leu Cys Phe Gly Asp Asn
545                 550                 555                 560
Lys Val Lys Met Glu Val Cys Arg Leu Gly Gly Ile Lys His Leu Val
                565                 570                 575
Asp Leu Leu Asp His Arg Val Leu Glu Val Gln Lys Asn Ala Cys Gly
                580                 585                 590
Ala Leu Arg Asn Leu Val Phe Gly Lys Ser Thr Asp Glu Asn Lys Ile
                595                 600                 605
Ala Met Lys Asn Val Gly Gly Ile Pro Ala Leu Leu Arg Leu Leu Arg
                610                 615                 620
Lys Ser Ile Asp Ala Glu Val Arg Glu Leu Val Thr Gly Val Leu Trp
625                 630                 635                 640
Asn Leu Ser Ser Cys Asp Ala Val Lys Met Thr Ile Ile Arg Asp Ala
                645                 650                 655
Leu Ser Thr Leu Thr Asn Thr Val Ile Val Pro His Ser Gly Trp Asn
                660                 665                 670
```

```
Asn Ser Ser Phe Asp Asp His Lys Ile Lys Phe Gln Thr Ser Leu
            675                 680                 685

Val Leu Arg Asn Thr Thr Gly Cys Leu Arg Asn Leu Thr Ser Ala Gly
690                 695                 700

Glu Glu Ala Arg Lys Gln Met Arg Ser Cys Glu Gly Leu Val Asp Ser
705                 710                 715                 720

Leu Leu Tyr Val Ile His Thr Cys Val Asn Thr Ser Asp Tyr Asp Ser
                725                 730                 735

Lys Thr Val Glu Asn Cys Val Cys Thr Leu Arg Asn Leu Ser Tyr Arg
            740                 745                 750

Leu Glu Leu Glu Val Pro Gln Ala Arg Leu Leu Gly Leu Asn Glu Leu
        755                 760                 765

Asp Asp Leu Leu Gly Lys Glu Ser Pro Ser Lys Asp Ser Glu Pro Ser
770                 775                 780

Cys Trp Gly Lys Lys Lys Lys Lys Arg Thr Pro Gln Glu Asp
785                 790                 795                 800

Gln Trp Asp Gly Val Gly Pro Ile Pro Gly Leu Ser Lys Ser Pro Lys
                805                 810                 815

Gly Val Glu Met Leu Trp His Pro Ser Val Val Lys Pro Tyr Leu Thr
            820                 825                 830

Leu Leu Ala Glu Ser Ser Asn Pro Ala Thr Leu Glu Gly Ser Ala Gly
        835                 840                 845

Ser Leu Gln Asn Leu Ser Ala Ser Asn Trp Lys Phe Ala Ala Tyr Ile
850                 855                 860

Arg Gly Gly Arg Pro Lys Arg Lys Gly Leu Pro Ile Leu Val Glu Leu
865                 870                 875                 880

Leu Arg Met Asp Asn Asp Arg Val Val Ser Ser Gly Ala Thr Ala Leu
                885                 890                 895

Arg Asn Met Ala Leu Asp Val Arg Asn Lys Glu Leu Ile Gly Lys Tyr
            900                 905                 910

Ala Met Arg Asp Leu Val Asn Arg Leu Pro Gly Gly Asn Gly Pro Ser
        915                 920                 925

Val Leu Ser Asp Glu Thr Met Ala Ala Ile Cys Cys Ala Leu His Glu
930                 935                 940

Val Thr Ser Lys Asn Met Glu Asn Ala Lys Ala Leu Ala Asp Ser Gly
945                 950                 955                 960

Gly Ile Glu Lys Leu Val Asn Ile Thr Lys Gly Arg Gly Asp Arg Ser
                965                 970                 975

Ser Leu Lys Val Val Lys Ala Ala Gln Val Leu Asn Thr Leu Trp
            980                 985                 990

Gln Tyr Arg Asp Leu Arg Ser Ile Tyr Lys Lys Asp Gly Trp Asn Gln
        995                 1000                1005

Asn His Phe Ile Thr Pro Val Ser Thr Leu Glu Arg Asp Arg Phe Lys
    1010                1015                1020

Ser His Pro Ser Leu Ser Thr Thr Asn Gln Gln Met Ser Pro Ile Ile
025                 1030                1035                1040

Gln Ser Val Gly Ser Thr Ser Ser Ser Pro Ala Leu Leu Gly Ile Arg
                1045                1050                1055

Asp Pro Arg Ser Glu Tyr Asp Arg Thr Gln Pro Pro Met Gln Tyr Tyr
            1060                1065                1070

Asn Ser Gln Gly Asp Ala Thr His Lys Gly Leu Tyr Pro Gly Ser Ser
        1075                1080                1085
```

```
Lys Pro Ser Pro Ile Tyr Ile Ser Ser Tyr Ser Ser Pro Ala Arg Glu
    1090                1095                1100

Gln Asn Arg Arg Leu Gln His Gln Gln Leu Tyr Tyr Ser Gln Asp Asp
105                 1110                1115                1120

Ser Asn Arg Lys Asn Phe Asp Ala Tyr Arg Leu Tyr Leu Gln Ser Pro
                1125                1130                1135

His Ser Tyr Glu Asp Pro Tyr Phe Asp Asp Arg Val His Phe Pro Ala
            1140                1145                1150

Ser Thr Asp Tyr Ser Thr Gln Tyr Gly Leu Lys Ser Thr Thr Asn Tyr
        1155                1160                1165

Val Asp Phe Tyr Ser Thr Lys Arg Pro Ser Tyr Arg Ala Glu Gln Tyr
    1170                1175                1180

Pro Gly Ser Pro Asp Ser Trp Val Tyr Asp Gln Asp Ala Gln Gln Arg
185                 1190                1195                1200

Asn Ser Phe Phe Leu Thr Leu Phe Arg Leu Arg
                1205                1210

<210> SEQ ID NO 15
<211> LENGTH: 1857
<212> TYPE: DNA
<213> ORGANISM: Homo sapiens
<220> FEATURE:
<221> NAME/KEY: CDS
<222> LOCATION: (70)..(1224)

<400> SEQUENCE: 15
gccccggccc cgccccagcc ctcctgatcc ctcgcagccc ggctccggcc gcccgcctct      60 gccgccgca atg atg atg atg gcg ctg agc aag acc ttc ggg cag aag ccc    111
         Met Met Met Met Ala Leu Ser Lys Thr Phe Gly Gln Lys Pro
           1               5                  10 gtg aag ttc cag ctg gag gac gac ggc gag ttc tac atg atc ggc tcc      159
Val Lys Phe Gln Leu Glu Asp Asp Gly Glu Phe Tyr Met Ile Gly Ser
 15                  20                  25                  30 gag gtg gga aac tac ctc cgt atg ttc cga ggt tct ctg tac aag aga      207
Glu Val Gly Asn Tyr Leu Arg Met Phe Arg Gly Ser Leu Tyr Lys Arg
                 35                  40                  45 tac ccc tca ctc tgg agg cga cta gcc act gtg gaa gag agg aag aaa      255
Tyr Pro Ser Leu Trp Arg Arg Leu Ala Thr Val Glu Glu Arg Lys Lys
             50                  55                  60 ata gtt gca tcg tca cat ggt aaa aaa aca aaa cct aac act aag gat      303
Ile Val Ala Ser Ser His Gly Lys Lys Thr Lys Pro Asn Thr Lys Asp
         65                  70                  75 cac gga tac acg act cta gcc acc agt gtg acc ctg tta aaa gcc tcg      351
His Gly Tyr Thr Thr Leu Ala Thr Ser Val Thr Leu Leu Lys Ala Ser
     80                  85                  90 gaa gtg gaa gag att ctg gat ggc aac gat gag aag tac aag gct gtg      399
Glu Val Glu Glu Ile Leu Asp Gly Asn Asp Glu Lys Tyr Lys Ala Val
 95                 100                 105                 110 tcc atc agc aca gag ccc ccc acc tac ctc agg gaa cag aag gcc aag      447
Ser Ile Ser Thr Glu Pro Pro Thr Tyr Leu Arg Glu Gln Lys Ala Lys
                115                 120                 125 agg aac agc cag tgg gta ccc acc ctg tcc aac agc tcc cac cac tta      495
Arg Asn Ser Gln Trp Val Pro Thr Leu Ser Asn Ser Ser His His Leu
            130                 135                 140 gat gcc gtg cca tgc tcc aca acc atc aac agg aac cgc atg ggc cga      543
Asp Ala Val Pro Cys Ser Thr Thr Ile Asn Arg Asn Arg Met Gly Arg
        145                 150                 155 gac aag aag aga acc ttc ccc ctt tgc ttt gat gac cat gac cca gct      591
Asp Lys Lys Arg Thr Phe Pro Leu Cys Phe Asp Asp His Asp Pro Ala
```

|  |  |  |  |  |  |  |  |  |  |  |  |  |  |  |  |
|---|---|---|---|---|---|---|---|---|---|---|---|---|---|---|---|
|  | 160 |  |  |  | 165 |  |  |  |  | 170 |  |  |  |  |  |
| gtg | atc | cat | gag | aac | gca | tct | cag | ccc | gag | gtg | ctg | gtc | ccc | atc | cgg | 639 |
| Val | Ile | His | Glu | Asn | Ala | Ser | Gln | Pro | Glu | Val | Leu | Val | Pro | Ile | Arg |  |
| 175 |  |  |  | 180 |  |  |  |  | 185 |  |  |  |  | 190 |  |  |
| ctg | gac | atg | gag | atc | gat | ggg | cag | aag | ctg | cga | gac | gcc | ttc | acc | tgg | 687 |
| Leu | Asp | Met | Glu | Ile | Asp | Gly | Gln | Lys | Leu | Arg | Asp | Ala | Phe | Thr | Trp |  |
|  |  |  |  |  | 195 |  |  |  |  | 200 |  |  |  |  | 205 |  |
| aac | atg | aat | gag | aag | ttg | atg | acg | cct | gag | atg | ttt | tca | gaa | atc | ctc | 735 |
| Asn | Met | Asn | Glu | Lys | Leu | Met | Thr | Pro | Glu | Met | Phe | Ser | Glu | Ile | Leu |  |
|  |  |  | 210 |  |  |  |  | 215 |  |  |  |  | 220 |  |  |  |
| tgt | gac | gat | ctg | gat | ttg | aac | ccg | ctg | acg | ttt | gtg | cca | gcc | atc | gcc | 783 |
| Cys | Asp | Asp | Leu | Asp | Leu | Asn | Pro | Leu | Thr | Phe | Val | Pro | Ala | Ile | Ala |  |
|  |  | 225 |  |  |  |  | 230 |  |  |  |  | 235 |  |  |  |  |
| tct | gcc | atc | aga | cag | cag | atc | gag | tcc | tac | ccc | acg | gac | agc | atc | ctg | 831 |
| Ser | Ala | Ile | Arg | Gln | Gln | Ile | Glu | Ser | Tyr | Pro | Thr | Asp | Ser | Ile | Leu |  |
|  | 240 |  |  |  |  | 245 |  |  |  |  | 250 |  |  |  |  |  |
| gag | gac | cag | tca | gac | cag | cgc | gtc | atc | atc | aag | ctg | aac | atc | cat | gtg | 879 |
| Glu | Asp | Gln | Ser | Asp | Gln | Arg | Val | Ile | Ile | Lys | Leu | Asn | Ile | His | Val |  |
| 255 |  |  |  |  | 260 |  |  |  |  | 265 |  |  |  |  | 270 |  |
| gga | aac | att | tcc | ctg | gtg | gac | cag | ttt | gag | tgg | gac | atg | tca | gag | aag | 927 |
| Gly | Asn | Ile | Ser | Leu | Val | Asp | Gln | Phe | Glu | Trp | Asp | Met | Ser | Glu | Lys |  |
|  |  |  |  | 275 |  |  |  |  | 280 |  |  |  |  | 285 |  |  |
| gag | aac | tca | cca | gag | aag | ttt | gcc | ctg | aag | ctg | tgc | tcg | gag | ctg | ggg | 975 |
| Glu | Asn | Ser | Pro | Glu | Lys | Phe | Ala | Leu | Lys | Leu | Cys | Ser | Glu | Leu | Gly |  |
|  |  |  | 290 |  |  |  |  | 295 |  |  |  |  | 300 |  |  |  |
| ttg | ggc | ggg | gag | ttt | gtc | acc | acc | atc | gca | tac | agc | atc | cgg | gga | cag | 1023 |
| Leu | Gly | Gly | Glu | Phe | Val | Thr | Thr | Ile | Ala | Tyr | Ser | Ile | Arg | Gly | Gln |  |
|  |  | 305 |  |  |  |  | 310 |  |  |  |  | 315 |  |  |  |  |
| ctg | agc | tgg | cat | cag | aag | acc | tac | gcc | ttc | agc | gag | aac | cct | ctg | ccc | 1071 |
| Leu | Ser | Trp | His | Gln | Lys | Thr | Tyr | Ala | Phe | Ser | Glu | Asn | Pro | Leu | Pro |  |
| 320 |  |  |  |  | 325 |  |  |  |  | 330 |  |  |  |  |  |  |
| aca | gtg | gag | att | gcc | atc | cgg | aac | acg | ggc | gat | gcg | gac | cag | tgg | tgc | 1119 |
| Thr | Val | Glu | Ile | Ala | Ile | Arg | Asn | Thr | Gly | Asp | Ala | Asp | Gln | Trp | Cys |  |
| 335 |  |  |  |  | 340 |  |  |  |  | 345 |  |  |  |  | 350 |  |
| cca | ctg | ctg | gag | act | ctg | aca | gac | gct | gag | atg | gag | aag | aag | atc | cgc | 1167 |
| Pro | Leu | Leu | Glu | Thr | Leu | Thr | Asp | Ala | Glu | Met | Glu | Lys | Lys | Ile | Arg |  |
|  |  |  |  | 355 |  |  |  |  | 360 |  |  |  |  | 365 |  |  |
| gac | cag | gac | agg | aac | acg | agg | cgg | atg | agg | cgt | ctt | gcc | aac | acg | ggc | 1215 |
| Asp | Gln | Asp | Arg | Asn | Thr | Arg | Arg | Met | Arg | Arg | Leu | Ala | Asn | Thr | Gly |  |
|  |  |  | 370 |  |  |  |  | 375 |  |  |  |  | 380 |  |  |  |
| ccg | gcc | tgg | taaccagccc | atcagcacac | ggctcccacg | gagcatctca |  |  |  |  |  |  |  |  |  | 1264 |
| Pro | Ala | Trp |  |  |  |  |  |  |  |  |  |  |  |  |  |  |
|  |  | 385 |  |  |  |  |  |  |  |  |  |  |  |  |  |  |

| | |
|---|---|
| gaagattggg ccgcctctcc tccatcttct ggcaaggaca gaggcgaggg gacagcccag | 1324 |
| cgccatcctg aggatcgggt gggggtggag tgggggcttc caggtggccc ttcccggtac | 1384 |
| acattccatt tgttgagccc cagtcctgcc ccccacccca ccctccctac ccctccccag | 1444 |
| tctctgggt caggaagaaa ccttatttta ggttgtgttt tgttttgta taggagcccc | 1504 |
| aggcagggct agtaacagtt tttaaataaa aggcaacagg tcatgttcaa ttcttaaat | 1564 |
| ctagtgtctt tatttcttct gttacaatag tgttgcttgt gtaagcaggt tagagtgcac | 1624 |
| agtgtcccca attgttcctg gcactgcaaa accaaattaa acaatcccac aaagaattct | 1684 |
| gacatcaatg tgttttcctc agtcaggtct atttcaagat tctagaagtt cctttgtaa | 1744 |
| aacttgcctt taaaactctt cctcctaatg ccatcagatc tcttaacatt ggctcactgt | 1804 |
| gggatctttc ctcttaggtt gaatttctac gtgaatatca aagtgccttt ttc | 1857 |

```
<210> SEQ ID NO 16
<211> LENGTH: 385
<212> TYPE: PRT
<213> ORGANISM: Homo sapiens

<400> SEQUENCE: 16

Met Met Met Met Ala Leu Ser Lys Thr Phe Gly Gln Lys Pro Val Lys
 1               5                  10                  15

Phe Gln Leu Glu Asp Asp Gly Glu Phe Tyr Met Ile Gly Ser Glu Val
                20                  25                  30

Gly Asn Tyr Leu Arg Met Phe Arg Gly Ser Leu Tyr Lys Arg Tyr Pro
            35                  40                  45

Ser Leu Trp Arg Arg Leu Ala Thr Val Glu Glu Arg Lys Lys Ile Val
    50                  55                  60

Ala Ser Ser His Gly Lys Lys Thr Lys Pro Asn Thr Lys Asp His Gly
65                  70                  75                  80

Tyr Thr Thr Leu Ala Thr Ser Val Thr Leu Leu Lys Ala Ser Glu Val
                85                  90                  95

Glu Glu Ile Leu Asp Gly Asn Asp Glu Lys Tyr Lys Ala Val Ser Ile
            100                 105                 110

Ser Thr Glu Pro Pro Thr Tyr Leu Arg Glu Gln Lys Ala Lys Arg Asn
        115                 120                 125

Ser Gln Trp Val Pro Thr Leu Ser Asn Ser Ser His His Leu Asp Ala
    130                 135                 140

Val Pro Cys Ser Thr Thr Ile Asn Arg Asn Arg Met Gly Arg Asp Lys
145                 150                 155                 160

Lys Arg Thr Phe Pro Leu Cys Phe Asp Asp His Asp Pro Ala Val Ile
                165                 170                 175

His Glu Asn Ala Ser Gln Pro Glu Val Leu Val Pro Ile Arg Leu Asp
            180                 185                 190

Met Glu Ile Asp Gly Gln Lys Leu Arg Asp Ala Phe Thr Trp Asn Met
        195                 200                 205

Asn Glu Lys Leu Met Thr Pro Glu Met Phe Ser Glu Ile Leu Cys Asp
    210                 215                 220

Asp Leu Asp Leu Asn Pro Leu Thr Phe Val Pro Ala Ile Ala Ser Ala
225                 230                 235                 240

Ile Arg Gln Gln Ile Glu Ser Tyr Pro Thr Asp Ser Ile Leu Glu Asp
                245                 250                 255

Gln Ser Asp Gln Arg Val Ile Ile Lys Leu Asn Ile His Val Gly Asn
            260                 265                 270

Ile Ser Leu Val Asp Gln Phe Glu Trp Asp Met Ser Glu Lys Glu Asn
        275                 280                 285

Ser Pro Glu Lys Phe Ala Leu Lys Leu Cys Ser Glu Leu Gly Leu Gly
    290                 295                 300

Gly Glu Phe Val Thr Thr Ile Ala Tyr Ser Ile Arg Gly Gln Leu Ser
305                 310                 315                 320

Trp His Gln Lys Thr Tyr Ala Phe Ser Glu Asn Pro Leu Pro Thr Val
                325                 330                 335

Glu Ile Ala Ile Arg Asn Thr Gly Asp Ala Asp Gln Trp Cys Pro Leu
            340                 345                 350

Leu Glu Thr Leu Thr Asp Ala Glu Met Glu Lys Lys Ile Arg Asp Gln
        355                 360                 365

Asp Arg Asn Thr Arg Arg Met Arg Leu Ala Asn Thr Gly Pro Ala
    370                 375                 380
```

Trp
385

```
<210> SEQ ID NO 17
<211> LENGTH: 364
<212> TYPE: DNA
<213> ORGANISM: Homo sapiens
<220> FEATURE:
<221> NAME/KEY: CDS
<222> LOCATION: (1)..(363)

<400> SEQUENCE: 17
```

| | | | | | | | | | | | | | | | | |
|---|---|---|---|---|---|---|---|---|---|---|---|---|---|---|---|---|
| agc | cgc | cgc | atc | gtg | gag | ctg | gag | gtg | ggg | gct | gag | atg | gac | gac | atg | 48 |
| Ser | Arg | Arg | Ile | Val | Glu | Leu | Glu | Val | Gly | Ala | Glu | Met | Asp | Asp | Met | |
| 1 | | | | 5 | | | | | 10 | | | | | 15 | | |
| aag | gat | cat | gga | ggt | ggc | tgt | ggg | gtg | gcc | ttc | tcc | gcg | ctg | ggt | ggc | 96 |
| Lys | Asp | His | Gly | Gly | Gly | Cys | Gly | Val | Ala | Phe | Ser | Ala | Leu | Gly | Gly | |
| | | | 20 | | | | | 25 | | | | | 30 | | | |
| gga | gag | tgc | ggg | gag | agc | ttg | gac | ctg | cag | ttt | gtc | gaa | gag | gag | gcc | 144 |
| Gly | Glu | Cys | Gly | Glu | Ser | Leu | Asp | Leu | Gln | Phe | Val | Glu | Glu | Glu | Ala | |
| | 35 | | | | | 40 | | | | | 45 | | | | | |
| gag | ctg | ctg | cgg | cgc | tcc | tac | cag | aac | aag | ctg | ctg | aac | gag | ctg | | 192 |
| Glu | Leu | Leu | Arg | Arg | Ser | Tyr | Gln | Asn | Lys | Leu | Leu | Asn | Glu | Leu | | |
| 50 | | | | | 55 | | | | | 60 | | | | | | |
| gcc | aag | ttc | cgc | tcg | gtg | gcg | ctg | tcg | gag | gac | agt | tgt | tct | gtg | ctc | 240 |
| Ala | Lys | Phe | Arg | Ser | Val | Ala | Leu | Ser | Glu | Asp | Ser | Cys | Ser | Val | Leu | |
| 65 | | | | 70 | | | | | 75 | | | | | 80 | | |
| agc | gaa | cct | tca | ccc | gca | agc | tgc | aga | tcg | gcg | agc | tca | gcg | gca | agg | 288 |
| Ser | Glu | Pro | Ser | Pro | Ala | Ser | Cys | Arg | Ser | Ala | Ser | Ser | Ala | Ala | Arg | |
| | | | 85 | | | | | 90 | | | | | 95 | | | |
| tca | aga | agc | tcg | tgc | tcc | tct | cca | acc | tcc | agc | gct | gtg | acc | tcg | cct | 336 |
| Ser | Arg | Ser | Ser | Cys | Ser | Ser | Pro | Thr | Ser | Ser | Ala | Val | Thr | Ser | Pro | |
| | 100 | | | | | 105 | | | | | 110 | | | | | |
| cct | gcc | agc | tgg | aga | cgg | acg | ccg | agg | c | | | | | | | 364 |
| Pro | Ala | Ser | Trp | Arg | Arg | Thr | Pro | Arg | | | | | | | | |
| | 115 | | | | 120 | | | | | | | | | | | |

```
<210> SEQ ID NO 18
<211> LENGTH: 121
<212> TYPE: PRT
<213> ORGANISM: Homo sapiens

<400> SEQUENCE: 18
```

Ser Arg Arg Ile Val Glu Leu Glu Val Gly Ala Glu Met Asp Asp Met
1               5                   10                  15

Lys Asp His Gly Gly Gly Cys Gly Val Ala Phe Ser Ala Leu Gly Gly
            20                  25                  30

Gly Glu Cys Gly Glu Ser Leu Asp Leu Gln Phe Val Glu Glu Glu Ala
        35                  40                  45

Glu Leu Leu Arg Arg Ser Tyr Gln Asn Lys Leu Leu Asn Glu Leu
    50                  55                  60

Ala Lys Phe Arg Ser Val Ala Leu Ser Glu Asp Ser Cys Ser Val Leu
65                  70                  75                  80

Ser Glu Pro Ser Pro Ala Ser Cys Arg Ser Ala Ser Ser Ala Ala Arg
                85                  90                  95

Ser Arg Ser Ser Cys Ser Ser Pro Thr Ser Ser Ala Val Thr Ser Pro
            100                 105                 110

Pro Ala Ser Trp Arg Arg Thr Pro Arg
            115                 120

```
<210> SEQ ID NO 19
<211> LENGTH: 599
<212> TYPE: DNA
<213> ORGANISM: Homo sapiens
<220> FEATURE:
<221> NAME/KEY: CDS
<222> LOCATION: (2)..(346)
<220> FEATURE:
<221> NAME/KEY: misc_difference
<222> LOCATION: (578)
<223> OTHER INFORMATION: n can be any nucleotide, thus n=a, t, c, or g

<400> SEQUENCE: 19
```

| | | | | | | | | | | | | | | | | |
|---|---|---|---|---|---|---|---|---|---|---|---|---|---|---|---|---|
| g | ccc | gct | gcg | gca | gag | gag | gag | gag | cag | cag | gga | gcc | gac | ggg | gcc gct | 49 |
| | Pro | Ala | Ala | Ala | Glu | Glu | Glu | Glu | Gln | Gln | Gly | Ala | Asp | Gly | Ala Ala | |
| | 1 | | | | 5 | | | | | 10 | | | | | 15 | |

| gcc | gag | gac | ggg | gcg | gac | gag | gcc | gag | gca | gag | atc | atc | cag | ctg ctg | 97 |
|---|---|---|---|---|---|---|---|---|---|---|---|---|---|---|---|
| Ala | Glu | Asp | Gly | Ala | Asp | Glu | Ala | Glu | Ala | Glu | Ile | Ile | Gln | Leu Leu | |
| | | | 20 | | | | | 25 | | | | | 30 | | |

| aag | cga | gcc | aag | ttg | agc | att | atg | aaa | gat | gag | cca | gaa | gag | gct gag | 145 |
|---|---|---|---|---|---|---|---|---|---|---|---|---|---|---|---|
| Lys | Arg | Ala | Lys | Leu | Ser | Ile | Met | Lys | Asp | Glu | Pro | Glu | Glu | Ala Glu | |
| | | 35 | | | | | 40 | | | | | 45 | | | |

| tta | att | ttg | cat | gac | gct | ctt | cgt | ctc | gcc | tat | cag | act | gat | aac aag | 193 |
|---|---|---|---|---|---|---|---|---|---|---|---|---|---|---|---|
| Leu | Ile | Leu | His | Asp | Ala | Leu | Arg | Leu | Ala | Tyr | Gln | Thr | Asp | Asn Lys | |
| | 50 | | | | | 55 | | | | | 60 | | | | |

| aag | gcc | atc | act | tac | act | tat | gat | ttg | atg | gcc | aac | tta | gca | ttt ata | 241 |
|---|---|---|---|---|---|---|---|---|---|---|---|---|---|---|---|
| Lys | Ala | Ile | Thr | Tyr | Thr | Tyr | Asp | Leu | Met | Ala | Asn | Leu | Ala | Phe Ile | |
| 65 | | | | | 70 | | | | | 75 | | | | | 80 | |

| cgg | ggt | cag | ctt | gaa | aat | gct | gaa | caa | ctt | ttt | aaa | gca | aca | atg agt | 289 |
|---|---|---|---|---|---|---|---|---|---|---|---|---|---|---|---|
| Arg | Gly | Gln | Leu | Glu | Asn | Ala | Glu | Gln | Leu | Phe | Lys | Ala | Thr | Met Ser | |
| | | | | 85 | | | | | 90 | | | | | 95 | |

| tac | ctc | ctt | gga | ggg | ggg | cat | gaa | gca | gga | gga | caa | tgc | aat | aat ttg | 337 |
|---|---|---|---|---|---|---|---|---|---|---|---|---|---|---|---|
| Tyr | Leu | Leu | Gly | Gly | Gly | His | Glu | Ala | Gly | Gly | Gln | Cys | Asn | Asn Leu | |
| | | | | 100 | | | | | 105 | | | | | 110 | |

| aaa | ttt | ccc | taaagctggc | cagtatctat | gcttgcgcag | aacagacagg | 386 |
|---|---|---|---|---|---|---|---|
| Lys | Phe | Pro | | | | | |
| | | 115 | | | | | |

```
aatttgctgt tgctggctat gaattctgca tttcaactct agaggaaaaa attgaaagag    446
aaaaggaatt agcagaagac attatgtcag tggaagagaa agccataccc acctcctctt    506
gggcatgtgc ttagacgcct gtgctcgcta ccttctgttc tccaagcagc cgtcacaggc    566
ccaaaggatg tntgaaaagc tctgcagatt tct                                 599

<210> SEQ ID NO 20
<211> LENGTH: 115
<212> TYPE: PRT
<213> ORGANISM: Homo sapiens

<400> SEQUENCE: 20

Pro Ala Ala Ala Glu Glu Glu Gln Gln Gly Ala Asp Gly Ala Ala
  1               5                  10                  15

Ala Glu Asp Gly Ala Asp Glu Ala Glu Ala Glu Ile Ile Gln Leu Leu
             20                  25                  30

Lys Arg Ala Lys Leu Ser Ile Met Lys Asp Glu Pro Glu Glu Ala Glu
         35                  40                  45

Leu Ile Leu His Asp Ala Leu Arg Leu Ala Tyr Gln Thr Asp Asn Lys
     50                  55                  60

Lys Ala Ile Thr Tyr Thr Tyr Asp Leu Met Ala Asn Leu Ala Phe Ile
 65                  70                  75                  80

Arg Gly Gln Leu Glu Asn Ala Glu Gln Leu Phe Lys Ala Thr Met Ser
                 85                  90                  95
```

```
            Tyr Leu Leu Gly Gly Gly His Glu Ala Gly Gly Gln Cys Asn Asn Leu
                            100                 105                 110

Lys Phe Pro
                    115

<210> SEQ ID NO 21
<211> LENGTH: 941
<212> TYPE: DNA
<213> ORGANISM: Homo sapiens
<220> FEATURE:
<221> NAME/KEY: CDS
<222> LOCATION: (67)..(939)

<400> SEQUENCE: 21 cttttttttaa atctaggaac aactgttaaa cctatatact tactacttgc agttccatga         60 tggcaa atg act gac aga aga tca tgt gtc cct agc tgg ttt tgg ggt            108
       Met Thr Asp Arg Arg Ser Cys Val Pro Ser Trp Phe Trp Gly
            1               5                  10 cca gta gta acc ttg caa gat tgt ctt gct gcc ttc ttt gcc aga gat           156
Pro Val Val Thr Leu Gln Asp Cys Leu Ala Ala Phe Phe Ala Arg Asp
 15              20                  25                  30 gaa cta aaa ggt gac aat atg tac agt tgt gaa aaa tgc aaa aag ctg           204
Glu Leu Lys Gly Asp Asn Met Tyr Ser Cys Glu Lys Cys Lys Lys Leu
                 35                  40                  45 aga aat gga gtg aag ttt tgt aaa gta caa aac ttt cct gag att ttg           252
Arg Asn Gly Val Lys Phe Cys Lys Val Gln Asn Phe Pro Glu Ile Leu
             50                  55                  60 tgc atc cac ctt aaa aga ttc aga cat gaa cta atg ttt tcc acc aaa           300
Cys Ile His Leu Lys Arg Phe Arg His Glu Leu Met Phe Ser Thr Lys
         65                  70                  75 atc agt acc cat gtt tca ttt ccg cta gaa ggc ttg gat ctt cag cca           348
Ile Ser Thr His Val Ser Phe Pro Leu Glu Gly Leu Asp Leu Gln Pro
     80                  85                  90 ttt ctt gct aag gat agt cca gct caa att gtg aca tat gat ctt ctg           396
Phe Leu Ala Lys Asp Ser Pro Ala Gln Ile Val Thr Tyr Asp Leu Leu
 95                 100                 105                 110 tca gtc att tgc cat cat gga act gca agt agt gga cac tat ata gcc           444
Ser Val Ile Cys His His Gly Thr Ala Ser Ser Gly His Tyr Ile Ala
                115                 120                 125 tac tgc cga aac aat cta aat aat ctc tgg tat gaa ttt gat gat cag           492
Tyr Cys Arg Asn Asn Leu Asn Asn Leu Trp Tyr Glu Phe Asp Asp Gln
            130                 135                 140 agt gtc act gaa gtt tca gaa tct act gta caa aat gca gaa gct tac           540
Ser Val Thr Glu Val Ser Glu Ser Thr Val Gln Asn Ala Glu Ala Tyr
        145                 150                 155 gtt ctt ttc tat agg aag agc agc gaa gag gca caa aaa gag agg aga           588
Val Leu Phe Tyr Arg Lys Ser Ser Glu Glu Ala Gln Lys Glu Arg Arg
    160                 165                 170 agg ata tca aat tta ttg aac ata atg gaa cca agc ctc ctt cag ttt           636
Arg Ile Ser Asn Leu Leu Asn Ile Met Glu Pro Ser Leu Leu Gln Phe
175                 180                 185                 190 tat att tct cga cag tgg ctt aat aaa ttt aag acc ttt gcc gaa cct           684
Tyr Ile Ser Arg Gln Trp Leu Asn Lys Phe Lys Thr Phe Ala Glu Pro
                195                 200                 205 ggc cct att tca aat aat gac ttt ctt tgt att cat gga ggt gtt cct           732
Gly Pro Ile Ser Asn Asn Asp Phe Leu Cys Ile His Gly Gly Val Pro
            210                 215                 220 cca aga aaa gct ggt tat att gaa gac ctg gtt ttg atg ctg cct cag           780
Pro Arg Lys Ala Gly Tyr Ile Glu Asp Leu Val Leu Met Leu Pro Gln
        225                 230                 235
```

```
aac att tgg gat aac cta tat agc agg tat ggt gga gga cca gct gtc    828
Asn Ile Trp Asp Asn Leu Tyr Ser Arg Tyr Gly Gly Gly Pro Ala Val
    240                 245                 250 aac cat ctg tac att tgt cat act tgc caa att gag gcg gag aaa att    876
Asn His Leu Tyr Ile Cys His Thr Cys Gln Ile Glu Ala Glu Lys Ile
255                 260                 265                 270 gaa aaa aga aga aaa act gaa ttg gaa att ttt att cgg ctt aac aga    924
Glu Lys Arg Arg Lys Thr Glu Leu Glu Ile Phe Ile Arg Leu Asn Arg
                275                 280                 285 gcg ttc caa aaa gag ga                                             941
Ala Phe Gln Lys Glu
            290
```

<210> SEQ ID NO 22
<211> LENGTH: 291
<212> TYPE: PRT
<213> ORGANISM: Homo sapiens

<400> SEQUENCE: 22

```
Met Thr Asp Arg Arg Ser Cys Val Pro Ser Trp Phe Trp Gly Pro Val
  1               5                  10                  15

Val Thr Leu Gln Asp Cys Leu Ala Ala Phe Ala Arg Asp Glu Leu
             20                  25                  30

Lys Gly Asp Asn Met Tyr Ser Cys Glu Lys Cys Lys Lys Leu Arg Asn
             35                  40                  45

Gly Val Lys Phe Cys Lys Val Gln Asn Phe Pro Glu Ile Leu Cys Ile
 50                  55                  60

His Leu Lys Arg Phe Arg His Glu Leu Met Phe Ser Thr Lys Ile Ser
 65                  70                  75                  80

Thr His Val Ser Phe Pro Leu Glu Gly Leu Asp Leu Gln Pro Phe Leu
                 85                  90                  95

Ala Lys Asp Ser Pro Ala Gln Ile Val Thr Tyr Asp Leu Leu Ser Val
            100                 105                 110

Ile Cys His His Gly Thr Ala Ser Ser Gly His Tyr Ile Ala Tyr Cys
            115                 120                 125

Arg Asn Asn Leu Asn Asn Leu Trp Tyr Glu Phe Asp Asp Gln Ser Val
130                 135                 140

Thr Glu Val Ser Glu Ser Thr Val Gln Asn Ala Glu Ala Tyr Val Leu
145                 150                 155                 160

Phe Tyr Arg Lys Ser Ser Glu Glu Ala Gln Lys Glu Arg Arg Arg Ile
                165                 170                 175

Ser Asn Leu Leu Asn Ile Met Glu Pro Ser Leu Leu Gln Phe Tyr Ile
            180                 185                 190

Ser Arg Gln Trp Leu Asn Lys Phe Lys Thr Phe Ala Glu Pro Gly Pro
        195                 200                 205

Ile Ser Asn Asn Asp Phe Leu Cys Ile His Gly Gly Val Pro Pro Arg
210                 215                 220

Lys Ala Gly Tyr Ile Glu Asp Leu Val Leu Met Leu Pro Gln Asn Ile
225                 230                 235                 240

Trp Asp Asn Leu Tyr Ser Arg Tyr Gly Gly Gly Pro Ala Val Asn His
                245                 250                 255

Leu Tyr Ile Cys His Thr Cys Gln Ile Glu Ala Glu Lys Ile Glu Lys
            260                 265                 270

Arg Arg Lys Thr Glu Leu Glu Ile Phe Ile Arg Leu Asn Arg Ala Phe
        275                 280                 285
```

Gln Lys Glu
   290

<210> SEQ ID NO 23
<211> LENGTH: 542
<212> TYPE: DNA
<213> ORGANISM: Homo sapiens
<220> FEATURE:
<221> NAME/KEY: CDS
<222> LOCATION: (1)..(213)

<400> SEQUENCE: 23

| | | | | | | | | | | | | | | | | |
|---|---|---|---|---|---|---|---|---|---|---|---|---|---|---|---|---|
| agg | ccg | gct | ttc | ggc | gcg | acg | gtc | gcc | gcg | ttc | cat | cgt | cgc | gcg | gcc | 48 |
| Arg | Pro | Ala | Phe | Gly | Ala | Thr | Val | Ala | Ala | Phe | His | Arg | Arg | Ala | Ala | |
| 1 | | | | 5 | | | | | 10 | | | | | 15 | | |
| ctt | cgg | ggc | ccg | agc | ccc | aat | gtc | ggg | ccc | caa | cgg | aga | cct | ggg | gat | 96 |
| Leu | Arg | Gly | Pro | Ser | Pro | Asn | Val | Gly | Pro | Gln | Arg | Arg | Pro | Gly | Asp | |
| | | | 20 | | | | | 25 | | | | | 30 | | | |
| gcc | ggt | gga | ggc | ggg | agc | gga | agg | cga | gga | gga | cgg | ctt | cgg | gga | agc | 144 |
| Ala | Gly | Gly | Gly | Gly | Ser | Gly | Arg | Arg | Gly | Gly | Arg | Leu | Arg | Gly | Ser | |
| | | | | 35 | | | | | 40 | | | | | 45 | | |
| aga | ata | cgc | tgc | cat | caa | ctc | cat | gct | gga | cca | gat | caa | ctc | ctg | tct | 192 |
| Arg | Ile | Arg | Cys | His | Gln | Leu | His | Ala | Gly | Pro | Asp | Gln | Leu | Leu | Ser | |
| | 50 | | | | | 55 | | | | | 60 | | | | | |
| gga | cca | cct | gga | gga | gaa | gaa | tgaccacctc cacgcccgcc tccaggagct | | | | | | | | | 243 |
| Gly | Pro | Pro | Gly | Gly | Glu | Glu | | | | | | | | | | |
| 65 | | | | | 70 | | | | | | | | | | | | gctggagtcc aaccggcaga cacgcctgga gttccagcag cagctcgggg aggcccccag    303 tgatgccagc ccctaggctc aagagcccc caaccgggac ccaaccctgc ctccctgggg     363 ctaagctctg gcctggggca ctcaccccct ggcttagaca acttctcaag ggcttggcct    423 tcagggggacc cttgtgggtc ttgccttgct ggggccacct tttcttgctt ggggcttccc   483 ctttggccta ccttggggcc aagcccctac caactttgga ttgccttctt gggggccaa    542

<210> SEQ ID NO 24
<211> LENGTH: 71
<212> TYPE: PRT
<213> ORGANISM: Homo sapiens

<400> SEQUENCE: 24

Arg Pro Ala Phe Gly Ala Thr Val Ala Ala Phe His Arg Arg Ala Ala
1               5                   10                  15

Leu Arg Gly Pro Ser Pro Asn Val Gly Pro Gln Arg Arg Pro Gly Asp
            20                  25                  30

Ala Gly Gly Gly Gly Ser Gly Arg Arg Gly Gly Arg Leu Arg Gly Ser
        35                  40                  45

Arg Ile Arg Cys His Gln Leu His Ala Gly Pro Asp Gln Leu Leu Ser
    50                  55                  60

Gly Pro Pro Gly Gly Glu Glu
65                  70

<210> SEQ ID NO 25
<211> LENGTH: 441
<212> TYPE: DNA
<213> ORGANISM: Homo sapiens
<220> FEATURE:
<221> NAME/KEY: CDS
<222> LOCATION: (1)..(246)

<400> SEQUENCE: 25 acg agg gct tat gca act aca agg att cgt agc caa att gga aac aca    48

```
                                                     -continued

Thr Arg Ala Tyr Ala Thr Thr Arg Ile Arg Ser Gln Ile Gly Asn Thr
  1               5                  10                  15 gag tct gcg ctg aag aaa ctt gct gaa gaa aac cca gat tta caa gaa           96
Glu Ser Ala Leu Lys Lys Leu Ala Glu Glu Asn Pro Asp Leu Gln Glu
                 20                  25                  30 gca tac att gca aaa cag ata cga ctt aaa tca aag ctg ctt gat cat          144
Ala Tyr Ile Ala Lys Gln Ile Arg Leu Lys Ser Lys Leu Leu Asp His
                 35                  40                  45 gac aat gtc aag tat ttg aag aaa att ctt gat gag ttg gag aaa gtc          192
Asp Asn Val Lys Tyr Leu Lys Lys Ile Leu Asp Glu Leu Glu Lys Val
     50                  55                  60 ttg gat cag gtt gaa act gaa ttg caa aga aga aat gaa gaa aac cca          240
Leu Asp Gln Val Glu Thr Glu Leu Gln Arg Arg Asn Glu Glu Asn Pro
 65                  70                  75                  80 ggt tct tgactgagct gctcctgtgc ttccatgaat ggctgcatct catctggacg           296
Gly Ser gggattccat cagcgccttc cctggccatt taatagatgg actcgccatc cttcaaggcc        356
ttgtgcaaat gtcaactttc taaaaattcg ctttattgga gctggaaggg actatcctat        416
tttctctagc cctttgtttt gccct                                              441

<210> SEQ ID NO 26
<211> LENGTH: 82
<212> TYPE: PRT
<213> ORGANISM: Homo sapiens

<400> SEQUENCE: 26

Thr Arg Ala Tyr Ala Thr Thr Arg Ile Arg Ser Gln Ile Gly Asn Thr
  1               5                  10                  15

Glu Ser Ala Leu Lys Lys Leu Ala Glu Glu Asn Pro Asp Leu Gln Glu
                 20                  25                  30

Ala Tyr Ile Ala Lys Gln Ile Arg Leu Lys Ser Lys Leu Leu Asp His
                 35                  40                  45

Asp Asn Val Lys Tyr Leu Lys Lys Ile Leu Asp Glu Leu Glu Lys Val
     50                  55                  60

Leu Asp Gln Val Glu Thr Glu Leu Gln Arg Arg Asn Glu Glu Asn Pro
 65                  70                  75                  80

Gly Ser
```

NLK1 PROTEIN AND NLK1 PROTEIN COMPLEXES

GRANT SUPPORT

This invention was made with United States Government support under award number 70NANB5H1066 awarded by the National Institute of Standards and Technology. The United States Government has certain rights in the invention.

FIELD OF THE INVENTION

The present invention disclosed herein relates to complexes of the Nlk1 protein with other proteins, in particular, complexes of the Nlk1 protein with the following proteins: TrkA, protein phosphatase-1α, 14-3-3ε, α-tropomyosin, vimentin, p0071, Ini-1, IP-1 (an intermediate filament associated protein), IP-2 (a tropomyosin homolog protein), IP-3 (a ubiquitin hydroxylase homolog protein), IP-4 (a collagen homolog protein) and IP-5 (a tropomyosin homolog protein). In addition, the present invention relates to the production of antibodies to the aforementioned Nlk1 protein complexes, and their use in, inter alia, screening, diagnosis, prognosis and therapy. The present invention further relates to the IP-1, IP-3, IP-4, and IP-5 genes and proteins, as well as derivatives, fragments, analogs and homologs, thereof.

BACKGROUND OF THE INVENTION

It is a well-established tenet in molecular biology that loss of control of cell proliferation may lead to severe diseases and disorders (e.g., neoplasia). Hence, the elucidation of the intricacies of the cell-cycle, and its deregulation during oncogenesis, will provide novel opportunities in the prophylactic, diagnostic and therapeutic management of cancer and other proliferation-related diseases. A better understanding of the cell-cycle could be achieved by the elucidation of the interactions of the various protein complexes, whose levels and biological activities are regulated through the cell-cycle. The identification and classification of these protein complexes will be useful in the development of treatment modalities and assays for various pathological processes including, but not limited to, hyperproliferative disorders (e.g., tumorigenesis and tumor progression), as well as other related genetic disorders.

It should be noted that the citation of a reference herein should not be construed as an admission that such is prior art to the present invention.

(1) The Nlk1 Protein

The Nlk1 protein (GenBank Acc. No. U11050) is a human homolog of the filamentous fungus *Aspergillus nidulans* mitotic regulator, NIMA kinase. The Nlk1 protein is a 48 Kdal serine/threonine-specific kinase which plays a key role in cell-cycle events leading to the onset of mitosis. The protein levels and activity of Nlk1 protein are regulated through the cell-cycle (see e.g., Schultz, et al., 1994. *Cell Growth Diff.* 5:625–632; Fry, et al., 1995. *J. Biol Chem.* 270:12899–12905). Analysis of the biochemical properties and in vitro substrate-specificity of Nlk1 protein have revealed striking similarities, but also some differences, between human Nlk1 protein and the fungal mitotic regulator, NIMA kinase. See e.g., Fry, et al., 1995. *J. Biol. Chem.* 270:12899–12905. Nlk1 protein is expressed during specific stages of the cell-cycle; with low levels of expression during mitosis (M) phase and in early gap phase (G1), and expression peaking during the DNA-synthesis (S) and late gap phase (G2) to reach a plateau in late G2 and M-phase. See e.g., Id. Accordingly, Nlk1 protein may function during an earlier phase of the cell-cycle than NIMA kinase, which displays maximum protein and activity levels during mitosis. See e.g., Osmani, et al., 1991. *EMBO J.* 10:2669–267; Pu, et al., 1995. *J. Biol Chem.* 270:18110–18116. The Nlk1 protein is associated with the centrosome throughout the cell-cycle, including all stages of mitosis, independent of microtubules. See e.g., Fry, et al., 1998. *EMBO J.* 17:470–481. Thus, one biological function of Nlk1 protein relates to the centrosome cycle.

In certain aspects, the Nlk1 protein appears to function in a similar manner to NIMA kinase. See generally, Pu, et al., 1995. *J. Biol. Chem.* 270:18110–18116. The activity of NIMA kinase is essential for the progression of cells into mitosis, and the full activation of the NIMA kinase depends on the cyclin-dependent kinase, CDC2. Both NIMA and CDC2 kinases have been demonstrated to be required for the progression from G2 to mitosis in Aspergillus, and following this cell-cycle progression, both kinases are rapidly degraded. See e.g., Pu & Osmani, 1995. *EMBO J.* 14:995–1003. Recent experimental evidence has demonstrated that the Aspergillus NIMA serine/threonine kinase is not only required for mitosis, in cooperation with CDC2, but is also implicated in chromatin condensation. See e.g., Lu & Hunter, 1995. *Cell* 81:413–424; Pu & Osmani, 1995. *EMBO J.* 14:993–1003. Additionally, the Nlk1 protein may also be involved in other events of meiosis including, but not limited to, chromosomal condensation. See e.g., Rhee & Wolgemuth, 1997. *Development* 124:2167–2177.

As previously discussed, CDC2 is responsible for the phosphorylation of the Aspergillus NIMA kinase (see Fry & Nigg, 1995. *Curr. Biol.* 5:1122–1125), interestingly, however, mammalian Nlk1 protein lacks the putative CDC2 phosphorylation sites. While Nlk1 protein has been shown to be active as a serine/threonine kinase, the precise sites which are phosphorylated by Nlk1 protein have not yet been mapped. Recently, a synthetic peptide possessing the amino acid sequence, IRRLSTRR, was found to be phosphorylated exclusively on serine residues, thus tending to suggest that basic amino acid residues may contribute to substrate recognition by Nlk1 protein. See e.g., Fry, et al., 1995. *J. Biol. Chem.* 270:12899–12905.

The Nlk1 protein possesses marked sequence homology with NIMA kinase, with the two kinases sharing a 48% sequence identity over their catalytic domains located at the amino-terminus. See e.g., Schultz, et al., 1994. *Cell Growth Diff.* 5:625–635. Another conserved feature of the NIMA-related kinase family is the position of an insertion (maximal 25 amino acids) between two kinase the subdomains, VIA and VIB. Interestingly, the carboxyl-terminal extensions display virtually no primary sequence conservation among the different members of the NIMA-related kinase family. However, the beginning of the highly basic carboxyl-terminal, non-catalytic extension contains a conserved secondary structural motif (i.e., a coiled-coil) in both NIMA kinase and Nlk1 protein, which functions in the degradation of NIMA kinase during the M-phase. Coiled-coil motifs are often found to be involved in protein-protein interaction, and such secondary structural motifs may have been conserved as a direct result of their putative biological function(s). See e.g., Fry & Nigg, 1997. *Meth. Enzym.* 283:270–282. The carboxyl-terminal non-catalytic domain within human Nlk1 protein are markedly shortened, and it is interesting to note that several putative CDC2 phosphorylation sites found within the carboxyl-terminal domain of NIMA, are not found to be present in the much shorter extension of Nlk1 protein.

The Aspergillus NIMA kinase interacts with CDC2-kinase (see e.g., Osmani, et al, 1994. *J. Cell Sci.*

107:1519–1528) and with the human Pin1 protein, a peptidyl-prolyl-isomerase (see e.g., Lu, et al, 1996. *Nature* 380:544–547). Heretofore the present invention, no interacting proteins have been described for the human NIMA kinase homologue Nlk1 protein. The Nlk1 protein differs from NIMA kinase in that: (i) Nlk1 protein activity peaks in the cell-cycle's S/G2 phase, and not in mitosis; (ii) Nlk1 protein lacks the putative CDC2 phosphorylation sites found in NIMA kinase and (iii) Nlk1 protein lacks the carboxyl-terminal PEST sequences found in NIMA kinase. Hence, the exact biological function(s) of the Nlk1 protein have yet to be elucidated, although along with the other members of the Nek family, it almost certainly functions in some form of cell-cycle mediation and control.

(2) Nlk1 protein-Interacting Proteins

The Nlk1 protein, a serine/threonine-specific kinase, plays an important role in cell-cycle events which lead to the onset of mitosis. Furthermore, Nlk1 protein is also involved in chromosome condensation and thus, in events of meiosis. Despite these aforementioned roles, heretofore the present invention, there has been no quantitative data regarding the interaction of the Nlk1 protein with other cellular proteins.

It is a well-established tenet in molecular biology that loss of control of cell proliferation may lead to severe diseases and disorders (e.g., neoplasia). As Nlk1 protein is involved in regulation of cell proliferation due to its role in the cell-cycle (mitosis and meiosis), it is likely that Nlk1 protein interacts with numerous cellular proteins to promote the profound structural reorganizations which accompany the entry of cells into, for example, mitosis. The elucidation of the intricacies of the cell-cycle, and its deregulation during oncogenesis, will provide novel opportunities in the prophylactic, diagnostic and therapeutic management of cancer and other proliferation-related diseases.

A better understanding of the cell-cycle could be achieved by the elucidation of the interactions of Nlk1 protein with other cellular proteins. As both the levels and biological activity of the Nlk1 protein are regulated through the cell-cycle, it is highly likely that this kinase will perform via protein-protein interactions. Although, as previously discussed, nothing is known within the prior art regarding Nlk1 protein's interaction with other cellular proteins. Therefore, what is lacking within the prior art, is the identification of protein complexes between Nlk1 protein and other cellular proteins and/or polypeptides. The identification of these protein complexes will be useful in the development of treatment modalities and assays for various pathological processes including, but not limited to, hyperproliferative disorders (e.g., tumorigenesis and tumor progression), as well as other related genetic disorders.

(A) Cytoskeletal Proteins and Cytoskeletal-Associated Proteins

Several proteins which were identified as Nlk1 protein-interactants in the present invention were classified either as cytoskeletal proteins or proteins associated with cytoskeletal filaments. These aforementioned proteins include: (i) the skeletal muscle protein α-tropomyosin, (ii) the intermediate filament vimentin and (iii) the desmosomal protein p0071 (which associates with intermediate filaments). Expressed sequences (hereinafter referred to as "ESTs") possessing homologies to cytoskeletal proteins or proteins associated with the cytoskeleton include: (i) the tropomyosin-homolog proteins encoded by IP-2 and IP-5 and (ii) the intermediate filament-associated protein encoded by IP-1.

The interaction between Nlk1 protein and cytoskeletal or cytoskeleton-associated proteins provides a link to hyperproliferative disorders, as it is known from prior art that the cytoskeleton undergoes extensive modification in those diseases. Cytoskeletal proteins provide the structural foundation which allows cells to exist in a highly organized manner. These cytoskeletal proteins not only maintain structural integrity, but might also be associated with signal transduction and suppression of tumorigenesis. Therefore, the interaction of Nlk1 protein with cytoskeletal or cytoskeleton-associated proteins may play a pivotal role in processes including, but not limited to, regulating tumor cell behavior during tumor development and metastasis, and neurodegenerative disorders. Furthermore, the interaction of Nlk1 protein with tropomyosin or tropomyosin-homolog proteins may also provide a link to cardiovascular diseases.

(i) α-Tropomyosin

Human skeletal muscle a-tropomyosin (hTM; GenBank Acc. No. M19713; MacLeod & Gooding, 1988. *Mol. Cell. Biol.* 8:433–440) is a structural protein of muscle. The tropomyosins are highly conserved, coiled-coil actin-binding proteins found in most eukaryotic cells. The actin cytoskeleton is an intracellular structure, which is involved in the onset and control of cell shape and function. Actin filaments play important roles in mitosis, cell signaling, and motility and thus, the actin cytoskeleton is affected in many disease states. Striated and smooth muscle α-tropomyosins differ as a consequence of alternative splicing of exons 2 and 9. See e.g. Ruiz-Opazo, et al., 1985. *Nature* 315:67–70. Non-acetylated, smooth tropomyosin binds actin with high affinity, whereas non-acetylated, striated tropomyosin requires the protein troponin, found only in striated muscle, for strong actin binding. See e.g., Hammell, et al., 1996. *J. Biol Chem.* 271:4236–4242.

Tropomyosin, in association with the troponin complexes (i.e., troponin-I, -T and -C) plays a central role in the $Ca^{2+}$-dependent regulation of vertebrate striated muscle contraction. The function of this protein in smooth muscle and non-muscle cells remains unknown. Three distinct α-tropomyosin messenger (mRNA) isoforms encode different protein isoforms; which are tissue-specific, developmentally regulated and (most probably) encoded by the same gene. Tissue-specific domains within these isoforms delineate the putative troponin-I and troponin-T binding domains of tropomyosin. See e.g., Ruiz-Opazo, et al., 1985. *Nature* 315:67–70.

Suppression of the specific muscle-type isoforms of tropomyosin is a common biochemical event in malignantly transformed cells. See e.g., Braverman, et al., 1996. *Oncogene* 13:537–545. For example, tropomyosins are commonly down-regulated in fibroblasts transformed by oncogenes and specific tropomyosin isoforms are down-regulated in human breast carcinoma cell lines. See e.g., Franzen, et al, 1996. *Br. J. Cancer* 73:909–913.

Additionally, mutations in the α-tropomyosin gene are linked to familial hypertrophic cardiomyopathy (i.e., mutation Asp175Asn, Glu180Gly). Hypertrophic cardiomyopathy is a disease with an autosomal dominant pattern of heritability and is the most common cause of sudden-death in youth (see e.g., Palmiter & Salaro, 1997. *Basic Res. Cardiol.* 92:63–74; Kimura, et al., 1997. *Nature Genet.* 16:379–382; Davies & McKenna, 1995. *Histopath.* 26:493–500) and is characterized by left ventricular hypertrophy in the absence of an increased external load, as well as extreme myofibrillar disarray. Mutations in seven genes, all encoding sarcomeric proteins, have been identified as causes of familial hypertrophic cardiomyopathy. See e.g., Towbin, 1998. *Curr. Opin. Cell Biol.* 10:131–139. The genes include those encoding the cytoskeletal proteins such as α-tropomyosin, β-myosin heavy chain, cardiac troponin-T, myosin binding protein-C, myosin essential light chain, myosin regulatory light chain, and troponin-I.

Thus, α-tropomyosin is involved in pathological processes including, but not limited to, tumorigenesis and hypertrophic cardiomyopathy.

(ii) IP-1 Protein

Within the present invention, IP-1 has been identified as a novel protein possessing homology to intermediate filaments associated proteins (e.g., the plectin proteins), which in-turn exhibit homologies to intermediate filaments (e.g., the keratin proteins). Thus, as discussed in the previous subsections, these aforementioned homologies serve to implicate IP-1 in various pathological processes including, but not limited to, tumorigenesis, neurodegenerative disorders and metabolic diseases.

(iii) IP-2 Protein

The Nlk1 protein-interacting protein (i.e., interactant), IP-2 (GenBank Acc. No. AA143467; Hillier, et al., 1997. Wash Univ.-NCI Human EST Project Proceedings) is an EST which, currently, has no published, ascribed biological function. However, as disclosed herein, the protein encoded by IP-2 is a α-tropomyosin homolog protein, and accordingly, IP-2 may also play an important role in pathological processes including, but not limited to, the genesis of neoplasia and cardiovascular disorders.

(iv) IP-4 Protein

As disclosed herein, IP-4 has been characterized as a novel, Nlk1 protein-interacting protein (i.e., an interactant) of the present invention. IP-4 possesses homology to type-I collagen proteins, which have been shown to be involved in the regulation of a protease which has been broadly implicated in the neoplastic processes of invasion and metastasis within many cancer model systems including, but not limited to, human breast cancer (HBC). See e.g. Thompson, et al., 1994. *Breast Cancer Res. Treat.* 31:357–370. The adhesion of metastatic tumor cells to connective tissue elements (e.g., type I collagen) is required for the movement of these tumor cells into the subendothelial stroma and their subsequent growth at new locations. Accordingly, the type I collagen homolog protein IP-4 may be implicated in tumorigenesis and, particularly, in the metastatic dissemination of neoplastic cells.

(v) IP-5 Protein

The Nlk1 protein-interactant IP-5 possesses homologies to the amino-terminus of tropomyosin and to myosins. Furthermore, IP-5 has been shown to be a homolog of the Sry-like transcription factor, Sox 4, a DNA-binding protein. Accordingly, it is likely that the novel IP-5 protein is also, similarly involved in pathological processes including, but not limited to, the genesis of neoplasia and cardiovascular disorders.

(vi) Vimentin

Vimentin is a cytoskeletal protein which assembles into intermediate filaments (IFs) and belongs to the type III IF family (GenBank Acc. No. X56134; Honore, et al., 1990. *Nuc. Acids Res.* 18:6692–6698. IFs, as an intrinsic component of the cytoskeleton, control a large number and variety of biological events. Vimentin is expressed within central and peripheral neurons (i.e., neuronal progenitor cells, adult neurons, glial progenitor cells, mature astrocytes (see e.g., Ho & Liem, 1996. *Cancer Metastasis Rev.* 15:483–497) and in tumors of the nervous system. The expression of vimentin is tissue-specific and developmentally regulated and, therefore, vimentin serves as an efficacious marker for the determination of cell origin and the differentiation of the status of tumor cells.

When neoplastic transformation has taken place, affected cells reveal altered immunolocalization of IFs within the cytoplasm. See e.g., Hirasawa, et al., 1996. *Nippon Rinsho* 54:1542–1550. Vimentin has been associated with many tumors and it is a potential diagnostic immunohistochemical marker of soft tissue tumors. See e.g. Hibshoosh & Lattes, 1997. *Sem. Oncol.* 24:515–525. Additionally, in some cancers (e.g., malignant melanoma and breast carcinoma), vimentin and keratin IFs are co-expressed, thus lending credence to a putative role for vimentin in cancer progression. Over-expression of vimentin IFs in breast carcinoma leads to augmentation of motility and invasiveness which can be down-regulated by treatment with anti-sense oligonucleotides to vimentin, in vitro. See e.g., Hendrix, et al., 1996. *Cancer Meta. Rev.* 15:507–525.

In addition to vimentin's role in tumorigenesis, the protein is also involved in all other cellular processes which are associated with IFs. For example, the rate of steroid synthesis is directly regulated by the rate of cholesterol transport to mitochondria which involves IFs, microfilaments and $Ca^{2+}$/cahnodulin. Phosphorylation of IF-associated vimentin, causes breakdown of the IFs, which results in decreased cholesterol transport. See e.g., Hall, 1997. *Steroids* 62:185–189. Thus, vimentin functions in cell growth, differentiation, and other cytoskeletal finctions, and in tumorigenesis and metastatic spread, disorders of steroid metabolism, and disorders of cholesterol transport, including, atherosclerosis and cardiovascular disease.

Vimentin has also been shown to interact with: (i) the microfilament protein actin (see e.g., Ito, et al., 1996. *Neurochem. Int.* 29:383–389); (ii) the desmosomal plaque protein desmoplakin (see e.g., Meng, et al., 1997. *J. Biol. Chem.* 272:21495–21503) and (iii) the small heat-shock chaperone B-crystalline (see e.g., Djabali, et al., 1997. *J. Cell Sci.* 110:2759–2769).

Therefore, while it has been previously demonstrated that the actin cytoskeleton is affected in many disease states, quantification of the mechanisms by which altered structure or expression of actin, or of actin-binding proteins, cause specific defects are only now beginning to be elucidated.

(vii) p0071 Protein

The p0071 protein is a member of the Armadillo protein family (GenBank Acc. No. X81889; Hatzfeld & Nachtsheim, 1996. *J. Cell Sci.* 109:2767–2778), which are proteins associated with the cell-cell adherens junctional plaque. These proteins play an important role in cell-cell signaling processes through intercellular junctions. p0071 has been found to be expressed in all tissues thus far examined, and is localized at cell-cell borders and within the desmosomal plaque. p0071 may also be involved in regulating junctional plaque organization and the function of the adherin protein. See e.g., Hatzfeld & Nachtsheim, 1996. *J. Cell Sci.* 109:2767–2778.

The p0071 protein has been shown to be closely related to: (i) the murine p120 protein (a substrate of protein tyrosine kinase receptors) and (ii) the desmosomal band 6-protein (B6P)/plakoglobin. p0071 is a basic protein of 1,211 amino acid residues possessing a central "armadillo" repeat domain which is highly conserved between the p120, B6P/plakoglobin, and p0071 proteins. Desmosomal and adherens junction plaque proteins (e.g., plakoglobin) have been shown to exhibit remarkable efficiency in suppressing tumorigenesis. See e.g., Simcha, et al., 1996. *J. Cell. Biol.* 133:199–209.

In accord, p0071 has been implicated in cell-cell signaling, and thus, tissue-specific differentiation and development, as well as in tumorigenesis and metastatic dissemination of neoplastic tissue.

(B) Proteins Involved in Signal Transduction

In the present invention, three proteins, involved in signal transduction, are disclosed which were found to interact with Nlk1 protein. These proteins are: 14-3-3ε, TrkA and protein phosphatase-1α. In addition, the novel protein IP-3, an ubiquitin-hydroxylase homolog, may also be implicated in similar physiological processes.

(i) 14-3-3ε

The highly conserved and ubiquitously expressed eukaryotic 14-3-3 family of proteins have been found to modulate a wide variety of cellular processes. Human 14-3-3ε (GenBank Acc. No. U28936; Conklin, et al., 1995. *Proc. Natl. Acad. Sci. USA* 92:7892–7896) is an acidic, 30 Kdal isoform within 14-3-3 protein family. The 14-3-3 proteins are specific, phosphoserine-binding proteins (see e.g., Muslin, et al., 1996. *Cell* 84:889–897) which possess a highly conserved carboxyl-terminal domain (helices 7 and 8) through which the 14-3-3 proteins bind target proteins (see e.g., Ichimura, et al., 1997. *FEBS Lett.* 413:273–276).

The 14-3-3 family of proteins associate with a range of cellular or viral polypeptides which are involved in signal transduction, cell-cycle regulation and/or oncogenesis. See e.g., Aitken 1995. *Trends Biochem. Sci.* 20:95–97. 14-3-3 proteins have been demonstrated to interact with a wide variety of cellular proteins, including, but not limited to: (i) the serine/threonine protein kinase Raf-1 (see e.g., Zhang, et al., 1997. *J. Biol. Chem.* 272:13717–13724; Michaud, et al., 1995. *MoL Cell. Biol.*15:3390–3397); (ii) Bcr kinase (see e.g., Braselman & McCormick 1995. *EMBO J.* 14:4839–4848); (iii) protein kinase C (see e.g., Wheeler-Jones, et al., 1996. *Biochem. J.* 315:41–47) and phosphatidylinositol 3-kinase (see e.g. Bonnefoy-Berard, et al., 1995. *Proc. Natl. Acad. Sci. USA* 92:10142–10146), implicating 14-3-3 proteins in intracellular signal transduction and growth regulation.

For example, the 14-3-3 family of proteins may act as "adapter" proteins which modulate interactions between the components of signal transduction pathways; wherein the phosphorylation of the 14-3-3 proteins and/or their binding partners, may regulate these interactions. See e.g., Dubois, et al., 1997. *J. Protein Chem.* 16:513–522. 14-3-3 proteins are also known to interact with cdc25 phosphatase, which in turn activates the CDK proteins, which serve a critical function in cell-cycle progression. See e.g., Conklin, et al., 1995. *Proc. Natl. Acad. Sci. USA* 92:7892–7896. Furthermore, they interact with phosphorylated tryptophan hydroxylase in brain, thus implicating 14-3-3 proteins in serotonin biosynthesis and its role in neurological disorders and psychosis. See e.g., Banik, et al., 1997. *J. Biol Chem.* 272:26219–26225. The 14-3-3 family of proteins (including 14-3-3ε) are localized in the centrosome and spindle apparatus, and may function to "link" mitogenic signaling, the cell-cycle and the centrosome duplication cycle. This intracellular localization is particularly interesting due to a recent experimental finding which links Nlk1 protein to the centrosome cycle. See e.g., Fry & Nigg, 1998. *EMBO J.* 18:179–186; Section 2(A), subsections i-vii, supra. More specifically, the 14-3-3ε protein has been shown to interact with the central domain of the insulin receptor substrate (IRS-1) and with phosposerine residues contained within the carboxyl-terminus of the insulin-like growth factor I receptor (IGFIR). See e.g., Craparo, et al., 1997. *J. Biol. Chem.* 272:11663–11669; Furlanetto, et al., 1997. *Biochem. J.* 327:765–771. Therefore, 14-3-3ε may function to regulate insulin signaling. See e.g., Ogihara, et al., 1997. *J. Biol. Chem.* 272:25267–25274.

Positionally, the 14-3-3ε protein lies telometric to the Lis1 gene on chromosome 17p13.3 outside the Miller-Dieker syndrome chromosome region. See e.g. Chong, et al., 1996. *Genome Res.* 6:735–741. This chromosomal region is often associated with small deletions or translocations in a human developmental disease called isolated lissencephaly sequence disorder. See Hirotsune, et al., 1997. *Genome Res.* 7:625–634. Furthermore, this is a chromosomal region which is frequently deleted in several types of cancer, and thus, 14-3-3ε may putatively function in a tumor suppressor capacity. For example, 14-3-3 proteins are expressed within lung cancer cells. See e.g., Setoguchi, et al., 1995. *Hum. Anti. Hybrid.* 6:137–144). The 14-3-3 proteins have also been demonstrated to be present in Alzheimer's Disease neurofibrillary tangles. These proteins putatively affect MAP kinase signaling, resulting in tau protein hyperphosphorylation, which in turn leads to the formation of the paired, helical filaments seen in the brains of individuals with Alzheimer's Disease. See e.g., Layfield, et al., 1996. *Neurosci. Lett.* 209:57–60. Similarly, 14-3-3 proteins have been identified within the cerebrospinal fluid of patients with Creutzfeldt-Jakob disease. See e.g., Rosenmann, et al., 1997. *Neurol.* 49:593–595.

Therefore, in conclusion, the 14-3-3 family of proteins are strongly implicated in various pathological disorders which include, but are not limited to, tumorigenesis and neurodegenerative disorders.

(ii) The Trk Oncogene (TrkA)

The human Trk oncogene (also known as the nerve growth factor receptor (TrkA); GenBank Acc. No. X03541; Martin-Zanca, et al., 1986. *Nature* 319:743–748)) belongs to the Trk family of tyrosine-protein kinases which function as signaling receptors that mediate the biological properties of the nerve growth factor (NGF) family of neutrophins. See e.g., Kaplan & Miller, 1997. *Curr. Op. Cell. Biol.* 9:213–221; Barbacid, 1995. *Curr. Op. Cell. Biol.* 7:148–155. TrkA, a protein of 641 amino acid residues, was initially isolated as a transforming oncogene in which most of the extracellular receptor domain is replaced by the coding sequence (i.e., the first 221 amino acid residues) of a tropomyosin-encoding gene. TrkA is primarily expressed in neuronal cells and mediates neurogenesis and survival of neurons. In addition, Trk receptors are implicated in the survival, differentiation, and growth of certain neurons and tumors of the nervous system. See e.g., Lucarelli, et al., 1995. *J. Biol. Chen.* 270:24725–24731. For example, human neuroblastoma (NB) cell lines have been shown to constitutively express low levels of TrkA mRNA, and such expression is associated with a favorable prognosis. See e.g., Tanaka, et al., 1995. *Cancer* 76:1086–1095.

Experimental evidence has demonstrated that the interaction of NGF with TrkA requires multiple contact sites involving at least five different domains of NGF. Additionally, phosphorylation of TrkA appears to be critical for the survival of neurons dependent upon NGF. See e.g., Nobes, et al., 1996. *Neurosci.* 70:1067–1079. In rodent models of diabetes there are marked deficits in the expression of NGF and its receptor TrkA. This deficient neurotrophic support generally leads to diabetic neuropathy. See e.g., Tomlinson, et al., 1996. *Philos. Trans. R. Soc. Lond. B Biol. Sc.* 351:455–462. In addition to their neurotrophic actions, NGF has been shown to exert specific effects on cells of the immune system, and TrkA has been found within cells of the immune system. See e.g., Burgi, et al., 1996. *J. Immunol.* 157:5582–5588; Ehrhard, et al., 1993. *Proc. Natl. Acad. Sci. USA* 90:5423–5427.

Other TrkA substrates include, but are not limited to: (i) phospholipase C (see e.g., Kaplan & Stephens, 1994. *J. Neurobiol.* 25:1404–1417); (ii) PI-3 kinase (see e.g., Holgado-Madruga, et al., 1997. *Proc. Natl. Acad. Sci. U.S.A.* 94:12419–12424); (iii) the adapter protein Shc (see e.g., Thomas & Bradshaw, 1997. *J. Biol. Chen.* 272:22293–22299); (iv) phosphotyrosine phosphatase SHP-2 (see e.g., Goldsmith & Koizumi, 1997. *J. Neurochem.* 69:1014–1019); (v) Ras GTPase activating protein (see e.g., Mattingly, et al., 1994. *Mol. Cell. Biol.* 14:7943–7952) and (vi) the mitogen-activated protein kinase ERKI (see e.g., Althaus, et al., 1997. *J. Neurosci. Res.* 50:729–742). It should be noted that most of these aforementioned proteins interact with different, conserved tyrosine residues within the carboxyl-terminal domain of TrkA (see e.g., Stephens, et al., 1994. *Neuron* 12:691–705; Obermeier, et al., 1994. *EMBO J.* 13:1585–1590), thus linking TrkA to several intracellular signaling pathways.

With respect to neuronal tissue, TrkA activity has been demonstrated to inhibit cell growth and neuritogenesis in PC12 pheochromocytoma and neuroblastoma cells (see e.g., Matsushima & Bogenmann, 1993. *Mol. Cell. Biol.* 13:7447–7456), wherein high expression of TrkA correlates with a generally favorable prognosis (see e.g., Hoehner, et al., 1995. *Am. J. Path.* 147:102–113). Similarly, NGF-stimulated TrkA activity also induced cellular apoptosis within 24 hours within medulloblastoma cells. See e.g., Muragaki, et al., 1997. *J. Neurosci.* 17:530–542. In Alzheimer disease, the number of neurons which express TrkA are markedly decreased in the nucleus basalis of Meynert as a consequence of cholinergic neuronal loss. See e.g., Boissiere, et al., 1996. *Mol. Chem. Neuropathol.* 28:219–223.

In addition to its presence in neuronal tissue, TrkA has also been demonstrated in a wide range of non-neuronal tissues. TrkA was originally identified in a colon carcinoma (see e.g., Mitra, et al., 1991 *Oncogene* 6:2237–2241), and subsequently, this transforming oncogene has been detected at various levels in all tissues examined thus far, except for the heart and liver (see e.g., Shibayama & Koizumi, 1996. *Am. J. Pathol.* 148:1807–1818). For example, mutations within the TrkA oncogene are frequently found in human thyroid tumors (see e.g., Salvatore, et al., 1996. *Eur. J. Endocrinol.* 134:177–183) and TrkA has also implicated in the transformation of the human melanoma cell line XP44RO (see e.g., Lafarge-Frayssinet, et al., 1995. *Anticancer Res.* 15:1205–1213).

Hence, the TrkA transforming oncogene has been implicated in the physiological processes of cell growth, survival and apoptosis, neurogenesis, neuritogenesis, immune system, secretion, and intracellular signal transduction. In addition, it has also been implicated in the pathophysiology of tumorigenesis, metastatic spread, Alzheimer's disease and neurodegeneration, diabetes, and disorders of the immune system.

(iii) Protein Phosphatase 1α (PP1α)

Protein phosphatase 1a (PPla; GenBank Acc. No. M63960; Song, et al., 1993. *Gene* 129:291–295) is a 330 amino acid residue, serine/threonine-specific, protein phosphatase which affect a wide variety of important signal transduction processes, including cell-cycle progression, T-cell activation and neurotransmitter receptor activity.

An isoform of PPla has been shown to associate with retinoblastoma protein during the M to G1 transition. See e.g., Durfee, et al., 1993. *Genes Dev.* 7:555–569. Additionally, PP1α interacts with the cellular oncogene Hox11 (an orphan homeobox gene which controls the genesis of the spleen and liver) which was originally isolated from a chromosomal breakpoint in human T-cell leukemia. Hox11 targets both PP1α and PP2α, which in turn are targets for oncogenic viruses and chemical tumor promoters. See e.g., Kawabe, et al., 1997. *Nature* 385:454–458. It has been hypothesized that inhibition of PP1α and PP2α by Hox 11 abrogates a G2 checkpoint, thus promoting genomic instability and oncogenesis. Similarly, in fission yeast, PP1α-like phosphatases have been shown to inhibit the cell-cycle protein p34cdc2/cyclin kinase and thereby negatively-regulate entry into mitosis. See e.g. Yanagida, et al., 1992. *Ciba Found. Symp.* 170:130–140.

PP1α is regulated by several inhibitory proteins (e.g., the dopamine- and cAMP-regulated phosphoprotein (DARPP-32); PPI-inhibitor-1; PPI-inhibitor-2 and the like) which inhibit by binding to the catalytic domain (amino acid residues 7–300). The protein is also inhibited by various toxins and tumor promoters (e.g., clayculin A, okadaic acid, dinophysitoxin 1, microcystin, nodularin, tautomycin and cantharidic acid) by interacting at a common inhibitor site on PP1α. See e.g., Huang, et al., 1997. *Proc. Natl. Acad. Sci. USA* 94:3530–3535; Fujiki & Sugamura, 1993. *Adv. Cancer Res.* 61:143–194).

The nuclear translocation of PP1α has also been implicated in monocyte differentiation (see e.g., Omay, et al., 1995. *Cancer Res.* 55:774–780), probably by effecting the relocation of associated proteins. Nuclear translocation has also been associated with a malignant phenotype in hepatomas. See e.g., Saadat, et al, 1995. *Cancer Lett.* 94:165–170. The inhibition of PP1α, which is expressed in high levels within mammalian brain, has been associated with the stimulated secretion of the Alzheimer amyloid precursor protein (APP), thus diverting the processing of APP to non-amyloidogenic production of the large extracellular domain APPS. The aberrant processing of the Alzheimer amyloid precursor protein, and its amyloidogenic A-β, fragment, is thought to be centrally involved in Alzheimer's disease See e.g., de Cruz e Silva, et al., 1995. *Mol. Med.* 1:535–541.

In addition, the catalytic subunit of rabbit muscle PP1α has been found to bind to the glycolytic enzyme muscle phosphofructokinase (see e.g., Zhao & Lee, 1997. *Biochem.* 36:8318–8324) indicating that PP1α can control glycolytic flux by protein phosphorylation and/or dephosphorylation. Interestingly, in addition to the glycogen-bound form of PP1α, a myosin-bound form of PP1α exist in skeletal and cardiac muscles which dephosphorylates myosin and the PP1α catalytic subunit has been shown to be highly enriched in isolated rat postsynaptic densities. See e.g., Chisholm & Cohen, 1988. *Biochem. Biophys. Acta* 971:163–169.

Four major rat brain PP1αα-binding proteins (with molecular weights of 216, 175, 134, 75 Kdal) have been characterized. See e.g., Colbran, et al., 1997. *J. Neurochem.* 69:920–929. As disclosed herein by the present invention, the dephosphorylation of rabbit brain tryptophan hydroxylase by PP1α can be inhibited by 14-3-3 proteins. See Section 2(B).

Therefore, in conclusion, PP1α has been implicated in pathological disorders including, but not limited to, tumorigenesis, neurodegenerative disorders, and metabolic disorders.

(iv) IP-3 Protein

IP-3 is a novel protein which has been shown to possess homology to ubiquitin-specific hydrolases. Therefore, IP-3 putatively encodes a protein which belongs to the ubiquitination/deubiquitination system which controls the degradation of many cellular proteins. See e.g., Kalderon, 1996. *Curr. Biol.* 6:662–665. The ubiquitinated proteins were initially found within neurons in several major human neurodegenerative diseases (e.g. Alzheimer's disease, diffuse Lewy body disease, motor neuron disease and the like). See e.g. Mayer, et al., 1991. *Acta Biol. Hung.* 42:21–26. There is also more recent evidence regarding a putative role for the members of the ubiquitin hydrolase family playing a role in oncogenesis. See e.g., Swanson, et al., 1996. *Hum. Mol. Genet.* 5:533–538. Specifically, ubiquitin carboxyl-terminal hydrolase MRNA was detected in a tumor-derived neuroblastoma cell line (Neuro-2a), in non-neuronal, acute lymphoblastic leukemia (see e.g., Maki, et al., 1997. *Biotech. Histochem.* 72(1):38–44), in undifferentiated embryonic neoplasms (e.g., primitive neuroectodermal tumors, medulloblastomas and in oat cell carcinomas of the lung; see e.g., Ermisch & Schwechheimer, 1995. *Clin. Neuropathol.* 14(3): 130–136). Accordingly, the presence of this protein could be utilized as a sensitive marker of these aforementioned tumor groups.

(C) DNA-Binding Proteins

As previously discussed, the Nlk1 protein is involved in chromosomal condensation. See Section 2(A). In the present invention, one DNA-binding protein was demonstrated to interact with Nlk1 protein—the integrase interactor 1 protein. However, recent experimental evidence has also shown a putative interaction of the Nlk1 protein with the newly discovered human nuclear protein HEC (see PCT Publication WO 98/27994).

(i) Integrase Interactor 1 Protein (Ini-1)

The integrase interactor 1 (Ini-1) cellular protein has been found to interact with, and activate human immunodeficiency virus (HIV-1) integrase. Ini-1, the human homolog to the yeast transcription faction SNF5 (see e.g., Kalpana, et al., 1994. *Science* 266:2002–2006), is part of a protein complex which is thought to alter nucleosomal structure and thus, influence the selection of site(s) for HIV-1 genomic integration. See e.g., Miller & Bushman, 1995. *Curr. Biol.* 5:368–370.

The early stages of HIV-1 replication involve reverse transcription of the viral RNA and integration of the resulting cDNA into the host genome. HIV-1 cDNA integration requires the binding of the human DNA prior to the connection of the viral and host DNAs. See e.g., Miller, et al., 1995. *Curr. Biol.* 5:1047–1056. Recent evidence suggests that the retroviral integrase protein Ini-1 functions as a nuclear factor which promotes the targeting and insertion of the viral DNA into host chromosomal targets. Conserved domains of Ini-1 (i.e., amino acid residues 220–270) are critical for the host DNA-binding and integration of the retroviral cDNA. See e.g., Drelich, et al., 1993. *J. Virol.* 67:5041–5044; Eijkelenboom, et al., 1995. *Nat. Struct. Biol.* 2:807–810. As the integration of viral DNA into the human genome is required for replication of HIV-1, Ini-1 is logical target for anti-retroviral strategies.

Ini-1 has also been shown to interact with the nuclear antigen 2, a viral nuclear protein expressed in latently infected B lymphocytes essential to the immortalization of B cells by the Epstein-Barr virus (EBV). See e.g., Wu, et al., 1996. *J. Virol.* 70:6020–6028. Thus, Ini-1 is also strongly implicated in the process of DNA viral infection.

As previously stated, the newly discovered human nuclear protein HEC (see PCT Publication WO 98/27994)HEC is believed to interact with other proteins which serve an important role in mitosis (e.g., Nlk1, sb1.8 and the like) through a leucine heptad repeat domain. HEC appears to be important in chromosomal segregation during M phase, as the highest levels of expression were found in rapidly-dividing cells (e.g., neoplastic cells) were it was localized to centromere during mitosis. Additionally, HEC inactivation was demonstrated to result in disordered sister chromatid alignment and separation.

SUMMARY OF THE INVENTION

In brief, the Nlk1 protein has been demonstrated to form complexes, which heretofore have not been described, with the following cellular proteins: TrkA, protein phosphatase 1α, 14-3-3ε, α tropomyosin, vimentin, p0071, Ini-1, IP-1, IP-2, IP-3, IP-4 and IP-5. In genes which encode the IP-1, IP-2, IP-3, IP-4 and IP-5 proteins have not been previously described.

The present invention discloses herein compositions and methodologies for the production of protein complexes comprised of the Nlk1 protein and various other proteins which interact with (i.e., bind to) said Nlk1 protein. The proteins which have been demonstrated to form complexes with the Nlk1 protein will be designated hereinafter as "Nlk1 protein-IP" for Nlk1 protein interacting protein; whereas a complex of the Nlk1 protein and a Nlk1 protein-IP will hereinafter be designated as "Nlk1 protein•Nlk1 protein-IP".

More specifically, the present invention relates to complexes of the Nlk1 protein, and derivatives, fragments and analogs thereof, with the following cellular proteins:
(i) TrkA; (ii) protein phosphatase 1α; (iii) 14-3-3ε; (iv) α tropomyosin; (v) vimentin; (vi) p0071; (vii) Ini-1; (viii) IP-1; (ix) IP-2; (x) IP-3; (xi) IP-4 and (xii) IP-5, as well as their derivatives, analogs and fragments.

Methods of production of the Nlk1 protein•Nlk1 protein-IP complexes, and derivatives and analogs of these aforementioned proteins and protein complexes by, for example, recombinant means, will also be disclosed herein. Various pharmaceutical compositions relating to the Nlk1 protein:Nlk1 protein-IPs, Nlk1 protein•Nlk1 protein-IP complexes, and derivatives, fragments and analog thereof, will also be disclosed by the present invention.

The present invention will further provide methodologies for the modulation (i.e., inhibiting or enhancing) of the activity of the Nlk1 protein•Nlk1 protein-IP complexes, particularly: the following complexes: Nlk1 protein•TrkA; Nlk1 protein•α tropomyosin; Nlk1 protein•vimentin; Nlk1 protein•p0071; Nlk1 protein•protein phosphatase 1α; Nlk1 protein•14-3-3ε; Nlk1 protein•Ini-1; Nlk1 protein•IP-1; Nlk1 protein•IP-2; Nlk1 protein•IP-3; Nlk1 protein•IP-4 and Nlk1 protein•IP-5. The protein components of these aforementioned complexes have been implicated in a plethora of cellular and physiological processes, including, but not limited to: (i) control of cell-cycle progression; (ii) cellular differentiation and apoptosis; (iii) regulation of transcription; (iv) control of intracellular signal transduction and (v) pathological processes including, but not restricted to, hyperproliferative disorders (e.g., tumorigenesis and tumor progression); neurodegenerative diseases; cardiovascular disease; metabolic diseases and viral infections.

Accordingly, the present invention provides methodologies for the screening of Nlk1 protein•Nlk1 protein-IP complexes, particularly complexes of the Nlk1 protein with TrkA, protein phosphatase 1α, 14-3-3ε, α tropomyosin, vimentin, p0071, Ini-1, IP-1, IP-2, IP-3, IP-4 and IP-5, as well as derivatives, fragments and analogs thereof, for the ability to modulate or alter cell functions, particularly those cell functions in which Nlk1 protein and/or a Nlk1 protein-IP has been implicated including, but not limited to: control of cell-cycle progression; cellular differentiation and apoptosis; regulation of transcription; control of intracellular signal transduction; and pathological processes including, but not restricted to, hyperproliferative disorders (e.g., tumorigenesis and tumor progression); neurodegenerative diseases; cardiovascular disease; metabolic diseases viral infections.

The present invention further relates to therapeutic and prophylactic, as well as diagnostic, prognostic and screening methodologies and pharmaceutical compositions which are based upon Nlk1 protein•Nlk1 protein-IP complexes (and the nucleic acids encoding the individual proteins constituents which participate in the complexes). Therapeutic compounds of the invention include, but are not limited to: (i) Nlk1 protein•Nlk1 protein-IP complexes, and complexes where one or both members of the complex is a derivative, fragment or analog of the Nlk1 protein or a Nlk1 protein-IP; (ii) antibodies to, and nucleic acids encoding the foregoing and (iii) antisense nucleic acids to the nucleotide sequences encoding the various protein complex components. Diagnostic, prognostic and screening kits will also be provided.

Animal models and methodologies of screening for various modulatory agents (i.e., agonists, antagonists and inhibitors) of the activity of the Nlk1 protein:Nlk1 protein-IPs and Nlk1 protein•Nlk1 protein-IP complexes, are also disclosed herein.

Methodologies for the identification of molecules which inhibit, or alternatively, which increase the formation/synthesis of the Nlk1 protein:Nlk1 protein-IPs and Nlk1 protein•Nlk1 protein-IP complexes will also be provided by the present invention.

BRIEF DESCRIPTION OF THE FIGURES

In order that the present invention disclosed herein is better understood and appreciated, the following detailed description is set forth.

FIG. 1: The nucleotide sequence of the Nlk1 protein (GenBank Accession No. U11050)(SEQ ID NO:1) and the associated inferred amino acid sequence (SEQ ID NO:2). A bait fragment, comprised of nucleotides 1089–1472 (indicated in bold), was utilized in the modified yeast two hybrid assay system in Section 6, infra.

FIG. 2: The nucleotide sequence (SEQ ID NO:3) and the associated inferred amino acid sequence (SEQ ID NO:4) of the Trk oncogene (TrkA) (GenBank Accession No. X03541). The underlined nucleotides indicate the 5'-terminus start sites of the identified prey sequences, utilized in the modified yeast two hybrid assay system, which occur at nucleotides 176, 182, 200, 224 and 230 (amino acid residues 1–641).

FIG. 3: The nucleotide sequence (SEQ ID NO:5) and the associated inferred amino acid sequence (SEQ ID NO:6) of protein phosphatase-1α (GenBank Accession No. M63960). The arrows indicate the 5'-start sites of identified prey sequences, utilized in the modified yeast two hybrid assay system, which occur at nucleotides 30, 33, 36, 48, 93, 96 and 150 (amino acid residues 1, 2, 3, 7, 22, 23, or 41 to 330). In addition, the first amino acid residue of the interacting domain is underlined.

FIG. 4: The nucleotide sequence (SEQ ID NO:7) and associated inferred amino acid sequence (SEQ ID NO:8) of the 14-3-3ε protein (GenBank Accession No. U28936). The arrows indicate the 5'-start sites of identified prey sequences, utilized in the modified yeast two hybrid assay system, which occur at nucleotides 214, 223 and 427 (amino acid residues 72, 75 and 143 to 263). In addition, the first amino acid of the interacting domain is underlined.

FIG. 5: The nucleotide sequence (SEQ ID NO:9) and associated inferred amino acid sequence (SEQ ID NO:10) of the α-tropomyosin protein (GenBank Accession No. M19713). The prey sequence, utilized in the modified yeast two hybrid assay system, begins at nucleotide 535 (amino acid residues 161–347) and is indicated by an arrow. In addition, the first amino acid residue of the interacting domain is underlined.

FIG. 6: The nucleotide sequence (SEQ ID NO:11) and associated inferred amino acid sequence (SEQ ID NO:12) of the vimentin protein (GenBank Accession No. X56134). The prey sequence, utilized in the modified yeast two hybrid assay system, begins at nucleotide 581 (amino acid residues 180–466) and is indicated by an arrow. In addition, the first amino acid of the interacting domain is underlined.

FIG. 7: The nucleotide sequence (SEQ ID NO:13) and associated inferred amino acid sequence ((SEQ ID NO:14) of the p0071 protein (GenBank Accession No. X81889). The prey sequence, utilized in the modified yeast two hybrid assay system, begins at nucleotides 708 and 711 (amino acid residues 189 and 190, respectively, up to amino acid residue 1208) and is indicated by arrows. In addition, the first amino acid of the interacting domain is underlined.

FIG. 8: The nucleotide acid sequence (SEQ ID NO:15) and associated inferred amino acid sequence (SEQ ID NO:16) of the integrase interactor 1 protein (Ini-1) (GenBank Accession No. U04847). The prey sequence, utilized in the modified yeast two hybrid assay system, begins at nucleotide 289 (amino acid 74–385) and is indicated by an arrow); the first amino acid of the interacting domain is underlined.

FIG. 9: The nucleotide sequence (SEQ ID NO:17) and associated inferred amino acid sequence (SEQ ID NO:18) of the IP-1 protein (EST cg30153.g5). The prey sequence, utilized in the modified yeast two hybrid assay system, begins at nucleotide 1 (shown by arrow). The sequence does not include an initiation codon, and therefore the residue at amino acid position 1 is denoted in bold, thus indicating that the sequence must be extended in the direction of the amino-terminus. Additionally, the sequence does not have a stop codon. The open reading frame (ORF), comprising nucleotides 1–364, encodes the core-portion of protein possessing homology to proteins which are associated with the cellular cytoskeleton.

FIG. 10: The nucleotide sequence (SEQ ID NO:19) and associated inferred amino acid sequence (SEQ ID NO:20) of the IP-2 protein (GenBank Accession No. AA143467). The prey sequence, utilized in the modified yeast two hybrid assay system, begins at nucleotide 31 and is indicated by an arrow. The open reading frame (ORF) of IP-2, comprising nucleotides 2–346, encodes a protein of 115 amino acid residues with homology to α-tropomyosin. Note, that no methionine start codon was found and thus, an extension to the 5'-terminus indicated in bold.

FIG. 11 The nucleotide sequence (SEQ ID NO:21), comprising a total of 941 nucleotides, and associated inferred amino acid sequence (SEQ ID NO:22) of the IP-3 protein. The prey, utilized in the modified yeast two hybrid assay system, utilized in the modified yeast two hybrid assay system, begins at nucleotide 514 and is indicated by an arrow. The nucleic acid sequence of the EST H67985 sequence is shown in bold lettering (nucleotides 269–701), EST AA255861 (nucleotides 1–429 of the assembled EST) is shown in italics and EST AA251528 is denoted by underline starting at nucleotide 524 of the assembled expressed sequence. An open reading frame (ORF) could be translated from nucleotide 67 to 939, comprising a total of 291 amino acid residues. It should be noted that the sequence does not have a stop codon and thus, represents the amino-terminal region of a protein possessing homology to ubiquitin carboxyl-terminal hydrolases.

FIG. 12: The nucleotide sequence (SEQ ID NO:23), comprising a total of 542 nucleotides, and associated inferred amino acid sequence (SEQ ID NO:24) of the IP-4 protein. Nucleotides 1–70 of cg50648e3 were extended at the 3'-terminus with nucleotides 1–472 of EST M62042 (GenBank Accession No. M62042). The prey sequences, utilized in the modified yeast two hybrid assay system, begin at nucleotides 1, 4, 40, 44, 54 and 65 and are indicated by arrows. It should be noted that the sequence does not include an initiation codon, and therefore the Arg residue at amino acid residue 1 is denoted in bold and indicates that the sequence must be extended in the direction of the amino-terminus. The open reading frame (ORF) from nucleotide 2 to 213 (comprising a total of 71 amino acids) encodes the carboxyl-terminal region of a protein possessing homology to the collagen family of proteins.

FIG. 13: The nucleotide sequence (SEQ ID NO:25), comprising a total of 441 nucleotides, and associated inferred amino acid sequence (SEQ ID NO:26) of the IP-5 protein. The prey sequence, utilized in the modified yeast two hybrid assay system, begins at nucleotide 1. It should be noted that the sequence does not include an initiation codon, and therefore the Thr amino acid residue at amino acid position 1 is denoted in bold and indicates that the sequence must be extended in the direction of the amino-terminus. The open reading frame (ORF) from nucleotides 1–246 encodes the carboxyl-terminal region of a protein possessing homology to tropomyosin and myosin.

FIG. 14: Matrix of the results of the modified yeast two hybrid system assays. The results of assays using the bait Nlk1 protein are indicated above the columns; whereas prey proteins comprised of: TrkA, protein phosphatase 1α, 14-3-3ε, α-tropomyosin, vimentin, p0071, Ini-1, IP-1, IP-2, IP-3, IP-4, IP-5, and CDK2 are indicated to the left of the rows. A positive interaction for a bait and prey protein is indicated as "+" within the box forming the intersection between the particular bait and prey proteins; whereas a "−" indicates the growth of yeast expressing vector, but no interaction with the Nlk1 protein.

Table 1: Overview of all Nlk1 protein interactants (Nlk1 protein-IPs) found in the modified yeast two hybrid assay system screening. In column one, the Nlk1 protein interactant (Nlk1 protein-IP) and its GenBank Accession Number (if available) is listed. In column 2, a brief description of the (putative) function and suggested utility is provided. In column 3, the nucleotides where the open reading frame (ORF) begin (start) and end (stop) are indicated, along with the total number of nucleotides in the case of expressed sequences. In column 4, the first nucleotide ("start") of the interacting domains is given. In column 5, the number of isolates obtained for the corresponding fragment found to interact with the Nlk1 protein in the two-hybrid screen is indicated. Column 6 shows the open reading frame (ORF) of the respective protein. Column 7 refers to the specific (SEQ ID NO:, and finally, column 8 illustrates the expressed sequences which were utilized for the assembly of the corresponding sequence.

DETAILED DESCRIPTION OF THE INVENTION

The present invention is based upon the identification of proteins which have been demonstrated to interact with the Nlk1 protein (hereinafter referred to as "Nlk1 protein-Ps") using an improved, modified form of the yeast two hybrid system. The following proteins (Nlk1 protein-IPs were found to form complexes under physiological conditions with the Nlk1 protein: (i) TrkA; (ii) protein phosphatase 1α; (iii) 14-3-3ε; (iv) α-tropomyosin; (v) vimentin; (vi) p0071; (vii) Ini-1; (viii) IP-1; (ix) IP-2; (x) IP-3; (xi) IP-4 and (xii) IP-5. Complexes of the Nlk1 protein with a Nlk1 protein-IP are hereinafter referred to as "Nlk1 protein•Nlk1 protein-IP" complexes. Nlk1 protein•Nlk1 protein-IP complexes are implicated in the modulation of functional activities of the Nlk1 protein and its binding partners (Nlk1 protein-IPs). Such functional activities include, but are not limited to: (i) control of cell-cycle progression (e.g., cellular differentiation and apoptosis); (ii) regulation of transcription; (iii) control of intracellular signal transduction and (iv) pathological processes including, but not restricted to, hyperproliferative disorders (e.g., tumorigenesis and tumor progression), neurodegenerative diseases, cardiovascular disease, metabolic diseases and viral infections.

The present invention, through utilization of an improved, modified form of the yeast two hybrid system, has identified novel proteins, encoded by the IP-1, IP-3, IP-4 and IP-5 nucleotide sequences. Accordingly, the invention further relates to nucleotide sequences IP-1, IP-3, IP-4, and IP-5 (preferably, the human IP-1, IP-3, IP-4, and IP-5 genes) and homologs of other species, as well as derivatives, fragments and analogs thereof. Nucleic acids which are able to hybridize to, or are complementary to, the aforementioned nucleotide sequence (e.g., the inverse complement) of the foregoing sequences are also provided. More specifically, the present invention discloses nucleic acids which comprise, are hybridizable (e.g., the inverse complement) or which are complementary to, at least a 5, 10 or 25 nucleotide region of the IP-1, IP-3, IP-4, and IP-5 nucleotide sequences.

The present invention also relates to IP-1, IP-3, IP-4 and IP-5 derivatives, fragments and analogs which are functionally active (i.e., they are capable of displaying one or more known functional activities of a wild-type IP-1, IP-3, IP-4 and IP-5 protein. Such functional activities include, but are not limited to: (i)the ability to bind with, or compete for binding with the Nlk1 protein; (ii) antigenicity (the ability to bind, or compete with, IP-1, IP-3, IP-4 and IP-5 for binding to an anti-IP-1, anti-IP-3, anti-IP-4 and anti-IP-5 antibody, respectively) and (iii) immunogenicity (the ability to generate an antibody which binds IP-1, IP-3, IP-4 and IP-5, respectively).

The present invention further discloses methodologies of screening for proteins which interact with (e.g., bind to) the Nlk1 protein. The invention also relates to Nlk1 protein complexes, in particular the Nlk1 protein complexed with one of the following proteins: TrkA, protein phosphatase 1α, 14-3-3ε, α-tropomyosin, vimentin, p0071, Ini-1, IP-1, IP-2, IP-3, IP-4 and IP-5. The invention further discloses complexes of the Nlk1 protein, or derivatives, analogs and fragments of the Nlk1 protein with TrkA, protein phosphatase 1α, 14-3-3ε, α-tropomyosin, vimentin, p0071, Ini-1, IP-1, IP-2, IP-3, IP-4 and IP-5, or derivatives, analogs and fragments thereof. In a preferred embodiment, such complexes bind an anti-Nlk1 protein•Nlk1 protein-IP complex antibody. In another specific embodiment, complexes of human Nlk1 protein with human proteins are disclosed.

The present invention also provides methodologies for the production and/or isolation of Nlk1 protein•Nlk1 protein-IP complexes. In a specific embodiment, the present invention provides methodologies of using recombinant DNA techniques to express both the Nlk1 protein and its binding partner (Nlk1 protein-IP), or fragments, derivatives or homologs of one or both members of the complex; wherein either both binding partners are under the control of one heterologous promoter (ie. a promoter which is not naturally associated with the native gene encoding the particular complex component) or where each is under the control of a separate heterologous promoter.

Methodologies of diagnosis, prognosis, and screening for diseases and disorders associated with aberrant levels of Nlk1 protein•Nlk1 protein-IP complexes are discloses. The present invention also provides methodologies for the treatment and prevention of diseases or disorders which are associated with aberrant levels of Nlk1 protein•Nlk1 protein-IP complexes, or aberrant levels or activity of one or more of the components of a Nlk1 protein•Nlk1 protein-IP complex, by the administration of Nlk1 protein•Nlk1 protein-IP complexes, or modulators of Nlk1 protein••Nlk1 protein-IP complex formation or activity (eg., antibodies which bind the Nlk1 protein•Nlk1 protein-IP complex, or non-complexed Nlk1 protein, or its binding partner (Nlk1 protein-IP), or a fragment thereof. Preferably, the aforementioned fragment contains: (i) the portion of the Nlk1 protein or the Nlk1 protein-IP which is directly involved in complex formation; (ii) mutants of the Nlk1 protein or the Nlk1 protein-IP which increase or decrease binding affinity; (iii) small molecule inhibitors/enhancers of complex formation; (iv) antibodies that either stabilize or neutralize the complex, and the like.

Methodologies of assaying Nlk1 protein•Nlk1 protein-IP complexes for biological activity as a therapeutic or diagnostic, as well as methods of screening for Nlk1 protein•Nlk1 protein-IP complex, or modulators thereof (i.e., inhibitors, agonists and antagonists) are also disclosed herein.

For clarity of disclosure and enablement, and not by way of limitation, the detailed description of the invention is divided into the subsections which follow.

(1) The Nlk1 Protein, Nlk1 Protein-IPs and Nlk1 Protein•Nlk1 Protein-IP Complexes The present invention discloses Nlk1 protein•Nlk1 protein-IP complexes and, in particular aspects, complexes of the Nlk1 protein with: TrkA, protein phosphatase 1α, 14-3-3ε, α-tropomyosin, vimentin, p0071, Ini-1, IP-1, IP-2, IP-3, IP-4 and IP-5. In a preferred embodiment, the Nlk1 protein•Nlk1 protein-IP complexes are complexes of human proteins. The present invention also relates to: (i) complexes of derivatives, fragments and analogs of the Nlk1 protein with a Nlk1 protein-IP; (ii) complexes of the Nlk1 protein with derivatives, fragments and analogs of a Nlk1 protein-IP and (iii) complexes of derivatives, fragments and analogs of the Nlk1 protein and a Nlk1 protein-IP. It should be noted that, as used herein, fragment, derivative or analog of a Nlk1 protein•Nlk1 protein-IP complex includes complexes where one or both members of the complex are fragments, derivatives or analogs of the wild-type Nlk1 protein or Nlk1 protein-IP.

Preferably, as disclosed by the present invention, the Nlk1 protein•Nlk1 protein-IP complexes in which one or both members of the complex are a fragment, derivative or analog of the wild-type protein are functionally active Nlk1 protein•Nlk1 protein-IP complexes. In particular aspects, the native proteins, derivatives or analogs of the Nlk1 protein and/or the Nlk1 protein-IPs are of animals (e.g., mouse, rat, pig, cow, dog, monkey, frog); insects (e.g., fly); plants or, most preferably, human. As utilized herein, the term "finctionally active Nlk1 protein•Nlk1 protein-IP complex" refers to species displaying one or more known functional attributes of a full-length Nlk1 protein complexed with a full-length Nlk1 protein-IP (e.g., TrkA, protein phosphatase 1α, 14-3-3ε, α-tropomyosin, vimentin, p0071, Ini-1, IP-1, IP-2, IP-3, IP-4 and IP-5) including, but not exclusive to, the control of cellular and physiological processes, such including, but not limited to: (i) control of cell-cycle progression (e.g., cellular differentiation and apoptosis); (ii) regulation of transcription; (iii) control of intracellular signal transduction and (v) pathological processes including but not limited to, hyperproliferative disorders (eg., tumorigenesis and tumor progression); neurodegenerative diseases; cardiovascular disease; metabolic diseases and viral infections.

In accord, the present invention provides methodologies for the screening of Nlk1 protein•Nlk1 protein-IP complexes, particularly complexes of the Nlk1 protein with: TrkA, protein phosphatase 1α, 14-3-3ε, α-tropomyosin, vimentin, p0071, Ini-1, IP-1, IP-2, IP-3, IP-4 and IP-5, as well as derivatives, fragments and analogs thereof, for the ability to alter and/or modulate cellular functions, particularly those functions in which the Nlk1 protein and/or Nlk1 protein-IP have been implicated. These functions include, but are not limited to: but not limited to: control of cell-cycle progression; regulation of transcription; control of intracellular signal transduction; and pathological processes, as well as various other biological activities (e.g., binding to an anti-Nlk1 protein•Nlk1 protein-IP complex antibody, and the like). The derivatives, fragments or analogs which possess the desired immunogenicity and/or antigenicity may be utilized in immunoassays, for immunization, for inhibition of Nlk1 protein•Nlk1 protein-IP complex activity, etc. For example, derivatives, fragments or analogs which retain, or alternatively lack or inhibit, a given property of interest (e.g., participation in a Nlk1 protein•Nlk1 protein-IP complex) may be utilized as inducers, or inhibitors, respectively, of such a property and its physiological correlates. In a specific embodiment, a Nlk1 protein•Nlk1 protein-IP complex of a fragment of the Nlk1 protein and/or a fragment of Nlk1 protein-IP which can be bound by an anti-Nlk1 protein and/or anti-Nlk1 protein-IP antibody or antibody specific for a Nlk1 protein•Nlk1 protein-IP complex when such a fragment is included within a given Nlk1 protein•Nlk1 protein-IP complex. Derivatives, fragments and analogs of Nlk1 protein•Nlk1 protein-IP complexes may be analyzed for the desired activity or activities by procedures known within the art.

Specific embodiments of the present invention disclose Nlk1 protein•Nlk1 protein-IP complexes comprised of fragments of one or both protein species of the complex. In a preferred embodiment, these aforementioned fragments may consist of, but are not limited to, fragments of: TrkA, protein phosphatase 1α, 14-3-3ε, α-tropomyosin, vimentin, p0071, Ini-1, IP-1, IP-2, IP-3, IP-4 and IP-5, which have previously been identified as interacting with the Nlk1 protein in an improved, modified yeast two hybrid assay. For example, amino acid residues 1–641 of the TrkA protein (depicted in FIG. 2; (SEQ ID NO:4); amino acid residues 1, 2, 3, 7, 22, 23, and 41–330 of protein phosphatase 1α (depicted in FIG. 3; (SEQ ID NO:6); amino acid residues 72, 75 and 143–263 of the 4-3-3ε protein (depicted in FIG. 4; (SEQ ID NO:8); amino acid residue 161–347 of the α-tropomyosin protein (depicted in FIG. 5; (SEQ ID NO:10); amino acid residues 180–466 of the vimentin protein (depicted in FIG. 6; (SEQ ID NO:12); amino acid residues 189, 190–1208 of the p0071 protein (depicted in FIG. 7; (SEQ ID NO:14); amino acid residues 74–385 of the Ini-1 protein (depicted in FIG. 8; (SEQ ID NO:16); at least amino acid residue 1 –122 of the IP-1 protein (depicted in FIG. 9; (SEQ ID NO:18); at least amino acid residues 10–115 of the IP-2 protein, a tropomyosin homolog (depicted in FIG. 10; (SEQ ID NO:20); at least amino acid residues 150–291 of the IP-3 protein, a ubiquitin hydrolase homolog (depicted in FIG. 11; (SEQ ID NO:22); at least amino acid residues 1–71 of the IP-4 protein, a collagen homolog (depicted in FIG. 12; (SEQ ID NO:24) and at least amino acid residues 1–82 of the IP-5 protein (depicted in FIG. 13; (SEQ ID NO:26). In addition, fragments (or proteins comprising fragments) which may lack some or all of the aforementioned regions of either member of the complex, as well as nucleic acids which encode the aforementioned proteins, are also disclosed herein.

The present invention further relates to the IP-1, IP-3, IP-4, and IP-5 proteins, as well as derivatives, fragments, analogs, homologs and paralogs thereof In a preferred embodiment, human IP-1, IP-3, IP-4, and IP-5 genes and/or proteins are disclosed. In a specific embodiments, the derivative, fragment, analog, homolog or paralog has the following attributes: (i) is functionally active (i.e., capable of exhibiting one or more finctional activities associated with full-length, wild-type IP-1, IP-3, IP-4, and IP-5; (ii) possesses the ability to bind the Nlk1 protein; (iii) is immunogenic or (iv) is antigenic.

The nucleotide sequences which encode, as well as the corresponding amino acid sequences of, human Nlk1 protein, TrkA, α-tropomyosin, vimentin, p0071, protein phosphatase 1α; 14-3-3ε and Ini-1 are known (GenBank Accession Nos. U11050; X03541; M63960; U28936; M19713; X56134; X81889 and U04847, respectively), are provided in FIGS. 1–8, respectively and are identified by (SEQ ID NOS:1–16, respectively. In addition, the nucleotide and inferred amino acid sequences of IP-1, IP-2 (GenBank Accession No. AA143467), IP-3, IP-4 and IP-5 are provided in FIGS. 9, 10, 11, 12 , and 13, respectively (SEQ ID NOS:17–26, respectively). Nucleic acids encoding TrkA, α-tropomyosin, vimentin, p0071, protein phosphatase 1α; 14-3-3ε and Ini-1, IP-1, IP-2, IP-3, IP-4 and IP-5 may be obtained by any method known within the art (e.g., by PCR amplification using synthetic primers hybridizable to the 3'- and 5'-termini of the sequence and/or by cloning from a cDNA or genomic library using an oligonucleotide sequence specific for the given gene sequence.

Homologs (i.e., nucleic acids encoding the aforementioned proteins derived from species other than human) or other related sequences (e.g., paralogs) can also be obtained by low, moderate or high stringency hybridization with all or a portion of the particular human sequence as a probe using methods well known in the art for nucleic acid hybridization and cloning.

The Nlk1 protein, TrkA, α-tropomyosin, vimentin, p0071, protein phosphatase 1α; 14-3-3ε and Ini-1, IP-1, IP-2, IP-3, IP-4 and IP-5 proteins, either alone or within a coplex, may be obtained by methods well-known in the art for protein purification and recombinant protein expression. For recombinant expression of one or more of the proteins, the nucleic acid containing all or a portion of the nucleotide sequence encoding the protein may be inserted into an appropriate expression vector (i.e., a vector which contains the necessary elements for the transcription and translation of the inserted protein coding sequence). In a preferred embodiment, the regulatory elements are heterologous (i.e., not the native gene promoter). Alternately, the necessary transcriptional and translational signals may also be supplied by the native promoter for the Nlk1 protein or any Nlk1 protein-IP genes and/or their flanking regions.

A variety of host-vector systems may be utilized to express the protein coding sequence(s). These include, but are not limited to: (i) mammalian cell systems which are infected with vaccinia virus, adenovirus, and the like; (ii) insect cell systems infected with baculovirus and the like; (iii) yeast containing yeast vectors or (iv) bacteria transformed with bacteriophage, DNA, plasmid DNA, or cosmid DNA. Depending upon the host-vector system utilized, any one of a number of suitable transcription and translation elements may be used.

In a preferred embodiment of the present invention, the Nlk1 protein•Nlk1 protein-IP complexes are obtained by expressing the entire Nlk1 protein coding sequence and a Nlk1 protein-IP coding sequence within the same cell, either under the control of the same promoter or two separate promoters. In another embodiment, a derivative, fragment or homolog of the Nlk1 protein and/or a derivative, fragment or homolog of a Nlk1 protein-IP are recombinantly expressed. Preferably, the derivative, fragment or homolog of the Nlk1 protein and/or the Nlk1 protein-IP form a complex with a binding partner which has been identified by a binding assay (e.g., the modified yeast two hybrid system assay) and, more preferably, form a complex which binds to an anti-Nlk1 protein•Nlk1 protein-IP complex antibody.

Any of the methodologies known within the relevant prior art regarding the insertion of nucleic acid fragments into a vector may be utilized to construct expression vectors which contain a chimeric gene comprised of the appropriate transcriptional/translational control signals and protein-coding sequences. These methodologies may include, but are not limited to, in vitro recombinant DNA and synthetic techniques, as well as in vivo recombination techniques (e.g., genetic recombination). The expression of nucleic acid sequences which encode the Nlk1 protein and a Nlk1 protein-IP, or derivatives, fragments, analogs or homologs thereof, may be regulated by a second nucleic acid sequence such that the genes or fragments thereof are expressed in a host which has been concomitantly transformed with the recombinant DNA molecule(s) of interest. The expression of the specific proteins may be controlled by any promoter/enhancer known in the art including, but not limited to: (i) the SV40 early promoter (see e.g., Bemoist & Chambon, 1981. Nature 290:304–310); (ii) the promoter contained within the 3'-terminus long terminal repeat of Rous Sarcoma Virus (RSV; see e.g., Yamamoto, et al., 1980. Cell 22:787–797); (iii) the Herpesvirus thymidine kinase promoter (see e.g., Wagner, et al., 1981. Proc. Natl. Acad. Sci. USA 78:1441–1445); (iv) the regulatory sequences of the metallothionein gene (see e.g., Brinster, et al., 1982. Nature 296:39–42); (v) prokaryotic expression vectors such as the β-lactamase promoter (see e.g. Villa-Kamaroff, et al., 1978. Proc. Natl. Acad. Sci. USA 75:3727–3731); (vi) the tac promoter (see e.g., DeBoer, et al., 1983. Proc. Natl. Acad. Sci. USA 80:21–25.

In addition, plant promoter/enhancer sequences within plant expression vectors may also be utilized including, but not limited to: (i) the nopaline synthetase promoter (see e.g., Herrar-Estrella, et al., 1984. Nature 303:209–213); (ii) the cauliflower mosaic virus 35S RNA promoter (see e.g., Garder, et al., 1981. Nuc. Acids Res. 9:2871) and (iii) the promoter of the photosynthetic enzyme ribulose bisphosphate carboxylase (see e.g., Herrera-Estrell α, et al., 1984. Nature 310:115–120).

Promoter/enhancer elements from yeast and other fungi (e.g., the Gal4 promoter, the alcohol dehydrogenase promoter, the phosphoglycerol kinase promoter, the alkaline phosphatase promoter), as well as the following animal transcriptional control regions, which possess tissue specificity and have been used in transgenic animals, may be utilized in the production of proteins of the present invention. Transcriptional control sequences derived from animals include, but are not limited to: (i) the elastase I gene control region active within pancreatic acinar cells (see e.g., Swift, et al., 1984. *Cell* 38:639–646; Omitz, et al., 1986. *Cold Spring Harbor Symp. Quant. Biol.* 50:399–409); (ii) the insulin gene control region active within pancreatic β-cells (see e.g., Hanahan, et al., 1985. *Nature* 315:115–122); (iii) the immunoglobulin gene control region active within lymphoid cells (see e.g., Grosschedl, et al., 1984. *Cell* 38:647–658); (iv) the mouse mammary tumor virus control region active within testicular, breast, lymphoid and mast cells (see e.g., Leder, et al., 1986. *Cell* 45:485–495); (v) the albumin gene control region active within liver (see e.g., Pinckert, et al., 1987. *Genes and Devel.* 1:268–276); (vi) the a-fetoprotein gene control region active within liver (see e.g., Krumlauf, et al., 1985. *Mol. Cell. Biol.* 5:1639–1648; (Hammer et al., 1987, *Science* 235:53–58), (vii) the α1 anti-trypsin gene control region active within liver (see e.g., Kelsey, et al., 1987. *Genes and Devel.* 1:161–171); (viii) the β-globin gene control region active within myeloid cells (see e.g., Mogram, et al., 1985. *Nature* 315:338–340; (ix) the myelin basic protein gene control region active within brain oligodendrocyte cells (see e.g., Readhead, et al., 1987. *Cell* 48:703–712); (x) the myosin light chain-2 gene control region active within skeletal muscle (see e.g., Sani, et al., 1985. *Nature* 314:283–286) and (xi) the gonadotrophin-releasing hormone gene control region active within the hypothalamus (see e.g., Mason, et al., 1986. *Science* 234:1372–1378).

In a specific embodiment of the present invention, a vector is utilized which comprises a promoter operably-linked to nucleic acid sequences which encode the Nlk1 protein and/or a Nlk1 protein-IP (e.g., TrkA, protein phosphatase 1α, 14-3-3ε, α-tropomyosin, vimentin, p0071, Ini-1, IP-1, IP-2, IP-3, IP-4 and IP-5), or a fragment, derivative or homolog, thereof, one or more origins of replication, and optionally, one or more selectable markers (e.g., an antibiotic resistance gene). In a preferred embodiment, a vector is utilized which is comprised of a promoter operably-linked to nucleic acid sequences encoding both the Nlk1 protein and a Nlk1 protein-IP, one or more origins of replication, and, optionally, one or more selectable markers.

In another specific embodiment, an expression vector containing the coding sequences (or portions thereof) of the Nlk1 protein and a Nlk1 protein-IP, either together or separately. The expression vector is generated by subcloning the aforementioned gene sequences into the EcoRI restriction site of each of the three available pGEX vectors (glutathione S-transferase expression vectors; see e.g., Smith & Johnson, 1988. *Gene* 7:31–40), thus allowing the expression of products in the correct reading frame. Expression vectors which contain the sequences of interest may be identified by three general approaches: (i) nucleic acid hybridization, (ii) presence or absence of "marker" gene function and/or (iii) expression of the inserted sequences. In the first approach, Nlk1 protein, TrkA, protein phosphatase 1α, 14-3-3ε, α-tropomyosin, vimentin, p0071, Ini-1, IP-1, IP-2, IP-3, IP-4 and IP-5 (or other Nlk1 protein-IP sequences) may be detected by nucleic acid hybridization using probes comprising sequences homologous and complementary to the inserted sequences of interest. In the second approach, the recombinant vector/host system may be identified and selected based upon the presence or absence of certain "marker" functions (e.g., binding to an antibody specific for the Nlk1 protein, a Nlk1 protein-IP, or a Nlk1 protein•Nlk1 protein-IP complex, resistance to antibiotics, occlusion-body formation in baculovirus, and the like) caused by the insertion of the sequences of interest into the vector. In the third approach, recombinant expression vectors may be identified by assaying for the expression of the Nlk1 protein concomitantly with expression of the aforementioned Nlk1 protein-IPs by the recombinant vector.

Once the recombinant Nlk1 protein and Nlk1 protein-IP molecules have been identified and the complexes or individual proteins isolated, and a suitable host system and growth conditions have been established, the recombinant expression vectors may be propagated and amplified in-quantity. As previously discussed, expression vectors or their derivatives which can be used include, but are not limited to, human or animal viruses (e.g., vaccinia virus or adenovirus); insect viruses (e.g., baculovirus); yeast vectors; bacteriophage vectors (e.g. lambda phage); plasmid vectors and cosmid vectors.

A host cell strain may then be selected which modulates the expression of the inserted sequences of interest, or modifies/processes the expressed proteins in the specific manner desired. In addition, expression from certain promoters may be enhanced in the presence of certain inducers; thus facilitating control of the expression of the genetically-engineered Nlk1 protein and/or Nlk1 protein-IP. Moreover, different host cells possess characteristic and specific mechanisms for the translational and post-translational processing and modification (e.g., glycosylation, phosphorylation, and the like) of expressed proteins. Appropriate cell lines or host systems may thus be chosen to ensure the desired modification and processing of the foreign protein is achieved. For example, protein expression within a bacterial system can be used to produce an unglycosylated core protein; whereas expression within mammalian cells ensures "native" glycosylation of a heterologous protein.

In other specific embodiments, the Nlk1 protein and/or Nlk1 protein-IPs (or derivatives, fragments, analogs and homologs thereof) may be expressed as fusion or chimeric protein products comprising the protein joined via a peptide bond to a heterologous protein sequence of a different protein. Such chimeric products may be produced by the ligation of the appropriate nucleic acid sequences encoding the desired amino acids to one another in the proper coding frame and subsequently expressing the chimeric products in a suitable host by methods known within the art. Alternatively, such a chimeric product can be made by protein synthetic techniques (e.g., by use of a peptide synthesizer). A specific embodiment of the present invention discloses a chimeric protein comprising a fragment of the Nlk1 protein and/or a Nlk1 protein-IP. In another specific embodiment, fusion proteins are provided which contain the domains of the Nlk1 protein and a Nlk1 protein-IP (which result in the direct formation of Nlk1 protein•Nlk1 protein-IP complexes) and, optionally, a heterofunctional reagent (e.g., a peptide linker) which serves to both link the two aforementioned proteins and promote the interaction of the Nlk1 protein and Nlk1 protein-IP binding domains. These fusion proteins may be particularly useful where the stability of the interaction is desirable (i.e., stability due to the formation of the complex as an intramolecular reaction), for example in production of antibodies specific to the Nlk1 protein•Nlk1 protein-IP complex.

In a specific embodiment of the present invention, the nucleic acids encoding proteins, and proteins consisting of, or comprising a fragment of the Nlk1 protein or a Nlk1 protein-IP which consists of at least 6 contiguous amino acid residues of the Nlk1 protein and/or a Nlk1 protein-IP, are provided herein. In another embodiment, the aforementioned protein fragment is comprised of at least 10, 20, 30, 40, or 50 amino acid residues (preferably not larger that 35, 100 or 200 amino acid residues) of the Nlk1 protein or Nlk1 protein-IP. Derivatives or analogs of the Nlk1 protein and Nlk1 protein-IPs include, but are not limited to, molecules comprising regions which are substantially homologous to the Nlk1 protein or the Nlk1 protein-IPs in various embodiments, of at least 30%, 40%, 50%, 60%, 70%, 80%, 90% or 95% amino acid identity when: (i) compared to an amino acid sequence of identical size; (ii) compared to an aligned sequence in which the alignment is done by a computer homology program known within the art or (iii) the encoding nucleic acid is capable of hybridizing to a sequence encoding the Nlk1 protein or a Nlk1 protein-IP under stringent, moderately stringent, or non-stringent conditions.

Nlk1 protein and/or Nlk1 protein-IP derivatives may be produced by alteration of their sequences by substitutions, additions or deletions which result in fiunctionally-equivalent molecules. In a specific embodiment of the present invention, the degeneracy of nucleotide coding sequences allows for the use of other DNA sequences which encode substantially the same amino acid sequence as the Nlk1 protein or Nlk1 protein-IP genes. In another specific embodiment, one or more amino acid residues within the sequence of interest may be substituted by another amino acid of a similar polarity and net charge, thus resulting in a silent alteration. Substitutes for an amino acid within the sequence may be selected from other members of the class to which the amino acid belongs. The Nlk1 protein or Nlk1 protein-IP derivatives and analogs of the present invention may be produced by various methodologies known within the art. For example, the cloned Nlk1 protein and Nlk1 protein-IP gene sequences may be modified by any of numerous methods known within the art. See e.g., Sambrook, et al., 1990. *Molecular Cloning: A Laboratory Manual*, 2nd ed., (Cold Spring Harbor Laboratory Press; Cold Spring Harbor, N.Y.). These sequences may be digested at appropriate sites with restriction endonuclease (s), followed by further enzymatic modification, if so desired, and the resultant fragments isolated and ligated in vitro. Additionally, the Nlk1 protein- or Nlk1 protein-IP-encoding nucleic acids may be mutated in vitro or in vivo to: (i) create variations in coding regions; (ii) create and/or destroy translation, initiation, and/or termination sequences and/or (iii) form new restriction endonuclease sites or destroy pre-existing ones, so as to facilitate further in vitro modification. Any technique for mutagenesis known within the art may be utilized, including but not limited to, chemical mutagenesis and in vitro site-directed mutagenesis (see e.g., Hutchinson, et al., 1978. *J. Biol. Chem* 253:6551–6558); by use of TABJ™ linkers (Pharmacia) and similar methodologies.

Once a recombinant cell expressing the Nlk1 protein and/or a Nlk1 protein-IP, or a fragment or derivative thereof, is identified, the individual gene product or complex may be isolated and analyzed. This is achieved by assays which are based upon the physical and/or functional properties of the protein or complex, including, but not limited to, radioactive labeling of the product followed by analysis by gel electrophoresis, immunoassay, cross-linking to marker-labeled products, and the like. The Nlk1 protein•Nlk1 protein-IP complexes may be isolated and purified by standard methods known in the art (either from natural sources or recombinant host cells expressing the proteins/protein complexes) including, but not limited to, column chromatography (e.g., ion exchange, affinity, gel exclusion, reverse-phase, high pressure, fast protein liquid, etc), differential centrifugation, differential solubility, or similar methodologies used for the purification of proteins. Alternatively, once Nlk1 protein or Nlk1 protein-IP or its derivative is identified, the amino acid sequence of the protein can be deduced from the nucleic acid sequence of the chimeric gene from which it was encoded. Hence, the protein or its derivative can be synthesized by standard chemical methodologies known in the art. See, e.g., Hunkapiller, et al., 1984. *Nature* 310:105–111.

In a specific embodiment of the present invention, such Nlk1 protein•Nlk1 protein-IP complexes, whether produced by recombinant DNA techniques, chemical synthesis methods or by purification from native sources, include, but are not limited to, those containing as a primary amino acid sequence, all or part of the amino acid sequences substantially as depicted in FIGS. 1–14 (SEQ ID NOS:2, 4, 6, 8, 10, 12, 14, 16, 18, 20, 22, 24, 26, and 28), as well as fragments, analogs and derivatives thereof, including proteins homologous thereto.

Manipulations of the Nlk1 protein and/or Nlk1 protein-IP sequences, may be made at the protein level. Included within the scope of the present invention are complexes of the Nlk1 protein or Nlk1 protein-IP fragments, derivatives, fragments or analogs which are differentially modified during or after translation (e.g., by glycosylation, acetylation, phosphorylation, amidation, derivatization by known protecting/blocking groups, proteolytic cleavage, linkage to an antibody molecule or other cellular ligand, and the like). Any of the numerous chemical modification methodologies known within the art may be utilized including, but not limited to, specific chemical cleavage by cyanogen bromide, trypsin, chymotrypsin, papain, V8 protease, $NaBH_4$, acetylation, formylation, oxidation, reduction, metabolic synthesis in the presence of tunicamycin, etc. In a specific embodiment, the Nlk1 protein and/or Nlk1 protein-IP sequences are modified to include a fluorescent label. In another specific embodiment, the Nlk1 protein and/or the Nlk1 protein-IP are modified by the incorporation of a heterofunctional reagent, wherein such heterofunctional reagent may be used to cross-link the members of the complex.

In addition, complexes of analogs and derivatives of the Nlk1 protein and/or a Nlk1 protein-IP can be chemically synthesized. For example, a peptide corresponding to a portion of the Nlk1 protein and/or a Nlk1 protein-IP, which comprises the desired domain or which mediates the desired activity in vitro (e.g., Nlk1 protein•Nlk1 protein-IP complex formation), may be synthesized by use of a peptide synthesizer. In cases where natural products are suspected of being "mutant" or are isolated from new species, the amino acid sequence of the Nlk1 protein, a Nlk1 protein-IP isolated from the natural source, as well as those expressed in vitro, or from synthesized expression vectors in vivo or in vitro, may be determined from analysis of the DNA sequence, or alternatively, by direct sequencing of the isolated protein. The Nlk1 protein•Nlk1 protein-IP complexes may also be analyzed by hydrophilicity analysis (see e.g., Hopp & Woods, 1981. *Proc. Natl. Acad. Sci. USA* 78:3824–3828) which can be utilized to identify the hydrophobic and hydrophilic regions of the proteins, thus aiding in the design of substrates for experimental manipulation, such as in binding experiments, antibody synthesis, etc. Secondary structural analysis may also be performed to identify regions of the Nlk1 protein and/or a Nlk1 protein-IP which assume specific structural motifs. See e.g., Chou & Fasman, 1974. *Biochem.* 13:222–223. Manipulation, translation, secondary structure prediction, hydrophilicity and hydrophobicity profiles, open reading frame prediction and plotting, and determination of sequence homologies, can be accomplished using computer software programs available in the art.

Other methods of structural analysis including, but not limited to, X-ray crystallography (see e.g., Engstrom, 1974. *Biochem. Exp. Biol.* 11:7–13); mass spectroscopy and gas chromatography (see e.g., *Methods in Protein Science*, 1997. J. Wiley and Sons, New York, N.Y.) and computer modeling (see e.g., Fletterick & Zoller, eds., 1986. Computer Graphics and Molecular Modeling, In: *Current Communications in Molecular Biology*, Cold Spring Harbor Laboratory Press, Cold Spring Harbor, N.Y.) may also be employed.

(2) Sequences Encoding IP-1, IP-3, IP4 and IP-5

The present invention discloses the nucleotide sequences of nucleic acids which encode IP-1, IP-3, IP-4 and IP-5. In specific embodiments, the nucleic acid sequences of IP-1, IP-3, IP-4, and IP-5 nucleic acids are set forth in (SEQ ID NOS:17, 21, 23, and 25, respectively; wherein the associated inferred amino acid sequences of these nucleic acids are set forth in (SEQ ID NOS:18, 22, 24, and 26, respectively. The present invention also relates to nucleic acids which are hybridizable or complementary to the aforementioned sequences. In specific aspects, nucleic acids are provided which comprise a sequence complementary to (specifically, are the inverse complement of) at least 10, 25, 50, 100, or 200 nucleotides, or the entire coding region, of an IP-1, IP-3, IP-4, and IP-5 gene.

In a specific embodiment of the present invention, a nucleic acid which is hybridizable to IP-1, IP-3, IP-4, or IP-5 nucleic acids (e.g. possessing a sequence which is anti-sense to (SEQ ID NOS:17, 21, 23, or 25, respectively), or derivatives thereof, under conditions of low stringency hybridization is disclosed herein. By way of example, and not of limitation, procedures using such conditions of low stringency hybridization were as follows (see e.g. Shilo & Weinberg, 1981. *Proc. Natl. Acad. Sci. USA* 78:6789–6792): filters containing DNA were prehybridized for 6 hours at 40° C. in a solution containing 35% formamide, 5×SSC, 50 mM Tris-HCl (pH 7.5), 5 mM EDTA, 0.1% PVP, 0.1% Ficoll, 1% BSA, and 500 µg/ml denatured salmon sperm DNA. Hybridizations were carried out in the same solution with the following modifications: 0.02% PVP, 0.02% Ficoll, 0.2% BSA, 100 µg/ml salmon sperm DNA, 10% (wt/vol) dextran sulfate, and 5–20×10$^6$ cpm $^{32}$P-labeled probe. The filters were incubated in the hybridization mixture for 18–20 hours at 40° C. and then washed for 1.5 hours at 50° C. in a solution containing 2×SSC 25 mM Tris-HCl (pH 7.4), 5 mM EDTA, and 0.1% SDS. The wash solution was replaced with fresh solution and re-incubated an additional 1.5 hours at 60° C. The filters were blotted dry and autoradiographed. If necessary, the filters were washed for a third time at 65–68° C. and re-exposed to film. It should be noted that other conditions of low stringency hybridizations which are well-known in the art may also be utilized in the practice of the present invention.

In another specific embodiment of the present invention, a nucleic acid, which is hybridizable to an IP-1, IP-3, IP-4 or IP-5 nucleic acid under conditions of moderate stringency is disclosed. By way of example, and not of limitation, the procedure utilized for the moderate stringency hybridization were as follows: filters containing DNA were pre-hybridized for 6 hours at 55° C. in a solution containing 6×SSC, 5×Denhart's solution, 0.5% SDS and 100 µg/ml denatured salmon sperm DNA. Hybridizations were carried out in the same solution with the addition of 5–20×10$^6$ cpm $^{32}$P-labeled probe. The filters were incubated in hybridization mixture for 18–20 hours at 55° C. and then washed twice for 30 minutes at 60° C. in a solution containing 1×SSC and 0.1% SDS. The filters were blotted dry and autoradiographed. Other conditions of moderate stringency which are well-known within the art may also be utilized in the practice of the present invention.

In yet other specific embodiment of the present invention, a nucleic acids which is hybridizable to an IP-1, IP-3, IP-4 or IP-5 nucleic acid under conditions of high stringency hybridization is disclosed. By way of example, and not of limitation, the procedure utilized for such conditions of high stringency were as follows: pre-hybridization of filters containing DNA was carried out for 8–16 hours at 65° C. in buffer comprised of 6×SSC, 50 mM Tris-HCl (pH 7.5), 1 mM EDTA, 0.02% PVP, 0.02% Ficoll, 0.02% BSA, and 500 µg/ml denatured salmon sperm DNA. The filters were hybridized for 48 hours at 65° C. in pre-hybridization mixture containing 100 µl denatured salmon sperm DNA and 5–20×10$^6$ cpm of $^{32}$P-labeled probe. Washing of filters was done at 37° C. for 1 hour in a solution containing 2×SSC, 0.01% PVP, 0.01% Ficoll, and 0.01% BSA. This was then followed by a wash in 0.1×SSC at 50° C. for 45 minutes prior to autoradiography. Other conditions of high stringency hybridization which well known within the art may also be utilized in the practice of the present invention.

Nucleic acids encoding derivatives, fragments and analogs of IP-1, IP-3, IP-4 and IP-5 proteins and IP-1, IP-3, IP-4 and IP-5 antisense nucleic acids are additionally disclosed. The amino acid and nucleotide sequences for IP-1, IP-3, IP-4, and IP-5 were determined in silico as described above. Any methodology available within the art may be utilized to obtain a full-length (i.e., encompassing the entire coding region) cDNA clone encoding IP-1, IP-3, IP-4 and IP-5. For example, the polymerase chain reaction (PCR) may be utilized to amplify the sequence within a cDNA library. Similarly, oligonucleotide primers may also be used to amplify by PCR sequences from a nucleic acid sample (RNA or DNA), preferably a cDNA library, from an appropriate source (e.g., the sample from which the initial cDNA library for the modified yeast two hybrid assay fusion population was derived).

PCR may be performed by use of, for example, a Perkin-Elmer Cetus thermal cycler and Taq polymerase. The DNA being amplified is preferably cDNA derived from any eukaryotic species. It should be noted that several different degenerate primers may be synthesized for use in the PCR reactions. It is also possible to vary the stringency of the hybridization conditions used in priming the PCR reactions, to amplify nucleic acid homologs by allowing for greater or lesser degrees of nucleotide sequence similarity between the known nucleotide sequence and the nucleic acid homolog being isolated. For cross species hybridization, low stringency conditions are preferred; whereas for same species hybridization, moderately stringent conditions are preferred.

Any eukaryotic cell may potentially serve as the nucleic acid source for the molecular cloning of the IP-1, IP-3, IP-4 and IP-5 sequences. The DNA may be obtained by standard procedures known in the art from cloned DNA (e.g., a DNA "library"), by chemical synthesis, by cDNA cloning, or by the cloning of genomic DNA, or fragments thereof, purified from the desired cell. See e.g., Sambrook, et al., 1989. *Molecular Cloning: A Laboratory Manual*, 2nd ed., (Cold Spring Harbor Laboratory Press, Cold Spring Harbor, N.Y.); Glover, 1985. *DNA Cloning: A Practical Approach* (MRL Press, Ltd., Oxford, U.K. Vol. I, II). Clones derived from genomic DNA may contain regulatory and intronic DNA regions in addition to exonic (coding) regions; whereas clones derived from cDNA will contain only exonic sequences.

In a preferable embodiment of the present invention, IP-1, IP-3, IP-4 and IP-5 nucleic acids are derived from a cDNA source. Identification of the specific cDNA containing the desired sequence may be accomplished in a number of ways. In one methodology, a portion of the IP-1, IP-3, IP-4 or IP-5 sequence (e.g., a PCR amplification product obtained as described supra), or an oligonucleotide possessing a sequence of a portion of the known nucleotide sequence, or its specific RNA, or a fragment thereof, may be purified, amplified, and labeled, and the generated nucleic acid fragments may be screened by nucleic acid hybridization utilizing a labeled probe. See e.g., Benton & Davis, 1977. *Science* 196:180. In a second methodology, the appropriate fragment is identified by restriction enzyme digestion(s) and comparison of fragment sizes with those expected from comparison to a known restriction map (if such is available) or by DNA sequence analysis and comparison to the known nucleotide sequence of IP-1, IP-3, IP-4 or IP-5. In a third methodology, the gene of interest may be detected utilizing assays based on the physical, chemical or immunological properties of its expressed product. For example, cDNA clones, or DNA clones which hybrid-select the proper mRNAs, may be selected as a function of their production of a protein which, for example, has similar or identical electrophoretic migration, isolectric focusing behavior, proteolytic digestion maps, antigenic properties or ability to bind the Nlk1 protein. In a fourth methodology, should an anti-IP-4 or anti-IP-5 antibody be available, the protein of interest may be identified by the binding of a labeled antibody to the putatively IP-1, IP-3, IP-4 or IP-5 clone in an enzyme-linked immunosorbent assay (ELISA).

In specific embodiments of the present invention, following isolation and identification, the nucleic acids may then be inserted into an appropriate cloning vector including, but are not limited to, bacteriophages (e.g., λ derivatives) or bacterial plasmids (e.g., pBR322, pUC, or the Bluescript® vector (Stratagene; La Jolla, Calif.). The insertion of the nucleic acid of interest into a cloning vector may be facilitated by, for example, ligating the DNA fragment into a vector possessing complementary cohesive termini or, if there are no complementary cohesive termini present in the cloning vector, the termini of the DNA insert or vector molecule may be enzymatically modified. Alternatively, any restriction site may be produced by the ligation of linker sequences onto the DNA termini; wherein these linker sequences may comprise specific chemically-synthesized oligonucleotides possessing restriction endonuclease recognition sequences. In an additional embodiment, both the cleaved vector and IP-1, IP-3, IP-4 and IP-5 sequence may be modified by complementary, homopolymeric tailing. Recombinant molecules may be introduced into host cells via transformation, transfection, infection, electroporation, and the like. In yet another embodiment, the desired gene may be identified and isolated after insertion into a suitable cloning vector in a "shotgun" approach. Enrichment for the desired gene (e.g., by size fractionation) may be done before insertion into the cloning vector.

The IP-1, IP-3, IP-4 and IP-5 sequences provided by the instant invention include those nucleotide sequences encoding substantially the same amino acid sequences as found in native IP-1, IP-3, IP-4 and IP-5 proteins, and those encoded amino acid sequences with functionally equivalent amino acids, as well as those encoding other IP-1, IP-3, IP-4 and IP-5 derivatives, fragments or analogs.

(3) Production of Antibodies to Nlk1 Protein•Nlk1 Protein-IP Complexes

As disclosed by the present invention herein, Nlk1 protein•Nlk1 protein-IP complexes, or derivatives, fragments, analogs or homologs thereof, may be utilized as immunogens in the generation of antibodies which immunospecifically-bind these protein components. Such antibodies include, but are not limited to, polyclonal, monoclonal, chimeric, single chain, $F_{ab}$ fragments and an $F_{ab}$ expression library. In a specific embodiment, antibodies to complexes of human Nlk1 protein and human Nlk1 protein-IP are disclosed. In another specific embodiment, complexes formed from fragments of the Nlk1 protein and a Nlk1 protein-IP; wherein these fragments contain the protein domain which interacts with the other member of the complex and are used as immunogens for antibody production. Various procedures known within the art may be used for the production of polyclonal or monoclonal antibodies to a Nlk1 protein•Nlk1 protein-IP complex, or derivative, fragment, analog or homolog thereof.

For the production of polyclonal antibodies, various host animals may be immunized by injection with the native Nlk1 protein•Nlk1 protein-IP complex, or a synthetic version, or a derivative of the foregoing (e.g., a cross-linked Nlk1 protein•Nlk1 protein-IP). Various adjuvants may be used to increase the immunological response and include, but are not limited to, Freund's (complete and incomplete), mineral gels (e.g., aluminum hydroxide), surface active substances (e.g., lysolecithin, pluronic polyols, polyanions, peptides, oil emulsions, dinitrophenol, etc.) and human adjuvants such as Bacille Calmette-Guerin (BCG) and *Corynebacterium parvum.*

For preparation of monoclonal antibodies directed towards a Nlk1 protein•Nlk1 protein-IP complex, or derivatives, fragments, analogs or homologs thereof, any technique which provides for the production of antibody molecules by continuous cell line culture may be utilized. Such techniques include, but are not limited to, the hybridoma technique (see Kohler & Milstein, 1975. *Nature* 256:495–497); the trioma technique; the human B-cell hybridoma technique (see Kozbor, et al., 1983. *Immunol. Today* 4:72) and the EBV hybridoma technique to produce human monoclonal antibodies (see Cole, et al., 1985. In: *Monoclonal Antibodies and Cancer Therapy* (Alan R. Liss, Inc., pp. 77–96). In an additional embodiment of the present invention, monoclonal antibodies may be produced in germ-free animals utilizing recently developed technology. See PCT Publication US 90/02545. Human monoclonal antibodies may be utilized in the practice of the present invention and may be produced by the use of human hybridomas (see Cote, et al., 1983. *Proc. Natl. Acad. Sci. USA* 80:2026–2030) or by transforming human B-cells with Epstein Barr Virus (EBV) in vitro (see Cole, et al., 1985. In: *Monoclonal Antibodies and Cancer Therapy* (Alan R. Liss, Inc., pp. 77–96).

In an additional embodiment of the present invention, techniques are disclosed for the production of single-chain antibodies (see e.g., U.S. Pat. No. 4,946,778) may be adapted for the production of Nlk1 protein•Nlk1 protein-IP complex-specific single-chain antibodies. In yet another embodiment, methodologies are disclosed for the construction of $F_{ab}$ expression libraries (see e.g., Huse, et al., 1989. *Science* 246:1275–1281) to allow rapid and effective identification of monoclonal $F_{ab}$ fragments with the desired specificity for Nlk1 protein•Nlk1 protein-IP or derivatives, fragments, analogs or homologs thereof. Furthermore, the present invention discloses methodologies for the "humanization" of non-human antibodies by techniques known within the art. See e.g., U.S. Pat. No. 5,225,539). Antibody fragments which contain the idiotypes of Nlk1 protein•Nlk1 protein-IP complexes may be produced by techniques known in the art including, but not limited to: (i) the F(ab')$_2$ fragment which is produced by pepsin digestion of an antibody molecule; (ii) the Fab fragments which may be generated by the reduction of the disulfide bridges of the F(ab')$_2$ fragment; (iii) the F$_{ab}$ fragments which may be generated by the treatment of the antibody molecule with papain and a reducing agent and (iv) F$_v$ fragments.

In one embodiment of the present invention, methodologies for the screening of antibodies which possess the desired specificity include, but are not limited to, enzyme-linked immunosorbent assay (ELISA) and other immunologically-mediated techniques known within the art. In a specific embodiment, selection of antibodies which are specific to a particular domain of the Nlk1 protein•Nlk1 protein-IP complex is facilitated by generation of hybridomas which binds to the fragment of the Nlk1 protein•Nlk1 protein-IP complex possessing such a domain. In another specific embodiment, methodologies for the selection of an antibody which specifically-binds a Nlk1 protein•Nlk1 protein-IP complex but which does not specifically-bind to the individual proteins of the Nlk1 protein•Nlk1 protein-IP complex (by selecting the antibody on the basis of positive-binding to the Nlk1 protein•Nlk1 protein-IP complex with a concomitant lack of binding to the individual Nlk1 protein and Nlk1 protein-IP proteins) are disclosed herein. Accordingly, antibodies which are specific for a domain within the Nlk1 protein•Nlk1 protein-IP complex, or derivative, fragments, analogs or homologs thereof, are also provided herein.

It should be noted that the aforementioned antibodies may be used in methods known within the art relating to the localization and/or quantitation of Nlk1 protein•Nlk1 protein-IP complexes (e.g., for use in measuring levels of the protein within appropriate physiological samples, for use in diagnostic methods, for use in imaging the protein, and the like). In yet another embodiment of the present invention, anti-Nlk1 protein•Nlk1 protein-IP complex antibodies, or derivatives, fragments, analogs or homologs thereof, which possess the protein binding domain, are utilized as pharmacologically-active compounds (hereinafter "Therapeutics").

(4) Use of Nlk1 Protein•Nlk1 Protein-IP Complexes in Diagnosis, Prognosis and Screening Nlk1 protein•Nlk1 protein-IP complexes (i.e., particularly the Nlk1 protein complexed with TrkA, protein phosphatase 1α, 14-3-3ε, α-tropomyosin, vimentin, p0071, Ini-1, IP-1, IP-2, IP-3, IP-4 and IP-5), may serve as "markers" for specific disease states which involve the disruption of physiological processes including, but not limited to: (i) cell-cycle progression, cellular apoptosis and/or differentiation; (ii) intracellular signal transduction; (iii) transcriptional regulation; (iv) metabolism and pathological processes (e.g., hyperproliferative disorders, tumorigenesis and tumor progression, neurodegeneration, vascular disorders, viral infection and various genetic disorder), and thus may have diagnostic utility. In accord, the differentiation and classification of particular groups of patients possessing elevations or deficiencies of a Nlk1 protein•Nlk1 protein-IP complex may lead to new nosological classifications of diseases, thus markedly advancing diagnostic ability.

The detection of Nlk1 protein•Nlk1 protein-IP complex levels, or the levels of the individual proteins which have been shown to form complexes with the Nlk1 protein, or detecting the levels of the mRNAs which encode the components of the Nlk1 protein•Nlk1 protein-IP complexes, may be utilized in diagnosis, prognosis, following the disease course, following the efficacy of administered therapeutics, of disease states, following therapeutic response, etc. Similarly, both the nucleic acid sequences (and sequences complementary thereto) and anti-Nlk1 protein•Nlk1 protein-IP complex antibodies and antibodies directed against the individual components that can form Nlk1 protein•Nlk1 protein-IP complexes, have uses in diagnostics. Such molecules may be utilized in assays (e.g., immunoassays) to detect, prognose, diagnose, or monitor various conditions, diseases, and disorders characterized by aberrant levels of Nlk1 protein•Nlk1 protein-IP complexes, or monitor the treatment thereof. The aforementioned immunoassay may be performed by a methodology comprising contacting a sample derived from a patient with an anti-Nlk1 protein•Nlk1 protein-IP complex antibody under conditions such that immunospecific-binding may occur, and subsequently detecting or measuring the amount of any immunospecific-binding by the antibody. In a specific embodiment, an antibody specific for a Nlk1 protein•Nlk1 protein-IP complex may be used to analyze a tissue or serum sample from a patient for the presence of Nlk1 protein•Nlk1 protein-IP complex; wherein an aberrant level of Nlk1 protein•Nlk1 protein-IP complex is indicative of a diseased condition. The immunoassays which may be utilized include, but are not limited to, competitive and non-competitive assay systems using techniques such as Western Blots, radioimmunoassays (RIA), enzyme linked immunosorbent assay (ELISA), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, and protein-A immunoassays, etc.

The nucleic acid species of the present invention encoding the associated protein components of the Nlk1 protein•Nlk1 protein-IP complexes, and related nucleotide sequences and subsequences, may also be used in hybridization assays. The Nlk1 protein and Nlk1 protein-IP nucleotide sequences, or subsequences thereof comprising at least 8 nucleotides, may be used as hybridization probes. Hybridization assays can be used to detect, prognose, diagnose, or monitor conditions, disorders, or disease states associated with aberrant levels of the mRNAs encoding the components of a Nlk1 protein•Nlk1 protein-IP complex, as described supra. In specific embodiments of the present invention, diseases and disorders involving or characterized by aberrant levels of Nlk1 protein•Nlk1 protein-IP complexes or a predisposition to develop such disorders may be diagnosed by detecting aberrant levels of Nlk1 protein•Nlk1 protein-IP complexes, or non-complexed Nlk1 protein and/or Nlk1 protein-IP proteins or nucleic acids for functional activity. This aforementioned functional activity may including, but is not restricted to, (i) binding to an interacting partner (e.g., the Nlk1 protein, TrkA, protein phosphatase 1α, 14-3-3ε, α-tropomyosin, vimentin, p0071, Ini-1, IP-1, IP-2, IP-3, IP-4 and IP-5) or mutations in Nlk1 protein and/or a Nlk1 protein-IP RNA, DNA or protein (e.g., translocations, truncations, changes in nucleotide or amino acid sequence relative to wild-type Nlk1 protein and/or the Nlk1 protein-IP) which can cause increased or decreased expression or activity of the Nlk1 protein, a Nlk1 protein-IP or a Nlk1 protein•:Nlk1 protein-IP complex.

Methodologies which are well-known within the art (e.g., immunoassays, nucleic acid hybridization assays, biological activity assays, and the like) may be used to determine whether one or more particular Nlk1 protein•Nlk1 protein-IP complexes are present at either increased or decreased levels, or are absent, within samples derived from patients suffering from a particular disease or disorder, or possessing a predisposition to develop such a disease or disorder, as compared to the levels in samples from subjects not having such disease or disorder or predisposition thereto. Additionally, these assays may be utilized to determine whether the ratio of the Nlk1 protein•Nlk1 protein-IP complex to the non-complexed components (i.e. the Nlk1 protein and/or the specific Nlk1 protein-IP) in the complex of interest is increased or decreased in samples from patients suffering from a particular disease or disorder or having a predisposition to develop such a disease or disorder as compared to the ratio in samples from subjects not having such a disease or disorder or predisposition thereto.

Accordingly, in specific embodiments of the present invention, diseases and disorders which involve increased/decreased levels of one or more Nlk1 protein•Nlk1 protein-IP complexes may be diagnosed, or their suspected presence may be screened for, or a predisposition to develop such diseases and disorders may be detected, by quantitatively ascertaining increased/decreased levels of: (i) the one or more Nlk1 protein•Nlk1 protein-IP complexes; (ii) the mRNA encoding both protein members of said complex; (iii) the complex functional activity or (iv) mutations in the Nlk1 protein or the Nlk1 protein-IP (e.g., translocations in nucleic acids, truncations in the gene or protein, changes in nucleotide or amino acid sequence relative to wild-type Nlk1 protein or the Nlk1 protein-IP) which enhance/inhibit or stabilize/destabilize Nlk1 protein•Nlk1 protein-IP complex formation.

In the practice of the present invention, the use of detection techniques, especially those involving antibodies directed against the Nlk1 protein•Nlk1 protein-IP complexes, provide methods for the detection of specific cells which express the protein or protein complex of interest. Using such assays, specific cell types may be quantitatively characterized in which one or more particular Nlk1 protein•Nlk1 protein-IP complex are expressed, and the presence of the protein or protein complex may be correlated with cell viability by techniques well-known within the art (e.g., florescence-activated cell sorting (FACS)). Also embodied herein are methodologies directed to the detection of a Nlk1 protein•Nlk1 protein-IP complex within in vitro cell culture models which express particular Nlk1 protein•Nlk1 protein-IP complexes, or derivatives thereof, for the purpose of characterizing and/or isolating Nlk1 protein•Nlk1 protein-IP complexes. These detection techniques include, but are not limited to, cell-sorting of prokaryotes (see e.g., Davey & Kell, 1996. *Microbiol Rev.* 60:641–696); primary cultures and tissue specimens from eukaryotes, including mammalian species such as human (see e.g., Steele, et al., 1996. *Clin. Obstet. Gynecol.* 39:801–813) and continuous cell cultures (see e.g., Orfao & Ruiz-Arguelles, 1996. *Clin. Biochem.* 29:5–9.

The present invention additionally provides kits for diagnostic use which are comprised of one or more containers containing an anti-Nlk1 protein•Nlk1 protein-IP complex antibody and, optionally, a labeled binding partner to said antibody. The label incorporated into the anti-Nlk1 protein•Nlk1 protein-IP complex antibody may include, but is not limited to, a chemiluminescent, enzymatic, fluorescent, calorimetric or radioactive moiety. In an alternative specific embodiment, the kit may comprise, in one or more containers, a pair of oligonucleotide primers (e.g., each 6–30 nucleotides in length) which are capable of acting as amplification primers for: polymerase chain reaction (PCR; see e.g., Innis, et al., 1990. *PCR Protocols* (Academic Press, Inc., San Diego, Calif.)); ligase chain reaction; cyclic probe reaction, or other methods known within the art. The kit may, optionally, further comprise a predetermined amount of a purified Nlk1 protein, Nlk1 protein-IP or Nek•Nlk1 protein-IP complex, or nucleic acids thereof, for use as a standard or control in the aforementioned assays.

(5) Therapeutic Uses of the Nlk1 Protein, Nlk1 Protein-IP and Nlk1 Protein•Nlk1 Protein-IP Complexes The present invention provides for treatment or prevention of various diseases and disorders by administration of a biologically-active, therapeutic compound (hereinafter "Therapeutic"). Such Therapeutics include, but are not limited to: (i) various Nlk1 protein•Nlk1 protein-IP complexes (e.g., the Nlk1 protein complexed with TrkA, protein phosphatase 1α, 14-3-3ε, α-tropomyosin, vimentin, p0071, Ini-1, IP-1, IP-2, IP-3, IP-4 and IP-5 ) and deri fragments, analogs and homologs thereof; (ii) antibodies directed against the aforementioned proteins and protein complexes thereof; (iii) nucleic acids encoding the Nlk1 protein and Nlk1 protein-IPs and derivatives, fragments, analogs and homologs thereof; (iv) antisense nucleic acids encoding the Nlk1 protein and (v)Nlk1 protein IPs and Nlk1 protein•Nlk1 protein-IP complex and modulators (i.e., inhibitors, agonists and antagonists) thereof.

As previously discussed, the Nlk1 protein and/or several of its binding partners (i.e., Nlk1 protein-IPs) have been implicated to play a significant role in disorders of cell-cycle progression, cell differentiation, and transcriptional control, including cancer and tumorigenesis and tumor progression. Disorders of neurodegeneration (e.g., Alzheimer's disease) may also involve the Nlk1 protein and/or Nek protein-IPs. A wide range of cellular diseases affected by intracellular signal transduction may involve proteins (e.g., the Nlk1 protein, TrkA, protein phosphatase-1α and 14-3-3ε) and may be treated or prevented by the administration of a Therapeutic which modulates (i.e. inhibits, antagonizes or promotes) Nlk1 protein•Nlk1 protein-IP complex activity. Cardiovascular disease may involve α-tropomyosin, IP-2 and IP-5. Aberrant DNA repair and transcriptional control frequently results in a variety of genetic disorders, including xeroderma pigmentosum, Cockayne's syndrome and trichothiodystrophy (see e.g., Seroz, et al., 1995. *Curr. Opin. Genet. Dev.* 5:217–222), and may involve the Nlk1 protein, Ini-1, and IP-1. Ini-1 is also putatively involved in viral (e.g., HIV) infection. In addition, TrkA, protein phosphatase-1α, 14-3-3 ε, vimentin, IP-4 and IP-1 are specifically implicated in numerous metabolic diseases and disorders.

(i) Disorders with Increased Nlk1 protein and Nlk1 protein•Nlk1 protein-IP Complex Levels Diseases and disorders which are characterized by increased (relative to a subject not suffering from said disease or disorder) Nlk1 protein•Nlk1 protein-IP levels or biological activity may be treated with Therapeutics which antagonize (i.e., reduce or inhibit) Nlk1 protein•Nlk1 protein-IP complex formation or activity. Therapeutics which antagonize Nlk1 protein•Nlk1 protein-IP complex formation or activity may be administered in a therapeutic or prophylactic manner. Therapeutics which may be utilized include, but are not limited to, the Nlk1 protein or Nlk1 protein-IPs, or analogs, derivatives, fragments or homologs thereof, (ii) anti-Nlk1 protein•Nlk1 protein-IP complex antibodies; (iii) nucleic acids encoding the Nlk1 protein or a Nlk1 protein-IP; (iv) concurrent administration of a Nlk1 protein and a Nlk1 protein-IP antisense nucleic acid and Nlk1 protein and/or Nlk1 protein-IP nucleic acids which are "dysfunctional" (i.e., due to a heterologous non-Nlk1 protein and/or non-Nlk1 protein-IP) insertion within the coding sequences of the Nlk1 protein and Nlk1 protein-IP coding sequences) are utilized to "knockout" endogenous Nlk1 protein and/or Nlk1 protein-IP function by homologous recombination (see e.g., Capecchi, 1989. *Science* 244:1288–1292). In an additionally embodiment of the present invention, mutants or derivatives of a first Nlk1 protein-IP which possess greater affinity for Nlk1 protein than the wild-type first Nlk1 protein-IP may be administered to compete with a second Nlk1 protein-IP for binding to the Nlk1 protein, thereby reducing the levels of complexes between the Nlk1 protein and the second Nlk1 protein-IP.

Increased levels of Nlk1 protein•Nlk1 protein-IP complexes can be readily detected by quantifying protein and/or RNA, by obtaining a patient tissue sample (e.g., from biopsy tissue) and assaying it in vitro for RNA or protein levels, structure and/or activity of the expressed Nlk1 protein•Nlk1 protein-IP complex (or the Nlk1 protein and Nlk1 protein-IP mRNAs). Methods which are well-known within the art including, but not limited to, immunoassays to detect Nlk1 protein•Nlk1 protein-IP complexes (e.g., by Western blot analysis, immunoprecipitation followed by sodium dodecyl sulfate (SDS) polyacrylamide gel electrophoresis, immunocytochemistry, etc.) and/or hybridization assays to detect concurrent expression of the Nlk1 protein and a Nlk1 protein-IP mRNAs (e.g., Northern assays, dot blots, in situ hybridization, etc.).

(ii) Disorders with Increased Nlk1 protein and Nlk1 protein•Nlk1 protein-IP Complex Levels A specific embodiment of the present invention discloses methods for the reduction of Nlk1 protein•Nlk1 protein-IP complex expression (i.e., the expression of the two protein components of the complex and/or formation of the complex) by targeting mRNAs which express the protein moieties. RNA Therapeutics are, currently, differentiated into three classes: (i) antisense species; (ii) ribozymes or (iii) RNA aptamers. See e.g. Good, et al., 1997. *Gene Therapy* 4:45–54. Antisense oligonucleotides have been the most widely utilized and will be discussed, infra. Ribozyme therapy involves the administration (i.e., induced expression) of small RNA molecules with enzymatic ability to cleave, bind, or otherwise inactivate specific RNAs, thus reducing or eliminating the expression of particular proteins. See e.g., Grassi & Marini, 1996. *Ann. Med.* 28:499–510. At present, the design of "hairpin" and/or "hammerhead" RNA ribozymes are necessary to specifically-target a particular mRNA (e.g., the Nlk1 protein mRNA). RNA aptamers are specific RNA ligands for proteins, such as for Tat and Rev RNA (see e.g., Good, et al., 1997. *Gene Therapy* 4:45–54) which can specifically inhibit their translation.

In a preferred embodiment of the present invention, the activity or level of the Nlk1 protein may be reduced by administration of a Nlk1 protein-IP, a nucleic acid which encodes the Nlk1 protein-IP or an antibody (or a derivative or fragment of the antibody possessing the binding domain thereof) which immunospecifically-binds to the Nlk1 protein-IP. Similarly, the levels or activity of a Nlk1 protein-IP may be reduced by administration of the Nlk1 protein, a nucleic acid encoding the Nlk1 protein or an antibody (or a derivative or fragment of the antibody possessing the binding domain thereof) which immunospecifically-binds the Nlk1 protein. In another embodiment of the present invention, diseases or disorders which are associated with increased levels of the Nlk1 protein, or a particular Nlk1 protein-IP, may be treated or prevented by administration of a Therapeutic which increases Nlk1 protein•Nlk1 protein-IP complex formation, if said complex formation acts to reduce or inactivate the Nlk1 protein or the particular Nlk1 protein-IP via Nlk1 protein•Nlk1 protein-IP complex formation. Such diseases or disorders may be treated or prevented by: (i) the administration of one member of the Nlk1 protein•Nlk1 protein-IP complex, including mutants of one or both of the proteins which possess increased affinity for the other member of the Nlk1 protein•Nlk1 protein-IP complex (so as to cause increased complex formation) or (ii) the administration of antibodies or other molecules which serve to stabilize the Nlk1 protein•Nlk1 protein-IP complex, or the like.

(6) Determnination of the Biological Effect of the Therapeutic

In preferred embodiments of the present invention, suitable in vitro or in vivo assays are utilized to determine the effect of a specific Therapeutic and whether its administration is indicated for treatment of the affected tissue.

In various specific embodiments, in vitro assays may be performed with representative cells of the type(s) involved in the patient's disorder, to determine if a given Therapeutic exerts the desired effect upon said cell type(s). Compounds for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

(i) Malignancies

Components of the Nlk1 protein•Nlk1 protein-IP complexes (i.e., the Nlk1 protein, TrkA, protein phosphatase 1α, 14-3-3ε, α-tropomyosin, vimentin, p0071, IP-1 (intermediate filament associated protein), IP-2 (tropomyosin homolog), IP-3 (ubiquitin homolog specific hydrolase), IP-4 (collagen homolog) and IP-5 (tropomyosin homolog) are involved in the regulation of cell proliferation. Accordingly, Therapeutics of the present invention may be useful in the therapeutic or prophylactic treatment of diseases or disorders which are associated with cell hyperproliferation and/or loss of control of cell proliferation (e.g., cancers, malignancies and tumors). For a review of such hyperproliferation disorders, see e.g., Fishman, et al., 1985. *Medicine*, 2nd ed. (J. B. Lippincott Co., Philadelphia, Pa.).

Therapeutics of the present invention may be assayed by any method known within the art for efficacy in treating or preventing malignancies and related disorders. Such assays include, but are not limited to, in vitro assays utilizing transformed cells or cells derived from the patient's tumor, as well as in vivo assays using animal models of cancer or malignancies. Potentially effective Therapeutics, for example, inhibit the proliferation of tumor-derived or transformed cells in culture or cause a regression of tumors in animal models, in comparison to the controls.

In the practice of the present invention, once a malignancy or cancer has been shown to be amenable to treatment by modulating (i.e., inhibiting, antagonizing or agonizing) Nlk1 protein•Nlk1 protein-IP complex activity, that cancer or malignancy may subsequently be treated or prevented by the administration of a Therapeutic which serves to modulate Nlk1 protein•Nlk1 protein-IP complex formation and function, including supplying Nlk1 protein•:Nlk1 protein-IP complexes and the individual binding partners of said protein complex (i.e., the Nlk1 protein and/or a Nlk1 protein protein-IP.

(ii) Pre-Malignant Conditions

The Therapeutics of the present invention which are effective in the therapeutic or prophylactic treatment of cancer or malignancies may also be administered for the treatment of pre-malignant conditions and/or to prevent the progression of a pre-malignancy to a neoplastic or malignant state. Such prophylactic or therapeutic use is indicated in conditions known or suspected of preceding progression to neoplasia or cancer, in particular, where non-neoplastic cell growth consisting of hyperplasia, metaplasia or, most particularly, dysplasia has occurred. For a review of such abnormal cell growth see e.g., Robbins & Angell, 1976. *Basic Pathology*, 2nd ed. (W. B. Saunders Co., Philadelphia, Pa.).

Hyperplasia is a form of controlled cell proliferation involving an increase in cell number in a tissue or organ, without significant alteration in its structure or function. For example, it has been demonstrated that endometrial hyperplasia often precedes endometrial cancer. Metaplasia is a form of controlled cell growth in which one type of mature or fully differentiated cell substitutes for another type of mature cell. Metaplasia may occur in epithelial or connective tissue cells; whereas atypical metaplasia involves a somewhat disorderly metaplastic epithelium. Dysplasia is generally considered a precursor of cancer, and is found mainly in the epithelia. Dysplasia is the most disorderly form of non-neoplastic cell growth, and involves a loss in individual cell uniformity and in the architectural orientation of cells. Dysplastic cells often have abnormally large, deeply stained nuclei, and exhibit pleomorphism. Dysplasia characteristically occurs where there exists chronic irritation or inflammation, and is often found in the cervix, respiratory passages, oral cavity, and gall bladder.

Alternatively, or in addition to the presence of abnormal cell growth characterized as hyperplasia, metaplasia, or dysplasia, the presence of one or more characteristics of a transformed or malignant phenotype displayed either in vivo or in vitro within a cell sample derived from a patient, is indicative of the desirability of prophylactic/therapeutic administration of a Therapeutic of the present invention which possesses the ability to modulate Nlk1 protein•Nlk1 protein-IP complex activity. Characteristics of a transformed phenotype include, but are not limited to: (i) morphological changes; (ii) looser substratum attachment; (iii) loss of cell-to-cell contact inhibition; (iv) loss of anchorage dependence; (v) protease release; (vi) increased sugar transport; (vii) decreased serum requirement; (viii) expression of fetal antigens, (ix) disappearance of the 250 Kdal cell-surface protein, and the like. See e.g., Richards, et al., 1986. *Molecular Pathology* (W. B. Saunders Co., Philadelphia, Pa.).

In a specific embodiment of the present invention, leukoplakia (a benign-appearing hyperplastic or dysplastic lesion of the epithelium) or Bowen's disease (a carcinoma in situ) are pre-neoplastic lesions which are illustrative of the desirability of prophylactic intervention to prevent transformation to a frankly malignant phenotype. In another specific embodiment, the Therapeutics of the present invention may be useful in the therapeutic or prophylactic treatment of fibrocystic diseases including, but not limited to, cystic hyperplasia, mammary dysplasia and, particularly, adenosis (benign epithelial hyperplasia).

In other preferred embodiments, a patient which exhibits one or more of the following predisposing factors for malignancy is treated by administration of an effective amount of a Therapeutic: (i) a chromosomal translocation associated with a malignancy (e.g., the Philadelphia chromosome (bcr/abl) for chronic myelogenous leukemia and t(14;18) for follicular lymphoma, etc.); (ii) familial polyposis or Gardner's syndrome (possible forerunners of colon cancer); (iii) monoclonal gammopathy of undetermined significance (MGUS; a possible precursor of multiple myeloma) and (iv) a first degree kinship with persons having a cancer or pre-cancerous disease showing a Mendelian (genetic) inheritance pattern (e.g., familial polyposis of the colon, Gardner's syndrome, hereditary exostosis, polyendocrine adenomatosis, medullary thyroid carcinoma with amyloid production and pheochromocytoma, Peutz-Jeghers syndrome, neurofibromatosis of Von Recklinghausen, retinoblastoma, carotid body tumor, cutaneous melanocarcinoma, intraocular melanocarcinoma, xeroderma pigmentosum, ataxia telangiectasia, Chediak-Higashi syndrome, albinism, Fanconi's aplastic anemia and Bloom's syndrome).

In another preferred embodiment, a Therapeutic of the present invention is administered to a human patient to prevent the progression to breast, colon, lung, pancreatic, or uterine cancer, or melanoma or sarcoma.

(iii) Hyperproliferative and Dysproliferative Disorders

In a preferred embodiment of the present invention, a Therapeutic is administered in the therapeutic or prophylactic treatment of hyperproliferative or benign dysproliferative disorders. The efficacy in treating or preventing hyperproliferative diseases or disorders of a Therapeutic of the present invention may be assayed by any method known within the art. Such assays include in vitro cell proliferation assays, in vitro or in vivo assays using animal models of hyperproliferative diseases or disorders, or the like. Potentially effective Therapeutics may, for example, promote cell proliferation in culture or cause growth or cell proliferation in animal models in comparison to controls.

In accord, once a hyperproliferative disorder has been shown to be amenable to treatment by modulation of Nlk1 protein•Nlk1 protein-IP complex activity, the hyperproliferative disease or disorder may be treated or prevented by the administration of a Therapeutic which modulates Nlk1 protein•Nlk1 protein-IP complex formation (including supplying Nlk1 protein•Nlk1 protein-IP complexes and the individual binding partners of a Nlk1 protein•Nlk1 protein-IP complex (e.g., the Nlk1 protein, TrkA, protein phosphatase 1α, 14-3-3ε, α-tropomyosin, vimentin, p0071, IP-1, IP-2, IP-3, IP-4 and IP-5).

Specific embodiments of the present invention are directed to the treatment or prevention of cirrhosis of the liver (a condition in which scarring has overtaken normal liver regeneration processes); treatment of keloid (hypertrophic scar) formation causing disfiguring of the skin in which the scarring process interferes with normal renewal; psoriasis (a common skin condition characterized by excessive proliferation of the skin and delay in proper cell fate determination); benign tumors; fibrocystic conditions and tissue hypertrophy (e.g., benign prostatic hypertrophy).

(iv) Neurodegenerative Disorders

Certain binding partners of the Nlk1 protein (i.e., Nlk1 protein-IPs) have been implicated in neurodegenerative disease, such as Alzheimer disease, and it appears likely that IP-3 (ubiquitin specific hydrolases homolog) and IP-4 (collagen-homolog) play an important role in these disorders. Accordingly, Therapeutics of the present invention (particularly those which modulate or supply complexes of the Nlk1 protein and a Nlk1 protein-IP) may prove effective in treating or preventing neurodegenerative diseases including, but not limited to: Alzheimer disease, Creutzfeuld Jakob disease, Lewy body disease and others. The efficacy of the Therapeutics of the present invention in treating or preventing such neurodegenerative diseases and disorders may be ascertained by any method known within the art for efficacy. Such assays include in vitro assays for regulated cell maturation or inhibition of apoptosis, in vivo assays using animal models of neurodegenerative diseases or disorders, or the like. Potentially effective Therapeutics, for example but not by way of limitation, promote regulated cell maturation and prevent cell apoptosis in culture or reduce neurodegeneration in animal models, in comparison to controls.

Once a neurodegenerative disease or disorder has been shown to be amenable to treatment by modulation of Nlk1 protein•Nlk1 protein-IP complex activity, that neurodegenerative disease or disorder may be treated or prevented by the administration of a Therapeutic which modulates Nlk1 protein•Nlk1 protein-IP complex formation or function.

(v) Cardiovascular Disease

Cardiomyopathies are serious heart muscle disorders in children and adults, which result in morbidity and premature death. These disorders include hypertrophic cardiomyopathy, dilated cardiomyopathy and restrictive cardiomyopathy. Hypertrophic cardiomyopathy is characterized by left ventricular hypertrophy in the absence of an increased external load, and myofibrillar disarray. Mutations in a total of seven genes, all encoding sarcomeric proteins, have been identified as causes of familial hypertrophic cardiomyopathy, and include those genes encoding cytoskeletal proteins (e.g., $\alpha$-tropomyosin, $\beta$-myosin heavy chain, cardiac troponin-T, myosin binding protein-C, myosin essential light chain, myosin regulatory light chain, troponin I, and probably the tropomyosin-homolog proteins, IP-2 and IP-5. Accordingly, Therapeutics of the present invention, particularly those that modulate or supply Nlk1 protein•-Nlk1 protein-IP complex activity, may be effective in treating or preventing cardiomyopathy-associated diseases or disorders.

A vast array of animal and in vitro cell culture models exist for processes involved in cardiovascular disorders. Potentially effective Therapeutics, for example but not by way of limitation, may be studied in: (i) a murine systems which express mutant tropomyosin or myosin as a model for familial hypertrophic cardiomyopathy (see e.g., Vikstrom, et al., 1996. *Mol. Med.* 2:556–567); (ii) in a pig model with naturally occurring hypertrophic cardiomyopathy (see e.g., Lee, et al., 1996. *FASEB J.* 10:1198–1204) or (iii) in a feline model of hypertrophic cardiomyopathy (see e.g., Fox, et al., 1995. *Circulation* 92:2645–2651).

In accord, once an cardiomyopathy-associated disease or disorder has been shown to be amenable to treatment by modulation of Nlk1 protein•Nlk1 protein-IP complex activity, that disease or disorder may be treated or prevented by the administration of a Therapeutic which modulates Nlk1 protein•Nlk1 protein-IP complex formation or function.

(vi) Viral Infection

The Nlk1 protein binding partner (i.e., a Nlk1 protein-IP), Ini-1, has been implicated in viral infections. Ini-1 is involved in the integration of the virus HIV-1 into the host genome by interacting with and activating the enzyme, HIV-1 integrase. It has also been shown to interact with the Epstein Barr virus (EBV) nuclear antigen 2. Therapeutics of the present invention, particularly those that modulate or supply Nlk1 protein:Ini-1 complex activity may be effective in treating or preventing viral infections and related diseases and disorders, including HIV infection and AIDS. Therapeutics of the invention (particularly Therapeutics which modulate the levels or biological activity of the Nlk1 protein:Ini-1 complex) may be assayed by any method known within the art to be efficacious in treating or preventing such viral infections and related diseases and disorders. Such assays include in vitro assays for using cell culture models or in vivo assays using animal models of viral diseases or disorders. Potentially effective Therapeutics, for example but not by way of limitation, reduce viral responses in animal models in comparison to controls.

Accordingly, once a viral disease or disorder has been shown to be amenable to treatment by modulation of Nlk1 protein:Ini-1 complex activity, that viral disease or disorder may be treated or prevented by the administration of a Therapeutic which modulates Nlk1 protein•Nlk1 protein-IP complex formation or function.

(vii) Metabolic Diseases and Disorders

Several Nlk1 protein binding partners (i.e., Nlk1 protein-IPs) have been implicated in metabolic diseases. The Trk oncogene (TrkA) shows an expression deficit in rodent diabetes model; PP1$\alpha$ controls glycolytic flux in muscles; 14-3-3$\epsilon$ regulates the insulin sensitivity and vimentin has a role in adrenal steroidogenesis. IP-1 (IF-associated protein homolog), IP-3 (ubiquitin-hydroxylase homolog) and IP-4 (collagen-homolog) all appear to have additional roles in metabolic diseases. Therapeutics of the present invention, particularly those which modulate or supply Nlk1 proteine•Nlk1 protein-IP complex formation and/or activity may be effective in treating or preventing related diseases and disorders. The Therapeutics of the present invention may be assayed by any method known within the art for efficacy in treating or preventing metabolic diseases and disorders. Such assays include in vitro assays for using cell culture models or in vivo assays using animal models of metabolic diseases or disorders. Potentially effective Therapeutics, for example but not by way of limitation, reduce metabolic diseases and their deleterious physiological consequences in animal models, in comparison to controls.

Accordingly, once an metabolic disease or disorder has been shown to be amenable to treatment by modulation of Nlk1 protein•Nek 2 protein IP complex activity, that metabolic disease or disorder may be treated or prevented by the administration of a Therapeutic which modulates Nlk1 protein•Nlk1 protein-IP complex formation or function.

(7) Gene Therapy

In a specific embodiment of the present invention, nucleic acids comprising a sequence which encodes the Nlk1 protein and/or a Nlk1 protein-IP, or functional derivatives thereof, are administered to modulate Nlk1 protein•Nlk1 protein-IP complex function, by way of gene therapy. In more specific embodiments, a nucleic acid or nucleic acids encoding both the Nlk1 protein and a Nlk1 protein-IP (e.g., TrkA, protein phosphatase 1$\alpha$, 14-3-3$\epsilon$, $\alpha$-tropomyosin, vimentin, p0071, Ini-1, IP-1, IP-2, IP-3, IP-4 and IP-5), or functional derivatives thereof, are administered by way of gene therapy. Gene therapy refers to therapy which is performed by the administration of a specific nucleic acid to a subject. In this embodiment of the present invention, the nucleic acid produces its encoded protein(s), which then serve to exert a therapeutic effect by modulating Nlk1 protein•Nlk1 protein-IP complex function. Any of the methodologies relating to gene therapy available within the art may be used in the practice of the present invention. See e.g., Goldspiel, et al., 1993. *Clin. Pharm.* 12:488–505.

In a preferred embodiment, the Therapeutic comprises a Nlk1 protein and a Nlk1 protein-IP nucleic acid which is part of an expression vector expressing both of the aforementioned proteins, or fragments or chimeric proteins thereof, within a suitable host. In a specific embodiment, such a nucleic acid possesses a promoter which is operably-linked to the Nlk1 protein and the Nlk1 protein-IP coding region(s), or, less preferably two separate promoters linked to the Nlk1 protein and the Nlk1 protein-IP coding regions separately; wherein said promoter is inducible or constitutive, and, optionally, tissue-specific. In another specific embodiment, a nucleic acid molecule is used in which the Nlk1 protein and Nlk1 protein-IP coding sequences (and any other desired sequences) are flanked by regions which promote homologous recombination at a desired site within the genome, thus providing for intra-chromosomal expression of the Nlk1 protein and the Nlk1 protein-IP nucleic acids. See e.g., Koller & Smithies, 1989. *Proc. Natl. Acad. Sci. USA* 86:8932–8935.

Delivery of the Therapeutic nucleic acid into a patient may be either direct (i.e., the patient is directly exposed to the nucleic acid or nucleic acid-containing vector) or indirect (i.e., cells are first transformed with the nucleic acid in vitro, then transplanted into the patient). These two approaches are known, respectively, as in vivo or ex vivo gene therapy. In a specific embodiment of the present invention, the nucleic acid is directly administered in vivo, where it is expressed to produce the encoded product. This may be accomplished by any of numerous methods known in the art including, but not limited to: (i) constructing it as part of an appropriate nucleic acid expression vector and administering in a manner such that it becomes intracellular (e.g., by infection using a defective or attenuated retroviral or other viral vector; see U.S. Pat. No. 4,980,286) or (ii) direct injection of naked DNA, or through the use of microparticle bombardment (e.g., a "Gene Gun®; Biolistic, Dupont), or by coating it with lipids, cell-surface receptors/ transfecting agents, or through encapsulation in liposomes, microparticles, or microcapsules, or by administering it in linkage to a peptide which is known to enter the nucleus, or by administering it in linkage to a ligand predisposed to receptor-mediated endocytosis (see e.g., Wu & Wu, 1987. *J. Biol. Chem.* 262:4429–4432), which can be used to "target" cell types which specifically express the receptors of interest, etc.

In another specific embodiment of the present invention, a nucleic acid-ligand complex may be produced in which the ligand comprises a fusogenic viral peptide designed so as to disrupt endosomes, thus allowing the nucleic acid to avoid subsequent lysosomal degradation. In yet another specific embodiment, the nucleic acid may be targeted in vivo for cell-specific endocytosis and expression, by targeting a specific receptor. See e.g., PCT Publications WO 92/06180; WO 93/14188 and WO 93/20221. Alternatively, the nucleic acid may be introduced intracellularly and incorporated within host cell genome for expression by homologous recombination. See e.g., Zijlstra, et al., 1989. *Nature* 342:435–438.

In yet another specific embodiment, a viral vector which contains the Nlk1 protein and/or the Nlk1 protein-IP nucleic acids is utilized. For example, retroviral vectors may be employed (see e.g., Miller, et al., 1993. *Meth. Enzymol.* 217:581–599) which have been modified to delete those retroviral-specific sequences which are not required for packaging of the viral genome and its subsequent integration into host cell DNA. The Nlk1 protein and/or Nlk1 protein-IP (preferably both protein species) nucleic acids are cloned into the vector, which facilitates delivery of the genes into a patient. See e.g., Boesen, et al, 1994. *Biotherapy* 6:291–302; Kiem, et al., 1994. *Blood* 83:1467–1473. Additionally, adenovirus is an especially efficacious "vehicle" for the delivery of genes to the respiratory epithelia. Other targets for adenovirus-based delivery systems are liver, the central nervous system, endothelial cells, and muscle. Adenoviruses also possess the advantageous ability to infect non-dividing cells. For a review see e.g., Kozarsky & Wilson, 1993. *Curr. Opin. Gen. Develop.* 3:499–503. Adenovirus-associated virus (AAV) has also been proposed for use in gene therapy. See e.g., Walsh, et al., 1993. *Proc. Soc. Exp. Biol. Med.* 204:289–300.

An additional approach to gene therapy in the practice of the present invention involves transferring a gene into cells in vitro tissue culture by such methods as electroporation, lipofection, calcium phosphate-mediated transfection, or viral infection. Generally, the methodology of transfer includes the transfer of a selectable marker to the cells. The cells are then placed under selection pressure (e.g., antibiotic resistance) so as facilitate the isolation of those cells which have taken up, and are expressing the transferred gene. Those cells are then delivered to a patient. In this specific embodiment, the nucleic acid is introduced into a cell prior to the in vivo administration of the resulting recombinant cell by any method known within the art including, but not limited to: transfection, electroporation, microinjection, infection with a viral or bacteriophage vector containing the nucleic acid sequences of interest, cell fusion, chromosome-mediated gene transfer, microcell-mediated gene transfer, spheroplast fusion, and similar methodologies which ensure that the necessary developmental and physiological functions of the recipient cells are not disrupted by the transfer. See e.g., Loeffler & Behr, 1993. *Meth. Enzymol.* 217:599–618. The technique should provide for the stable transfer of the nucleic acid to the cell, so that the nucleic acid is expressible by the cell and preferably heritable and expressible by its cell progeny.

In preferred embodiments of the present invention, the resulting recombinant cells may be delivered to a patient by various methods known within the art including, but not limited to: injection of epithelial cells (e.g., subcutaneously); the application of recombinant skin cells as a skin graft onto the patient and the intravenous injection of recombinant blood cells (e.g., hematopoetic stem or progenitor cells). The total amount of cells which are envisioned for use depend upon the desired effect, patient state, etc., and may be determined by one skilled within the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes and blood cells (e.g., T-lymphocytes, B-lymphocytes, monocytes, macrophages, neutrophils, eosinophils, megakaryocytes, granulocytes and hematopoetic stem or progenitor cells obtained from bone marrow, umbilical cord blood, peripheral blood, fetal liver, etc.). In a preferred embodiment of the present invention, the cell utilized for gene therapy may be autologous to the patient.

In a specific embodiment in which recombinant cells are used in gene therapy, stem or progenitor cells, which can be isolated and maintained in vitro, may be utilized. Such stem cells include, but are not limited to, hematopoetic stem cells (HSC), stem cells of epithelial tissues (e.g., skin, lining of the gut, embryonic heart muscle cells, liver stem cells) and neural stem cells (see e.g., Stemple & Anderson, 1992. *Cell* 71:973–985). With respect to hematopoetic stem cells (HSC), any technique which provides for the isolation, propagation, and maintenance in vitro of HSC may be used in this specific embodiment of the invention. As previously discussed, the HSCs utilized for gene therapy are, preferably, autologous to the patient. Hence, non-autologous HSCs are, preferably, utilized in conjunction with a method of suppressing transplantation immune reactions of the future host/patient. See e.g., Kodo, et al., 1984. *J. Clin. Invest.* 73:1377–1384. In another preferred embodiment of the present invention, HSCs may be highly enriched (or produced in a substantially-pure form), by any techniques known within the art, prior to administration to the patient. See e.g., Witlock & Witte, 1982. *Proc. Natl. Acad. Sci. USA* 79:3608–3612.

(8) Utilization of Anti-Sense Oligonucleotides

In a specific embodiment of the present invention, Nlk1 protein•Nlk1 protein-IP complex formation and function may be inhibited by the use of anti-sense nucleic acids for the Nlk1 protein and/or a Nlk1 protein-IP (e.g. TrkA, protein phosphatase 1α, 14-3-3ε, α-tropomyosin, vimentin, p0071, Ini-1, IP-1, IP-2, IP-3, IP-4 and IP-5 ), and is preferably comprised of both the Nlk1 protein and the Nlk1 protein-IP. In addition, the present invention discloses the therapeutic or prophylactic use of nucleic acids (of at least six nucleotides in length) which are anti-sense to a genomic sequence (gene) or cDNA encoding the Nlk1 protein and/or a Nlk1 protein-IP, or portions thereof. Such anti-sense nucleic acids have utility as Therapeutics which inhibit Nlk1 protein•Nlk1 protein-IP complex formation or activity, and may be utilized in a therapeutic or prophylactic manner.

Another specific embodiment of the present invention discloses methodologies for the inhibition of the expression of the Nlk1 protein and a Nlk1 protein-IP nucleic acid sequences, within a prokaryotic or eukaryotic cell, which is comprised of providing the cell with an therapeutically-effective amount of an anti-sense nucleic acid of the Nlk1 protein and a Nlk1 protein-IP, or derivatives thereof.

The anti-sense nucleic acids of the present invention may be oligonucleotides which may either be directly administered to a cell or which may be produced in vivo by transcription of the exogenous, introduced sequences. In addition, the anti-sense nucleic acid may be complementary to either a coding (i.e., exonic) and/or non-coding (i.e., intronic) region of the Nlk1 protein or Nlk1 protein-IP mRNAs. The Nlk1 protein and Nlk1 protein-IP anti-sense nucleic acids are, at least, six nucleotides in length and are, preferably, oligonucleotides ranging from 6–200 nucleotides in length. In specific embodiments, the anti-sense oligonucleotide is at least 10 nucleotides, at least 15 nucleotides, at least 100 nucleotides, or at least 200 nucleotides. The anti-sense oligonucleotides may be DNA or RNA (or chimeric mixtures, derivatives or modified versions thereof), may be either single-stranded or double-stranded and may be modified at a base, sugar or phosphate backbone moiety.

In addition, the anti-sense oligonucleotide of the present invention may include other associated functional groups, such as peptides, moieties which facilitate the transport of the oligonucleotide across the cell membrane, a hybridization-triggered cross-linking agent, a hybridization-triggered cleavage-agent, and the like. See e.g., Letsinger, et al., 1989. *Proc. Natl. Acad. Sci. U.S.A.* 86:6553–6556; PCT Publication No. WO 88/09810. In a specific embodiment, the Nlk1 protein and Nlk1 protein-IP antisense oligonucleotides comprise catalytic RNAs or ribozymes. See, e.g., Sarver, et al., 1990. *Science* 247:1222–1225.

The anti-sense oligonucleotides of the present invention may be synthesized by standard methodologies known within the art including, but not limited to: (i) automated phosphorothioate-mediated oligonucleotide synthesis (see e.g., Stein, et al., 1988. *Nuc. Acids Res.* 16:3209) or (ii) methylphosphonate oligonucleotides can be prepared by use of controlled pore glass polymer supports (see e.g., Sarin, et al., 1988. *Proc. Natl. Acad. Sci. U.S.A.* 85:7448–7451).

In an alternative embodiment, the Nlk1 protein and Nlk1 protein-IP antisense nucleic acids are produced intracellularly by transcription of an exogenous sequence. For example, a vector may be produced which (upon being exocytosed by the cell) is transcribed in vivo, thus producing an antisense nucleic acid (RNA) species. The aforementioned vector may either remain episomal or become chromosomally-integrated, so long as it can be transcribed to produce the desired antisense RNA. The vectors utilized in the practice of the present invention may be derived from bacterial, viral, yeast or other sources known within the art, which are utilized for replication and expression in mammalian cells. Expression of the sequences encoding the Nlk1 protein and Nlk1 protein-IP antisense RNAs may be facilitated by any promoter known within the art to function in mammalian, preferably, human cells. Such promoters may be inducible or constitutive and include, but are not limited to: (i) the SV40 early promoter region; (ii) the promoter contained in the 3'-terminus long terminal repeat of Rous sarcoma virus (RSV); (iii) the Herpesvirus thymidine kinase promoter and (iv) the regulatory sequences of the metallothionein gene.

The Nlk1 protein and Nlk1 protein-IP antisense nucleic acids may be utilized prophylactically or therapeutically in the treatment or prevention of disorders of a cell type which expresses (or preferably over-expresses) the Nlk1 protein•Nlk1 protein-IP complex. Cell types which express or over-express the Nlk1 protein and Nlk1 protein-IP RNA, or IP-1, IP-3, IP-4 and IP-5 RNA, may be identified by various methods known within the art including, but are not limited to, hybridization with Nlk1 protein- and Nlk1 protein-IP-specific nucleic acids (e.g. by Northern hybridization, dot blot hybridization, in situ hybridization) or by observing the ability of RNA from the specific cell type to be translated in vitro into the Nlk1 protein and the Nlk1 protein-IP by immunohistochemistry. In a preferred aspect, primary tissue from a patient may be assayed for the Nlk1 protein and/or Nlk1 protein-IP expression prior to actual treatment by, for example, immunocytochemistry or in situ hybridization.

Pharmaceutical compositions of the present invention, comprising an effective amount of a Nlk1 protein and a Nlk1 protein-IP antisense nucleic acid contained within a pharmaceutically-acceptable carrier may be administered to a patient having a disease or disorder which is of a type that expresses or over-expresses Nlk1 protein•Nlk1 protein-IP complex RNA or protein. The amount of Nlk1 protein and/or Nlk1 protein-IP antisense nucleic acid which will be effective in the treatment of a particular disorder or condition will be dependant upon the nature of the disorder or condition, and may be determined by standard clinical techniques. Where possible, it is desirable to determine the antisense cytotoxicity in vitro, and then in useful animal model systems prior to testing and use in humans. In a specific embodiment, pharmaceutical compositions comprising Nlk1 protein and Nlk1 protein-IP antisense nucleic acids may be administered via liposomes, microparticles, or microcapsules. See e.g., Leonetti, et al., 1990. *Proc. Natl. Acad. Sci. U.S.A.* 87:2448–2451.

(9) Nlk1 Protein•Nlk1 Protein-IP Complex Assays

The functional activity of Nlk1 protein•Nlk1 protein-IP complexes (and derivatives, fragments, analogs and homologs thereof) may be assayed by a number of methods known within the art. For example, putative modulators (e.g., inhibitors, agonists and antagonists) of Nlk1 protein•Nlk1 protein complex activity (e.g., anti-Nlk1 protein•Nlk1 protein-IP complex antibodies, as well as Nlk1 protein or Nlk1 protein-IP antisense nucleic acids) may be assayed for their ability to modulate Nlk1 protein•Nlk1 protein-IP complex formation and/or activity.

(i) Immunoassays

In a specific embodiment of the present invention, immunoassay-based methodologies are disclosed where one is assaying for: (i) the ability to bind to, or compete with, wild-type Nlk1 protein•Nlk1 protein-IP complex or IP-1, IP-2, IP-3, IP-4, and IP-5 or (ii) the ability to bind to an anti-Nlk1 protein•Nlk1 protein-IP complex antibody. These immunoassays include, but are not limited to, competitive and non-competitive assay systems utilizing techniques such as radioimmunoassays, enzyme linked immunosorbent assay(ELISA), "sandwich" immunoassays, immunoradiometric assays, gel diffusion precipitin reactions, immunodiffusion assays, in situ immunoassays (e.g., using colloidal gold, enzyme or radioisotope labels), Western blots, Northwestern blots, precipitation reactions, agglutination assays (e.g., gel agglutination assays, hemagglutination assays), complement fixation assays, immunofluorescence assays, protein-A assays and immunoelectrophoresis assays, and the like. In one specific embodiment of the present invention, antibody binding is detected by assaying for a label on the primary antibody. In another specific embodiment, the binding of the primary antibody is ascertained by the detection of the binding of a secondary antibody (or reagent) specific for the primary antibody. In a further embodiment, the secondary antibody is labeled.

(ii) Gene Expression Assays

The expression of the Nlk1 protein or Nlk1 protein-IP genes (both endogenous genes and those expressed from recombinant DNA) may be detected using techniques known within the art including, but not limited to: Southern hybridization, Northern hybridization, restriction endonuclease mapping, DNA sequence analysis and polymerase chain reaction amplification (PCR) followed by Southern hybridization or RNase protection (see e.g., *Current Protocols in Molecular Biology* 1997. (John Wiley and Sons, New York, N.Y.)) with probes specific for the Nlk1 protein and Nlk1 protein-IP genes in various cell types.

In one specific embodiment of the present invention, Southern hybridization may be used to detect genetic linkage of the Nlk1 protein and/or Nlk1 protein-IP gene mutations to physiological or pathological states. Numerous cell types, at various stages of development, may be characterized for their expression of the Nlk1 protein and a Nlk1 protein-IP (particularly the concomitant expression of the Nlk1 protein and Nlk1 protein-IP within the same cells). The stringency of the hybridization conditions for Northern or Southern blot analysis may be manipulated to ensure detection of nucleic acids with the desired degree of relatedness to the specific probes used. Modification of these aforementioned methods, as well as other methods well-known within the art, may be utilized in the practice of the present invention.

(iii) Binding Assays

Derivatives, fragments, analogs and homologs of Nlk1 protein-IPs may be assayed for binding to the Nlk1 protein by any method known within the art including, but not limited to: (i) the modified yeast two hybrid assay system; (ii) immunoprecipitation with an antibody which binds to the Nlk1 protein within a complex, followed by analysis by size fractionation of the immunoprecipitated proteins (e.g., by denaturing or non-denaturing polyacrylamide gel electrophoresis); (iii) Western analysis; (v) non-denaturing gel electrophoresis, and the like.

(iii) Assays for Biological Activity

A specific embodiment of the present invention provides a methodology for the screening of a derivative, fragment, analog or homolog of the Nlk1 protein for biological activity which is comprised of contacting a derivative, fragment, analog or homolog of the Nlk1 protein with one of the Nlk1 Protein-IPs (e.g., TrkA, protein phosphatase 1α, 14-3-3ε, α-tropomyosin, vimentin, p0071, Ini-1, IP-1, IP-2, IP-3, IP-4 and IP-5) and detecting the formation of a complex between said derivative, fragment, analog or homolog of the Nlk1 protein and the specific Nlk1 protein-IP; wherein the detection of the formation of said complex indicates that the Nlk1 protein derivative, fragment, analog or homolog, possesses biological (e.g., binding) activity. Similarly, an additional embodiment discloses a methodology for the screening a derivative, fragment, analog or homolog of a Nlk1 protein-IP for biological activity comprising contacting said derivative, fragment, analog or homolog of said protein with the Nlk1 protein; and detecting the formation of a complex between said derivative, fragment, analog or homolog of the Nlk1 protein-IP and the Nlk1 protein; wherein detecting the formation of said complex indicates that said the Nlk1 protein-IP derivative, fragment, analog, or homolog possesses biological activity.

(10) Modulation of Nlk1 Protein•Nlk1 Protein-IP Complex Activity

The present invention discloses methodologies relating to the modulation of the activity of a protein moiety which possesses the ability to participate in a Nlk1 protein•Nlk1 protein-IP complex (e.g., the Nlk1 protein of TrkA, protein phosphatase 1α, 14-3-3, α-tropomyosin, vimentin, p0071, Ini-1, IP-1, IP-2, IP-3, IP-4 and IP-5) by the administration of a binding partner of that protein (or derivative, fragment, analog or homolog thereof). The Nlk1 protein (and derivatives, fragments, analogs and homologs thereof) may be assayed for their ability to modulate the activity or levels of a Nlk1 protein-IP by contacting a cell, or administering to an animal expressing a Nlk1 protein-IP gene, with the Nlk1 protein, or a nucleic acid encoding the Nlk1 protein or an antibody which immunospecifically-binds the Nlk1 protein, or a derivative, fragment, analog or homolog of said antibody which contains the binding domain thereof, and measuring a change in Nlk1 protein-IP levels or activity; wherein a change in Nlk1 protein-IP levels or activity indicates that the Nlk1 protein possesses the ability to modulate Nlk1 protein-IP levels or activity. In another embodiment, a Nlk1 protein-IP may be assayed for the ability to modulate the activity or levels of the Nlk1 protein in an analogous manner.

In a specific embodiment, the Nlk1 protein is active as a protein phosphatase which phosphorylates serine/threonine residues of proteins involved early in the cell-cycle. Accordingly, proteins and protein complexes of the present invention may be screened for the ability to modulate (i.e., increase or decrease) effects on critical cell-cycle proteins. For example, the Nlk1 protein has been shown to interact with retinoblastoma protein. Hence, the proteins and protein complexes of the present invention may be screened by assaying for changes in the level of retinoblastoma protein phosphorylation, and the like. See e.g., Milne, et al., 1994. *J. Biol. Chem.* 269:9253–9260. Furthermore, the Nlk1 protein has been shown to be associated with the centrosome during the cell-cycle, including all stages of mitosis. See e.g., Fry, et al., 1998. *EMBO J*. 17:470–481. Accordingly, the protein and protein complexes of the present invention may be screened for the ability to modulate (i.e., increase or decrease) effects on the centrosome.

In addition, TrkA is an essential component of the signal transducing receptor which mediates the biological properties of the nerve growth factor (NGF) family of neutrophins. Other TrkA substrates include: phospholipase C, PI-3 kinase, SHP-2, Ras GTPase activating protein, and ERK. TrkA is implicated in the growth of many tumors, including, but not limited to, those of the nervous system, colon carcinomas, thyroid tumors, and melanomas. Therefore, the proteins and protein complexes of the present invention may be screened for the ability to modulate (i.e., increase or decrease) the ability of TrkA to effect the biological properties and functions of its substrates. Protein phosphatase 1α (PP 1α) is a protein phosphatase affecting several signal transduction processes, including cell-cycle progression and neurotransmitter receptor activity. In particular, PP1α interacts with several proteins, including the retinoblastoma protein, Hox 11, DARPP-32, and toxins. Accordingly, the proteins and protein complexes of the present invention may be screened for the ability to modulate effects of PP 1α on these proteins.

The 14-3-3ε protein associates with a range of cellular proteins involved in signal transduction and/or cell-cycle regulation and oncogenesis. In addition, 14-3-3ε is present in the brains of patients with Alzheimer's disease and Creutzfeldt-Jakob disease. Accordingly, complexes and proteins of the invention can be screened for the ability to modulate effects of 14-3-3ε on cell-cycle regulation and neurodegenerative diseases and disorders. The ubiquitin specific hydrolase-homolog protein, IP-3, is implicated in degradation of cellular proteins. Accordingly, the proteins and protein complexes of the present invention may be screened for the ability to modulate the putative ability of IP-3 to influence degradation of cellular proteins.

Alpha-tropomyosin is a structural protein of the muscle which binds to actin and/or troponin and the homolog proteins, IP-2 and IP-5, have been shown to possess similar properties. Tropomyosins are found to be down-regulated in malignantly transformed cells and other tumors and a mutation in the gene for α-tropomyosin (and other structural cytoskeletal proteins) has been identified as cause of familial hypertrophic cardiomyopathy. Accordingly, complexes and proteins of the invention can be screened for the ability to modulate the expression of, and ability of α-tropomyosin, IP-2 and IP-5 to bind to actin and/or troponin. The vimentin protein assembles to intermediate filaments. Vimentin filaments have been demonstrated in many tumors and vimentin is believed to be involved in migration, invasion and metastasis. Accordingly, the proteins and protein complexes of the present invention may be screened for the ability to modulate the ability of vimentin to assemble to intermediate filaments, as well as to modulate the effects of vimentin on tumor migration, invasion and metastasis. In addition, vinentin may be utilized as marker for different cancers.

IP-1 is a protein homolog to intermediate filament associated proteins and homolog to keratins. Intermediate filaments are found in many tumors and are believed to be involved in migration, invasion and metastasis. Accordingly, the proteins and protein complexes of the present invention may be screened for the ability to modulate the ability of IP-1 to associate with intermediate filaments, as well as the ability to modulate the effects of IP-1 on tumor migration, invasion and metastasis. In addition, IP-1 may be utilized as marker for different cancers.

IP-4 shows homologies to collagen proteins. Metastatic tumor cell adhesion to connective tissue elements type I collagen is required for the movement of tumor cells into the sub-endothelial stroma and subsequent growth at these new sites. Accordingly, the proteins and protein complexes of the present invention may be screened for the ability to modulate the ability of IP-4 to influence the metastatic growth of tumor cells. The p0071 protein (an Armadillo protein) is associated with the cell-cell adherens junctional plaque (desmosomes). Accordingly, the proteins and protein complexes of the present invention may be screened for the ability to modulate the ability of p0071 to associate with desmosomal plaques. In addition, both Nlk1 protein•Nlk1 protein-IP complexes and individual Nlk1 protein-IPs may be screened by assaying for changes in levels of p0071-association with the desmosomal plaque (e.g., by immunoassays with anti-p0071 antibodies).

Integrase interactor 1 (Ini-1) protein has been demonstrated to interact with and activate HIV-1 integrase. Accordingly, the proteins and protein complexes of the present invention may be screened for the ability to modulate the ability of Ini-1 to influence the HIV-1 integration and replication.

(11) Nlk1-Related Treatment Assays
(i) Tumorigenesis

The Nlk1 protein, and several of the identified binding partners of the Nlk1 protein (i.e., Nlk1 protein-IPs) have roles in the control of cell proliferation and, therefore, cell-transformation and tumorigenesis. Accordingly, the present invention discloses methodologies for screening Nlk1 protein•Nlk1 protein-IP complexes and Nlk1 protein-IPs (and derivatives, fragments, analogs and homologs, thereof) for the ability to alter cell proliferation, cell transformation and/or tumorigenesis in vitro and in vivo. For example, but not by way of limitation, cell proliferation may be assayed by measuring $^3$H-thymidine incorporation, by direct cell count, by detecting changes in transcriptional activity of known genes such as proto-oncogenes (e.g., c-fos, c-myc) cell-cycle markers, and the like.

The Nlk1 protein•Nlk1 protein-IP complexes and Nlk1 protein-IPs (and derivatives, fragments, analogs and homologs, thereof) may also be screened for activity in inducing or inhibiting cell transformation (or the progression to malignant phenotype) in vitro. The proteins and protein complexes of the present invention may be screened by contacting either cells with a normal phenotype (for assaying for cell transformation) or a transformed cell phenotype (for assaying for inhibition of cell transformation) with the protein or protein complex of the present invention and examining the cells for acquisition or loss of characteristics associated with a transformed phenotype (a set of in vitro characteristics associated with a tumorigenic ability in vivo) including, but not limited to: colony formation in soft agar, a more rounded cell morphology, looser substratum attachment, loss of contact inhibition, loss of anchorage dependence, release of proteases such as plasminogen activator, increased sugar transport, decreased serum requirement, expression of fetal antigens, disappearance of the 250 Kdal cell-surface protein, and the like. See e.g., Luria, et al., 1978. *General Virology*, 3rd ed. (John Wiley & Sons, New York, N.Y.).

The Nlk1 protein•Nlk1 protein-IP complexes (and derivatives, fragments, analogs and homologs, thereof) may also be screened for activity to promote or inhibit tumor formation in vivo in non-human test animal. A vast number of animal models of hyperproliferative disorders (e.g., tumorigenesis and metastatic spread) are known within the art. See e.g., Lovejoy, et al., 1997. *J. Pathol.* 181:130–135. In a specific embodiment of the present invention, the proteins and protein complexes may be administered to a non-human test animal (preferably a test animal predisposed to develop a type of tumor) and the non-human test animals is subsequently examined for an increased incidence of tumor formation in comparison with controls animals which were not administered the proteins or protein complex of the present invention. Alternatively, the proteins and protein complexes may be administered to non-human test animals possessing tumors (e.g., animals in which tumors have been induced by introduction of malignant, neoplastic, or transformed cells or by administration of a carcinogen) and subsequently examining the tumors within the test animals for tumor regression in comparison to controls. Accordingly, once a hyperproliferative disease or disorder has been shown to be amenable to treatment by modulation of Nlk1 protein•Nlk1 protein-IP complex activity that disease or disorder may be treated or prevented by administration of a Therapeutic which modulates Nlk1 protein•Nlk1 protein-IP complex formation.

(ii) Neurodezenerative Diseases

In an embodiment of the present invention, a Therapeutic of the present invention may be assayed for activity in the treatment or prevention of neurodegenerative disease by administering the Therapeutic to: (i) culture cells in vitro or (ii) a test animal, such as but not limited to the PDAPP transgenic mouse model of Alzheimer disease (see e.g. Johnson-Wood. et al., 1997. *Proc. Natl. Acad. Sci. USA* 94:1550–1555), which exhibits symptoms of a neurodegenerative disease, or that is predisposed to develop symptoms of a neurodegenerative disease, and measuring the change in said symptoms or predisposition of the neurodegenerative disease after the administration of said Therapeutic; wherein a reduction in the predisposition or the severity of the symptoms of the neurodegenerative or prevention of the symptoms of the neurodegenerative disease indicates that the Therapeutic possesses activity in treating or preventing neurodegenerative disease.

Specific embodiments of such cultured cell models for neurodegenerative disease include, but are not limited to: cultured rat endothelial cells from affected and unaffected individual humans (see e.g., Maneiro, et al., 1997. *Methods Find. Exp. Clin. Pharmacol.* 19:5–12) including, but not limited to, cultured rat endothelial cells from affected and unaffected individual humans (see e.g., Maneiro, et al., 1997. *Methods Find. Exp. Clin. Pharmacol.* 19:5–12); P19 murine embryonic carcinoma cells (see e.g., Hung, et al., 1992. *Proc Natl Acad Sci USA* 89:9439–9443) and dissociated cell cultures of cholinergic neurons from nucleus basalis of Meynert (see e.g., Nakajima, et al., 1985. *Proc Natl Acad Sci USA* 82:6325–6329).

Specific embodiments of such test animal models neurodegenerative disease include, but are not limited to: partial trisomy 16 mouse (see e.g., Holtzman, et al., 1996. *Proc. Natl. Acad. Sci. USA* 93:13333–13338); bilateral nucleus basalis magnocellularis-lesioned rats (see e.g., Popovic, et al., 1996. *Int. J. Neurosci.* 86:281–299); the aged rat (see e.g., Muir, 1997. *Phannacol. Biochem. Behav.* 56:687–696); the PDAPP transgenic mouse model of Alzheimer disease (see e.g., Johnson-Wood, et al., 1997. *Proc. Natl. Acad. Sci. USA* 94:1550–1555) and experimental autoimmune dementia (see e.g., Oron, et al., 1997. *J. Neural. Transm.* 49:77–84).

Accordingly, once a neurodegeneration disease or disorder has been shown to be amenable to treatment by modulation of Nlk1 protein•Nlk1 protein-IP complex activity, that disease or disorder may be treated or prevented by administration of a Therapeutic which modulates Nlk1 protein•Nlk1 protein-IP complex formation and/or biological function.

(iii) Cardiomyopathy

As previously discussed, α-tropomyosin and is implicated in hypertrophic cardiomyopathy and associated disorders. Furthermore, due to their overall degree of homology to α-tropomyosin, the IP-2 and IP-5 proteins may also be implicated in these aforementioned disorders. Accordingly, in one embodiment of the present invention, a Therapeutic may be assayed for activity in treating or preventing cardiomyopathy (and associated disorders) by contacting: (i) cultured cells in vitro or (ii) animal models which exhibit an indicator or symptoms of cardiomyopathy with the Therapeutic, and subsequently comparing the level of said indicator in the cells or symptoms of the test animals contacted with the Therapeutic, with the level of said indicator in cells or symptoms in test animals not so contacted; wherein a diminution of these level in said contacted cells or test animals indicates that the Therapeutic possesses activity in treating or preventing cardiomyopathy and associated disorders.

Examples of cultured cells utilized in the practice of the present invention include, but are not limited to: cultured cardiac myocytes from neonates or adults (see e.g. Wall, et al., 1996. *Eur. J. Pharmacol.* 306:165–174) and cultured autoreactive T-lymphocytes in autoimmune myocarditis (see e.g, Perez-Leiros, et al, 1997. *Neuroimmunomodulation* 4:91–97). In another embodiment of the present invention, examples of test animals which may be utilized for the determination of whether a Therapeutic possesses activity in treating or preventing cardiomyopathy include, but not limited to: the aryl-hydrocarbon receptor-deficient mouse model of cardiomyopathy (see e.g., Femandez-Salguero, et al., 1997. *Vet. Pathol.* 34:605–614); experimental autoimmune myocarditis in mice (see e.g., Perez-Leiros, et al., 1997. *Neuroimmunomodulation* 4:91–97), transgenic mice over-expressing tropomodulin (see e.g., Sussman, et al., 1998. *J. Clin. Invest.* 101:51–61); guinea pigs immunized with adenine nucleotide transporter type I (see e.g., Domer, et al., 1997. *Mol. Cell. Biochem.* 174:261–269) and MLP-deficient mice (see e.g., Arber, et al., 1997. *Cell* 88:393–403).

(iv) Viral Infection

The Nlk1 protein interactant (Nlk1 protein-IP), Ini-1, is strongly implicated in viral infection mechanisms, including that for the AIDS virus, HIV-1. An enormous number of human diseases result from virulent and opportunistic viral infection. Accordingly, the Nlk1-related proteins and protein complexes, nucleic acids, and antibodies of the present invention may be tested for activity in treating or preventing viral diseases by the use of in vitro and in vivo assays.

Specifically, a Therapeutic of the present invention may be assayed for activity in the treatment or prevention of viral disease and/or infection by contacting: (i) cultured cells in vitro or (ii) animals models which exhibit an indicator or symptoms a viral infection reaction with the Therapeutic, and comparing the level of said indicator in the cells or symptoms in the test animals contacted with the Therapeutic with said level of said indicator in cells or symptoms in the test animals not so contacted; wherein a lower level in said contacted cells or test animals indicates that the Therapeutic possesses activity in treating or preventing viral infection and/or disease.

In vitro cell culture models which may be used for such assays include, but are not limited to: viral infection of T-lymphocytes (see e.g., Selin, et al., 1996. *J. Exp. Med.* 183:2489–2499); hepatitis B infection of dedifferentiated hepatoma cells (see e.g., Raney, et al., 1997. *J. Virol.* 71:1058–1071) and synchronous HIV-1 infection of CD4+ lymphocytic cell lines (see e.g., Wainberg, et al., 1997. *Virology* 233:364–373). Animal models of the present invention which can be utilized for such assays include, but are not limited to: neurotrophic virus infection of mice (see e.g., Bama, et al., 1996. *Virology* 223:331–343); encephalomyocarditis infection of mice (see e.g., Hirasawa, et al., 1997. *J. Virol.* 71:4024–4031) and cytomegalovirus (CMV) infection of mice (see e.g., Orange & Biron, 1996. *J. Immunol* 156:1138–1142).

(v) Metabolic Disorders

In specific embodiments of the present invention, Nlk1-related proteins, protein complexes, nucleic acids, and antibodies (as well as derivatives, fragments, analogs and homologs thereof) may be tested for activity in the treatment or prevention of diabetic neuropathy, glycolytic disorders, disorders involved in cholesterol transport and related disorders and diseases by the use of in vitro and in vivo assays.

Therapeutics of the present invention may be assayed for activity in treating or preventing diabetes by contacting: (i) cultured cells in vitro or (ii) animal models with the Therapeutic, and comparing the level of disease indicators in the cells or symptoms in the test animals contacted with the Therapeutic, with said level of said indicator in cells or animals not so contacted; wherein a lower level in said contacted cells or said test animals indicates that the Therapeutic possesses activity in treating or preventing diabetes or its sequelae.

Specific examples of cell culture models include, but are not limited to: (i) diabetes—cultured rat endothelial cells from diabetes-affected and -nonaffected humans (see e.g. Bazan, et al., 1997. *Therapie* 52:447–451) and (ii) cholesterol transport—cultured Chinese hamster ovary cells (see e.g., Underwood, et al., 1998. *J. Biol. Chem.* 273:4266–4274). Specific examples of animal models include, but are not limited to: (i) diabetes—IL-2-expressing transgenic mice (see e.g., Elliot & Flavell, 1994. *Int. Immunol.* 6:1629–1637) and (ii) cholesterol transport—obese murine model of hypercholesterolemia (see e.g., Hassel, 1998. *Curr. Opin. Lipidol.* 9:7–10).

(12) Protein-Protein Interaction Assays

The present invention discloses methodologies for assaying and screening derivatives, fragments, analogs and homologs of Nlk1 protein-interacting proteins (Nlk1 protein-IPs) for binding to Nlk1 protein. The derivatives, fragments, analogs and homologs of the Nlk1 protein-IPs which interact with Nlk1 protein may be identified by means of a yeast two hybrid assay system (see e.g., Fields & Song, 1989. *Nature* 340:245–246) or; preferably, a modification and improvement thereof, as described in U.S. patent applications Ser. Nos. 08/663,824 (filed Jun. 14, 1996) and 08/874,825 (filed Jun. 13, 1997), both of which are entitled "Identification and Comparison of Protein-Protein Interactions that Occur in Populations and Identification of Inhibitors of These Interactions," to Nandabalan, et al., and which are incorporated by reference herein in their entireties.

The identification of interacting proteins by the improved yeast two hybrid system is based upon the detection of the expression of a reporter gene (hereinafter "Reporter Gene"), the transcription of which is dependent upon the reconstitution of a transcriptional regulator by the interaction of two proteins, each fused to one half of the transcriptional regulator. The bait Nlk1 protein (or derivative, fragment, analog or homolog) and prey protein (proteins to be tested for ability to interact with the bait protein) are expressed as fusion proteins to a DNA-binding domain, and to a transcriptional regulatory domain, respectively, or vice versa. In a specific embodiment of the present invention, the prey population may be one or more nucleic acids encoding mutants of a Nlk1 protein-IP (e.g., as generated by site-directed mutagenesis or another method of producing mutations in a nucleotide sequence). Preferably, the prey populations are proteins encoded by DNA (e.g., cDNA, genomic DNA or synthetically generated DNA). For example, the populations may be expressed from chimeric genes comprising cDNA sequences derived from a non-characterized sample of a population of cDNA from mammalian RNA. In another specific embodiment, recombinant biological libraries expressing random peptides may be used as the source of prey nucleic acids.

The present invention discloses methods for the screening for inhibitors of the interacting proteins (Nlk1 protein-IPs). In brief, the protein-protein interaction assay may be performed as previously described herein, with the exception that it is performed in the presence of one or more candidate molecules. A resulting increase or decrease in Reporter Gene activity, in relation to that which was present when the one or more candidate molecules are absent, indicates that the candidate molecule exerts an effect on the interacting pair. In a preferred embodiment, inhibition of the protein interaction is necessary for the yeast cells to survive, for example, where a non-attenuated protein interaction causes the activation of the URA3 gene, causing yeast to die in medium containing the chemical 5-fluoroorotic acid. See e.g., Rothstein, 1983. *Meth. Enzymol.* 101:167–180.

In general, the proteins comprising the bait and prey populations are provided as fusion (chimeric) proteins, preferably by recombinant expression of a chimeric coding sequence containing each protein contiguous to a pre-selected sequence. For one population, the pre-selected sequence is a DNA-binding domain which may be any DNA-binding domain, so long as it specifically recognizes a DNA sequence within a promoter (e.g., a transcriptional activator or inhibitor). For the other population, the pre-selected sequence is an activator or inhibitor domain of a transcriptional activator or inhibitor, respectively. The regulatory domain alone (not as a fusion to a protein sequence) and the DNA-binding domain alone (not as a fusion to a protein sequence) preferably, do not detectably interact, so as to avoid false-positives in the assay. The assay system further includes a reporter gene operably linked to a promoter which contains a binding site for the DNA-binding domain of the transcriptional activator (or inhibitor). Accordingly, in the practice of the present invention, the binding of the Nlk1 protein fusion protein to a prey fusion protein leads to reconstitution of a transcriptional activator (or inhibitor), which concomitantly activates (or inhibits) expression of the Reporter Gene.

In a specific embodiment, the present invention discloses a methodology for detecting one or more protein-protein interactions comprising the following steps: (i) recombinantly-expressing the Nlk1 protein (or a derivative, fragment, analog or homolog thereof) in a first population of yeast cells of a first mating type and possessing a first fusion protein containing the Nlk1 protein sequence and a DNA-binding domain; wherein said first population of yeast cells contains a first nucleotide sequence operably-linked to a promoter which is "driven" by one or more DNA-binding sites recognized by said DNA-binding domain such that an interaction of said first fusion protein with a second fusion protein (comprising a transcriptional activation domain) results in increased transcription of said first nucleotide sequence; (ii) negatively selecting to eliminate those yeast cells in said first population in which said increased transcription of said first nucleotide sequence occurs in the absence of said second fusion protein; (iii) recombinantly expressing in a second population of yeast cells of a second mating type different from said first mating type, a plurality of said second fusion proteins; wherein said second fusion protein is comprised of a sequence of a derivative, fragment, analog or homolog of a Nlk1 protein-IP and an activation domain of a transcriptional activator, in which the activation domain is the same in each said second fusion protein; (iv) mating said first population of yeast cells with said second population of yeast cells to form a third population of diploid yeast cells, wherein said third population of diploid yeast cells contains a second nucleotide sequence operably linked to a promoter "driven" by a DNA-binding site recognized by said DNA-binding domain such that an interaction of a first fusion protein with a second fusion protein results in increased transcription of said second nucleotide sequence, in which the first and second nucleotide sequences can be the same or different and (v) detecting said increased transcription of said first and/or second nucleotide sequence, thereby detecting an interaction between a first fusion protein and a second fusion protein.

In a preferred embodiment, the bait (a Nlk1 protein sequence) and the prey (a library of chimeric genes) are combined by mating the two yeast strains on solid media for a period of approximately 6–8 hours. In a less preferred embodiment, the mating is performed in liquid media. The resulting diploids contain both types of chimeric genes (i.e., the DNA-binding domain fusion and the activation domain fusion). After an interactive population is obtained, the DNA sequences encoding the pairs of interactive proteins are isolated by a method wherein either the DNA-binding domain hybrids or the activation domain hybrids are amplified, in separate reactions. Preferably, the amplification is carried out by polymerase chain reaction (PCR; see e.g., Innis, et al., 1990. *PCR Protocols* (Academic Press, Inc., San Diego, Calif.)) utilizing pairs of oligonucleotide primers specific for either the DNA-binding domain hybrids or the activation domain hybrids. The PCR amplification reaction may also be performed on pooled cells expressing interacting protein pairs, preferably pooled arrays of interactants. Other amplification methods known within the art may also be used including, but not limited to, ligase chain reaction; Qβ-replicase or the like. See e.g., Kricka, et al., 1995. *Molecular Probing, Blotting, and Sequencing* (Academic Press, New York, N.Y.).

In an additional embodiment of the present invention, the plasmids encoding the DNA-binding domain hybrid and the activation domain hybrid proteins may also be isolated and cloned by any of the methods well-known within the art. For example, but not by way of limitation, if a shuttle (yeast to *E. coli*) vector is used to express the fusion proteins, the genes may be subsequently recovered by transforming the yeast DNA into *E. coli* and recovering the plasmids from the bacteria. See e.g., Hoffinan ,et al., 1987. *Gene* 57:267–272.

(13) Pharmaceutical Compositions

The invention present discloses methods of treatment and prophylaxis by the administration to a subject of an pharmaceutically-effective amount of a Therapeutic of the invention. In a preferred embodiment, the Therapeutic is substantially purified and the subject is a mammal, and most preferably, human.

Formulations and methods of administration that can be employed when the Therapeutic comprises a nucleic acid are described in Sections 6(i) and 6(ii), supra. Various delivery systems are known and can be used to administer a Therapeutic of the present invention including, but not limited to: (i) encapsulation in liposomes, microparticles, microcapsules; (ii) recombinant cells capable of expressing the Therapeutic; (iii) receptor-mediated endocytosis (see, e.g. Wu & Wu, 1987. *J. Biol. Chem.* 262:4429–4432); (iv) construction of a Therapeutic nucleic acid as part of a retroviral or other vector, and the like.

Methods of administration include, but are not limited to, intradermal, intramuscular, intraperitoneal, intravenous, subcutaneous, intranasal, epidural, and oral routes. The Therapeutics of the present invention may be administered by any convenient route, for example by infusion or bolus injection, by absorption through epithelial or mucocutaneous linings (e.g., oral mucosa, rectal and intestinal mucosa, etc.) and may be administered together with other biologically-active agents. Administration can be systemic or local. In addition, it may be advantageous to administer the Therapeutic into the central nervous system by any suitable route, including intraventricular and intrathecal injection. Intraventricular injection may be facilitated by an intraventricular catheter attached to a reservoir (e.g., an Ommaya reservoir). Pulmonary administration may also be employed by use of an inhaler or nebulizer, and formulation with an aerosolizing agent. It may also be desirable to administer the Therapeutic locally to the area in need of treatment; this may be achieved by, for example, and not by way of limitation, local infusion during surgery, topical application, by injection, by means of a catheter, by means of a suppository, or by means of an implant. In a specific embodiment, administration may be by direct injection at the site (or former site) of a malignant tumor or neoplastic or pre-neoplastic tissue.

In another embodiment of the present invention, the Therapeutic may be delivered in a vesicle, in particular a liposome. See e.g., Langer, 1990. *Science* 249:1527–1533. In yet another embodiment, the Therapeutic can be delivered in a controlled release system including ,but not limited to: a delivery pump (see e.g., Saudek, et al., 1989. *New Engl. J. Med.* 321:574 and a semi-permeable polymeric material (see e.g., Howard, et al., 1989. *J. Neurosurg.* 71:105). Additionally, the controlled release system can be placed in proximity of the therapeutic target (e.g., the brain), thus requiring only a fraction of the systemic dose. See, e.g., Goodson, In: *Medical Applications of Controlled Release* 1984. (CRC Press, Bocca Raton, Fla.).

In a specific embodiment of the present invention, where the Therapeutic is a nucleic acid encoding a protein, the Therapeutic nucleic acid may be administered in vivo to promote expression of its encoded protein, by constructing it as part of an appropriate nucleic acid expression vector and administering it so that it becomes intracellular (e.g., by use of a retroviral vector, by direct injection, by use of microparticle bombardment, by coating with lipids or cell-surface receptors or transfecting agents, or by administering it in linkage to a homeobox-like peptide which is known to enter the nucleus (see e.g., Joliot, et al., 1991. *Proc. Natl. Acad. Sci. USA* 88:1864–1868), and the like. Alternatively, a nucleic acid Therapeutic can be introduced intracellularly and incorporated within host cell DNA for expression, by homologous recombination.

The present invention also provides pharmaceutical compositions. Such compositions comprise a therapeutically-effective amount of a Therapeutic, and a pharmaceutically acceptable carrier. As utilized herein, the term "pharmaceutically acceptable" means approved by a regulatory agency of the Federal or a state government or listed in the U.S. Pharmacopoeia or other generally recognized pharmacopoeia for use in animals and, more particularly, in humans. The term "carrier" refers to a diluent, adjuvant, excipient, or vehicle with which the therapeutic is administered and includes, but is not limited to such sterile liquids as water and oils.

The amount of the Therapeutic of the invention which will be effective in the treatment of a particular disorder or condition will depend on the nature of the disorder or condition, and may be determined by standard clinical techniques by those of average skill within the art. In addition, in vitro assays may optionally be employed to help identify optimal dosage ranges. The precise dose to be employed in the formulation will also depend on the route of administration, and the overall seriousness of the disease or disorder, and should be decided according to the judgment of the practitioner and each patient's circumstances. However, suitable dosage ranges for intravenous administration of the Therapeutics of the present invention are generally about 20–500 micrograms ($\mu$g) of active compound per kilogram (Kg) body weight. Suitable dosage ranges for intranasal administration are generally about 0.01 pg/kg body weight to 1 mg/kg body weight. Effective doses may be extrapolated from dose-response curves derived from in vitro or animal model test systems. Suppositories generally contain active ingredient in the range of 0.5% to 10% by weight; oral formulations preferably contain 10% to 95% active ingredient.

The present invention also provides a pharmaceutical pack or kit, comprising one or more containers filled with one or more of the ingredients of the pharmaceutical compositions and Therapeutics of the present invention. Optionally associated with such container(s) may be a notice in the form prescribed by a governmental agency regulating the manufacture, use or sale of pharmaceuticals or biological products, which notice reflects approval by the agency of manufacture, use or sale for human administration.

(14) Specific Examples (i) Identification of Nlk1 Protein•Nlk1 Protein-IP Complexes A modified, improved yeast two hybrid system was used to identify protein interactions of the present invention. Yeast is a eukaryot, and therefore any intermolecular protein interactions detected in this type of system demonstrate protein interactions that occur under physiological conditions. See e.g., Chien, et al., 1991. *Proc. Natl. Acad. Sci. USA* 88:9578–9581. Expression vectors were constructed to encode two hybrid proteins. In a "reverse" screen methodology of the present invention, a portion of the Nlk1 protein was fused to the Gal4 activator domain, and the prey protein sequences of the mammalian cDNA library were fused to the DNA-binding domain. Each of the resulting vectors was then inserted into complementary mating types of yeast (an a mating type and an a mating type) by use of techniques well-known within the art. See e.g., Chien, et al., 1991., supra. Mating was carried out to express both vector constructs within the same yeast cells, thus allowing protein-protein interaction to occur. Interaction between the bait and prey domains led to transcriptional activation of Reporter Genes containing cis-binding elements for Gal4. The Reporter Genes encoding the indicator protein $\beta$-galactosidase, and metabolic markers for uracil and histidine auxotrophy, were included in a specific fashion, in one or the other of the yeast strains utilized in the mating. In this manner, yeast were selected for successful mating, expression of both fusion constructs and expression of Nlk1 protein-IPs. Yeast clones which were found to contain interacting regions were selected and grown in individual wells of 96-well microtiter plates. The plasmids containing the Nlk1 protein-IP sequences were then isolated and characterized.

The prey cDNAs were obtained from a fetal brain cDNA library of 1.5×10$^6$ independent isolates. The library was synthesized from aho 1-digested and T15-primed fetal brain mRNA (derived from five male/female, 19–22 week fetuses) which was directionally cloned into pBD-GAL4 (Stratagene; La Jolla, Calif.), a yeast Gal4 activation domain cloning vector including the TRP1 gene for selection of yeast deficient in tryptophan biosynthesis.

Two reverse screens were performed in order to test the interaction of prey cDNA products against an array of 20 and 22 bait proteins, respectively. The bait was encoded by the Nlk1 protein nucleotide sequence comprised of nucleotides 1089–1472 encoding the carboxyl-terminal region of the Nlk1 protein, as depicted in FIG. 1 (SEQ ID NO:1) and (SEQ ID NO:2), respectively. The Nlk1 protein was obtained by use of a yeast two-hybrid screen in which it served as an Retinoblastoma (Rb)-interactant.

The nucleic acid encoding the introduced bait was then expressed by lithium acetate-polyethylene glycol-mediated transformation (see e.g., Ito, et al., 1983. *J. Bacteriol.* 153:163–168) into the yeast strain N106r (mating type a, ura3, his3, ade2, trp1, leu2, gal4, gal80, cyh$^r$, Lys2::GAL1$_{UAS}$-HIS3$_{TATA}$-HIS3, ura3::GAL1$_{UAS}$-GAL$_{TATA}$-lacZ); whereas the prey sequences were introduced by transformation into the yeast strain YULH (mating type a, ura3, his3, lys2, Ade2, trp1, leu2, gal4, gal80, GAL1-URA3, GAL1-lacZ), The two transformed yeast populations were then mated using standard methods in the art. See e.g., Sherman, et al., 1991. Getting Started with Yeast (Academic Press; New York, N.Y.). In brief, the yeast were grown until mid- to late-log phase on media which selected for the presence of the appropriate plasmids. The two mating strains ($\alpha$ and a) were then diluted in YAPD media, filtered onto nitrocellulose membranes and incubated at 30° C. for 6–8 hours. The yeast cells were then transferred to media selective for the desired diploids (i.e., yeast harboring Reporter Genes for $\beta$-galactosidase, uracil auxotrophy, and histidine auxotrophy and expression of the vectors encoding the bait and prey). The mating products were then plated onto synthetic complete (SC) media (see e.g., Kaiser, et al., 1994. *Methods in Yeast Genetics* (Cold Spring Harbor Laboratory Press; Cold Spring Harbor, N.Y.)) lacking adenine and lysine (to facilitate the selection of successful matings), leucine and tryptophan (to facilitate the selection for expression of genes encoded by both the bait and prey plasmids) and uracil and histidine (to facilitate the selection for protein interactions). This medium containing the aforementioned compounds is referred to as SC Selective medium (hereinafter "SCS medium").

Selected clones were examined for expression of $\beta$-galactosidase to confirm the formation of a Nlk1 protein•Nlk1 protein-IP interaction. Filter-lift $\beta$-galactosidase assays were then performed as per a modified of the protocol of Breeden & Nasmyth (1985. *Cold Spring Harbor Quant. Biol.* 50: 643–650). Colonies were patched onto SCS plates, grown overnight and replica-plated onto Whatman No. 1 filters. The replica filters were subsequently assayed for $\beta$-galactosidase activity (i.e., colonies which were positive turned a visible blue).

The cells contained within colonies which were positive for protein interaction contained a mixture of DNA-binding and activation-domain plasmids and these cells were individually plated and regrown as single isolates in the individual wells of 96-well microtiter plates. Ten microliters (µl) of each isolate was lysed, the inserts contained within the pACT2 and pBD-GAL4 plasmids were amplified by PCR using primers specific for the flanking sequences of each vector and approximately 200 amino-terminal nucleotides of each insert sequence was determined using an ABI Model 377 sequenator. Comparison to known sequences was made using the "BLAST" computer program publicly available through the National Center for Biotechnology Information.

During a subsequent screening procedure utilizing a fragment of the Nlk1 protein consisting of nucleotides 1089–1472, five unique isolates were identified, which were determined to be identical to known Trk oncogene (TrkA) nucleic acid sequence (GenBank Acc. No. X03541) starting at nucleotides 176, 182, 200, 224 and 230 (as depicted in FIG. 2 ((SEQ ID NO:3) and Table 1). Other identified sequences included: (i) eight isolates identical to the protein phosphatase Iα sequence (GenBank Acc. No. M63960), starting at nucleotides 30, 33, 36, 48, 93, 96, and 150 (as depicted in FIG. 3 (SEQ ID NO:5); (ii) seven isolates identical to the 14-3-3ε sequence (GenBank Acc. No. U28936), starting at nucleotides 214 (2 isolates), 223 (4 isolates) and 427 (as depicted in FIG. 4 (SEQ ID NO:7); (iii) two isolates identical to the α-tropomyosin sequence (GenBank Acc. No. M19713), starting from nucleotide 535 (as depicted in FIG. 5 (SEQ ID NO:9); (iv) one isolate identical to the vimentin sequence (GenBank Acc. No. X56134), starting at nucleotide 581 (as depicted in FIG. 6 (SEQ ID NO:11); (v) four isolates identical to the p0071 sequence (GenBank Acc. No. X81889), starting at nucleotide 708 (3 isolates) and 711 (as depicted in FIG. 7 (SEQ ID NO:13); (vi) one isolate identical to the Ini-1 sequence (GenBank Acc. No. U04847), starting at nucleotide 289 (as depicted in FIG. 8 (SEQ ID NO:15); (vii) one isolate identical to the ESTS cg30153.1.g5 sequence (referred to herein as IP-1), starting at nucleotide 1 (as depicted in FIG. 9 ((SEQ ID NO:17); (viii) one isolate identical to the EST AA143367 sequence (referred to herein as IP-2) (GenBank Acc. No. AA143367), starting at nucleotide 29 (as depicted in FIG. 10 (SEQ ID NO:19); (ix) one isolate identical to the sequence referred to herein as IP-3, starting at nucleotide 514 (as depicted in FIG. 11 (SEQ ID NO:21); (x) 24 isolates identical to the cg50648.e3 sequence (referred to herein as IP-4), starting at nucleotide 1 (15 isolates), 4 (3 isolates), 40 (3 isolates), 43, 52, and 64 (as depicted in FIG. 12 (SEQ ID NO:23) and (xi) one isolate identical to the cg50424.b2 sequence (referred to herein as IP-5), at nucleotide 1 (as depicted in FIG. 13 (SEQ ID NO:25). As previously discussed herein, the nucleotide sequences for IP-1, IP-3, IP-4 and IP-5 have never been disclosed within the prior art and are considered to be sequences of novel genes. The determined nucleic acid sequences for IP-1, IP-2, IP-3, IP-4 and IP-5 and their corresponding inferred amino acid sequences are shown in FIGS. 2, 3, 4, 5, 6, 7, 8, 9, 10, 11, 12, and 13, respectively. A summary of the Nlk1 protein-interactants identified herein is shown in Table 1.

(ii) Verification of the Specificity of the Nlk1 Protein-Interactions

To determine the overall degree of specificity for the bait:prey interaction, two general assays were performed. In the first assay, N106r yeast cells were produced which expressed the individual plasmids encoding the Nlk1 proteins. These yeast cells were plated on SCS plates, grown overnight, and examined for growth. No growth was found for all five proteins, thus confirming that they were not "self-activating" proteins (i.e., these proteins require interaction with a second protein domain for a functional activation complex).

In the second assay, plasmids containing TrkA, protein phosphatase 1α, 14-3-3ε, α-tropomyosin, vimentin, p0071, Ini-1, IP-1, IP-2, IP-3, IP-4 and IP-5 inserts were transformed into strain YULH yeast (mating type a) and mated with yeast strain N106r (mating type α) expressing proteins other than the Nlk1 protein. Promiscuous binders (i.e., inserts able to bind with many other proteins in a non-specific manner) would interact in a non-specific manner with non-Nlk1 protein domains, and would subsequently be discarded as non-specific interactants. It should be noted that none of the interactants of the present invention showed binding to protein other than those described in the following paragraph.

In order to recapitulate the aforementioned detected interactions, and further demonstrate their specificity, the isolated bait plasmid for the Nlk1 protein was used to transform yeast N 106r (mating type α). The interacting domains from TrkA, protein phosphatase 1α, 14-3-3ε, α-tropomyosin, vimentin, p0071, Ini-1, IP-1, IP-2, IP-3, IP-4 and IP-5 were transformed into strain YULH (mating type a). The transformants were re-amplified and a mating was performed to recapitulate the identified Nlk1 protein•Nlk1 protein-IP interactions. As shown in FIG. 14, the Nlk1 protein was shown to complex in a specific manner with the aforementioned Nlk1 protein-IPs. In addition, the Nlk1 protein was also shown not to react non-specifically with the CDK2 protein and the vector controls. As illustrated in FIG. 14, the intersection of the Nlk1 protein row (top) with the TrkA, protein phosphatase 1α, 14-3-3ε, α-tropomyosin, vimentin, p0071, Ini-1, IP-1, IP-2, IP-3, IP-4 and IP-5 columns, indicates growth (i.e. a positive protein-protein interaction), but the intersection of the Nlk1 protein row with the columns for CDK2 and vector control, indicates no growth (i.e., no protein-protein interaction). The control using p27(Kip1) also showed no reaction with any of the Nlk1 protein interacting proteins (intersection of the column p27(Kip1) and TrkA, protein phosphatase 1α, 14-3-3ε, α-tropomyosin, vimentin, p0071, Ini-1, IP-1, IP-2, IP-3, IP-4 and IP-5 or vector). In contrast, the intersection of the p27(Kip1) indicates growth (i.e. a positive protein-protein interaction) with CDK2.

(iii) Analysis of the Sequences Encoding IP-1, IP-2, IP-3, IP-4 and IP-5

The general procedure for the assembly and identity searches of the sequences encoding human EST were performed using publicly-available EST assembly databases such as the National Center for Biotechnology Information (N.C.B.I.) BlastN 2.0 program. See Altschul, et al, 1990. *J. Mol Biol* 215:403–410.

Sequences which were demonstrated to align with 95% or greater identity at the nucleic acid level over their terminal sequences comprised of, at least, 30 nucleotides, were utilized if the alignment resulted in 5'-extension or 3'-extension of the EST sequence of interest. Once this first assembly procedure was complete, the extended sequence was again subjected to comparison with the BlastN 2.0 program in order to detect potential new homologies to the added extensions. The sequence was extended in both directions until new, related sequences which allowed extension of the assembled sequence were no longer detected.

The assembled EST sequence was then subjected to further homology searches using the BlastN 2.0 program for the identification of protein coding regions by database similarity search. See e.g., Gish & States, 1993. *Nat. Genet.*

3:266–272. The BlastN 2.0 program translates the DNA sequence in all six reading frames and compares the translated protein sequence with those within protein databases. The statistical significance is estimated under the assumption that the equivalent of one entire reading frame in the query sequence codes for protein and that significant alignments will involve only coding reading frames. Only those sequences which produce high-scoring segment pairs are shown in the BlastN 2.0 program results.

Additionally, the sequences were analyzed for open reading frames (ORFs) using proprietary software which translates the DNA sequence in all six reading frames of the (assembled) DNA sequence using the standard genetic code. The interacting ESTs were obtained from directionally-cloned libraries, and thus the direction of translation of the assembled EST is known to be in the 5' to 3' orientation. Within the translations obtained, all ORFs found in frames 1–3 were analyzed. ORFs which were found to be comprised of: (i) amino acid sequences greater than 50 amino acids which followed an initiator codon or (ii) an ORF with no initiator methionine at the 5'-terminus were determined to be possible protein products, and were compared to sequences in protein data bases using the BlastN 2.0 program.

Further protein sequence analysis was performed after selecting a suitable ORF. The protein sequence was then compared to previously characterized protein domains present in the PROSITE, BLOCKS and PRODOM motif databases. See e.g., Nakai & Kanehisa, 1992. *Genomics* 14:897–891; Wallace & Henikoff, 1992. *Cabios* 8:249–254. The BLIMPS program found matches to entries in the BLOCKS; wherein the BLOCKS analysis aligns similar sequence domains found in proteins and reveals the corresponding protein families. The BlastN 2.0 program found matches to entries in the PRODOM database; wherein the PRODOM analysis displays the alignment that constitutes protein domains with high identities and similarities. The Prosite-Scan program found matches to entries in the PROSITE database; wherein the PROSITE analysis reveals shorter functional domains, such as myristylation or phosphorylation sites or targeting signals.

(a) IP-1 (EST cg30153.g5)

One identified prey sequence of the present invention which was found to interact with the Nlk1 protein was identical to EST cg30153.g5, a human cDNA clone of 552 nucleotides. No other expressed sequences which were identical or highly homologous to the cg30153.g5 sequence were found. EST cg30153.g5 could not be extended to in either the 5' or 3' direction.

A search was performed with the IP-1 nucleotide sequence and revealed significant homologies to proteins which are associated with the cytoskeleton. An identity of 61% (nucleotides 68 to 453) was seen with human plectin gene (GenBank Acc. Nos. Z54367 (gene), U63610 (gene, exon 3–320) and U53204 (mRNA). In addition, an identity of 64% of nucleotides 66–344 was found to rat α-intemexin (GenBank Acc. No. X52017).

An open reading frame (ORF) from nucleotides 1–363 could be translated and the resulting protein was designated IP-1. This aforementioned translational frame had no initiator methionine codon (ATG) and no stop codon, thus it may represent the core region of a protein. A BlastN 2.0 search with the IP-1 sequence showed: (i) 42% identities and 50% similarities of amino acid residues 20–74 to human high-sulfur keratins (GenBank Acc. No. X63755); (ii) 51% similarity of amino acids 51–97 to KAP5.4 keratin protein (GenBank Acc. No. X73434) and (iii) 25 amino acids (amino acid residue 68–92) showed 64% homology to metallothionein (GenBank Acc. No. U67347). A search using the PRODOM program also revealed homology to high-sulfur keratin (38% homology of amino acid residues 51–94 and 45% homologies to amino acid residues 66–105). The IP-1 nucleotide and amino acid sequences are illustrated in FIG. 9 (SEQ ID NOS:17 and 18, respectively).

The homology of IP-1 to intermediate-filament-associated proteins such as plectin, intemexin and keratin are quite promising, due to the fact that vimentin (an intermediate filament protein) and p0071 (a protein of the adherens junctions) were found to be another interactant of the Nlk1 protein. In addition, PROSITE analysis showed three phosphorylation sites and an N-myristolation site within the ORF of IP-1.

Accordingly, the Nlk1 protein interactant, IP-1, represents a core region of a novel protein with homologies to intermediate-filament associated proteins.

(b) IP-2 (EST AA143467)

Another of the identified prey sequences of the present invention which were found to interact with the Nlk1 protein was identical to EST AA143467, a human cDNA clone of 599 nucleotides initially derived from a pancreas library. See Hillier, et al., 1997. Wash Univ.-NCI Human EST Project. Further homology searches resulted in no significant identities to published EST sequences being found, nor could the expressed sequence AA14346 be extended in the 5' or 3' direction. The IP-2 nucleotide and amino acid sequences are illustrated in FIG. 10 (SEQ ID NOS:19 and 21, respectively).

No significant homology to known proteins was detected using the IP-2 sequence by the BlastN 2.0 program. An open reading frame (ORF) was found to be capable of translation from nucleotides 2–346 (a 115 amino acid residue ORF) and the resulting protein was designated IP-2. The IP-2 ORF has no initiator methionine codon (ATG), thus it may represent the carboxyl-terminus of a protein following further 5' extension of the EST sequence. IP-2 showed a 28% identity and a 46% similarity of amino acid residues 3–98 to the amino-terminal region of a contractile system protein. A domain search utilizing the PRODOM database showed a 32% identities and a 47% similarity of amino acid residues 17–89 to the amino-terminal region of the α-tropomyosin chain from skeletal muscle. This result is promising due to the fact that α-tropomyosin was found to be an interactant with the Nlk1 protein.

Thus, the Nlk1 protein-interactant, IP-2, represents a novel tropomyosin-homolog protein.

(c) IP-3

An additional identified prey sequence of the present invention which was demonstrated to interact with the Nlk1 protein was found to be identical to EST H67985, a 371 nucleotide sequence derived from a human fetal liver/spleen library, which may function as a ubiquitin carboxyl-terminal hydrolase (see e.g., Hillier, et al., 1995. Wash Univ.-Merck EST Project). The 5'-terminus of this EST was able to be extended with EST AA255861 (NCI Cancer Genome Anatomy Project, 1997 Tumor Gene Index) and the 3'-terminus could be extended with EST AA251528 (NCI Cancer Genome Anatomy Project, 1997 Tumor Gene Index), resulting in an assembled EST 941 nucleotides in length. The complete assembled EST sequence of 941 nucleotides is shown in FIG. 11, with the nucleic acid sequence of EST H67985 shown in bold lettering (nucleotides 269–701), the nucleic acid sequence of EST AA255861 (nucleotides 1–429 of the assembled EST) shown in italics and the nucleic acid sequence of EST AA251528 denoted by underline starting at nucleotide 524 of the assembled expressed sequence.

The nucleotide sequence of the assembled EST showed high homology to ubiquitin carboxyl-terminal hydrolase-homolog ESTs. Specifically, EST AA236822 showed a 94% identity to nucleotides 9–98; EST AA081709 showed a 98% identity to nucleotides 336–674; EST AA 592337 showed an 87% identity to nucleotides 1–183; EST AA 410216 showed a 94% identity to nucleotides 1–74 and EST R52765 showed a 99% identity to nucleotides 597–941. Nonetheless, no sequence could be utilized for further extension of the assembled EST. The IP-3 nucleotide and amino acid sequences are illustrated in FIG. 11 (SEQ ID NO:21 and 22, respectively).

The translated protein was found to encompass an open reading frame (ORF) from nucleotides 67–939 (291 amino acid ORF) and was designated IP-3. This translational frame had an initiator methionine codon (ATG) but no stop codon, thus it may represent the amino-terminal region of a protein. A domain search utilizing the PRODOM program was performed and showed identities to ubiquitin carboxyl-terminal hydrolases 1, 2, 3 and 4. These identities were all revealed within the region between amino acid residues 17 and 172, and showed a 38% identity and 55% similarity. In addition, the PRODOM search was found to be in good agreement with the PROSITE analysis, which showed, in addition to several phosphorylation and a N-myristylation site, a ubiquitin carboxyl-terminal hydrolases family 2 signature.

Therefore, the Nlk1 protein-interactant, IP-3, represents a novel ubiquitin processing enzyme homolog.

(d) IP-4 (EST cg 50648e3

Another identified prey sequence of the present invention which was found to interact with the Nlk1 protein was EST cg50648e3, a human cDNA clone of 439 nucleotides. EST cg50648e3 was shown to exhibit a high degree of identity to EST M62042 (GenBank Acc. No. M62042; see e.g., Adams, et al., 1991. *Science* 252:1651–1656) and thus, the expressed sequence was assembled as follows. Nucleotides 1–70 of cg50648e3 were extended at the 3'-terminus with nucleotides 1–472 of EST M62042, resulting in an expressed sequence 542 nucleotides in length. Further homology searches resulted in no significant identity to other published EST sequences, and therefore, the extended expressed sequence could not be further extended. The IP-4 nucleotide and amino acid sequences are illustrated in FIG. 12 [SEQ ID NO:23 and 24, respectively].

The extended sequence of 542 nucleotides showed a 65% identity (nucleotides 55–297) to the *Caenorhabditis elegans* collagen encoding gene Col-2 (GenBank Acc. No. V00148). A 62% identity of nucleotides 154–435 were found to the human zinc finger transcriptional regulator (GenBank Acc. No. M92844).

The open reading frame (ORF) from nucleotides 1–213 (71 amino acid ORF) was shown not to possess a methionine start codon, thus it may represent the carboxyl-terminal region of the protein designated IP-4 herein. IP-4 showed a 53% homology to the human pro-α 1 type-I collagen (GenBank Acc. No. K03179) and to several collagens of *C. elegans* (GenBank Acc. Nos. C0965 and AF016671) and of *Canis familiaris* (GenBank Acc. Nos. U07888 and A55267).

Thus, the Nlk1 protein-interactant, IP-4, represents a novel protein with homologies to collagens.

(e) IP-5 (EST cg50424 b2)

Yet another identified prey sequence which was demonstrated to interact with the Nlk1 protein was shown to be identical to EST cg50424.b2, a human cDNA clone of 441 nucleotides. Further homology searches resulted in no significant identities to other published EST sequences and EST cg50424.b2 could not be extended in either the 5' or 3' direction. The IP-5 nucleotide and amino acid sequences are illustrated in FIG. 13 [SEQ ID NO:25 and 26, respectively].

An open reading frame (ORF) from nucleotides 1–246 (82 amino acid ORF) was found to be translated and was designated IP-5. This ORF was shown not to possess an initiator methionine codon and thus, it may represent the carboxyl-terminus of a protein. IP-5 showed a 28% identity and a 54% similarity of amino acid residues 9–81 to tropomyosins of different species including, but not limited to, *Homo sapiens*, horse, rat, *S. cerevisiae*. In addition, IP-5 showed a 61% similarity to amino acid residues 44–116 of the cytoskeletal (muscle-type) tropomyosin isoform (GenBank Acc. No. M12127; total of 131 amino acid residues) and a 54% similarity to amino acid residues 156–232 of human tropomyosin (GenBank Acc. No. X05276; total of 248 amino acid residues), to the human fibroblast tropomyosin (GenBank Acc. No. S07282) and the human non-muscle type fibroblast tropomyosin (GenBank Acc. No. P07226). A domain search utilizing the PRODOM program showed a 32% identity and a 47% similarity of amino acid residues 17–89 to the amino-terminal region of the α-tropomyosin chain from skeletal muscle.

In addition to the aforementioned homology to the tropomyosins, amino acid residues 21–56 of IP-5 showed a 32% identity and a 70% homology to amino acid residues 6–42 of the Sry-like transcription factor Sox (GenBank Acc. No. X65661). Sox genes share a particular DNA-binding domain (HMG) with Sry-like proteins. A search using the PRODOM program revealed a 56% homology of amino acid residues 15–74 (identities of 30%) to the a negative regulator of transcription and amino acid residues 64–80 were 76% homologous to a positive regulator of late transcription (Protein C).

The homologies demonstrated by IP-5 are quite promising due to the fact that α-tropomyosin was found to be an interactant of the Nlk1 protein. This result is similar to that found for IP-2 and these two proteins may different tropomyosin homolog proteins. Further analysis using a domain search (BLOCKS) revealed homology to intermediate filament proteins. PROSITE analysis showed a protein kinase C phosphorylation site and a N-myristolation site within the ORF.

In accord, the Nlk1 protein interactant, IP-5, represents a carboxy-terminal region of a novel, tropomyosin-homolog protein.

The present invention is not to be limited in scope by the specific embodiments described herein. Indeed, various modifications of the invention, in addition to those described herein, will become apparent to those skilled within the art from the foregoing description and accompanying figures. Such modifications are intended to fall within the scope of the appended claims.

Various publications are cited herein, and the disclosures of which are incorporated by reference in their entireties.

What is claimed is:

1. A purified complex of a Nlk1 protein and Nlk1 protein-IP (interacting protein), wherein said Nlk1 protein-IP is selected from the group consisting of: TrkA, protein phosphatase 1α, 14-3-3ε, α-tropomyosin, vimentin, p0071, Ini-1, IP-1 (SEO ID NO:18), IP-2 ((SEQ ID NO:20), IP-3 (SEQ ID NO:22), IP-4 (SEQ ID NO:24) and IP-5 (SEQ ID NO:26).

2. The purified complex of claim 1, wherein said proteins are human proteins.

3. A chimeric protein comprising a fragment of an Nlk1 protein consisting of at least 6 amino acid residues fused, via a covalent bond to a fragment of Nlk1 protein-IP also consisting of at least 6 amino acid residues, wherein said Nlk1 protein-IP is selected from the group consisting of: TrkA, protein phosphatase 1α, 14-3-3ε, α-tropomyosin, vimentin, p0071, Ini-1, IP-1 (SEQ ID NO:18), IP-2 (SEQ ID NO:20), IP-3 (SEQ ID NO:22), IP-4 ((SEQ ID NO:24) and IP-5 (SEQ ID NO:26), and wherein said fragment of the Nlk1 protein is a fragment that binds to the Nlk1 protein-IP and wherein said fragment of the Nlk1 protein-IP is a fragment capable of binding the Nlk1 protein.

4. The chimeric protein of claim 3, wherein said fragment of the Nlk1 protein and said fragment of the Nlk1 protein-IP form a Nlk1 protein•Nlk1 protein-IP complex.

5. A purified IP selected from the group consisting of IP-1 (SEQ ID NO:18), IP-2 (SEQ ID NO:20), IP-3 (SEQ ID NO:22), IP-4 (SEQ ID NO:24) and IP-5 (SEQ ID NO:26).

6. The protein of claim 5, wherein protein is a human protein.

7. The protein of claim 6, which comprises an amino acid sequence selected from the group consisting of: SEQ ID NO:18; SEQ ID NO:20; SEQ ID NO:22; SEQ ID NO:24 and SEQ ID NO:26.

8. A purified protein encoded by a nucleic acid which is hybridizable under high stringent hybridization condition to the inverse complement of a DNA possessing a nucleotide sequence comprising at least 10 nucleotides of the nucleotide sequence selected from the group consisting of SEQ ID NO:17; SEQ ID NO:19; SEQ ID NO:21; SEQ ID NO:23, and SEQ ID NO:25, wherein the encoded protein binds the Nlk1 protein.

9. A purified fragment of a protein selected from the group consisting of: TrkA, protein phosphatase 1α, 14-3-3ε, α-tropomyosin, vimentin, p0071, Ini-1, IP-1 (SEQ ID NO:18), IP-2 (SEQ ID NO:20), IP-3 (SEQ ID NO:22), IP-4 (SEQ ID NO:24) and IP-5 (SEQ ID NO:26), wherein said fragment possesses the ability to bind the Nlk1 protein.

10. The purified complex of claim 1, wherein said Nlk1 protein-IP protein) is TrkA.

11. The purified complex of claim 1, wherein said Nlk1 protein-IP is protein phosphatase 1α.

12. The purified complex of claim 1, wherein said Nlk1 protein-IP is 14-3-3ε.

13. The purified complex of claim 1, wherein said Nlk1 protein-IP protein) is α-tropomyosin.

14. The purified complex of claim 1, wherein said Nlk1 protein-IP is vimentin.

15. The purified complex of claim 1, wherein said Nlk1 protein-IP is p0071.

16. The purified complex of claim 1, wherein said Nlk1 protein-IP is Ini-1.

17. The purified complex of claim 1, wherein said Nlk1 protein-IP is IP-1.

18. The purified complex of claim 1, wherein said Nlk1 protein-IP is IP-2.

19. The purified complex of claim 1, wherein said Nlk1 protein-IP is IP-3.

20. The purified complex of claim 1, wherein said Nlk1 protein-IP is IP-4.

21. The purified complex of claim 1, wherein said Nlk1 protein-IP is IP-5.

22. The purified complex of claim 1, wherein said Nlk1 protein-IP comprises amino acids 1–641 of SEQ ID NO:4 (TrkA).

23. The purified complex of claim 1, wherein said Nlk1 protein-IP comprises amino acids 41–330 of SEQ ID NO:6 (protein phosphatase 1α).

24. The purified complex of claim 1, wherein said Nlk1 protein-IP comprises amino acids 143–263 of SEQ ID NO:8 (14-3-3ε).

25. The purified complex of claim 1, wherein said Nlk1 protein-IP comprises amino acids 161–347 of SEQ ID NO:10 (α-tropomyosin).

26. The purified complex of claim 1, wherein said Nlk1 protein-IP comprises amino acids 180–466 of SEQ ID NO:12 (vimentin).

27. The purified complex of claim 2, wherein said Nlk1 protein-IP comprises amino acids 161–347 of SEQ ID NO:10 (α-tropomyosin).

28. The purified complex of claim 1, wherein said Nlk1 protein-IP comprises amino acids 190–1208 of SEQ ID NO:14 (p0071).

29. The purified complex of claim 1, wherein said Nlk1 protein-IP comprises amino acids 74–385 of SEQ ID NO:16 (Ini-1).

30. The purified complex of claim 1, wherein said Nlk1 protein-IP comprises amino acids 1–363 of SEQ ID NO:18.

31. The purified complex of claim 1, wherein said Nlk1 protein-IP comprises amino acids 10–115 of SEQ ID NO:20.

32. The purified complex of claim 1, wherein said Nlk1 protein-IP comprises amino acids 150–291 of SEQ ID NO:22.

33. The purified complex of claim 1, wherein said Nlk1 protein-IP comprises amino acids 1–71 of SEQ ID NO:24.

34. The purified-complex of claim 1, wherein said Nlk1 protein-IP comprises amino acids 1–82 of SEQ ID NO:26.

35. The purified complex of claim 1, wherein said Nlk1 protein-IP comprises the amino acid sequence encoded by nucleotides 1089–1472 of SEQ ID NO: 1.

36. The purified IP of claim 5, wherein said IP is IP-1.

37. The purified IP of claim 5, wherein said IP is IP-2.

38. The purified IP of claim 5, wherein said IP is IP-3.

39. The purified IP of claim 5, wherein said IP is IP-4.

40. The purified IP of claim 5, wherein said IP is IP-5.

41. The purified IP of claim 5, wherein said IP comprises amino acids 1–363 of SEQ ID NO:18.

42. The purified IP of claim 5, wherein said IP comprises amino acids 10–115 of SEQ ID NO:20.

43. The purified IP of claim 5, wherein said IP comprises amino acids 150–291 of SEQ ID NO:22.

44. The purified IP of claim 5, wherein said IP comprises amino acids 1–71 of SEQ ID NO:24.

45. The purified IP of claim 5, wherein said IP comprises amino acids 1–82 of SEQ ID NO:26.

46. A kit comprising a Nlk1 protein and aNlk1 protein-IP, wherein said Nlk1 protein-IP is selected from the group consisting of: TrkA, protein phosphatase 1α, 14-3-3ε, α-tropomyosin, vimentin, p0071, Ini-1, IP-1 (SEQ ID NO:18), IP-2 (SEQ ID NO:20), IP-3 (SEQ ID NO:22), IP-4 (SEQ ID NO:24) and IP-5 (SEQ ID NO:26).

* * * * *